US012797442B2

(12) United States Patent
Huh et al.

(10) Patent No.: US 12,797,442 B2
(45) Date of Patent: Nov. 17, 2026

(54) HARNESSING INFLAMMATION TO TREAT NEURODEVELOPMENTAL DISORDERS

(71) Applicants: President and Fellows of Harvard College, Cambridge, MA (US); Massachusetts Institute of Technology, Cambridge, MA (US)

(72) Inventors: Jun Huh, Newton, MA (US); Bohyun Gloria Choi, Newton, MA (US)

(73) Assignees: President and Fellows of Harvard College; Massachusetts Institute of Technology

( * ) Notice: Subject to any disclaimer, the term of this patent is extended or adjusted under 35 U.S.C. 154(b) by 1369 days.

(21) Appl. No.: 17/419,870

(22) PCT Filed: Jan. 9, 2020

(86) PCT No.: PCT/US2020/012903
§ 371 (c)(1),
(2) Date: Jun. 30, 2021

(87) PCT Pub. No.: WO2020/146610
PCT Pub. Date: Jul. 16, 2020

(65) Prior Publication Data

US 2022/0072101 A1 Mar. 10, 2022

Related U.S. Application Data

(60) Provisional application No. 62/913,945, filed on Oct. 11, 2019, provisional application No. 62/791,368, filed on Jan. 11, 2019.

(51) Int. Cl.
*A61K 38/20* (2006.01)
*A61K 38/21* (2006.01)
*A61P 25/28* (2006.01)
*C07K 16/28* (2006.01)

(52) U.S. Cl.
CPC ............ *A61K 38/20* (2013.01); *A61K 38/217* (2013.01); *A61P 25/28* (2018.01); *C07K 16/2809* (2013.01)

(58) Field of Classification Search
CPC ....... A61K 38/20; A61K 38/217; A61P 25/28; C07K 16/249; C07K 16/244
See application file for complete search history.

(56) References Cited

U.S. PATENT DOCUMENTS

| | | | | |
|---|---|---|---|---|
| 2016/0311897 | A1 | 10/2016 | Jaspers et al. | |
| 2017/0028061 | A1 | 2/2017 | Honda et al. | |
| 2017/0326356 | A1* | 11/2017 | Huh | A61K 38/217 |

OTHER PUBLICATIONS

U.S. Appl. No. 18/853,224, filed Oct. 1, 2024, Huh; Jun R.*
Hofstetter et al. Cytokine 34 (2006) 184-197 (Year: 2006).*
Gupta et al. J Clin Immunol (2010) 30 (Suppl 1):S90-S96 (Year: 2010).*
Magid-Bernstein et al. Journal of Child Neurology 2015, vol. 30(3) 386-390 (Year: 2015).*
Kuhn et al. Immunotherapy. Jul. 2016;8(8):889-906. Epub May 10, 2016. (Year: 2016).*
Choi et al. "The maternal interleukin-17a pathway in mice promotes autism-like phenotypes in offspring." Science 351 (6276): 933-939 (2016).
Grzadzinski et al. "Children with autism spectrum disorder who improve with fever: insights from the Simons Simplex Collection." Autism Research 11(1): 175-184 (2018).
Yim et al. "Reversing behavioural abnormalities in mice exposed to maternal inflammation." Nature 549(7673): 482-487 (2017).

* cited by examiner

*Primary Examiner* — Jeffrey Stucker
*Assistant Examiner* — Sarah Cooper Patterson
(74) *Attorney, Agent, or Firm* — NIXON PEABODY LLP; David S. Resnick; Nicole D. Kling

(57) ABSTRACT

Described herein are methods and compositions related to a method of treating a neurodevelopmental disorder in a subject in need thereof, the method comprises administering to the subject an agent that increases the level or activity of interleukin-17a (IL-17a) in the brain. The method can further comprise administering an agent that increases the permeability of the blood brain barrier.

12 Claims, 100 Drawing Sheets

Specification includes a Sequence Listing.

| | | | | | |
|---|---|---|---|---|---|
| + | - | + | - | - | - |
| - | + | - | + | + | + |
| + | + | + | + | - | - |
| - | - | - | - | + | - |
| - | - | - | - | - | + |

| | Pre/Test | Pre/Test | Pre/Test | Pre/Test | Pre/Test | Pre/Test |
|---|---|---|---|---|---|---|
| Veh | + | - | + | - | - | - |
| LPS | - | + | - | + | + | + |
| Isotype | + | + | + | + | - | - |
| αIL-17a | - | - | - | - | + | - |
| αIFNγ | - | - | - | - | - | + |

SEQUENCE LISTING

<160> NUMBER OF SEQ ID NOS: 12

<210> SEQ ID NO 1
<211> LENGTH: 155
<212> TYPE: PRT
<213> ORGANISM: Homo sapiens

<400> SEQUENCE: 1

```
Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
            20                  25                  30

Cys Pro Asn Ser Glu Asp Lys Asn Phe Pro Arg Thr Val Met Val Asn
        35                  40                  45

Leu Asn Ile His Asn Arg Asn Thr Asn Thr Asn Pro Lys Arg Ser Ser
    50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155
```

<210> SEQ ID NO 2
<211> LENGTH: 866
<212> TYPE: PRT
<213> ORGANISM: Homo sapiens

<400> SEQUENCE: 2

```
Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110
```

```
Glu Leu Ser Val Leu Gln Leu Asn Thr Asn Glu Arg Leu Cys Val Arg
        115                 120                 125

Phe Glu Phe Leu Ser Lys Leu Arg His His His Arg Arg Trp Arg Phe
    130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Val Tyr Trp Phe Ile Thr Gly Ile Ser Ile Leu Leu Val Gly Ser Val
                325                 330                 335

Ile Leu Leu Ile Val Cys Met Thr Trp Arg Leu Ala Gly Pro Gly Ser
            340                 345                 350

Glu Lys Tyr Ser Asp Asp Thr Lys Tyr Thr Asp Gly Leu Pro Ala Ala
        355                 360                 365

Asp Leu Ile Pro Pro Pro Leu Lys Pro Arg Lys Val Trp Ile Ile Tyr
    370                 375                 380

Ser Ala Asp His Pro Leu Tyr Val Asp Val Val Leu Lys Phe Ala Gln
385                 390                 395                 400

Phe Leu Leu Thr Ala Cys Gly Thr Glu Val Ala Leu Asp Leu Leu Glu
                405                 410                 415

Glu Gln Ala Ile Ser Glu Ala Gly Val Met Thr Trp Val Gly Arg Gln
            420                 425                 430

Lys Gln Glu Met Val Glu Ser Asn Ser Lys Ile Ile Val Leu Cys Ser
        435                 440                 445

Arg Gly Thr Arg Ala Lys Trp Gln Ala Leu Leu Gly Arg Gly Ala Pro
    450                 455                 460

Val Arg Leu Arg Cys Asp His Gly Lys Pro Val Gly Asp Leu Phe Thr
465                 470                 475                 480

Ala Ala Met Asn Met Ile Leu Pro Asp Phe Lys Arg Pro Ala Cys Phe
                485                 490                 495

Gly Thr Tyr Val Val Cys Tyr Phe Ser Glu Val Ser Cys Asp Gly Asp
            500                 505                 510

Val Pro Asp Leu Phe Gly Ala Ala Pro Arg Tyr Pro Leu Met Asp Arg
        515                 520                 525
```

```
Phe Glu Glu Val Tyr Phe Arg Ile Gln Asp Leu Glu Met Phe Gln Pro
    530                 535                 540

Gly Arg Met His Arg Val Gly Glu Leu Ser Gly Asp Asn Tyr Leu Arg
545                 550                 555                 560

Ser Pro Gly Gly Arg Gln Leu Arg Ala Ala Leu Asp Arg Phe Arg Asp
                565                 570                 575

Trp Gln Val Arg Cys Pro Asp Trp Phe Glu Cys Glu Asn Leu Tyr Ser
            580                 585                 590

Ala Asp Asp Gln Asp Ala Pro Ser Leu Asp Glu Glu Val Phe Glu Glu
        595                 600                 605

Pro Leu Leu Pro Pro Gly Thr Gly Ile Val Lys Arg Ala Pro Leu Val
    610                 615                 620

Arg Glu Pro Gly Ser Gln Ala Cys Leu Ala Ile Asp Pro Leu Val Gly
625                 630                 635                 640

Glu Glu Gly Gly Ala Ala Val Ala Lys Leu Glu Pro His Leu Gln Pro
                645                 650                 655

Arg Gly Gln Pro Ala Pro Gln Pro Leu His Thr Leu Val Leu Ala Ala
            660                 665                 670

Glu Glu Gly Ala Leu Val Ala Ala Val Glu Pro Gly Pro Leu Ala Asp
        675                 680                 685

Gly Ala Ala Val Arg Leu Ala Leu Ala Gly Glu Gly Glu Ala Cys Pro
    690                 695                 700

Leu Leu Gly Ser Pro Gly Ala Gly Arg Asn Ser Val Leu Phe Leu Pro
705                 710                 715                 720

Val Asp Pro Glu Asp Ser Pro Leu Gly Ser Ser Thr Pro Met Ala Ser
                725                 730                 735

Pro Asp Leu Leu Pro Glu Asp Val Arg Glu His Leu Glu Gly Leu Met
            740                 745                 750

Leu Ser Leu Phe Glu Gln Ser Leu Ser Cys Gln Ala Gln Gly Gly Cys
        755                 760                 765

Ser Arg Pro Ala Met Val Leu Thr Asp Pro His Thr Pro Tyr Glu Glu
    770                 775                 780

Glu Gln Arg Gln Ser Val Gln Ser Asp Gln Gly Tyr Ile Ser Arg Ser
785                 790                 795                 800

Ser Pro Gln Pro Pro Glu Gly Leu Thr Glu Met Glu Glu Glu Glu Glu
                805                 810                 815

Glu Glu Gln Asp Pro Gly Lys Pro Ala Leu Pro Leu Ser Pro Glu Asp
            820                 825                 830

Leu Glu Ser Leu Arg Ser Leu Gln Arg Gln Leu Leu Phe Arg Gln Leu
        835                 840                 845

Gln Lys Asn Ser Gly Trp Asp Thr Met Gly Ser Glu Ser Glu Gly Pro
    850                 855                 860

Ser Ala
865


<210> SEQ ID NO 3
<211> LENGTH: 832
<212> TYPE: PRT
<213> ORGANISM: Homo sapiens

<400> SEQUENCE: 3

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30
```

```
Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His His Arg Arg Trp Arg Phe
    130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Gly Pro Gly Ser Glu Lys
305                 310                 315                 320

Tyr Ser Asp Asp Thr Lys Tyr Thr Asp Gly Leu Pro Ala Ala Asp Leu
                325                 330                 335

Ile Pro Pro Pro Leu Lys Pro Arg Lys Val Trp Ile Ile Tyr Ser Ala
            340                 345                 350

Asp His Pro Leu Tyr Val Asp Val Val Leu Lys Phe Ala Gln Phe Leu
        355                 360                 365

Leu Thr Ala Cys Gly Thr Glu Val Ala Leu Asp Leu Leu Glu Glu Gln
    370                 375                 380

Ala Ile Ser Glu Ala Gly Val Met Thr Trp Val Gly Arg Gln Lys Gln
385                 390                 395                 400

Glu Met Val Glu Ser Asn Ser Lys Ile Ile Val Leu Cys Ser Arg Gly
                405                 410                 415

Thr Arg Ala Lys Trp Gln Ala Leu Leu Gly Arg Gly Ala Pro Val Arg
            420                 425                 430

Leu Arg Cys Asp His Gly Lys Pro Val Gly Asp Leu Phe Thr Ala Ala
        435                 440                 445
```

```
Met Asn Met Ile Leu Pro Asp Phe Lys Arg Pro Ala Cys Phe Gly Thr
    450                 455                 460

Tyr Val Val Cys Tyr Phe Ser Glu Val Ser Cys Asp Gly Asp Val Pro
465                 470                 475                 480

Asp Leu Phe Gly Ala Ala Pro Arg Tyr Pro Leu Met Asp Arg Phe Glu
                485                 490                 495

Glu Val Tyr Phe Arg Ile Gln Asp Leu Glu Met Phe Gln Pro Gly Arg
            500                 505                 510

Met His Arg Val Gly Glu Leu Ser Gly Asp Asn Tyr Leu Arg Ser Pro
        515                 520                 525

Gly Gly Arg Gln Leu Arg Ala Ala Leu Asp Arg Phe Arg Asp Trp Gln
    530                 535                 540

Val Arg Cys Pro Asp Trp Phe Glu Cys Glu Asn Leu Tyr Ser Ala Asp
545                 550                 555                 560

Asp Gln Asp Ala Pro Ser Leu Asp Glu Glu Val Phe Glu Glu Pro Leu
                565                 570                 575

Leu Pro Pro Gly Thr Gly Ile Val Lys Arg Ala Pro Leu Val Arg Glu
            580                 585                 590

Pro Gly Ser Gln Ala Cys Leu Ala Ile Asp Pro Leu Val Gly Glu Glu
        595                 600                 605

Gly Gly Ala Ala Val Ala Lys Leu Glu Pro His Leu Gln Pro Arg Gly
    610                 615                 620

Gln Pro Ala Pro Gln Pro Leu His Thr Leu Val Leu Ala Ala Glu Glu
625                 630                 635                 640

Gly Ala Leu Val Ala Ala Val Glu Pro Gly Pro Leu Ala Asp Gly Ala
                645                 650                 655

Ala Val Arg Leu Ala Leu Ala Gly Glu Gly Glu Ala Cys Pro Leu Leu
            660                 665                 670

Gly Ser Pro Gly Ala Gly Arg Asn Ser Val Leu Phe Leu Pro Val Asp
        675                 680                 685

Pro Glu Asp Ser Pro Leu Gly Ser Ser Thr Pro Met Ala Ser Pro Asp
    690                 695                 700

Leu Leu Pro Glu Asp Val Arg Glu His Leu Glu Gly Leu Met Leu Ser
705                 710                 715                 720

Leu Phe Glu Gln Ser Leu Ser Cys Gln Ala Gln Gly Gly Cys Ser Arg
                725                 730                 735

Pro Ala Met Val Leu Thr Asp Pro His Thr Pro Tyr Glu Glu Glu Gln
            740                 745                 750

Arg Gln Ser Val Gln Ser Asp Gln Gly Tyr Ile Ser Arg Ser Ser Pro
        755                 760                 765

Gln Pro Pro Glu Gly Leu Thr Glu Met Glu Glu Glu Glu Glu Glu Glu
    770                 775                 780

Gln Asp Pro Gly Lys Pro Ala Leu Pro Leu Ser Pro Glu Asp Leu Glu
785                 790                 795                 800

Ser Leu Arg Ser Leu Gln Arg Gln Leu Leu Phe Arg Gln Leu Gln Lys
                805                 810                 815

Asn Ser Gly Trp Asp Thr Met Gly Ser Glu Ser Glu Gly Pro Ser Ala
            820                 825                 830
```

<210> SEQ ID NO 4
<211> LENGTH: 166
<212> TYPE: PRT
<213> ORGANISM: Homo sapiens

<400> SEQUENCE: 4

```
Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
agatgccagc atcctgtacc 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
cacagtcaca gcgtgtctca 20

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
gacttcaaca gcctcccact cttcc 25

<210> SEQ ID NO 8
<211> LENGTH: 26
<212> TYPE: DNA

-continued

```
<213> ORGANISM: Artificial Sequence
<220> FEATURE:
<223> OTHER INFORMATION: Description of Artificial Sequence: Synthetic
      primer

<400> SEQUENCE: 8

tgggtggtcc aggtttctta ctcctt                                          26


<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

gacgctgagg catgatgaga gcat                                            24


<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

gacggcacgg attgttattc a                                               21


<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

actcctacgg gaggcagcag t                                               21


<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

attaccgcgg ctgctggc                                                   18
```

HARNESSING INFLAMMATION TO TREAT NEURODEVELOPMENTAL DISORDERS

CROSS-REFEREENCE TO RELATED APPLICATIONS

This application is a 35 U.S.C. § 371 National Phase Entry Application of International Application No. PCT/US2020/012903 filed Jan. 9, 2020, which designates the U.S. and claims benefit under 35 U.S.C. § 119(e) of U.S. Provisional Application No. 62/791,368 filed Jan. 11, 2019, and U.S. Provisional Application No. 62/913,945 filed Oct. 11, 2019, the contents of which are incorporated herein by reference in their entireties.

GOVERNMENT SUPPORT

This invention was made with government support under MH115037 awarded by National Institutes of Health (NIH). The government has certain rights in this invention.

SEQUENCE LISTING

The instant application contains a Sequence Listing which has been submitted electronically in ASCII format and is hereby incorporated by reference in its entirety. Said ASCII copy, created on Dec. 3, 2019, is named 002806-094070WOPT_SL.txt and is 19,614 bytes in size.

TECHNICAL FIELD

The technology described herein relates to methods and compositions for treating neurodevelopmental disorders and uses thereof.

BACKGROUND

Neurodevelopmental disorders such as autism can be characterized by difficulty socializing or communicating and repetitive behaviors. Interestingly, for many patients with neurodevelopmental disorders, fever is correlated with an improvement in behavioral symptoms. During the course of a fever, patients show decreased severity of the core symptoms of the neurodevelopmental disease or disorder. The maternal immune activation (MIA) mouse model is a useful tool to gain a mechanistic understanding of how this phenomenon occurs. However, the exact mechanisms of how the immune system influences the brain are currently unknown and there are currently no effective therapeutic agents for neurodevelopmental disorders. Thus, new targets and treatments for neurodevelopmental disorders are needed to prevent and improve the quality of life for affected individuals.

SUMMARY

In one aspect, described herein is a method of treating a neurodevelopmental disorder in a subject in need thereof, the method comprises: administering to the subject an agent that increases the level or activity of interleukin (IL)-17a (IL-17a) in the brain.

In another aspect, described herein is a method of treating a neurodevelopmental disorder in a subject in need thereof, the method comprises: administering IL-17a and IFNγ to the subject.

In another aspect, described herein is a method of treating a neurodevelopmental disorder in a subject in need thereof, the method comprises: administering to the subject at least one genetically engineered microorganism or population thereof, that expresses an agent that increases the level or activity of interleukin (IL)-17a (IL-17a).

In another aspect, described herein is a method of treating a neurodevelopmental disorder in a subject in need thereof, the method comprising: administering to the subject an antibody or antibody fragment thereof that increases the level or activity of interleukin (IL)-17a (IL-17a).

In another aspect, described herein is a pharmaceutical composition formulated for the treatment of a neurodevelopmental disease, the pharmaceutical composition comprising: an agent that increases the level or activity of IL-17a in the brain of a subject; and a pharmaceutically acceptable carrier.

In one embodiment of any of the aspects, the agent increases the level or activity of the interleukin-17 receptor (IL-17Ra) in the brain. In another embodiment of any of the aspects, the agent is selected from the group consisting of: a small molecule, an antibody, a peptide, a genome editing system, a vector, a miRNA, and a siRNA.

In another embodiment of any of the aspects, the peptide is a cytokine. In another embodiment of any of the aspects, the cytokine is IL-17a, IL-17f, or IL-25. In another embodiment of any of the aspects, the cytokine is recombinant.

In another embodiment of any of the aspects, the antibody is an anti-cluster of differentiation 3 (CD3) antibody or antibody fragment thereof. In another embodiment of any of the aspects, the antibody or antibody fragment thereof promotes an increase in the level of IL-17a in the brain of the subject. In another embodiment of any of the aspects, the antibody or antibody fragment thereof increases the population of T helper-17 cells (Th17) in the gut. In another embodiment of any of the aspects, the antibody or antibody fragment thereof increases the population of IL-17 positive immune cells in the brain.

In another embodiment of any of the aspects, the method further comprises administering an agent that increases the permeability of the blood brain barrier. In another embodiment of any of the aspects, the agent that increases permeability of the blood brain barrier is a peptide. In another embodiment of any of the aspects, the peptide is an interferon. In another embodiment of any of the aspects, the interferon is interferon gamma (IFNγ).

In another embodiment of any of the aspects, the IL-17a and IFNγ are recombinant.

In another embodiment of any of the aspects, the agent modulates the neural activity in a brain region selected from the group consisting of: the dysgranular zone of the primary somatosensory cortex (S1DZ), prefrontal cortex (PFC), cerebellum, temporal association cortex (TeA), temporal parietal junction (TPJ), secondary somatosensory cortex, and the parietal association area.

In another embodiment of any of the aspects, the neurodevelopmental disorder is selected from the group consisting of: autism spectrum disorder (ASD), Asperger's syndrome, learning disabilities, anxiety disorders, schizophrenia, attention deficit hyperactivity disorder (ADHD), sensory processing disorder, epilepsy, fragile X syndrome, sleep disorder, obsessive compulsive disorder (OCD), and non-verbal learning disorder.

In another embodiment of any of the aspects, the agent is formulated in a pharmaceutical composition. In another embodiment of any of the aspects, the pharmaceutical composition is formulated to restrict delivery of the agent to the brain. In another embodiment of any of the aspects, the composition further comprises an enteric coating.

In another embodiment of any of the aspects, the agent is administered by direct injection, subcutaneous injection, muscular injection, oral, or nasal administration.

In another embodiment of any of the aspects, the level or activity of IL-17a is increased by at least 50%, at least 60%, at least 70%, at least 80%, at least 90%, or more as compared to an appropriate control.

In another embodiment of any of the aspects, the subject is a mammal. In another embodiment of any of the aspects, the subject is a human.

In another embodiment of any of the aspects, the genetically engineered microorganism is a bacterium. In another embodiment of any of the aspects, the genetically engineered microorganism increases the population of T helper-17 cells (Th17) in the gut. In another embodiment of any of the aspects, the genetically engineered microorganism is administered by oral administration. In another embodiment of any of the aspects, the genetically engineered microorganism is formulated in a pharmaceutical composition.

In another embodiment of any of the aspects, the pharmaceutical composition is formulated to restrict delivery of the agent to the gastrointestinal tract.

In another aspect, described herein is a pharmaceutical composition formulated for the treatment of a neurodevelopmental disease, the pharmaceutical composition comprising: (a) an agent that increases the level or activity of IL-17a in the brain of a subject; and (b) a pharmaceutically acceptable carrier.

In one embodiment of any of the aspects, the agent is an anti-CD3 antibody reagent.

In another embodiment of any of the aspects, the agent is a microorganism or group of microorganisms. In another embodiment, the microorganism or group of microorganisms comprises at least one commensal bacteria. In another embodiment of any of the aspects, the microorganism is genetically engineered.

In another embodiment of any of the aspects, the agent or pharmaceutical composition increases the population of T helper-17 cells (Th17) in the gut of the subject.

BRIEF DESCRIPTION OF THE DRAWINGS

FIG. 1A shows body temperature profile following LPS or Veh injection in PBS-offspring (Veh n=11, LPS n=11; from 5 independent experiments). Veh, Vehicle; LPS, lipopolysaccharide. FIG. 1B shows mice were tested for sociability (% time investigating social object/total time investigating both social and inanimate objects) one day prior to LPS injection (Pre). Mice were then assessed on sociability four hours after LPS injection (Test). FIG. 1C shows performance on sociability for mice described in (FIG. 1B) (n=11 for all groups; from 3 independent experiments). FIG. 1D shows representative images illustrating c-Fos (green) expression in the S1DZ following Veh or LPS injection in PBS and MIA offspring. Scale bar represents 200 μm. Numerals indicate cortical layer. S1DZ, Primary somatosensory cortex, dysgranular zone. FIG. 1E shows quantification of c-Fos expressing cells in the S1DZ following LPS injection in PBS and MIA offspring (PBS-Veh n=8, PBS-LPS n=9, MIA-Veh n=13, MIA-LPS n=11; from 4 independent experiments). FIG. 1F shows action potential (AP) frequency as a function of injected current calculated from whole-cell current-clamp recordings of layer 2/3 pyramidal neurons in S1DZ from Veh- and LPS-injected MIA offspring (Veh n=7 cells, 5 mice, 5 independent experiments, LPS n=7 cells, 3 mice, 3 independent experiments). Inset shows example voltage traces following a 350 ms, 600 pA current step from the cell's resting potential (Veh: −78.7 mV, LPS: −78.1 mV). Current step is illustrated beneath traces. Scale bar represents 50 mV, 50 ms. $^{*}p<0.05$, $^{}p<0.01$ as calculated by two-way repeated measures ANOVA (FIG. 1F) with Bonferroni's post-hoc test (FIG. 1A), three-way repeated measures ANOVA with Bonferroni's post-hoc test (FIG. 1C), and two-way ANOVA with Tukey's post-hoc test (FIG. 1**E). Graphs indicate mean±s.e.m.

FIG. 2A shows a virus encoding inhibitory DREADD (AAV2-hSyn-DIO-hM4D(Gi)-mCherry) was targeted to the vLPO of Vgat-Cre MIA mice. Scale bar represents 2 mm. vLPO, ventral part of the lateral preoptic nucleus. FIG. 2B shows body temperature profile following Veh or CNO injection (n=9 for all groups; from 2 independent experiments). FIG. 2C shows mice were tested for sociability one day prior to injection (Pre). The following two days, mice received counterbalanced injections of either Veh or CNO. Sociability was assessed two hours following injection (n=9 for all groups; from 2 independent experiments). FIG. 2D shows IL-17a and IFNγ levels in plasma and brain following Veh or LPS injection in PBS and MIA and offspring of wild-type (WT), IL-17a KO and IFNγ KO background (WT-MIA-Veh n=9, WT-MIA-LPS n=9, IL-17a KO-PBS-LPS n=6, IL-17a KO-MIA-LPS n=6, IFNγ KO-PBS-LPS n=9, IFNγ KO-MIA-LPS n=9; from 3 independent experiments). FIG. 2E shows performance on sociability was assessed before (Pre) and four hours after Veh or LPS injection (Test) in WT, IL-17a KO and IFNγ KO PBS or MIA offspring (WT-MIA-Veh n=9, WT-MIA-LPS n=9, IL-17a KO-PBS-LPS n=6, IL-17a KO-MIA-LPS n=6, IFNγ KO-PBS-LPS n=9, IFNγ KO-MIA-LPS n=9; from 3 independent experiments). $^{*}p<0.05$, $^{}p<0.01$ as calculated by two-way repeated measures ANOVA with Bonferroni's post-hoc test (FIG. 2B, E), one-way ANOVA repeated measures (FIG. 2C) and one-way ANOVA with Tukey's post-hoc test (FIG. 2**D). Graphs indicate mean±s.e.m.

FIG. 3A shows mice were tested for sociability one day prior to injection (Pre). The following day blocking antibody against IL-17a or IFNγ, or control isotype antibody was administered i.e.v. 30 minutes prior to Veh or LPS injection. Sociability was assessed four hours following Veh or LPS injection (Test) (PBS-Veh-Isotype n=9, PBS-LPS-Isotype n=11, MIA-Veh-Isotype n=10, MIA-LPS-Isotype n=10, MIA-LPS-aIL-17a n=10, MIA-LPS-aIFNγ n=10; from 7 independent experiments). FIG. 3B shows mice were tested for sociability one day prior to injection (Pre) and following bilateral administration of Veh or IL-17a into the S1DZ (Test). (PBS-Veh n=11, PBS-IL-17a n=12, MIA-Veh n=14, MIA-IL-17a n=10; from 9 independent experiments). FIG. 3C shows lentivirus encoding either EYFP or EGFP fused to nuclearCre (nCre) was bilaterally injected into the S1DZ of IL-17Ra$^{fl/fl}$ MIA offspring. Scale bar represents 200 μm. FIG. 3D shows mice were tested for sociability one day prior to injection (Pre). The following day, mice were tested for sociability four hours after LPS injection (Test). (IL-17Ra$^{fl/fl}$;EYFP n=9, IL-17Ra$^{fl/fl}$, EGFP:nCre n=10; from 5 independent experiments). $^{}p<0.01$ as calculated by two-way repeated measures ANOVA with Bonferroni's post-hoc test (FIG. 3A, 3D) and three-way repeated measures ANOVA with Bonferroni's post-hoc test (FIG. 3**B). Graphs indicate mean±s.e.m.

FIG. 4A shows 3 weeks prior to sociability testing, antibiotics (Vancomycin; Vanco, and Metronidazole; Metro.) were orally administered every other day. FIG. 4B shows performance on sociability test before (Pre) and after (Test) Veh or LPS injection in antibiotic pretreated PBS or MIA offspring. FIG. 4C shows IL-17a and IFNγ levels in plasma and brain tissue for animals described in (FIG. 4B) (For FIG. 4B and FIG. 4C, PBS-Veh n=11, PBS-LPS-Vanco n=11, PBS-LPS-Metro n=10, MIA-Veh n=11, MIA-LPS n=11, MIA-LPS-Vanco n=12, MIA-LPS-Metro n=10; from 3 independent experiments). FIG. 4D shows mice born to SFB-present dams were transferred to SFB-absent dams at birth for rearing. FIG. 4E shows sociability was assessed one week after SFB colonization protocol. FIG. 4F shows performance on sociability before (Pre) and after (Test) LPS administration in SFB-colonized and SFB− non-colonized MIA offspring (SFB+ n=10, SFB− n=11; from 2 independent experiments). FIG. 4G shows IL-17a and IFNγ levels in plasma and brain tissue following LPS injection in SFB-colonized and SFB− non-colonized MIA offspring (SFB+ n=5, SFB− n=6; from 2 independent experiments). **p<0.01 as calculated by two-way repeated measures ANOVA with Bonferroni's post-hoc test (FIG. 4B, 4F), one-way ANOVA with Tukey's post-hoc test (FIG. 4C) and unpaired two-tailed t-test (FIG. 4G). Graphs indicate mean±s.e.m.

FIG. 6C shows quantification of c-Fos expression in a series of cortical regions and the central amygdala following Veh or LPS injection in PBS or MIA offspring (For S1BF, M2, M1, AuD, and CeA; PBS-Veh n=8, PBS-LPS n=9, MIA-Veh n=13, MIA-LPS n=11. For mPFC; PBS-Veh n=8, PBS-LPS n=9, MIA-Veh n=12, MIA-LPS n=11. For V1; PBS-Veh n=7, PBS-LPS n=8, MIA-Veh n=12, MIA-LPS n=9; from 4 independent experiments). *p<0.05, **p<0.01 as calculated by two-way ANOVA with Tukey's post-hoc test (FIG. 6C). Graphs indicate mean±s.e.m.

Figure 4A:
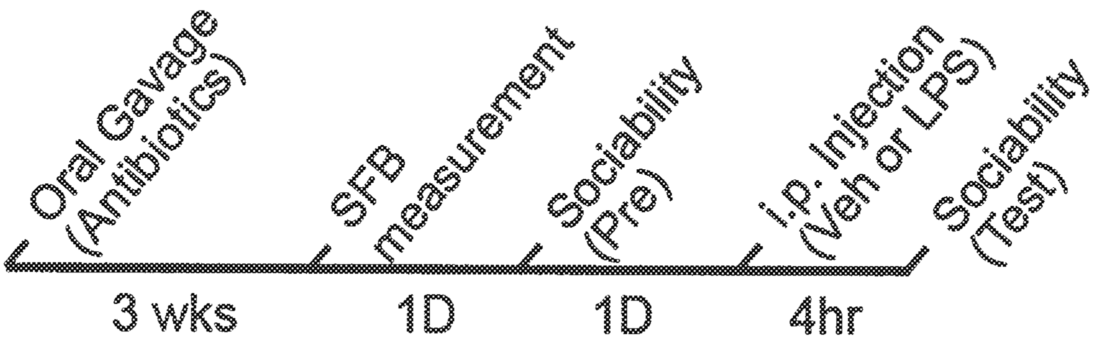
FIG. 4A-4G shows Th17 cell promoting gut bacteria are crucial for LPS-induced rescue of sociability deficits in MIA offspring.
Figure 4B:
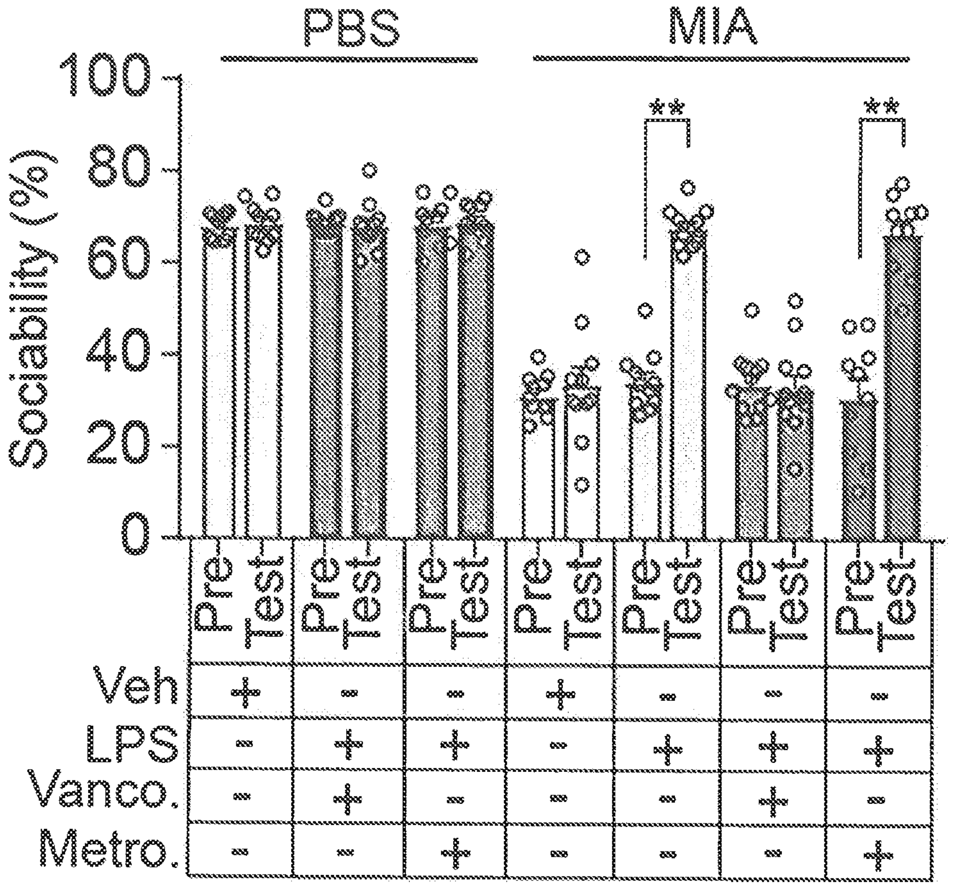
Figure 12A:
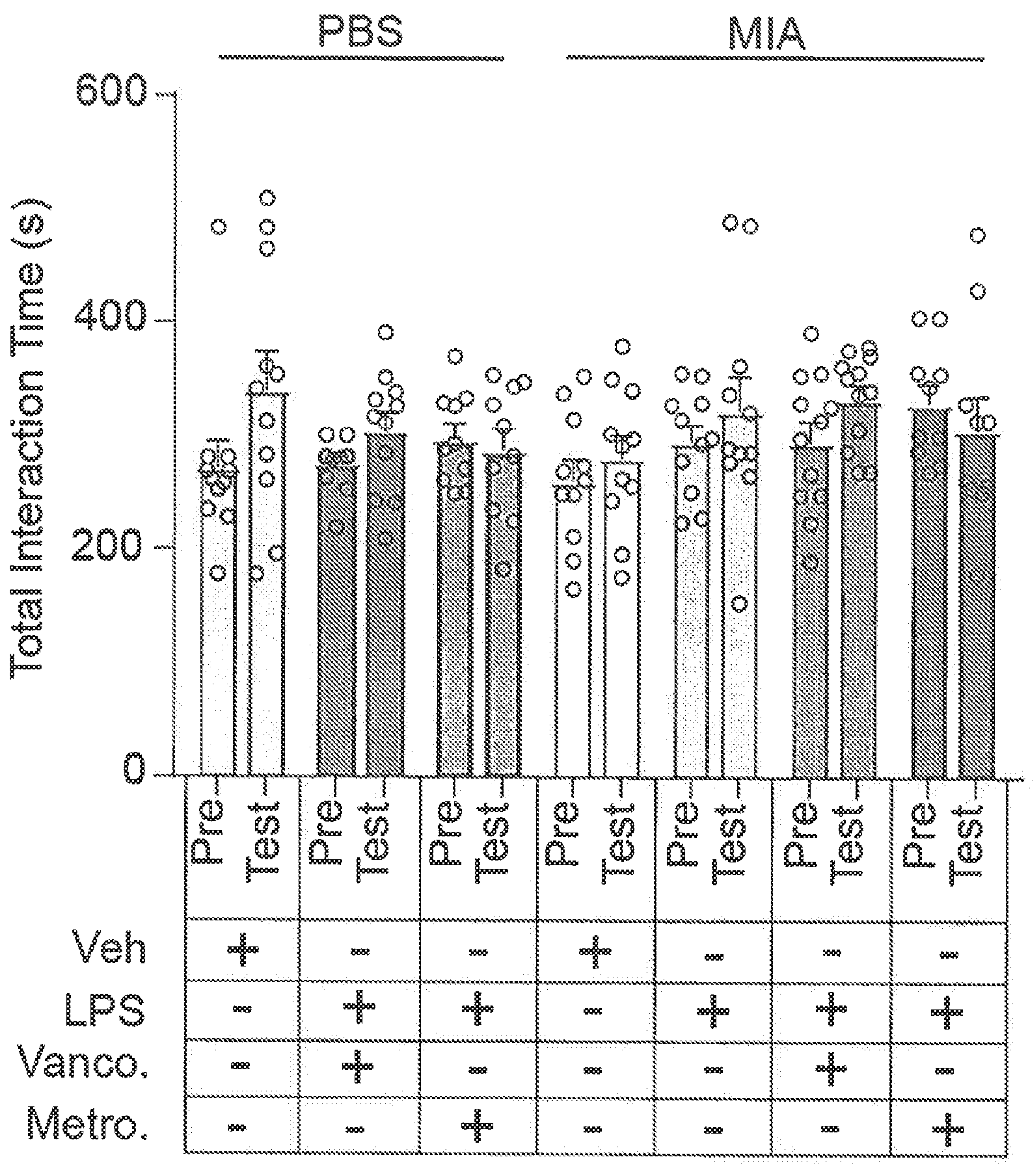
Figure 12B:
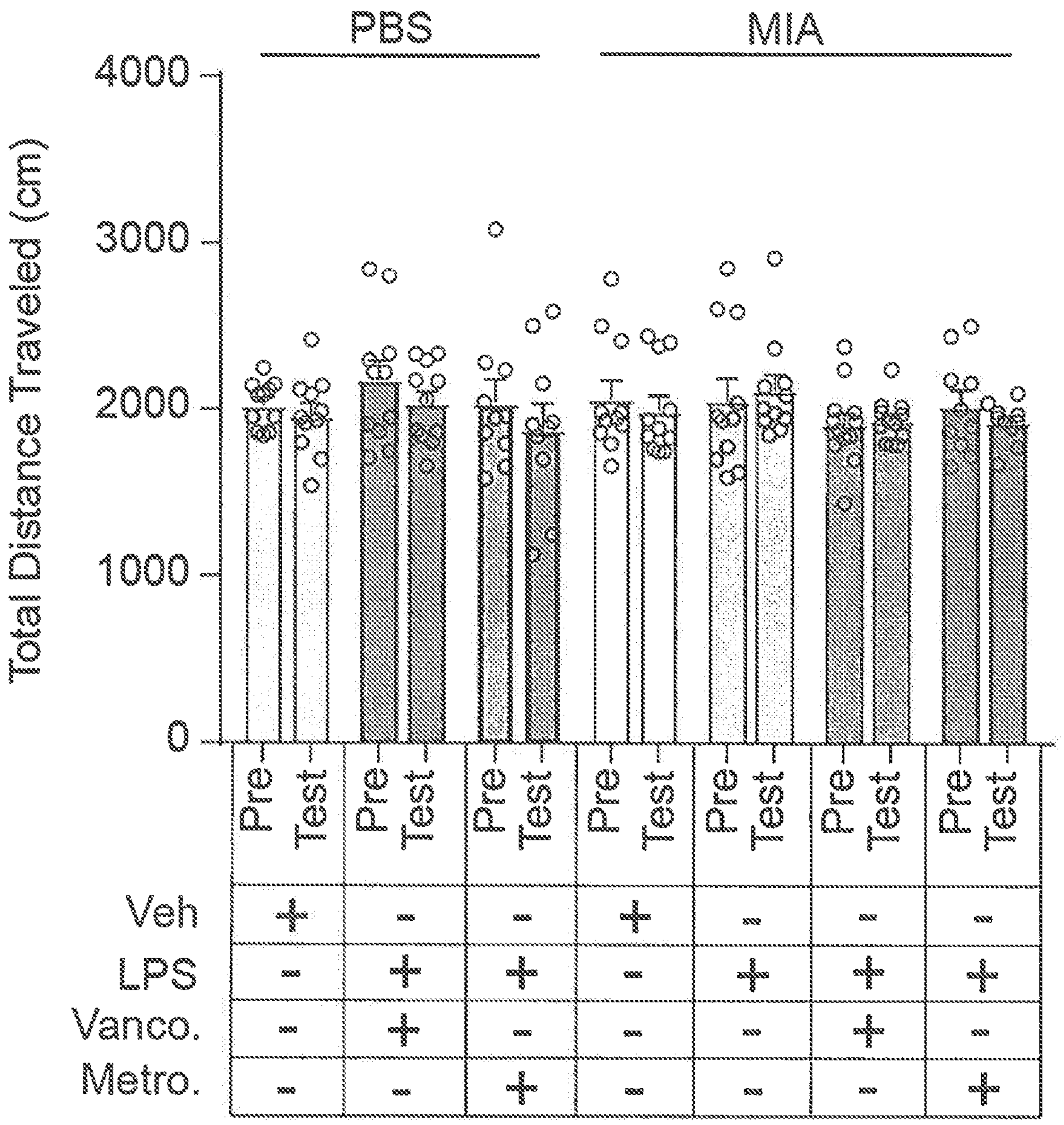
Figure 12C:
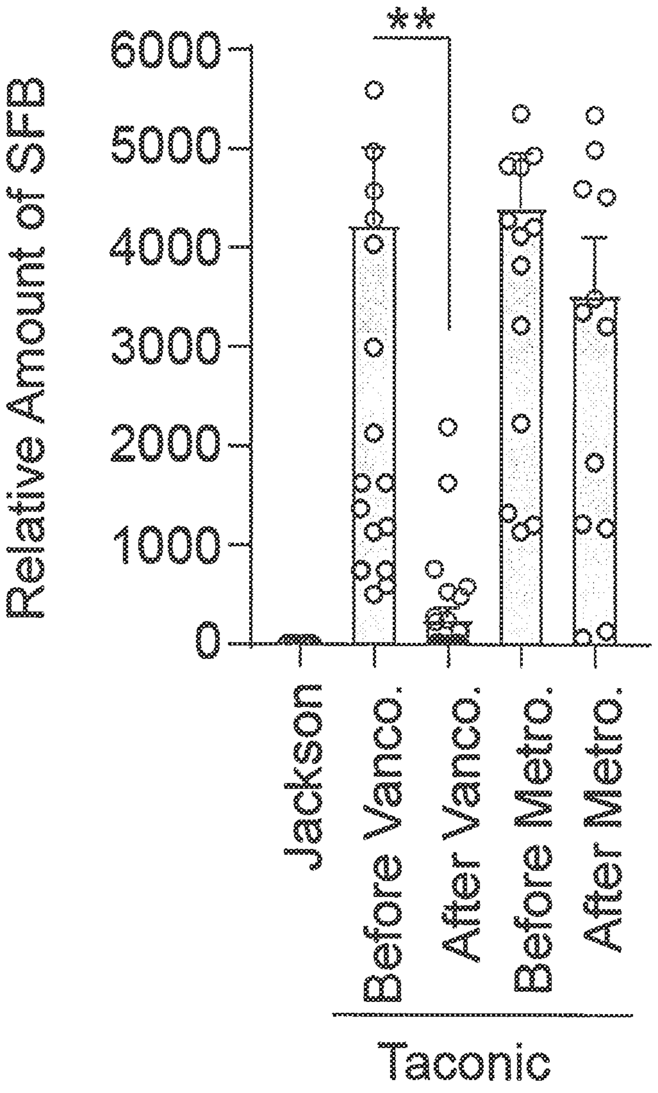
Figure 12D:
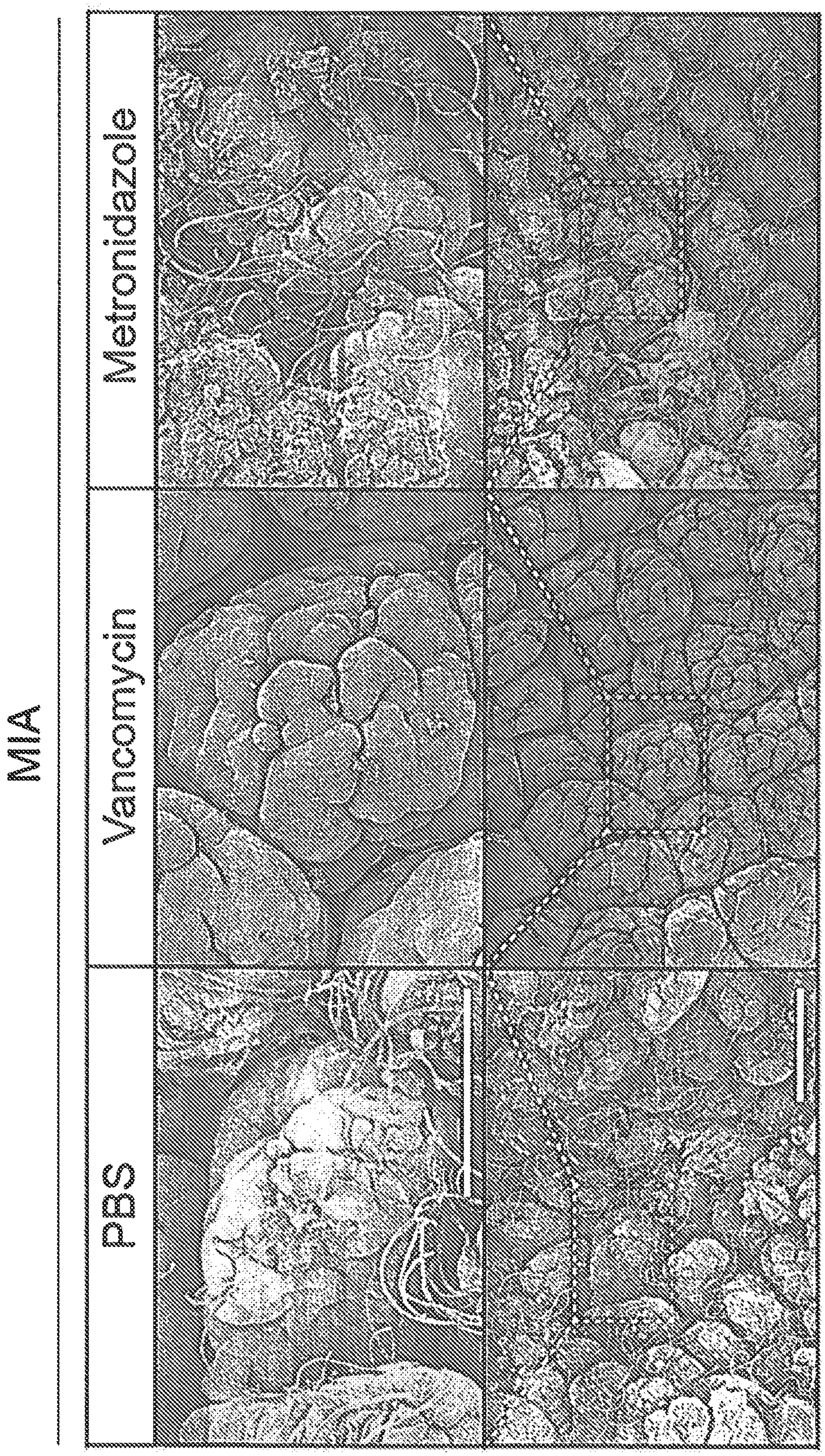

FIG. 12A-12B shows total interaction time (FIG. 12A) and total distance traveled (FIG. 12B) during the sociability assay for offspring described in FIG. 4B. (PBS-Veh n=11, PBS-LPS-Vanco n=11, PBS-LPS-Metro n=10, MIA-Veh n=11, MIA-LPS n=11, MIA-LPS-Vanco n=12, MIA-LPS-Metro n=10; from 3 independent experiments). FIG. 12C shows SFB levels as measured by qPCR in mice received from Jackson and mice received from Taconic before and after antibiotic treatment (Jackson n=10, Tac-Before Vanco n=23, Tac-After Vanco n=27, Tac-Before Metro n=17, Tac-After Metro n=15; from 4 independent experiments). FIG. 12D shows representative SEM images of epithelial surfaces in the ilea of MIA offspring following LPS injection, pre-treated with vehicle, vancomycin or metronidazole treatment. Scale bar indicates 50 μm and 100 μm for top and bottom row, respectively. Dashed inset demarcates magnified image in top row. p<0.01 as calculated by one-way ANOVA with Tukey's post-hoc test (FIG. 12C). Data analyzed by two-way repeated measures ANOVA (FIG. 12A-12**B). Graphs indicate mean±s.e.m.

Figure 4C:
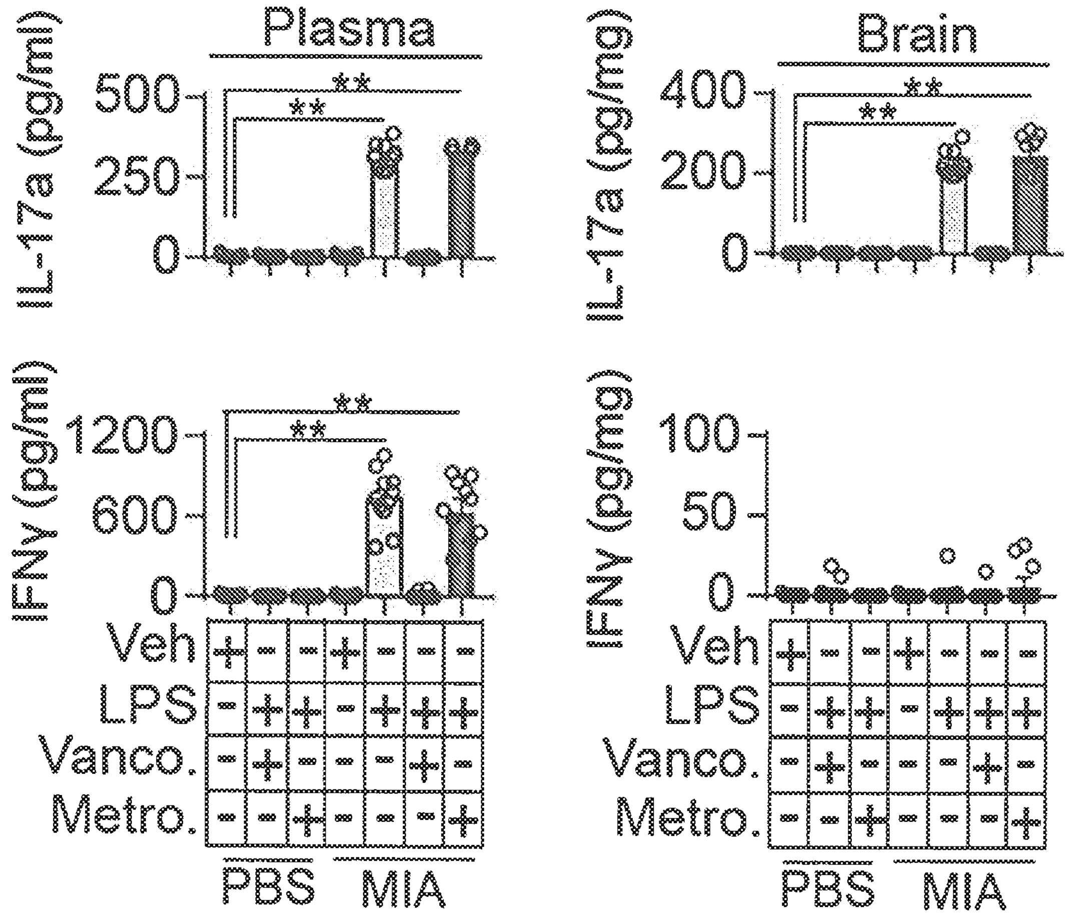
Figure 4D:
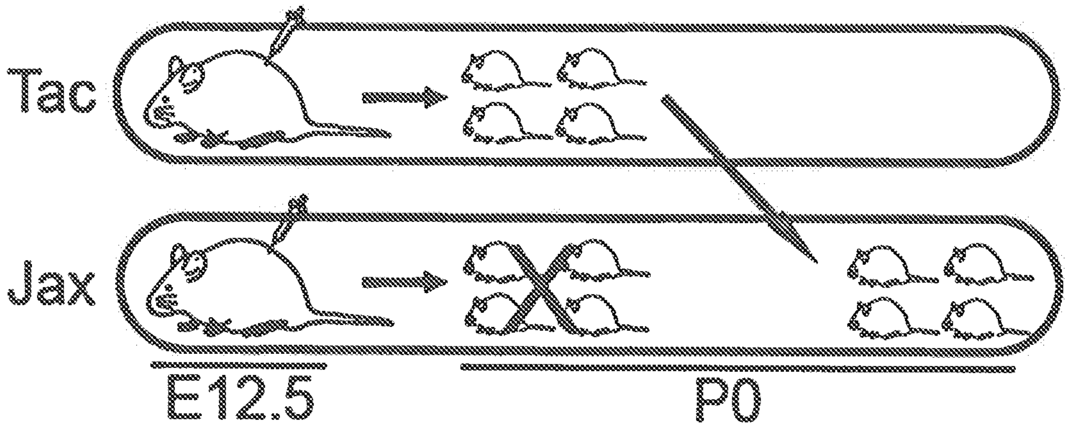
Figure 4E:
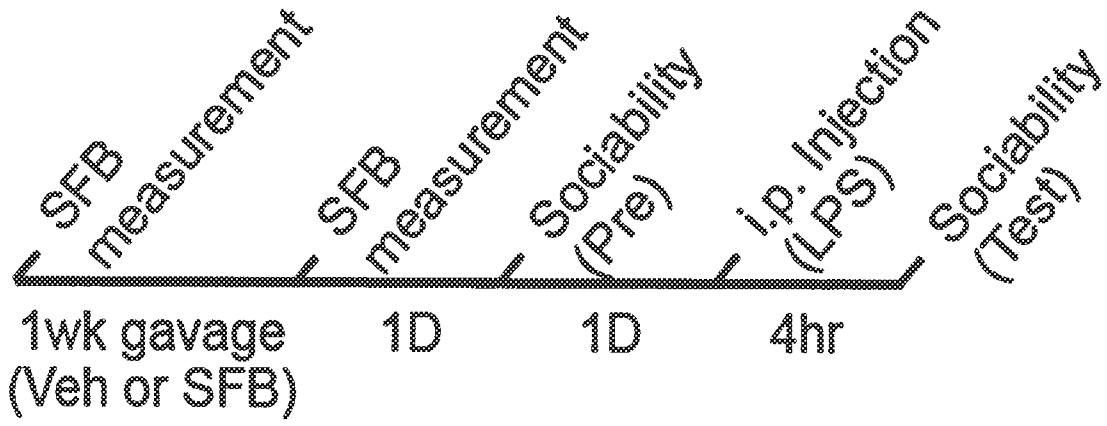
Figure 4F:
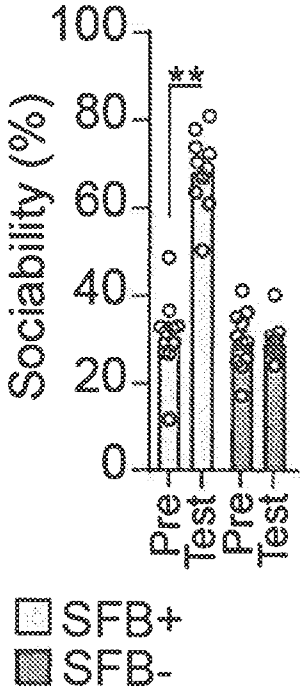
Figure 13A:
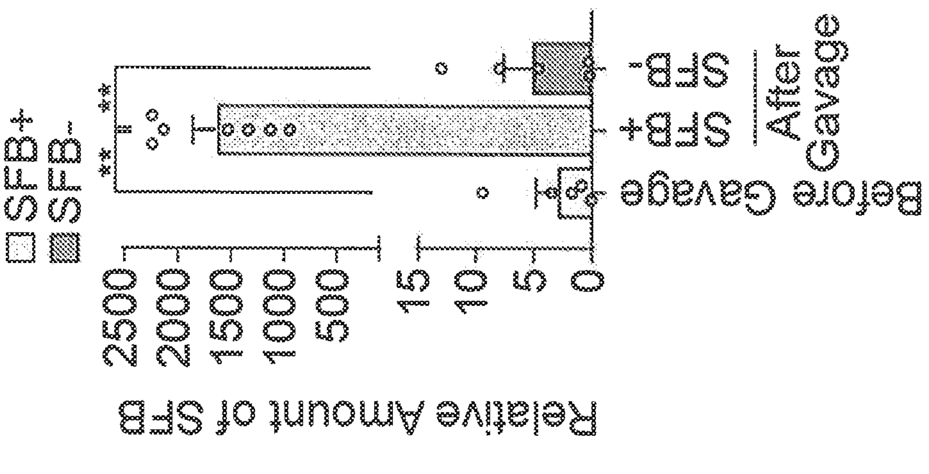
Figure 13B:
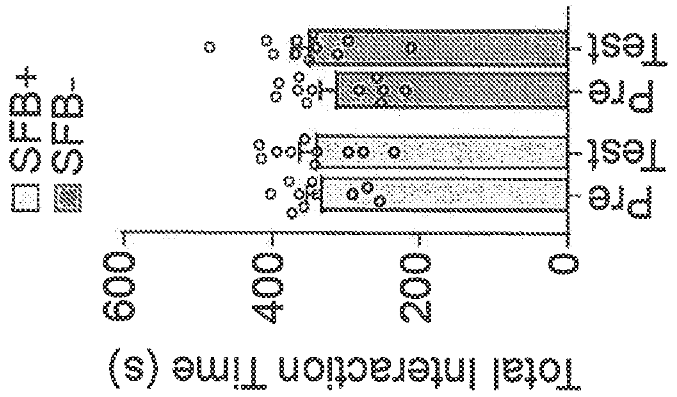
Figure 13C:
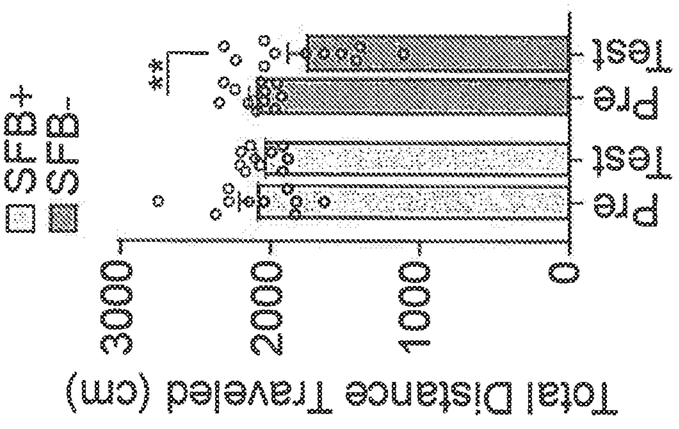
Figure 13D:
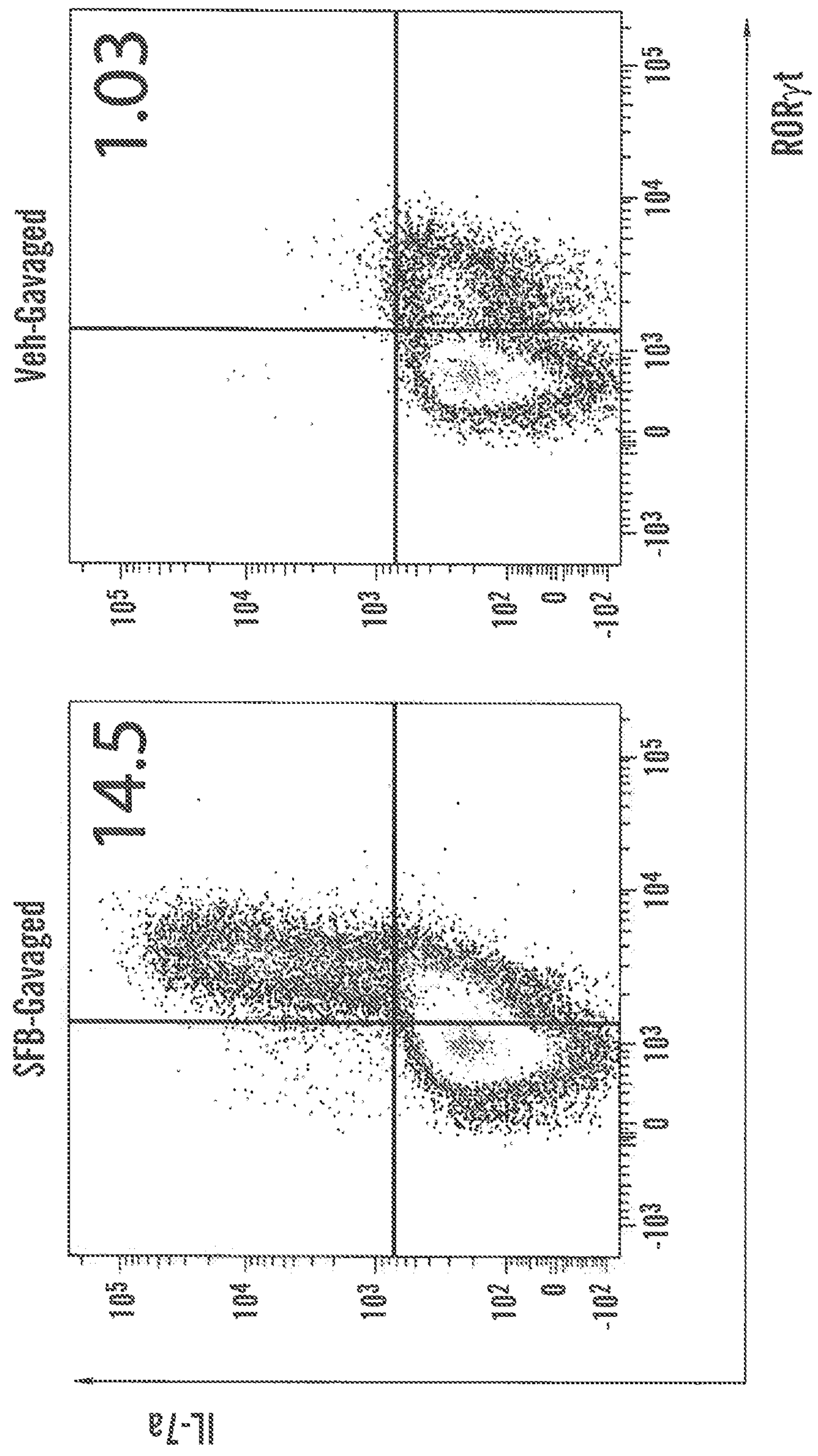

FIG. 13A shows SFB levels as measured by qPCR prior to and after SFB colonization protocol described in FIG. 4E (Before gavage n=5, After gavage-SFB+ n=7, After gavage-SFB− n=5; from 2 independent experiments). FIG. 13B-13C shows total interaction time (FIG. 13B) and total distance traveled (FIG. 13C) during sociability assay for offspring described in FIG. 4F (SFB+ n=10, SFB− n=11; from 2 independent experiments). FIG. 13D shows flow cytometry of $CD4^+$ T cells (gated on $TCR\beta^+CD4^+$ cells) stained intracellularly for IL-17a and RORγt. Mononuclear cells were collected from the ilea of SFB- or vehicle-gavaged mice after behavioral test. p<0.01 as calculated by one-way ANOVA with Tukey's post-hoc test (FIG. 13A). Data analyzed by two-way repeated measures ANOVA (FIG. 13B-13**C). Graphs indicate mean±s.e.m.

Figure 14:
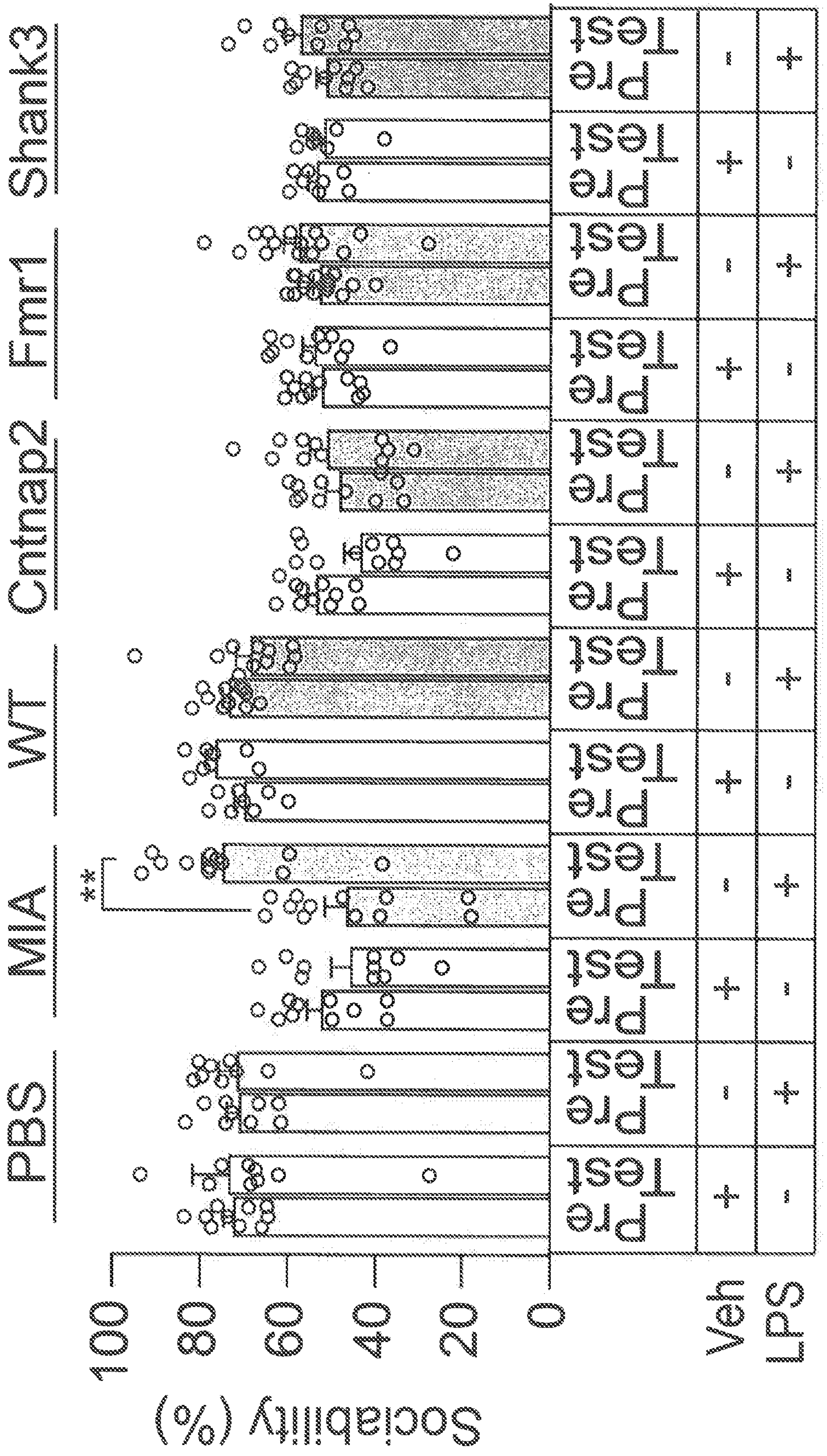

FIG. 14 shows mice were tested for sociability (% time investigating social object/total time investigating both social and inanimate objects) one day prior to LPS injection (Pre). Mice were then tested for sociability four hours after either Veh or LPS injection (Test) (PBS-Veh n=10, PBS-LPS n=9, MIA-Veh n=10, MIA-LPS n=12, WT-Veh n=8, WT-LPS n=11, Cntnap2-Veh n=11, Cntnap2-LPS n=11, Fmr1-Veh n=11, Fmr1-LPS n=15, Shank3-Veh n=8, Shank3-LPS n=10; from 3 independent experiments).

Figure 15A:
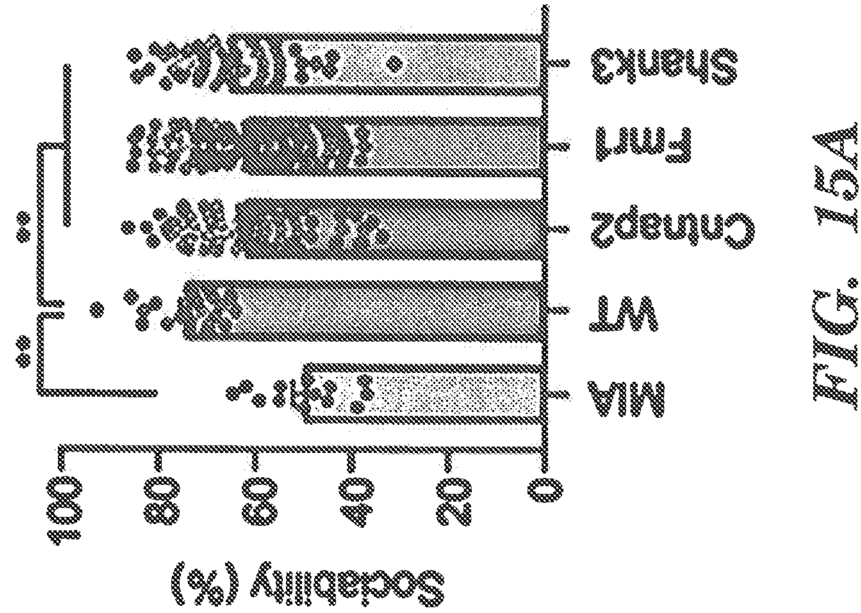
Figure 15B:
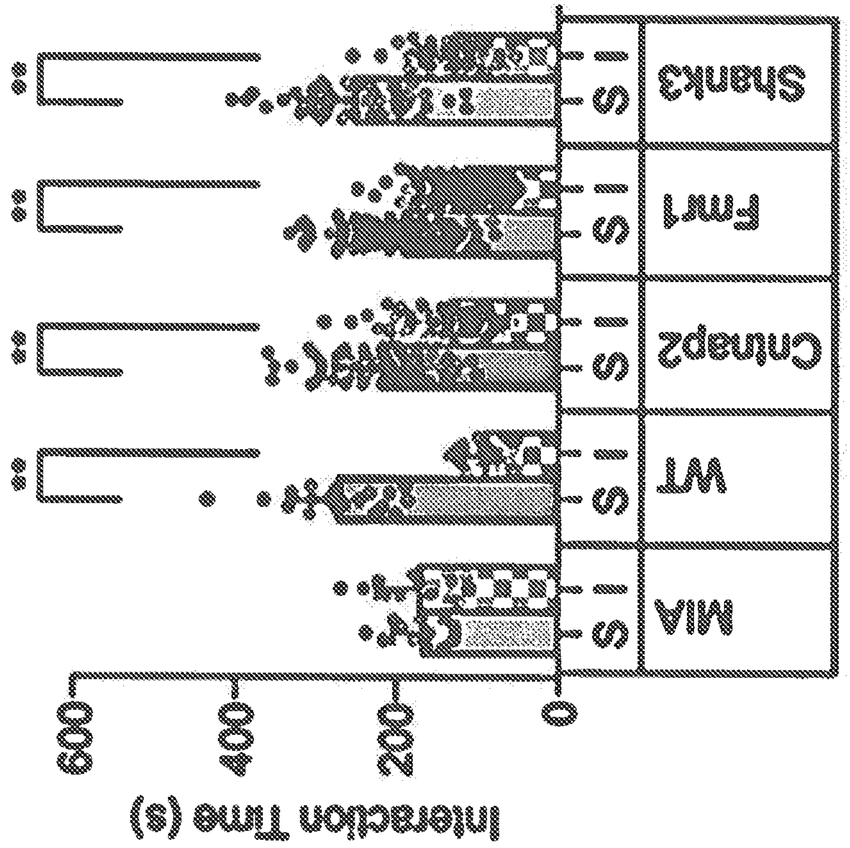
Figure 15D:
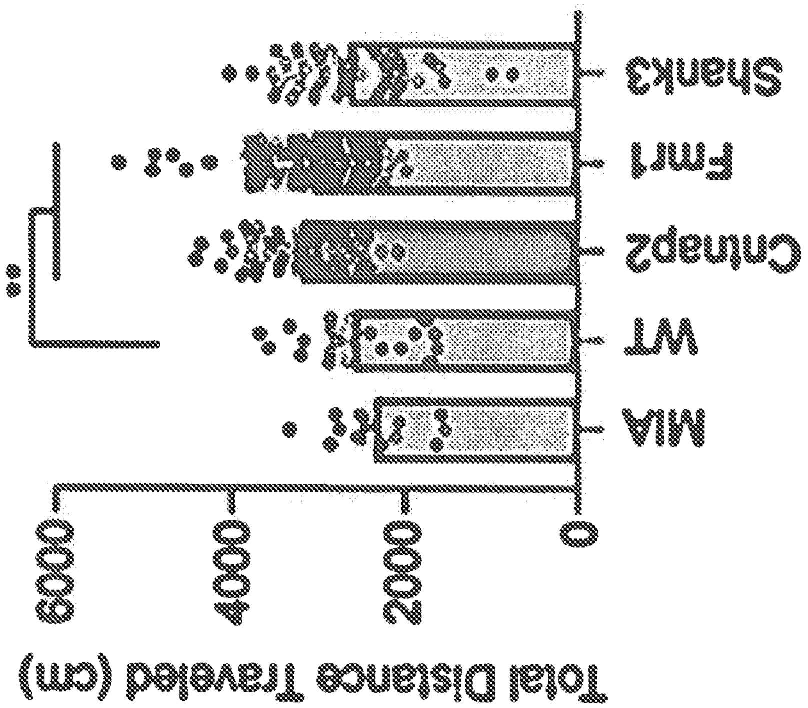
Figure 15C:
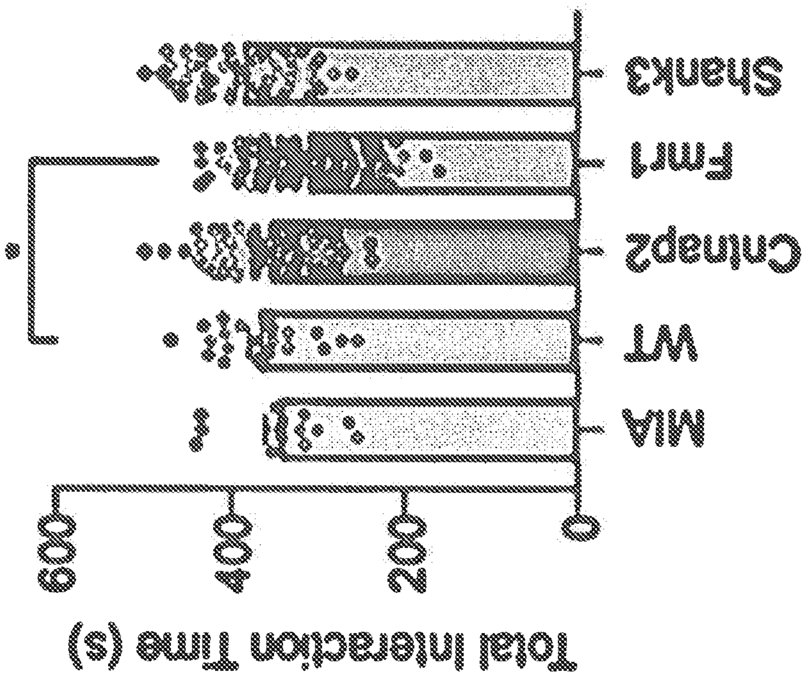

FIG. 15A-15D shows Cntnap2, Fmr1, and Shank3 mutant mice show variable sociability performance. FIG. 15A demonstrates the sociability performance (MIA n=13, WT n=22, Cntnap2 n=71, Fmr1 n=165, Shank3 n=50; from 30 independent experiments). FIG. 15B shows the time spent investigating social (S) versus inanimate (I) objects for mice described in (FIG. 15A). FIG. 15C-15D demonstrates the total interaction time (FIG. 15C) and distance traveled (FIG. 15D) during three-chambered sociability experiments described in (FIG. 15A). *P<0.05, P<0.01 calculated by one-way ANOVA with Dunnett's post-hoc test (FIG. 15A, 15C, 15D) and two-way ANOVA with Dunnett's post-hoc test (FIG. 15**B). Graphs indicate mean±s.e.m.

Figure 16A:
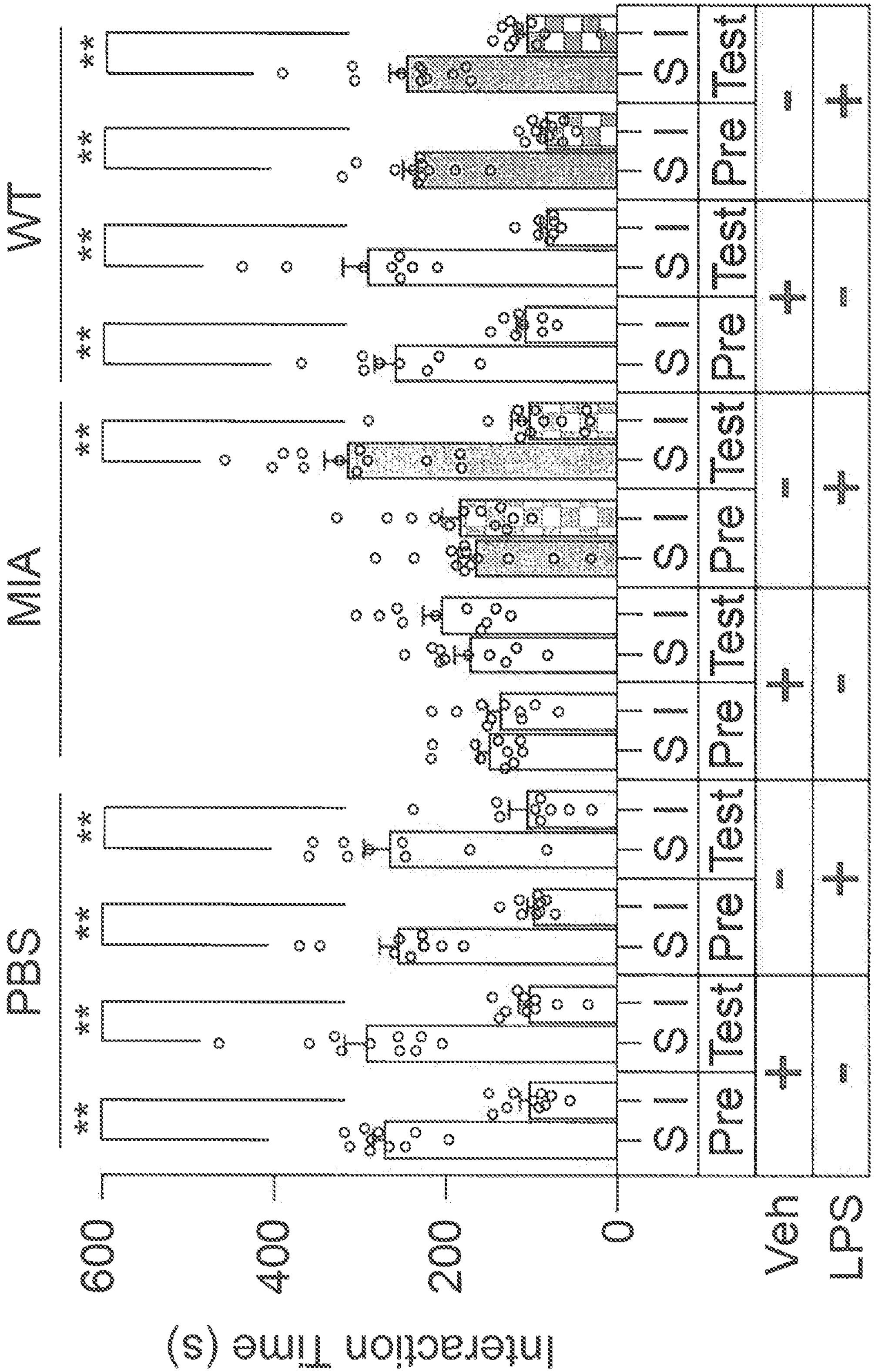
Figure 16A:
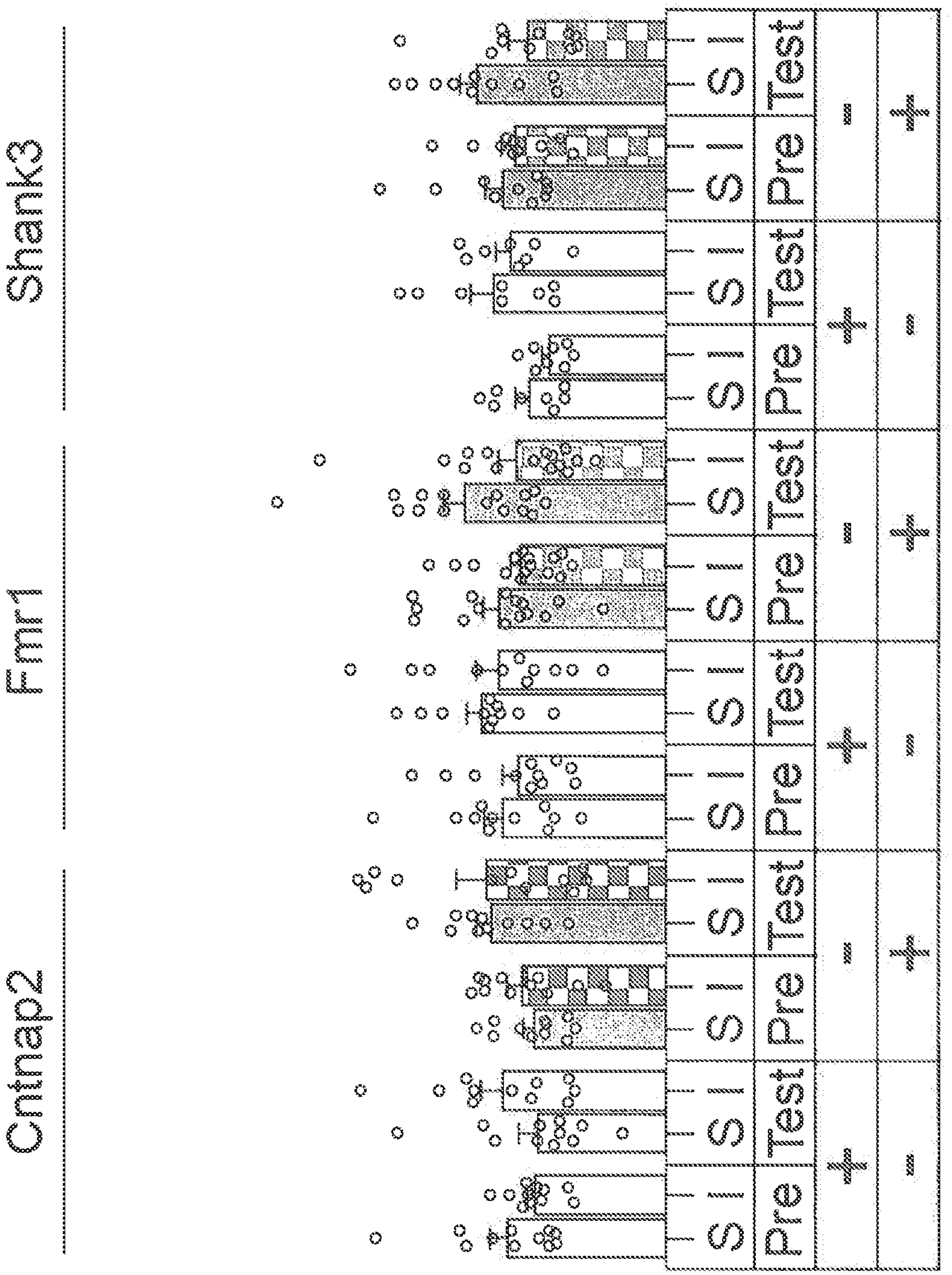
Figure 16B:
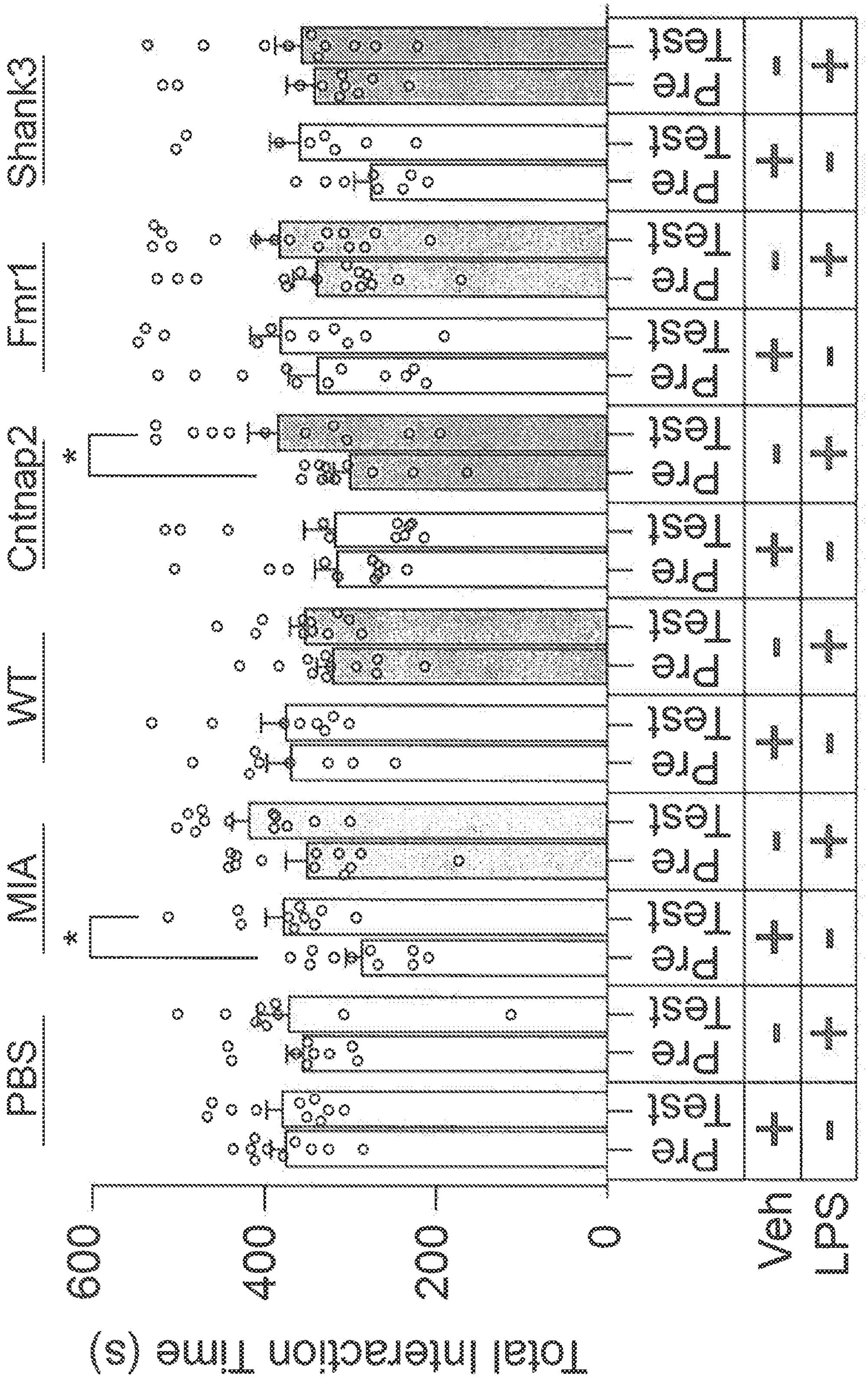
Figure 16C:
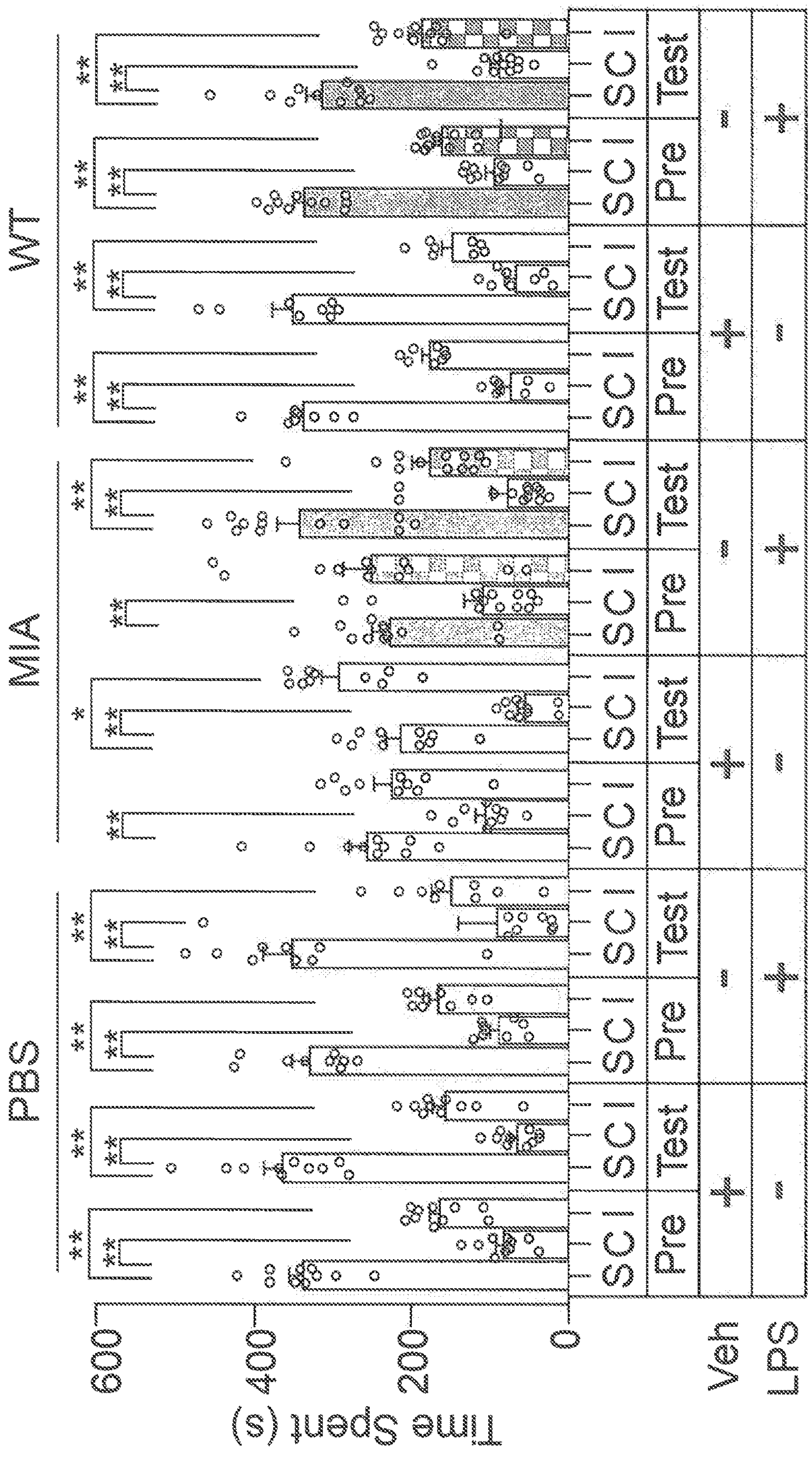
Figure 16C:
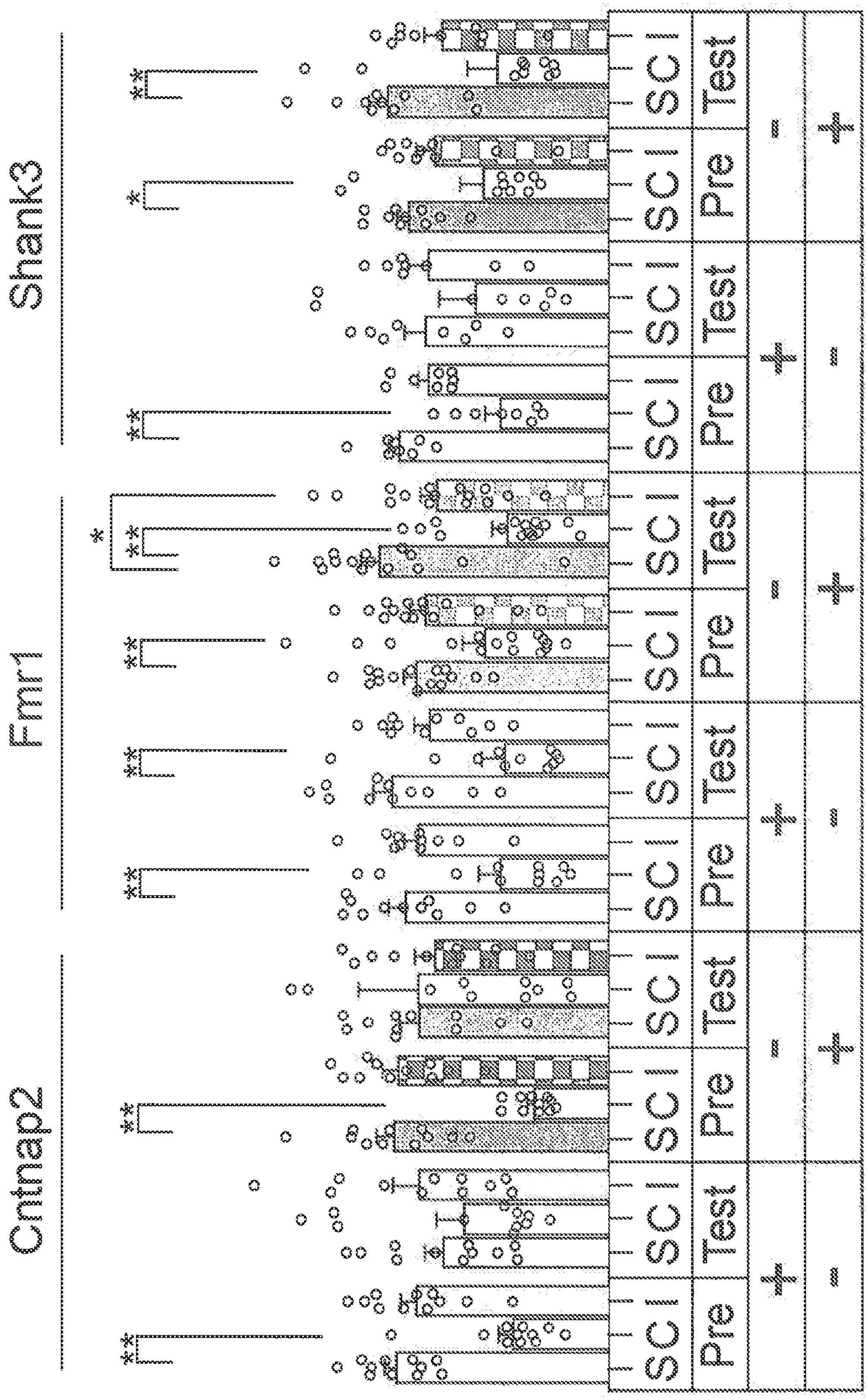
Figure 16D:
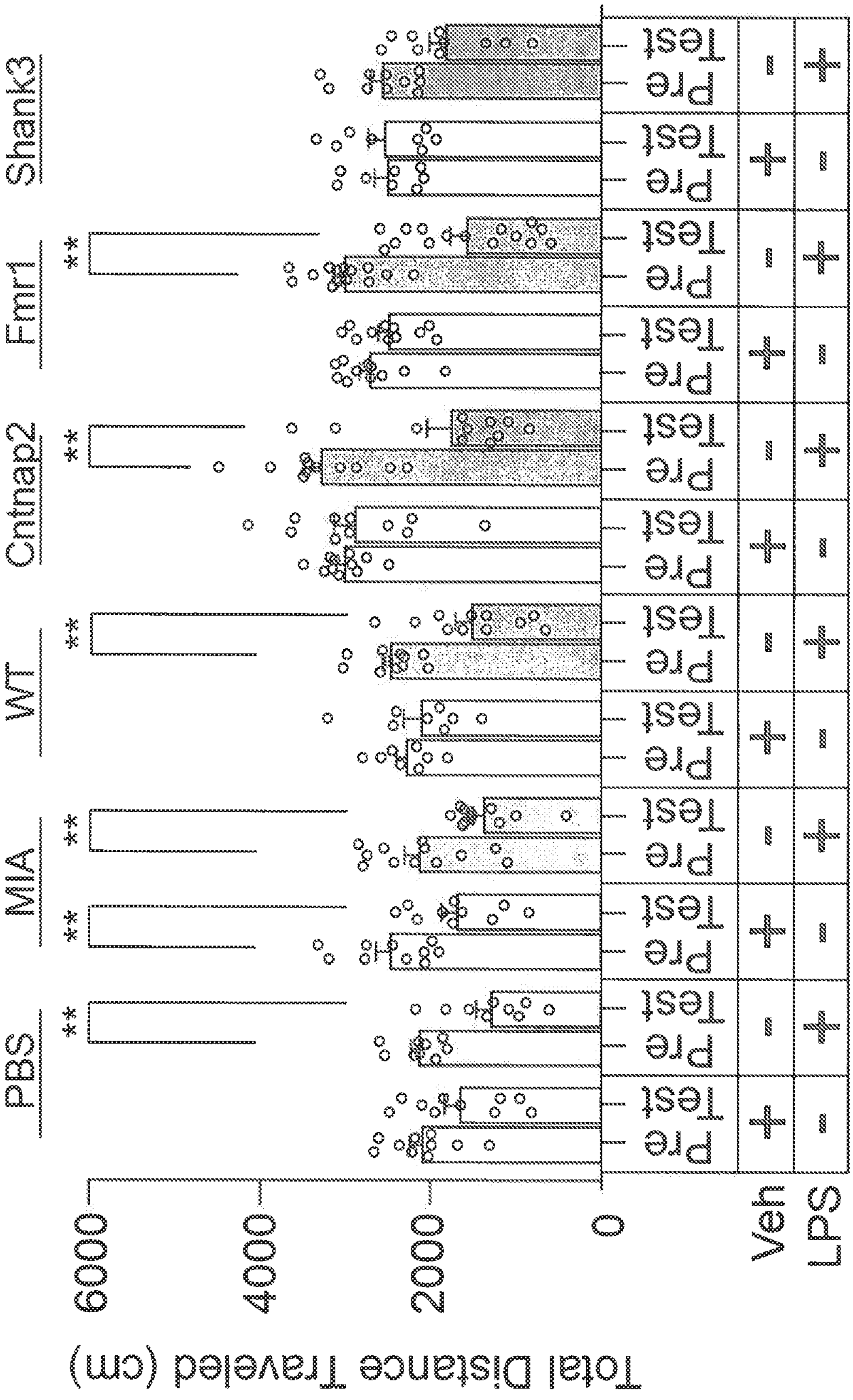

FIG. 16A-16D shows further behavioral analyses for sociability performance following LPS treatment in PBS and MIA offspring, and monogenic mutant mice. FIG. 16A demonstrates the time spent investigating social (S) versus inanimate (I) objects (a), total interaction time (FIG. 16B), time spent in social (S), center (C) or inanimate (I) chamber (FIG. 16C), and distance traveled (FIG. 16D) for sociability experiments in FIG. 1C. *P<0.05, P<0.01 calculated by two-way ANOVA with Sidak's (FIG. 16A) Dunnett's (FIG. 16C) post-hoc test and two-way repeated measures ANOVA with Sidak's post-hoc test (FIGS. 16**B and D). Graphs indicate mean±s.e.m.

Figure 17C:
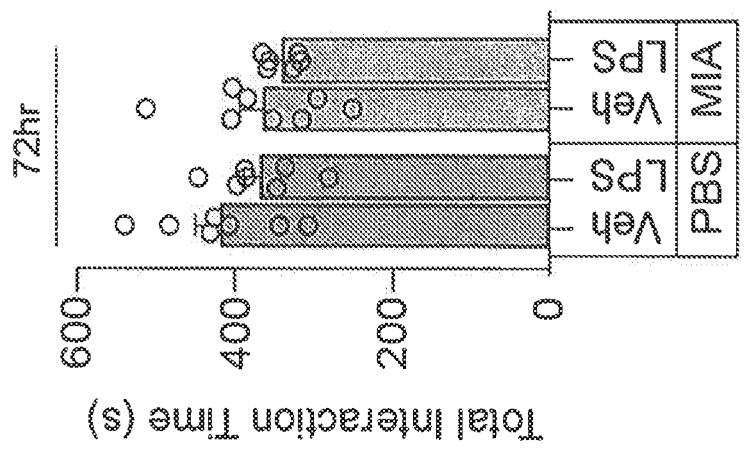
Figure 17B:
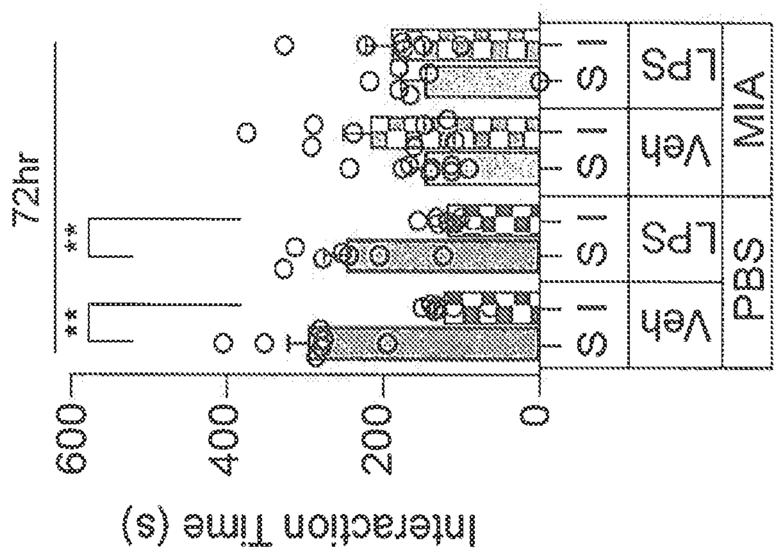
Figure 17A:
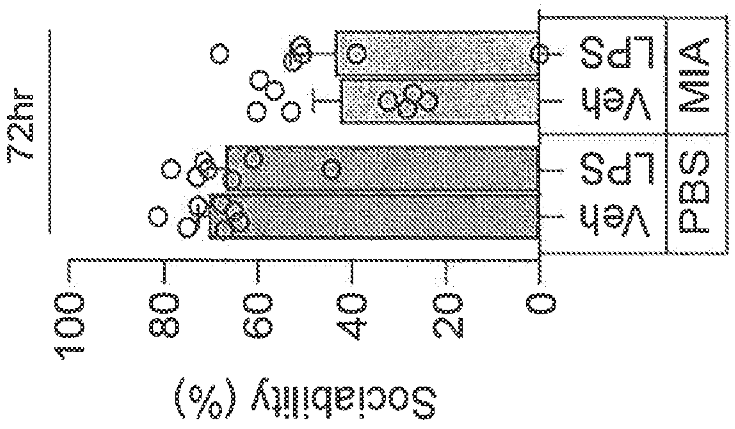
Figure 17D:
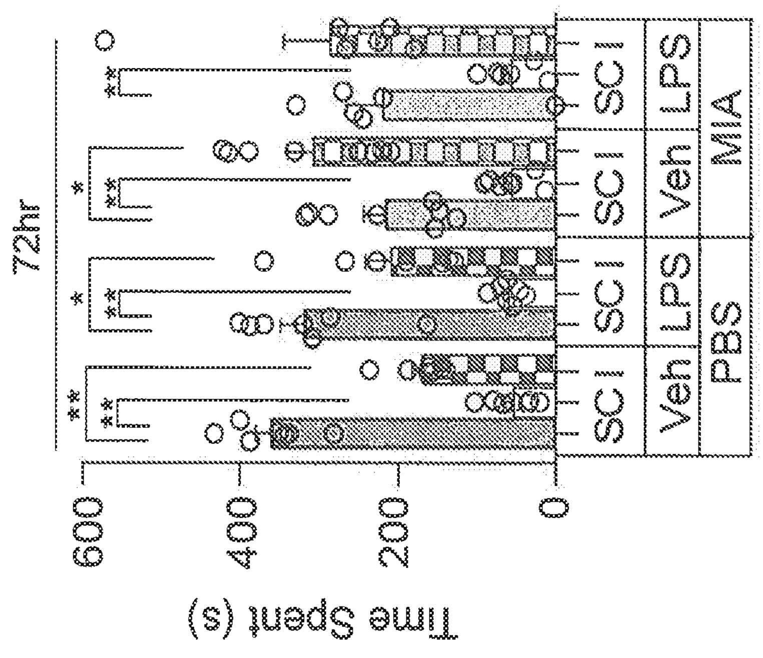
Figure 17E:
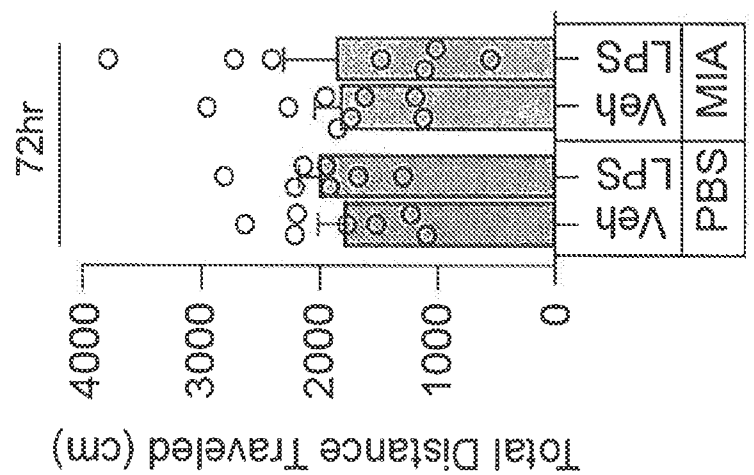
Figure 17H:
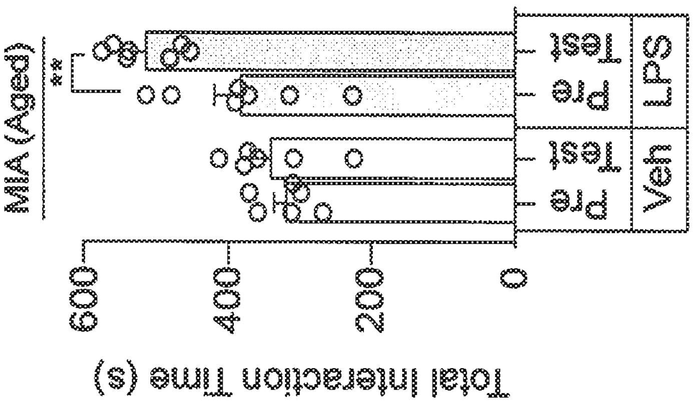
Figure 17G:
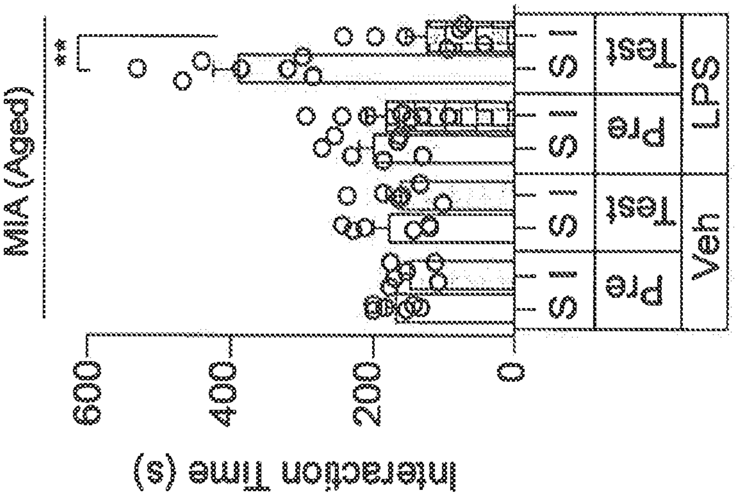
Figure 17F:
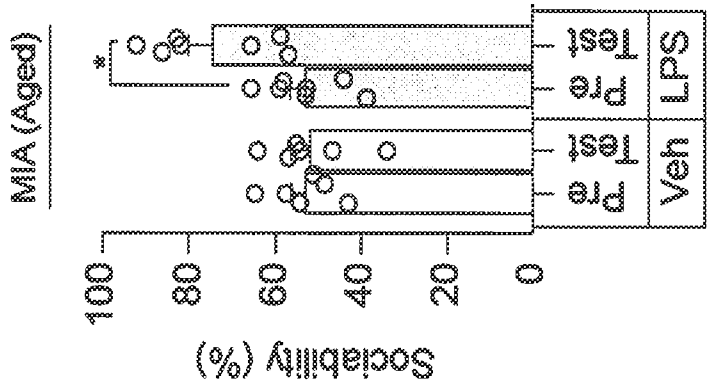
Figure 17J:
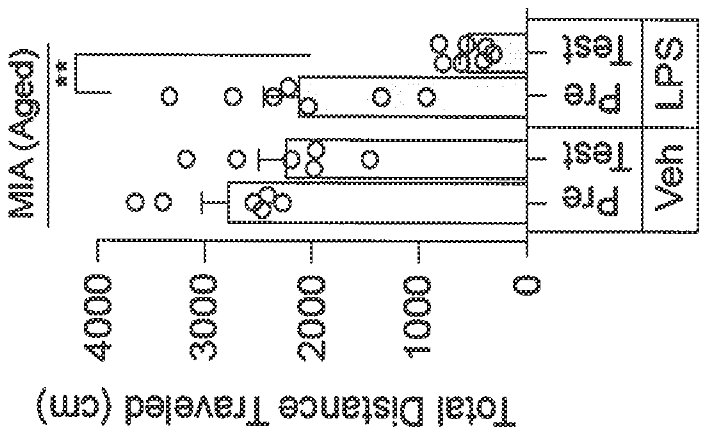
Figure 17I:
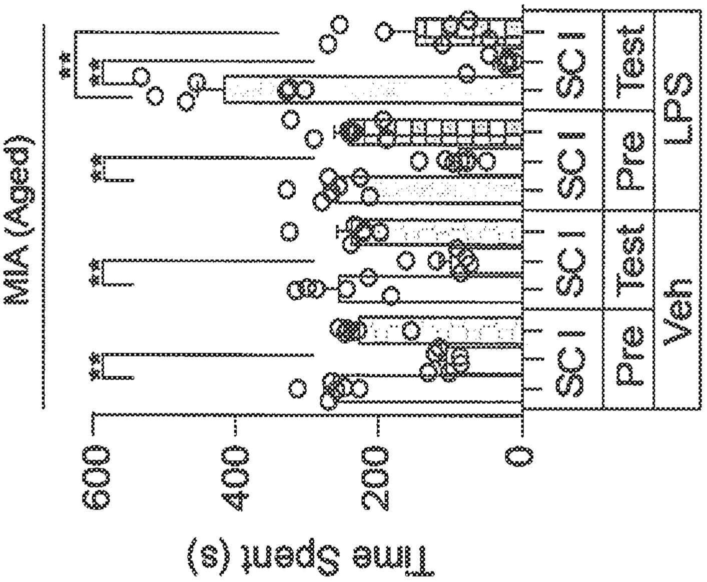
Figure 17L:
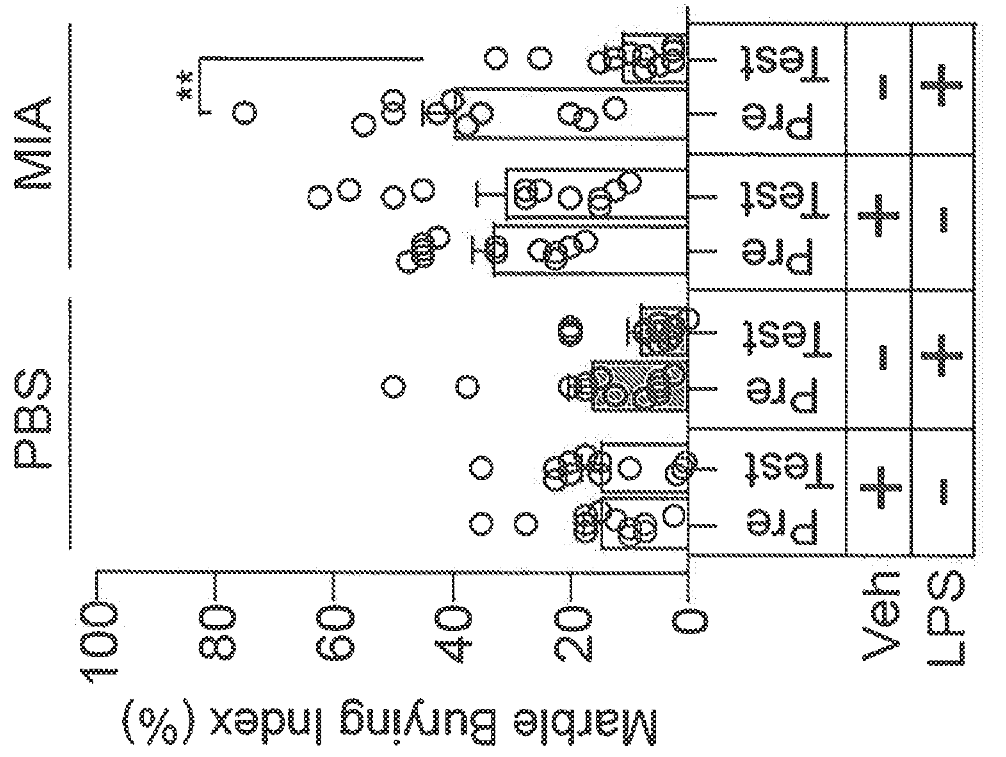
Figure 17K:
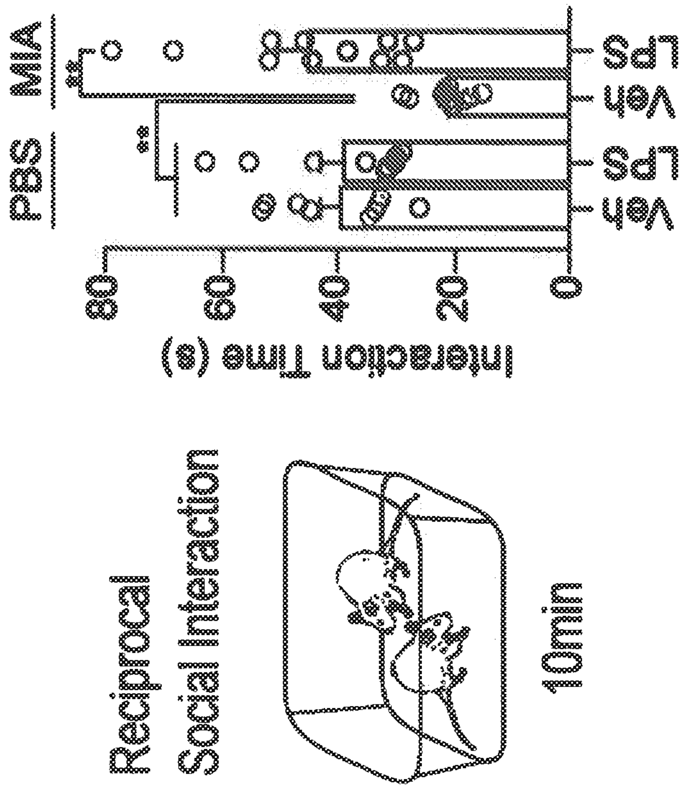

FIG. 17A-17L shows LPS-induced rescue of MIA behavioral phenotypes is transient, effective in aged mice, and extends beyond three-chambered sociability. FIG. 17A-17E demonstrates the sociability measured 72 hrs following Veh or LPS injection in PBS and MIA offspring from FIG. 14. Data expressed as percent sociability (FIG. 17A), time spent investigating social (S) versus inanimate (I) objects (FIG. 17B), total interaction time (FIG. 17C), time spent in social (S), center (C) or inanimate (I) chamber (FIG. 17D), and distance traveled (FIG. 17E) during three-chambered sociability experiments (PBS-Veh n=7, PBS-LPS n=7, MIA-Veh n=8, MIA-LPS n=6; from 2 independent experiments). FIG. 17F-17J demonstrates the sociability measured before and 4 hr after Veh or LPS injection in aged MIA mice (9-12 months). Data expressed as percent sociability (FIG. 17F), time spent investigating social (S) versus inanimate (I) objects (FIG. 17G), total interaction time (FIG. 17H), time spent in social (S), center (C) or inanimate (I) chamber (FIG. 17I), and distance traveled (FIG. 17J) during three-chambered sociability experiments (MIA-Veh n=6, MIA-LPS n=7: from 2 independent experiments). FIG. 17K shows reciprocal social interactions measured upon Veh or LPS treatment in PBS or MIA offspring (PBS-Veh n=9, PBS-LPS n=9, MIA-Veh n=11, MIA-LPS n=11; from 4 independent experiments). FIG. 17L shows marble burying index (% of buried marbles) measured before and 4 hr after Veh or LPS treatment in PBS or MIA offspring (PBS-Veh n=12, PBS-LPS n=12, MIA-Veh n=12, MIA-LPS n=11; from 5 independent experiments). *P<0.05, P<0.01 calculated by two-way ANOVA with Sidak's (FIG. 17A-17C, 17E, 17G), Dunnett's (FIG. 17D, 17I), and Tukey's (FIG. 17K) post-hoc tests, and two-way repeated measures ANOVA with Sidak's post-hoc test (FIGS. 17F, 17H, 17J, and 17**L). Graphs indicate mean±s.e.m.

Figure 18A:
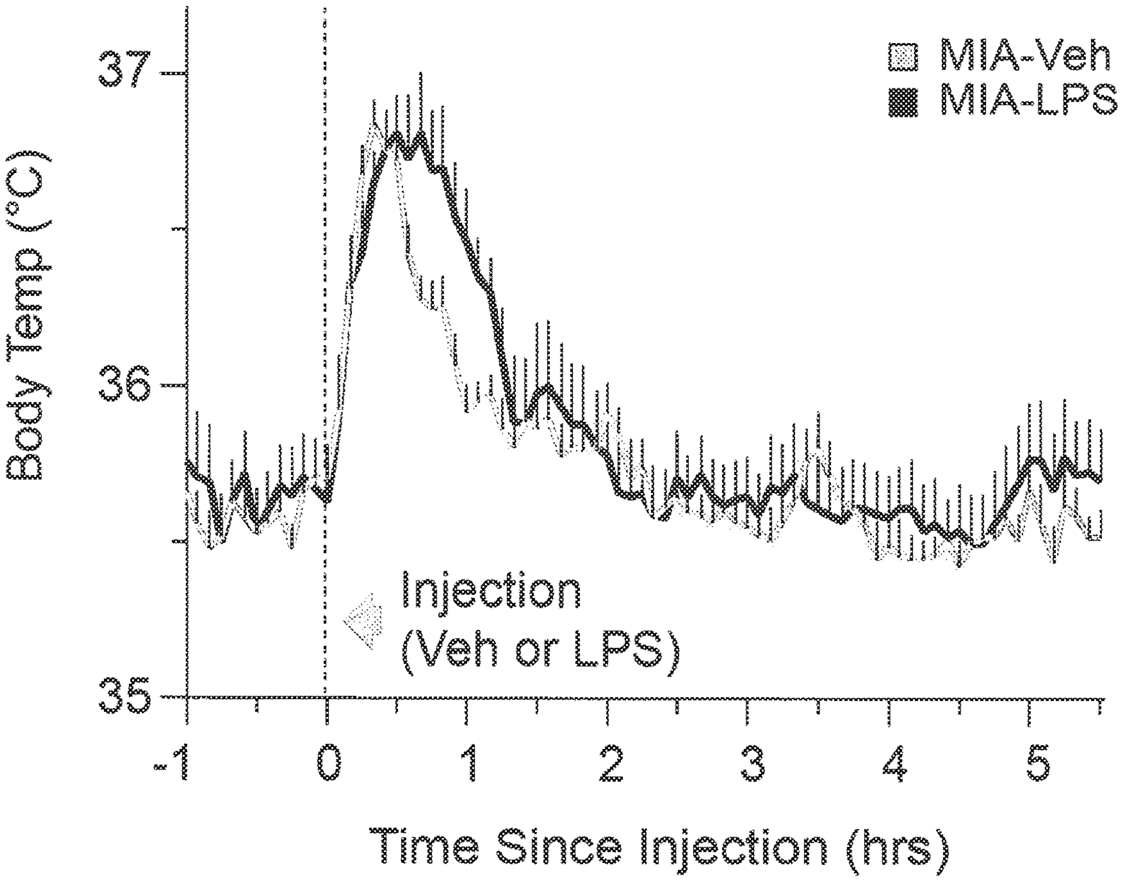
Figure 18B:
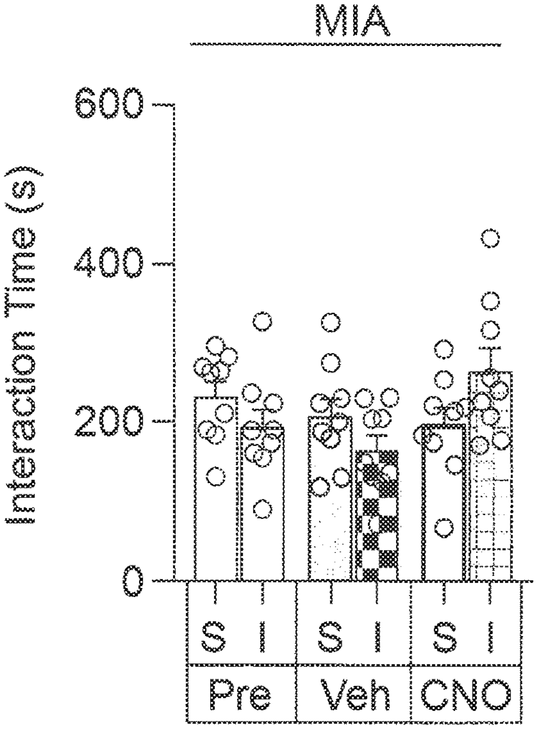
Figure 18C:
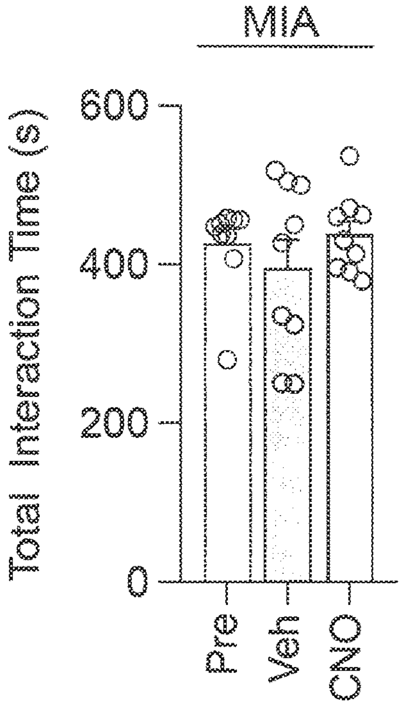
Figure 18D:
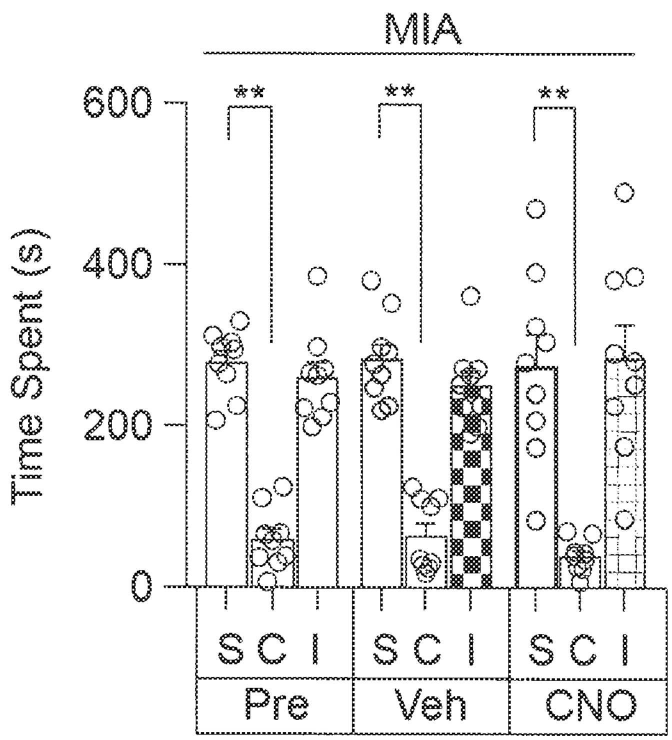
Figure 18E:
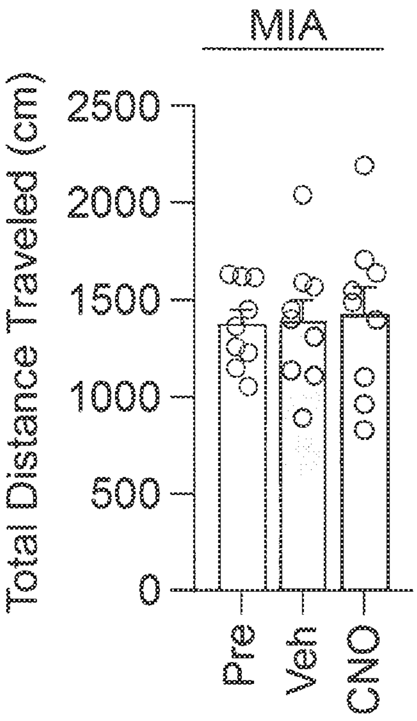
Figure 18F:
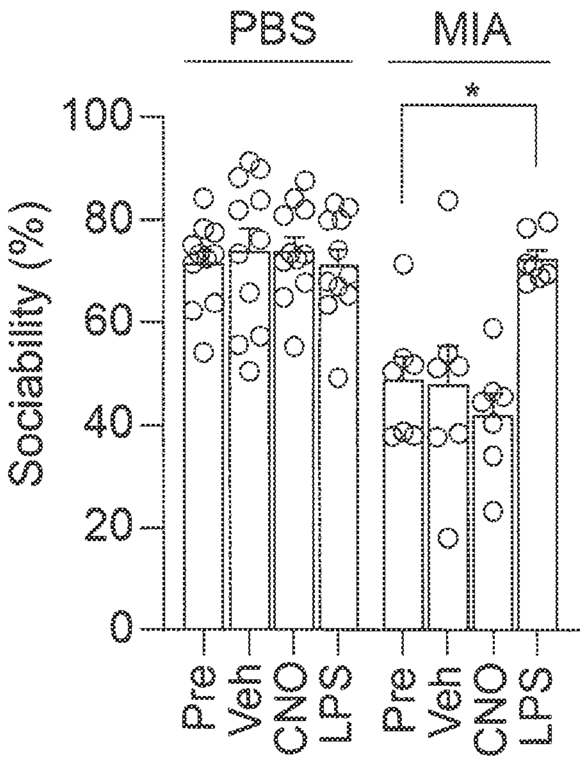
Figure 18G:
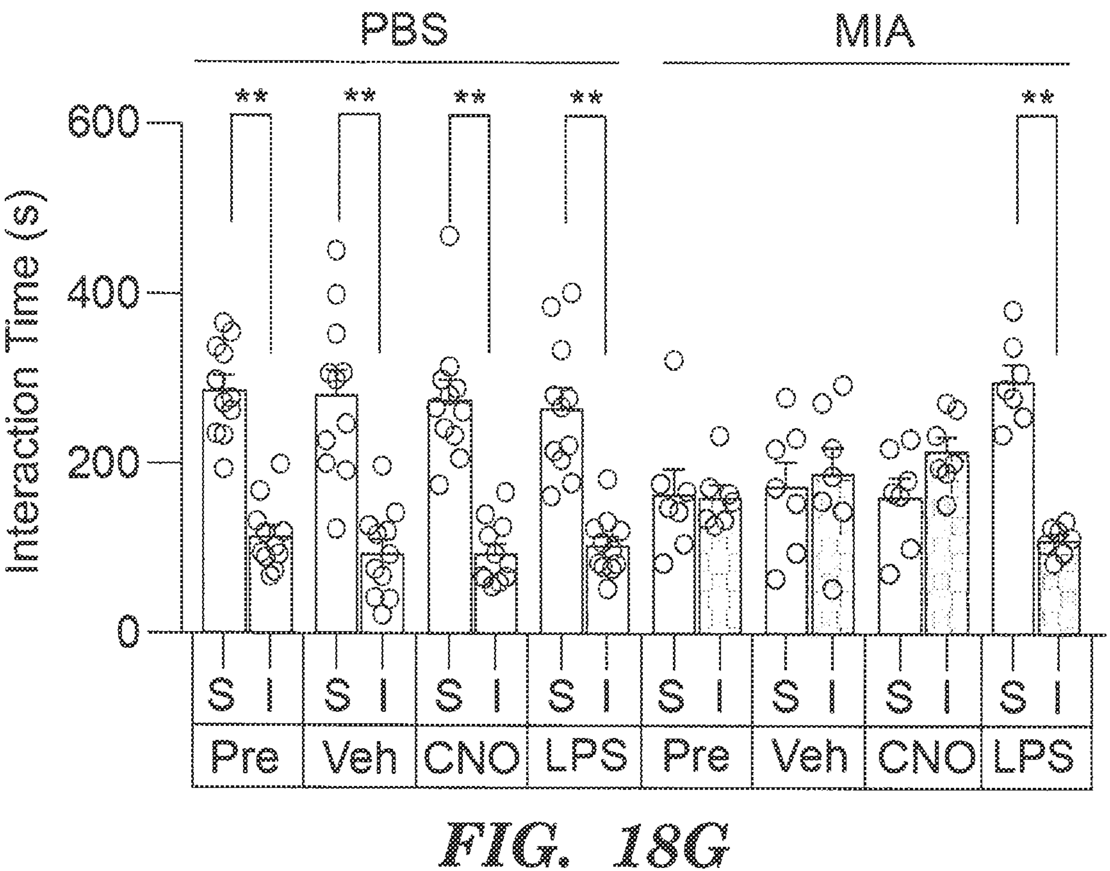
Figure 18H:
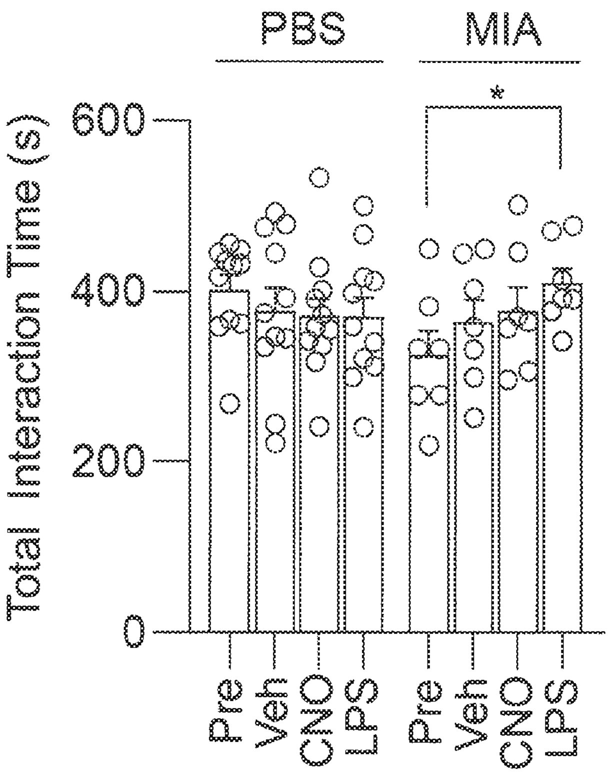
Figure 18I:
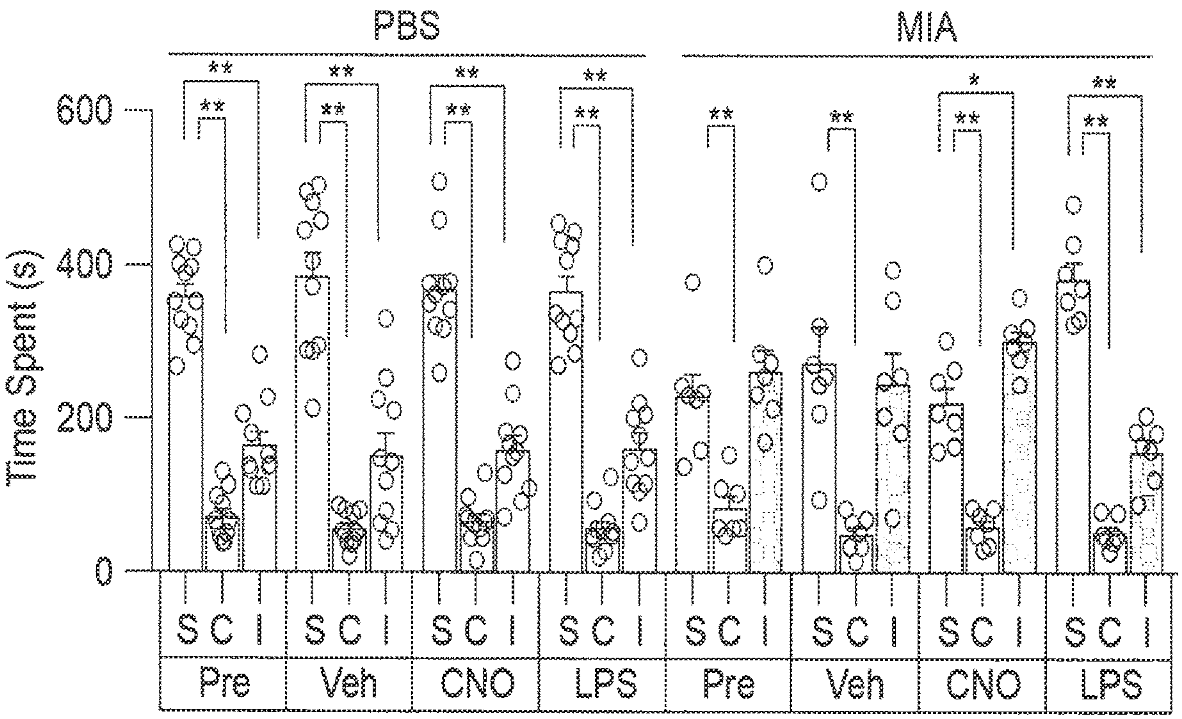
Figure 18J:
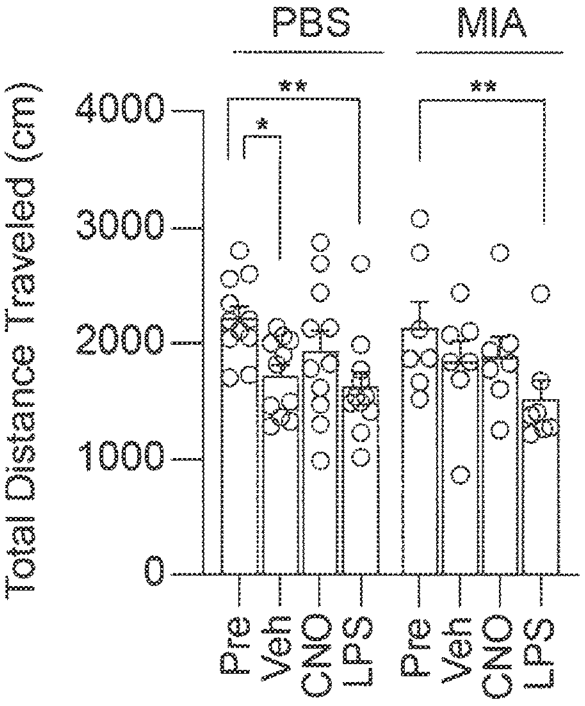

FIG. 18A-18J shows an acute increase in body temperature is insufficient to promote sociability. FIG. 18A shows the body temperature profile following Veh or LPS injection in MIA offspring (Veh n=10, LPS n=10; from 4 independent experiments). Initial spike in body temperature is due to handling stress. FIG. 18B-18E shows the data expressed as time spent investigating social (S) versus inanimate (I) objects (FIG. 18B), total interaction time (FIG. 18C), time spent in social (S), center (C) or inanimate (I) chamber (FIG. 18D), and distance traveled (FIG. 18E) during three-chambered sociability experiments described in FIG. 2C. FIG. 18F-18J demonstrates the sociability performance in Vgat-Cre PBS and MIA offspring following Veh, CNO, or LPS treatment. Data expressed as percent sociability (FIG. 18F), time spent investigating social (S) versus inanimate (I) objects (FIG. 18G), total interaction time (FIG. 18H), time spent in social (S), center (C) or inanimate (I) chamber (FIG. 18I), and distance traveled (FIG. 18J) during three-chambered sociability experiments (PBS n=11, MIA n=7; from 2 independent experiments). *P<0.05, P<0.01 calculated by two-way repeated measures ANOVA with Bonferroni's (a) and Dunnett's (FIG. 18F, 18H, 18J) post-hoc tests, and two-way ANOVA with Sidak's (FIG. 18B, 18G) and Dunnett's (FIG. 18D, 18I) post-hoc tests, and one-way repeated measures ANOVA with Tukey's post-hoc test (FIG. 18C, 18**E). Graphs indicate mean±s.e.m.

Figure 19A:
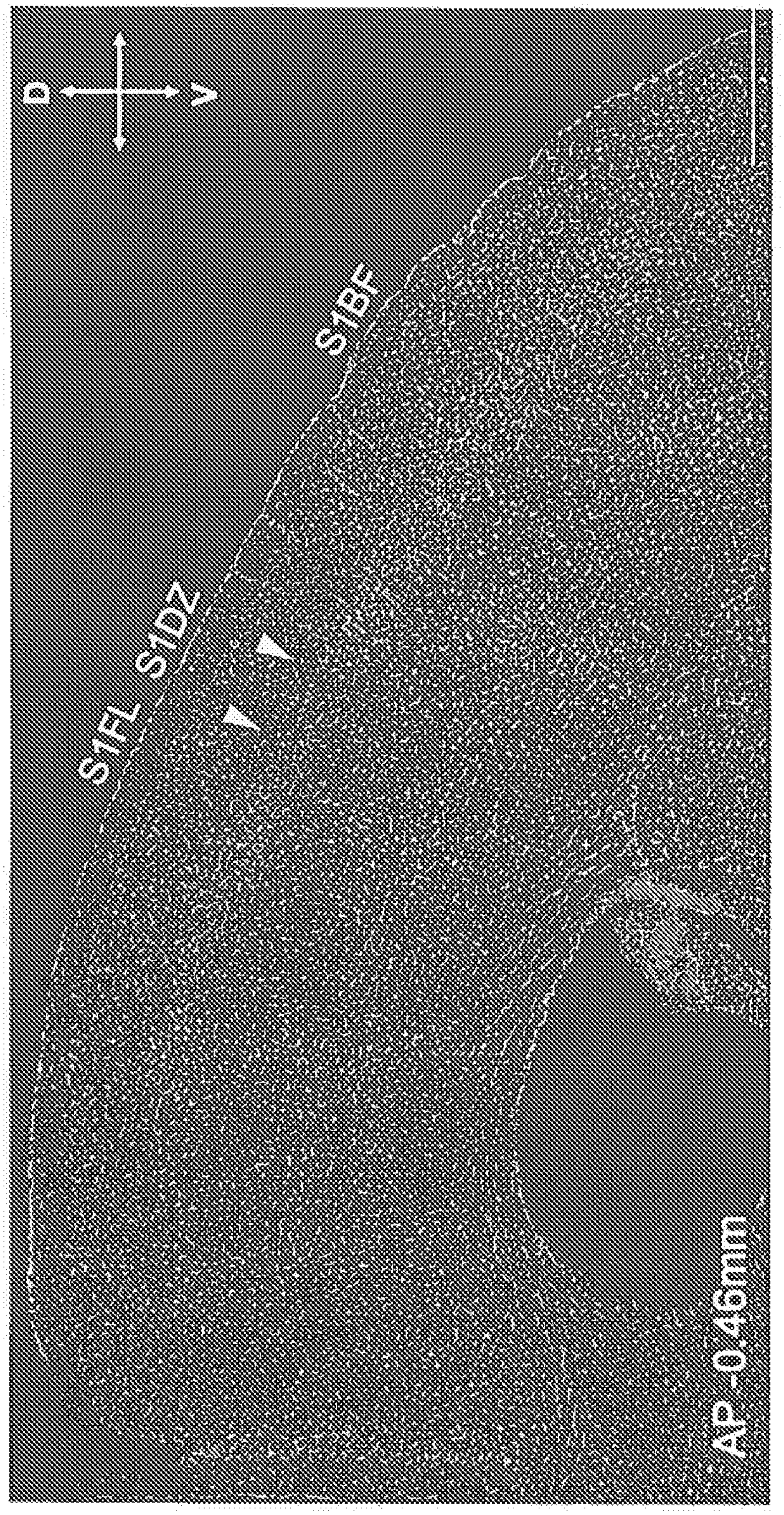
Figure 19B:
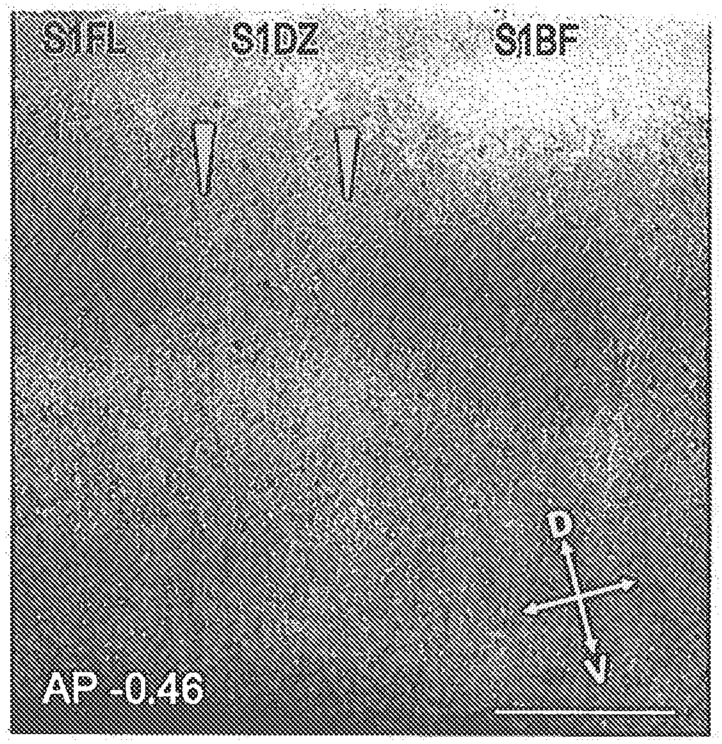

FIG. 19A-19B show histological identification of S1DZ. FIG. 19A demonstrates the coronal section of the cortex counterstained with DAPI to highlight the abrupt reduction in cell density in layer 4 between the S1DZ and the S1BF at AP−0.46 mm. FIG. 19B demonstrates the coronal section of the cortex imaged with differential interference contrast further highlighting the reduced layer 4 in the S1DZ at AP−0.46 mm. White arrows indicate borders of S1DZ. Scare bar represents 500 μm (FIG. 19A) and 300 μm (FIG. 19B). D: dorsal, V: ventral.

Figure 20A:
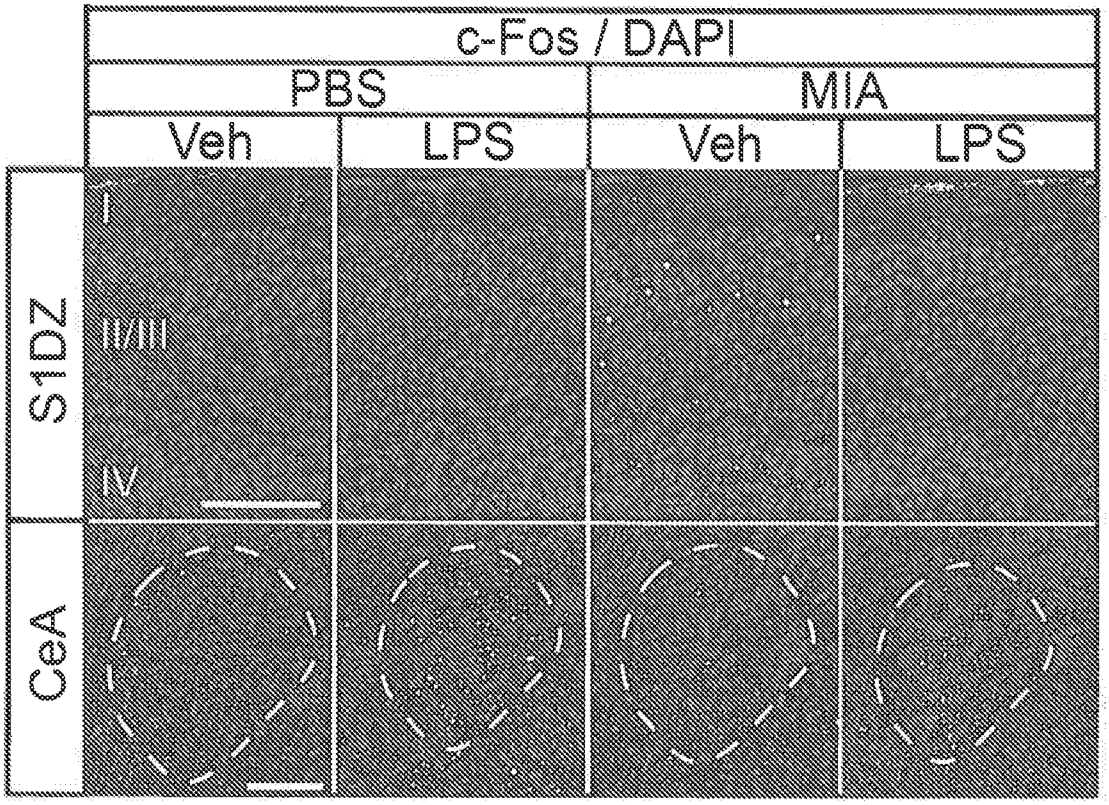
Figure 20B:
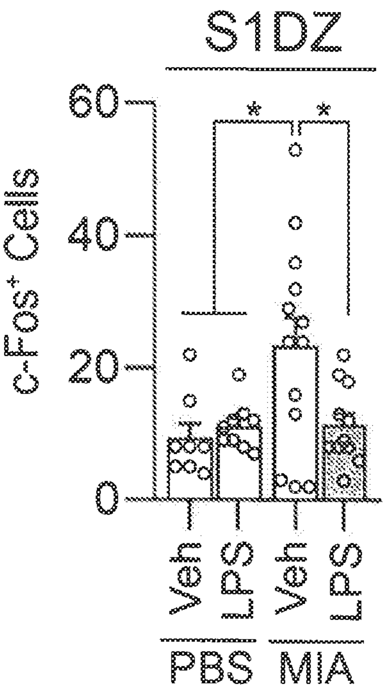
Figure 20C:
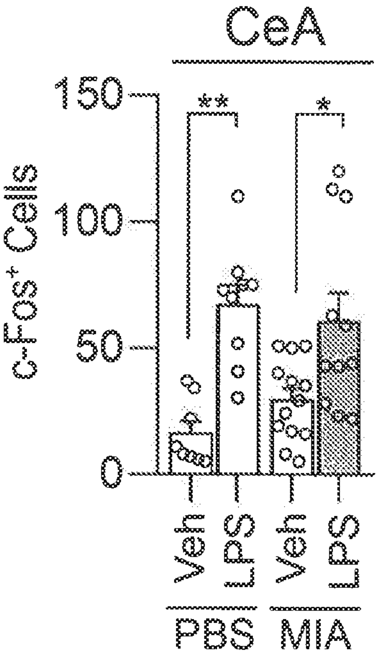
Figure 20D:
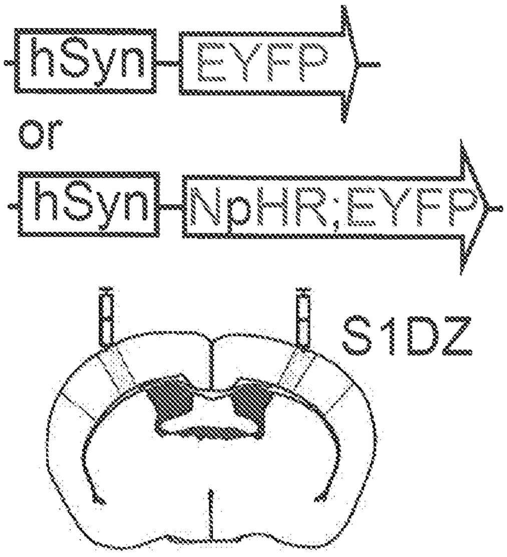
Figure 20E:
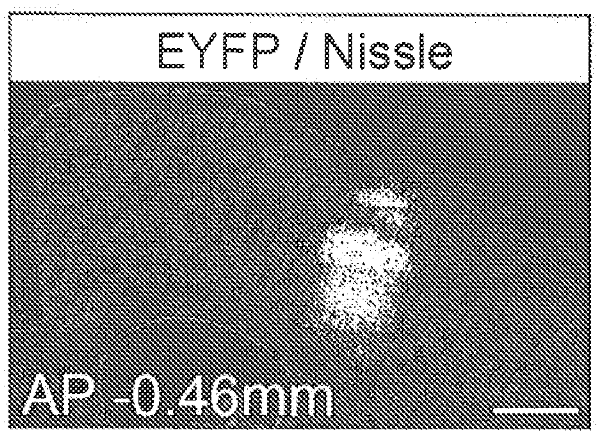
Figure 20F:
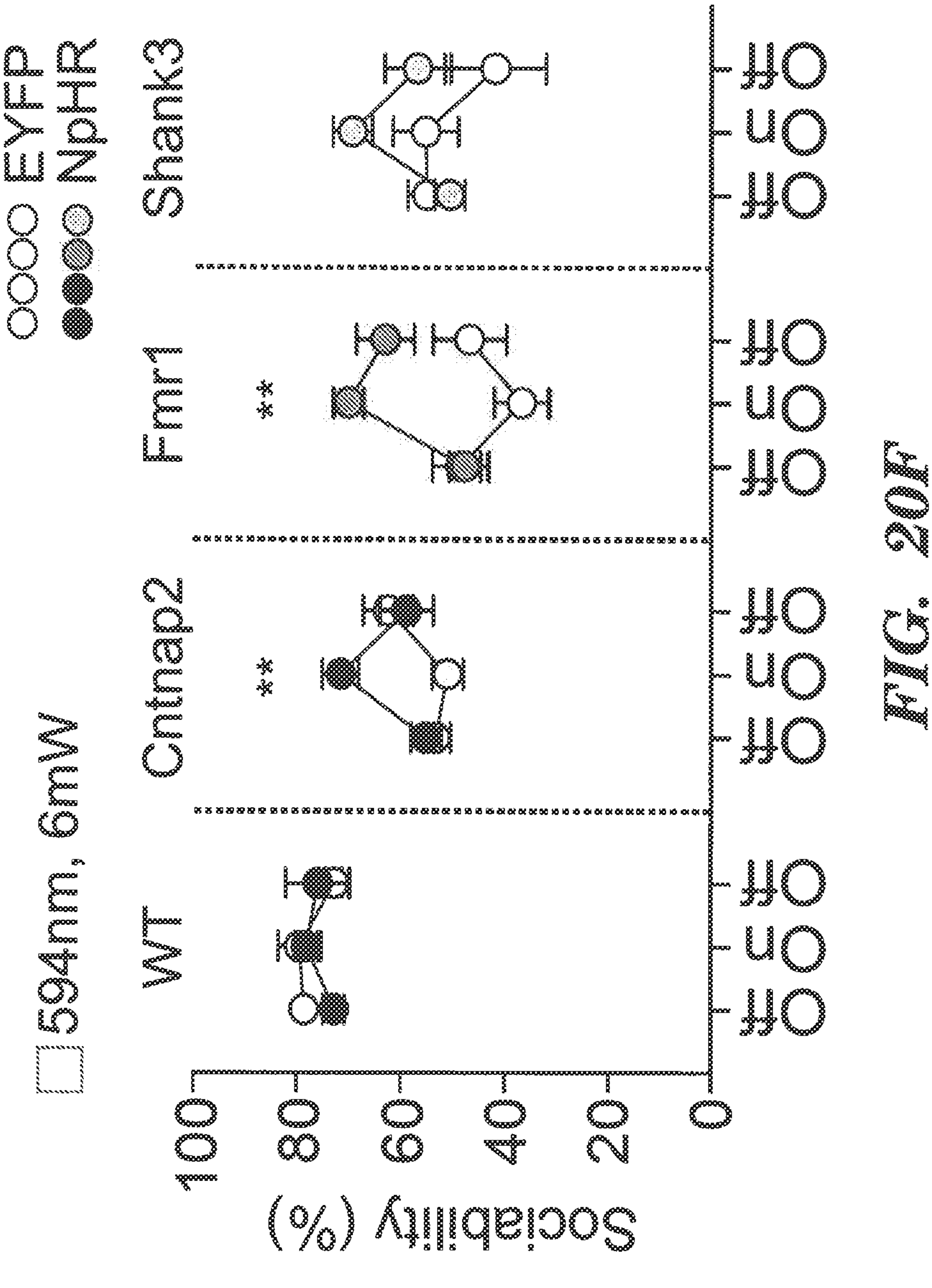
Figure 20G:
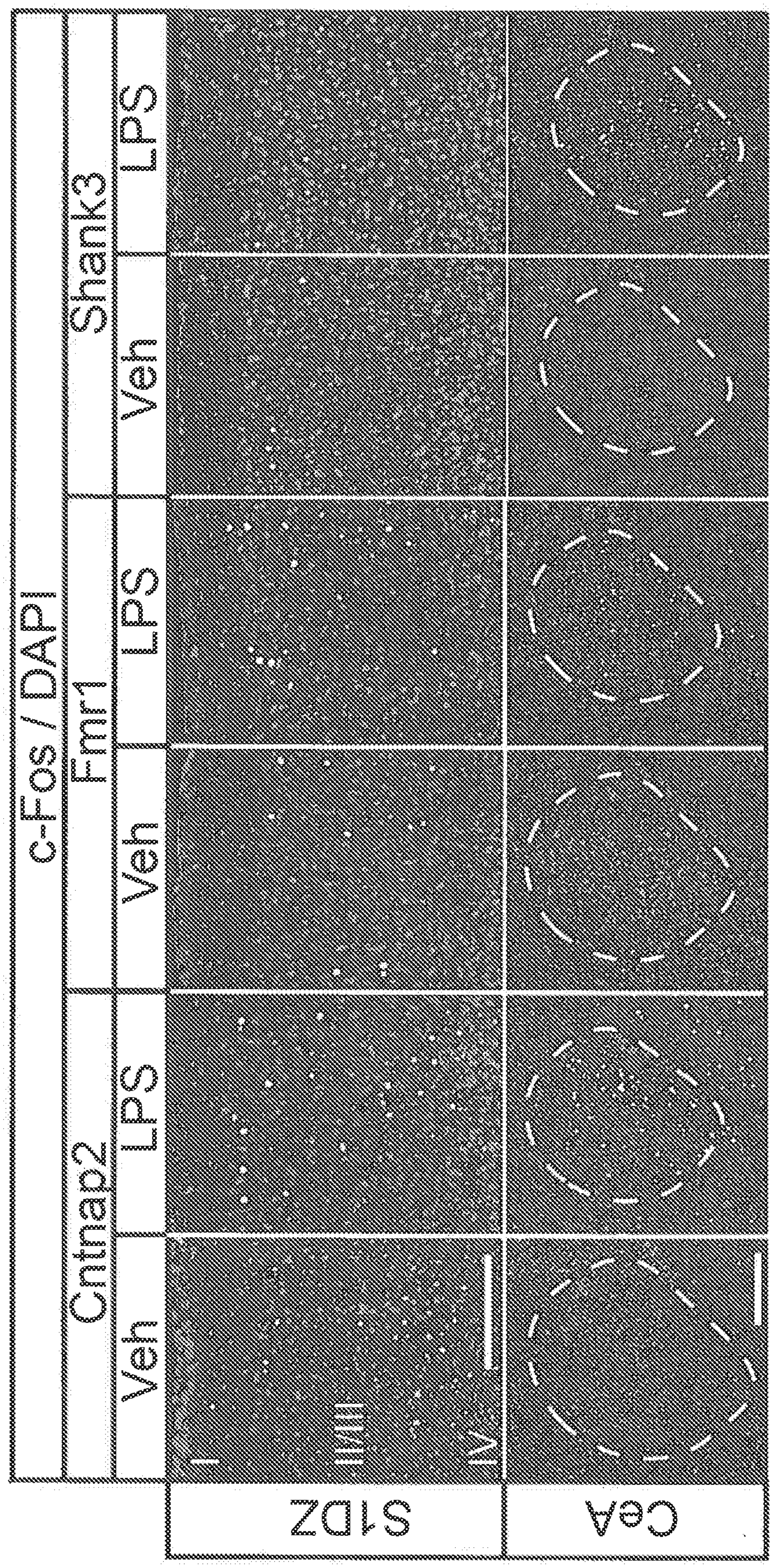
Figure 20H:
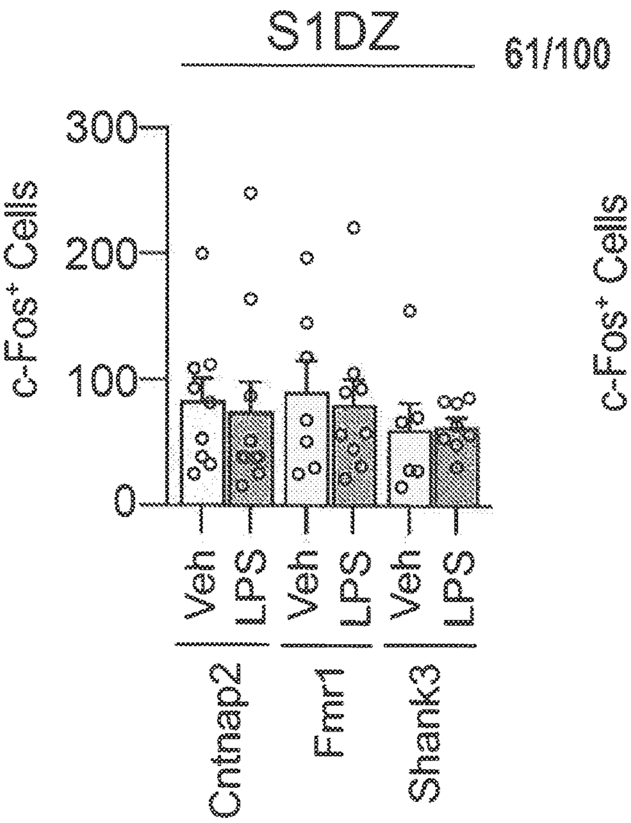
Figure 20I:
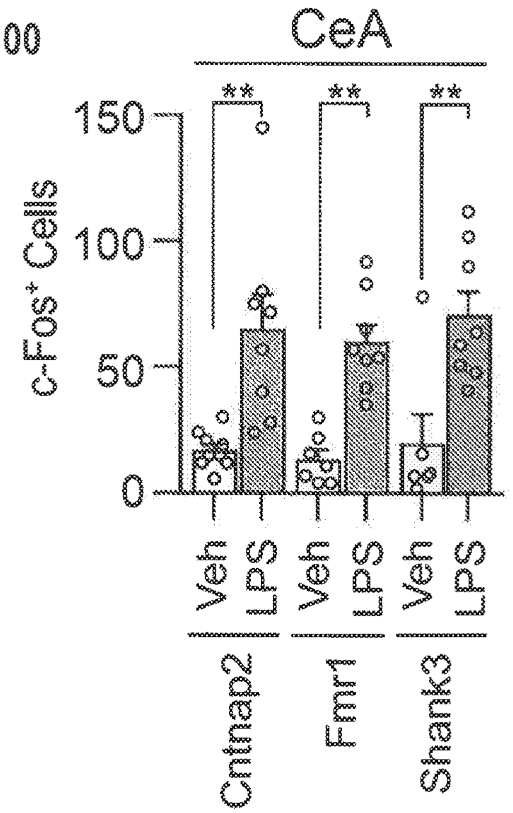

FIG. 20A-20I demonstrates that immune stimulation reduces hyperactivation in the S1DZ of MIA offspring. FIG. 20A shows representative images illustrating c-Fos expression in the S1DZ and CeA following Veh or LPS injection. Scale bar represents 200 μm. Numerals indicate cortical layers. S1DZ, Primary somatosensory cortex, dysgranular zone; CeA, Central amygdala. FIG. 20B, 20C show quantification of c-Fos expressing cells following Veh or LPS injection in the S1DZ (FIG. 20B) and CeA (FIG. 20C) (PBS-Veh n=8, PBS-LPS n=9, MIA-Veh n=13, MIA-LPS n=11; from 3 independent experiments). FIG. 20D, 20E shows the AAV encoding either EYFP or EYFP fused to eNpHR was bilaterally injected into the S1DZ of monogenic mutant animals. Scale bar represents 500 μm. FIG. 20F demonstrates the performance on sociability was assessed in the presence and absence of optical inhibition (WT-EYFP n=7, WT-eNpHR n=8, Cntnap2-EYFP n=11, Cntnap2-eNpHR n=9, Fmr1-EYFP n=8, Fmr1-eNpHR n=12, Shank3-EYFP n=8, Shank3-eNpHR n=10; from 6 independent experiments). FIG. 20G shows representative images illustrating c-Fos expression in the S1DZ and CeA following Veh or LPS injection in monogenic mutant mice. Scale bar represents 200 μm. FIG. 20H-20I shows the quantification of c-Fos expressing cells following Veh or LPS injection in the S1DZ (FIG. 20H) and CeA (FIG. 20I) (Cntnap2-Veh n=9, Cntnap2-LPS n=8, Fmr1-Veh n=7, Fmr1-LPS n=8, Shank3-Veh n=6, Shank3-LPS n=8; from 3 independent experiments). *P<0.05, P<0.01 calculated by two-way ANOVA with Tukey's post-hoc test (FIG. 20B, 20C) and Sidak's post-hoc test (FIG. 20H, 20I), and two-way repeated measures ANOVA with Sidak's post-hoc test (FIG. 20**F). Graphs indicate mean #s.e.m.

Figure 21A:
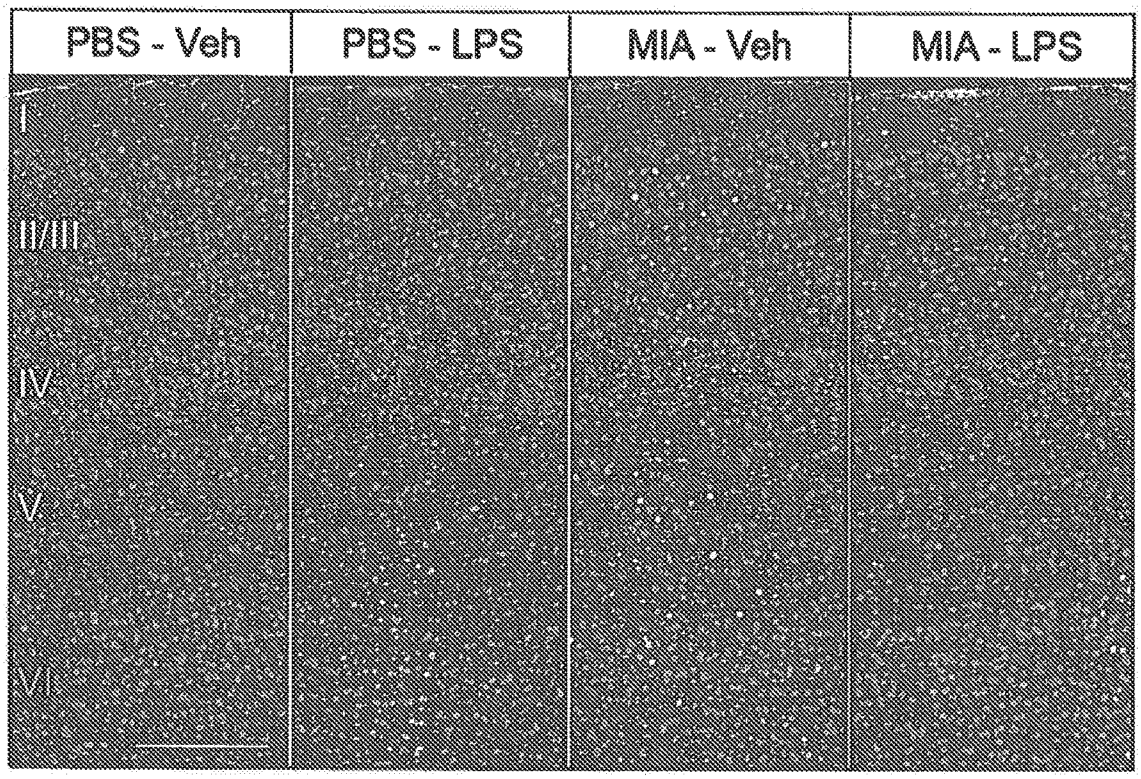
Figure 21B:
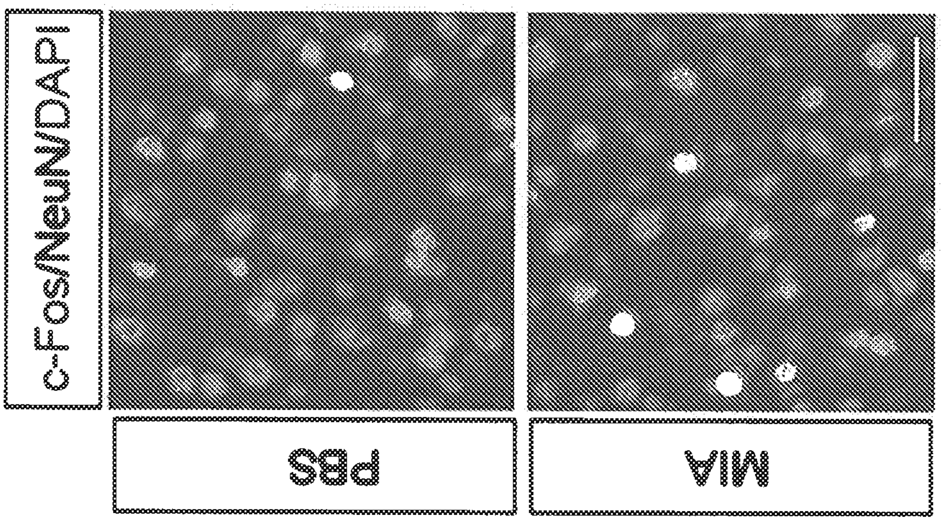
Figure 21C:
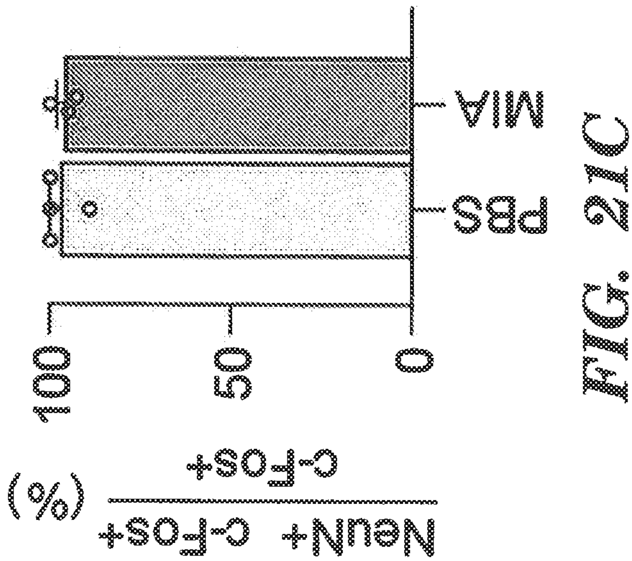
Figure 21D:
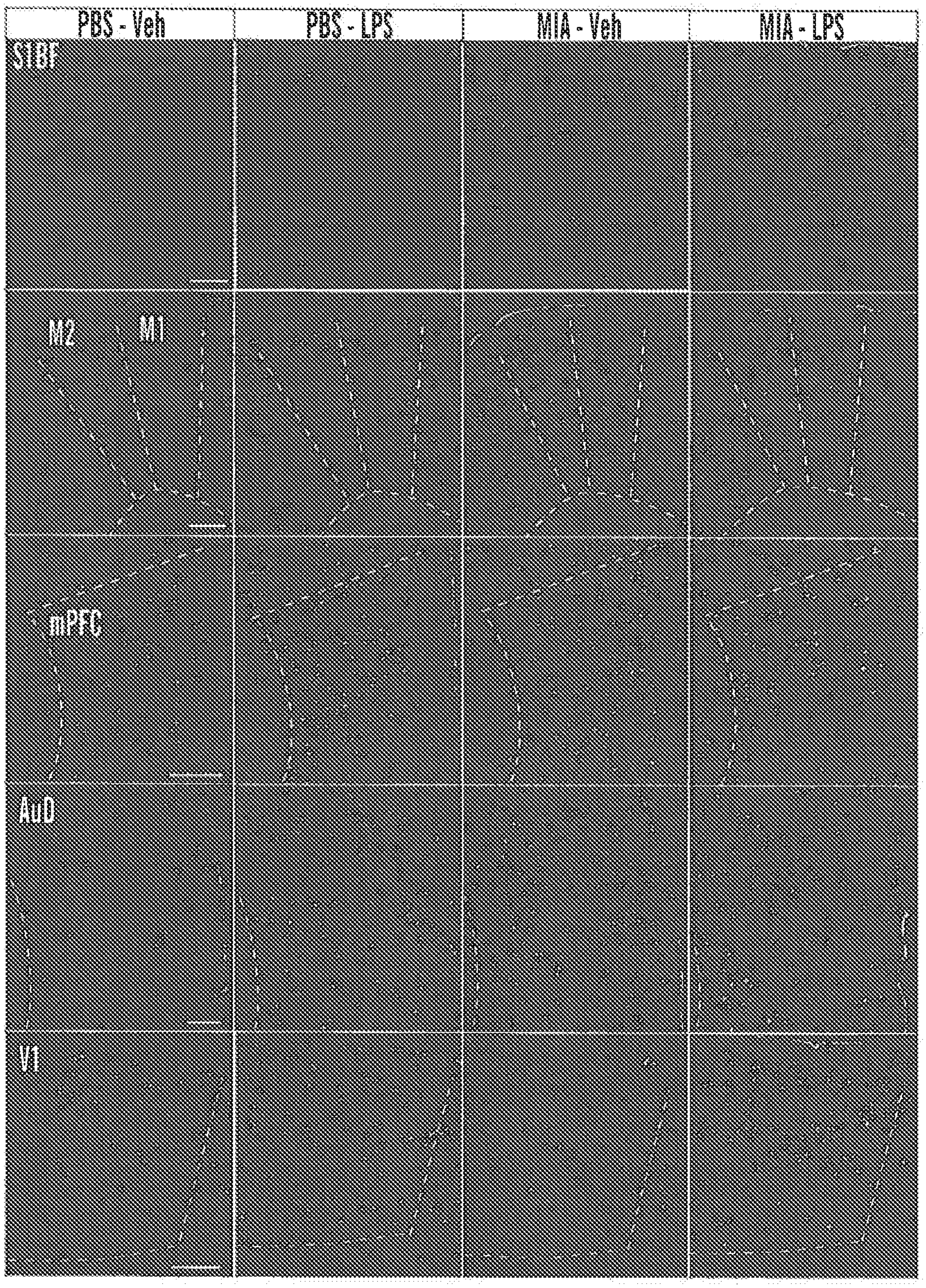
Figure 21E:
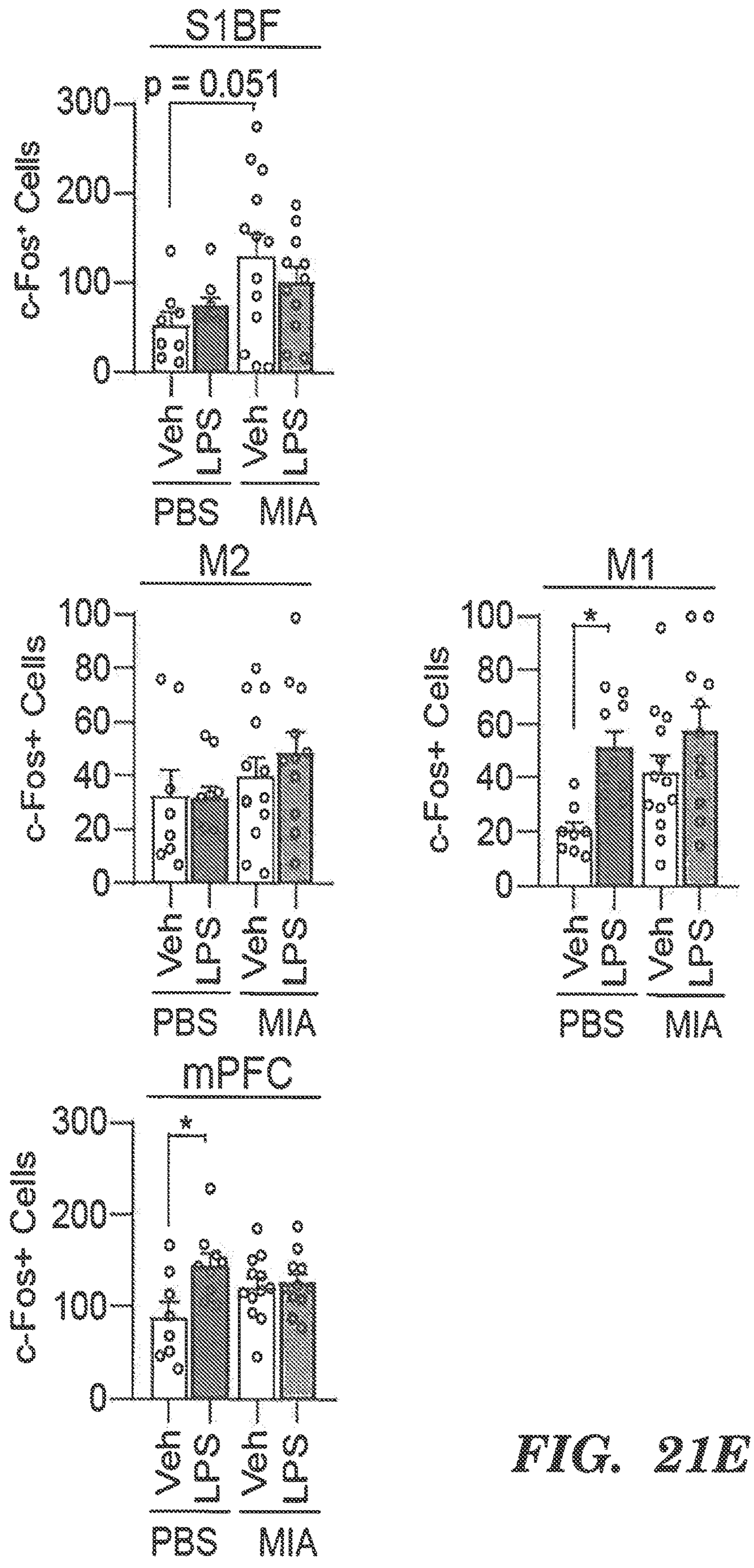
Figure 21E:
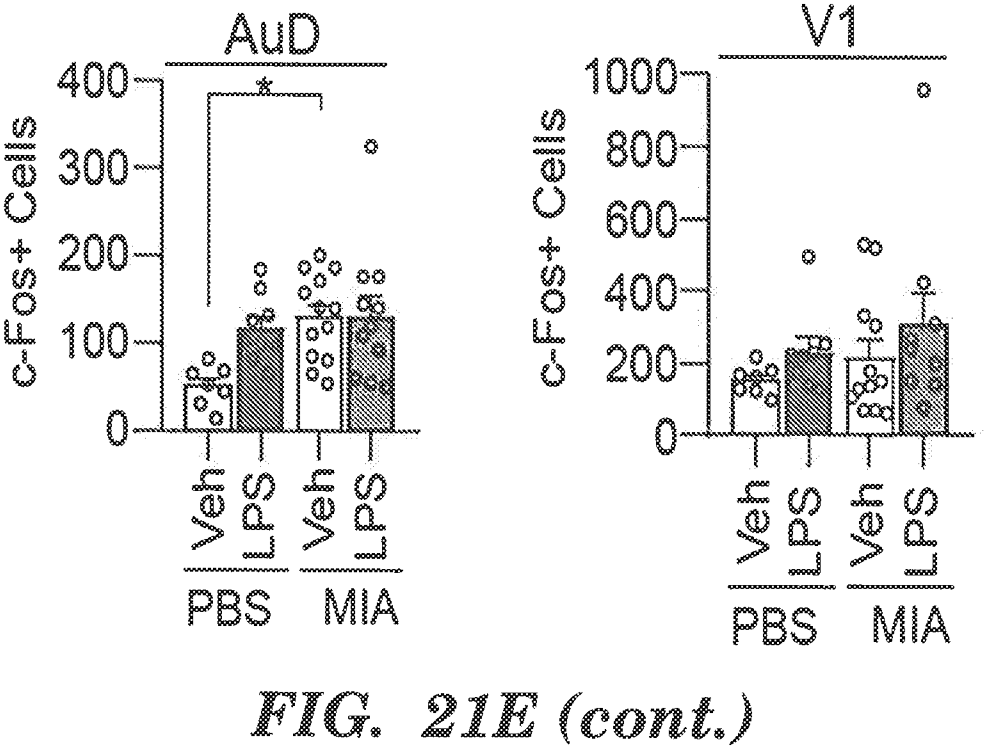

FIG. 21A-21E shows LPS treatment in MIA offspring does not have a distinguishable effect on c-Fos expression in other cortical regions analyzed. a, Full cortical depth of S1DZ c-Fos staining as shown in FIG. 20A for PBS and MIA offspring after Veh or LPS administration. Scare bar represents 200 μm. FIG. 21B-21C demonstrate representative images (FIG. 21B) and quantification (FIG. 21C) of c-Fos/NeuN co-labeled cells within the S1DZ of PBS and MIA offspring (PBS n=4, MIA n=3; from 1 independent experiment). Scale bar represents 50 μm. FIG. 21D-21E, Representative images (FIG. 21D) and quantification (FIG. 21E) of c-Fos expression in a series of cortical regions and following Veh or LPS injection in PBS or MIA offspring. Sections are stained for c-Fos and DAPI. Scale bar represents 200 μm. S1BF, Primary somatosensory cortex, barrel field; M1, Primary motor cortex; M2, Secondary motor cortex; mPFC, medial prefrontal cortex (prelimbic and infralimbic cortex); AuD, Primary auditory cortex; V1, Primary visual cortex (For S1BF, M2, M1, and AuD; PBS-Veh n=8, PBS-LPS n=9, MIA-Veh n=13, MIA-LPS n=11. For mPFC; PBS-Veh n=8, PBS-LPS n=9, MIA-Veh n=12, MIA-LPS n=11. For V1; PBS-Veh n=7, PBS-LPS n=8, MIA-Veh n=12, MIA-LPS n=9; from 4 independent experiments). *p<0.05, p<0.01 as calculated by unpaired t-test (FIG. 21C) and two-way ANOVA with Tukey's post-hoc test (FIG. 21**E). Graphs indicate mean±s.e.m.

Figure 22A:
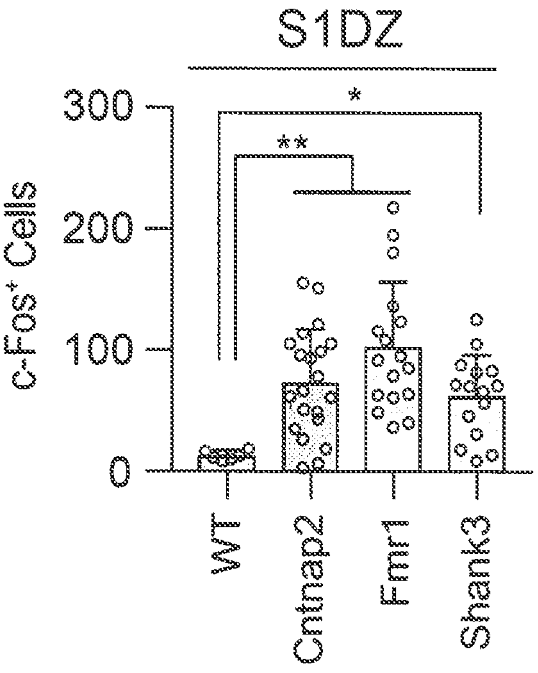
Figure 22B:
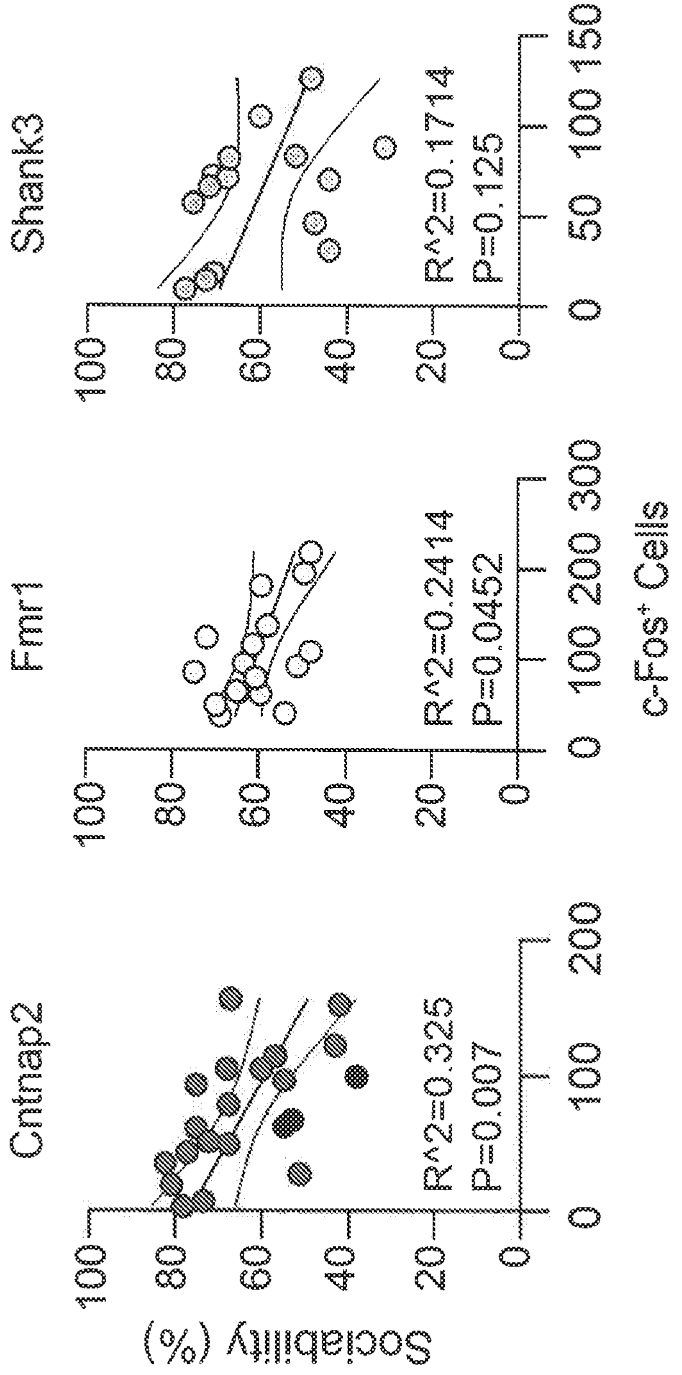
Figure 22C:
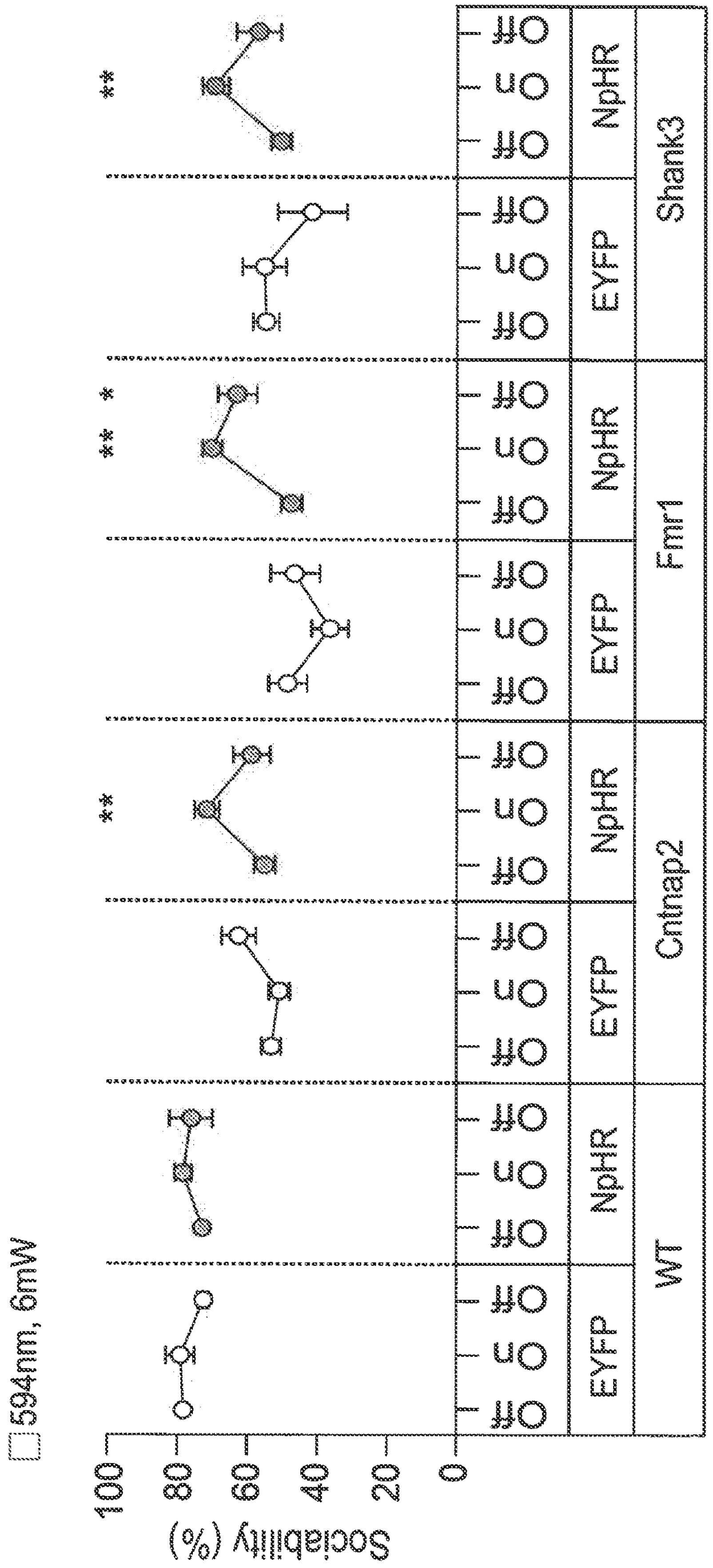
Figure 22D:
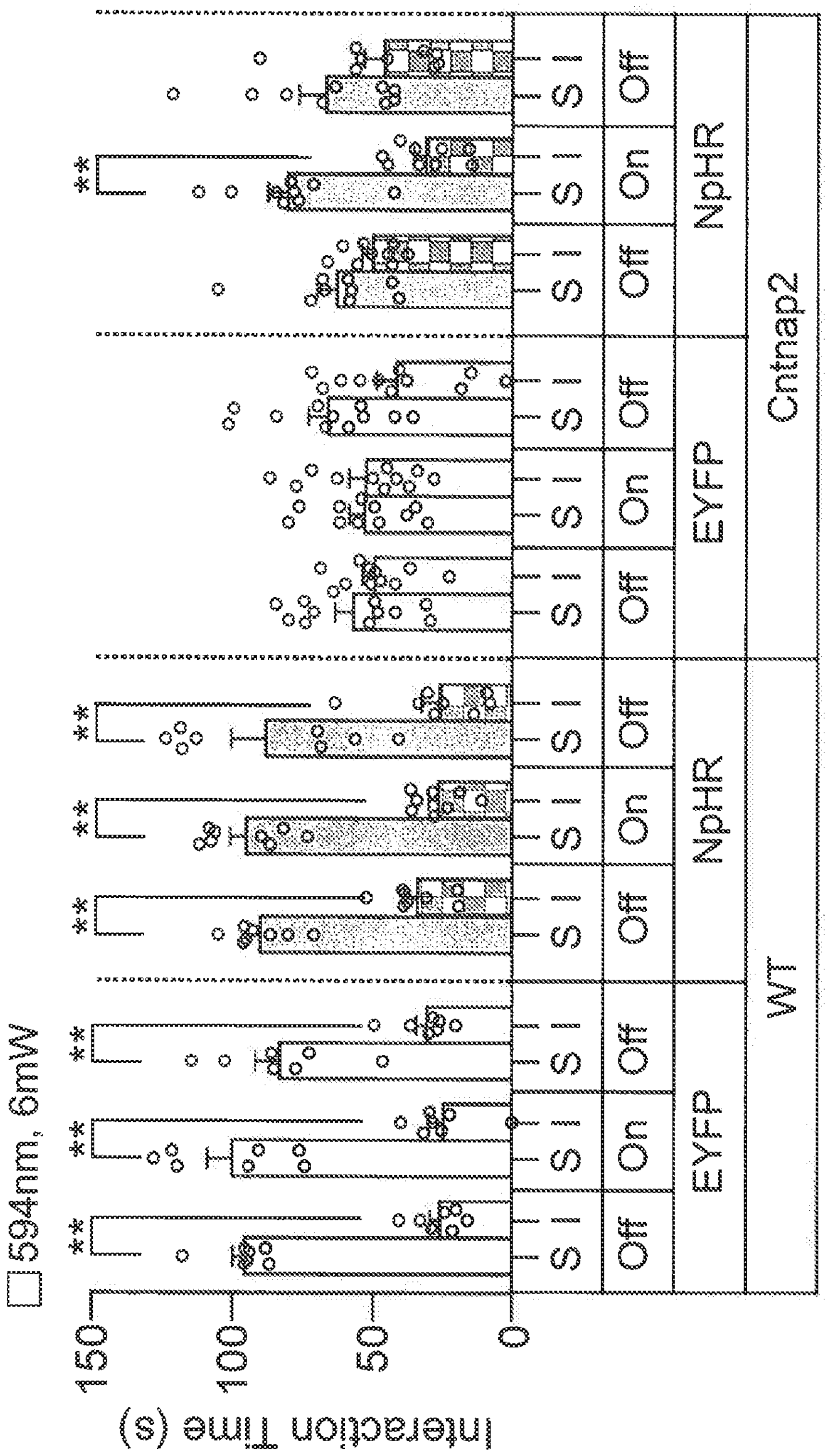
Figure 22D:
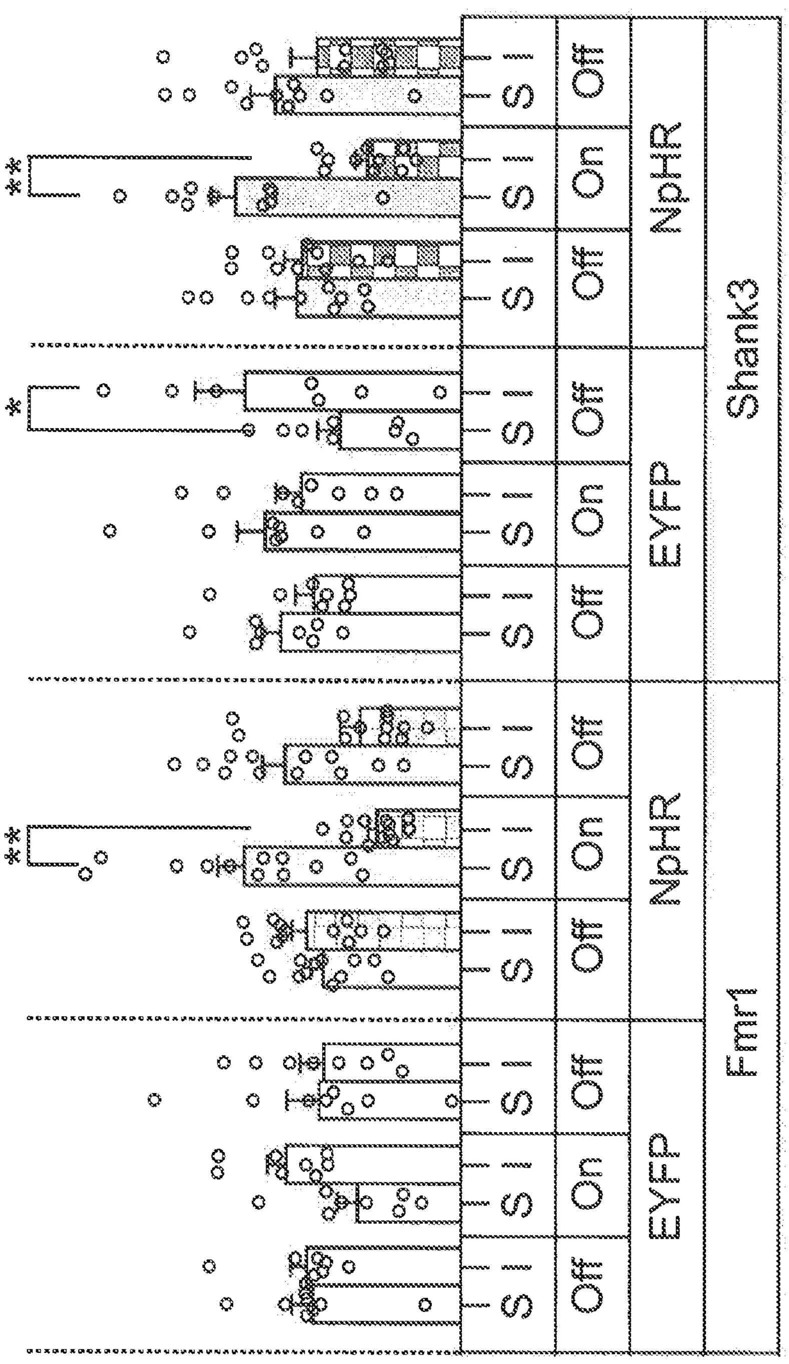
Figure 22E:
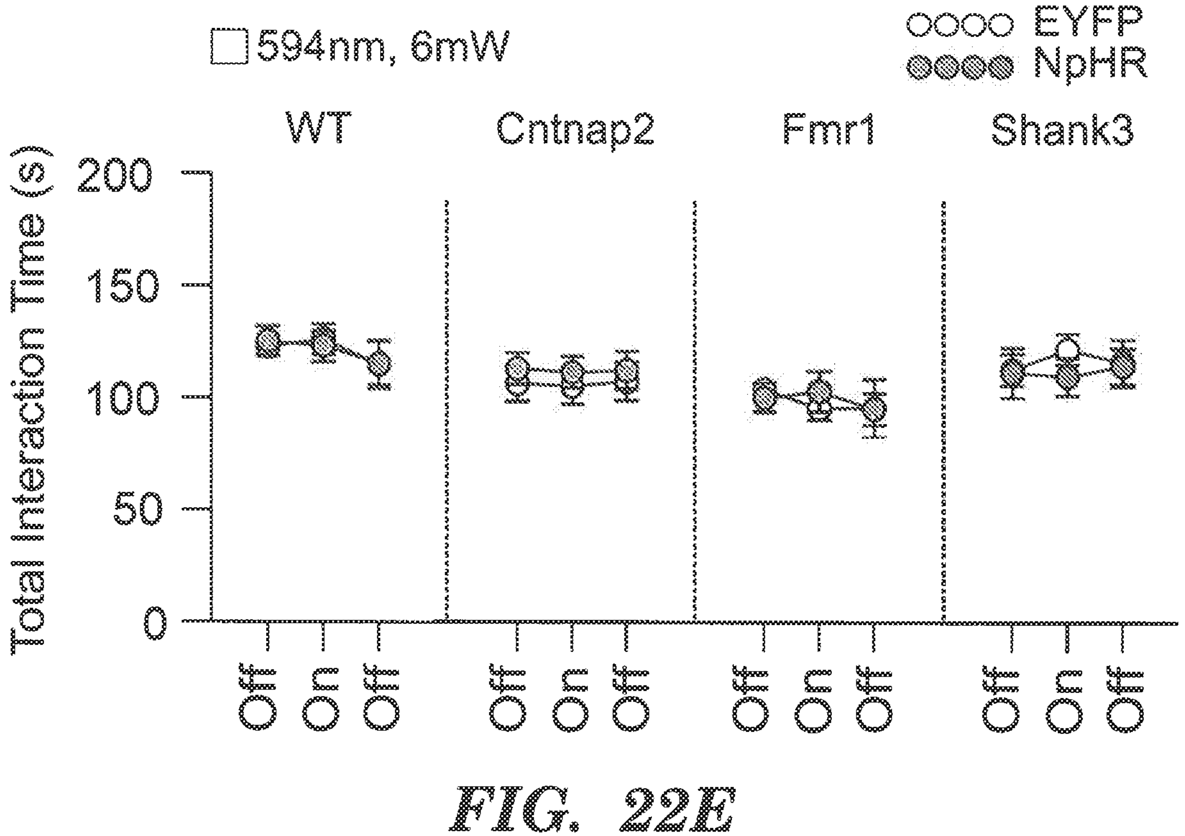
Figure 22F:
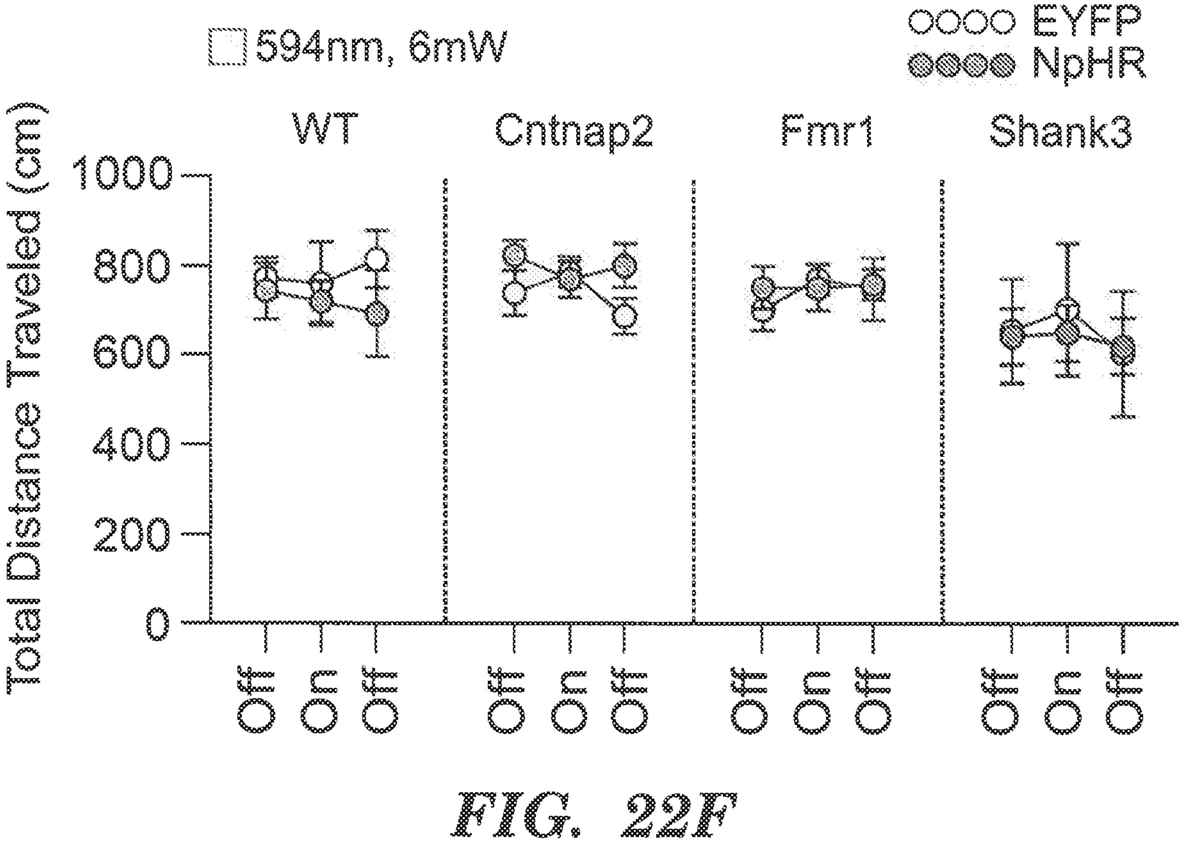

FIG. 22A-22F shows further behavioral analyses of S1DZ optical inhibition-mediated rescue of sociability in monogenic mutant mice. FIG. 22A shows the quantification of c-Fos expressing cells in the S1DZ of monogenic mutant mice (WT n=6, Cntnap2 n=21, Fmr1 n=17, Shank3 n=15: from 5 independent experiments). FIG. 22B shows the correlation of c-Fos expression in the S1DZ with severity of sociability deficits across monogenic mutant mice (Cntnap2 n=21, Fmr1 n=17, Shank3 n=15; from 4 independent experiments). Black solid lines represent regression line; grey lines indicate 90% confidence intervals. FIG. 22C shows individual data for experiments in FIG. 20F. FIG. 22D-22F shows the data expressed as time spent investigating social (S) versus inanimate (I) objects (FIG. 22D), total interaction time (FIG. 22E) and distance traveled (FIG. 22F) during three-chambered sociability experiments described in FIG. 2F. *p<0.05, p<0.01 as calculated by one-way ANOVA with Dunnett's post-hoc test (FIG. 22A), linear regression (FIG. 22B), one-way repeated measures ANOVA with Dunnet's post-hoc test (FIG. 22C), two-way ANOVA with Sidak's post-hoc test (FIG. 22D), and two-way repeated measures ANOVA with Sidak's post-hoc test (FIG. 22E, 22**F). Graphs indicate mean±s.e.m.

Figure 23A:
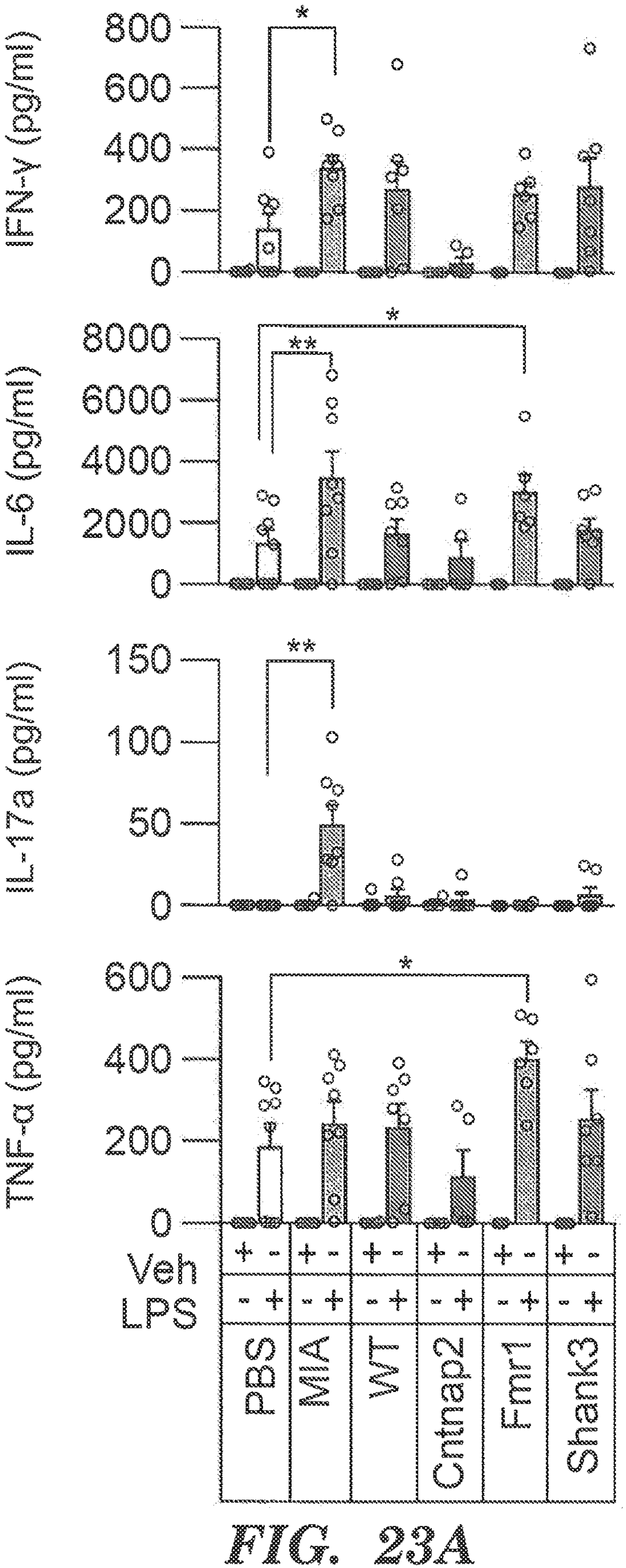
Figure 23B:
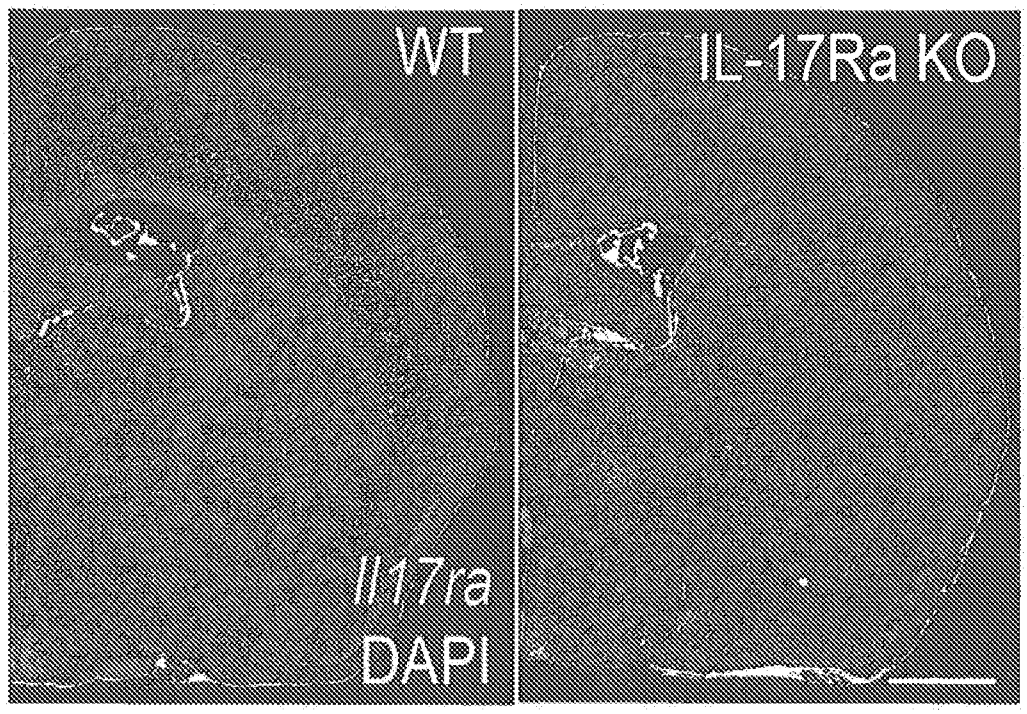
Figure 23C:
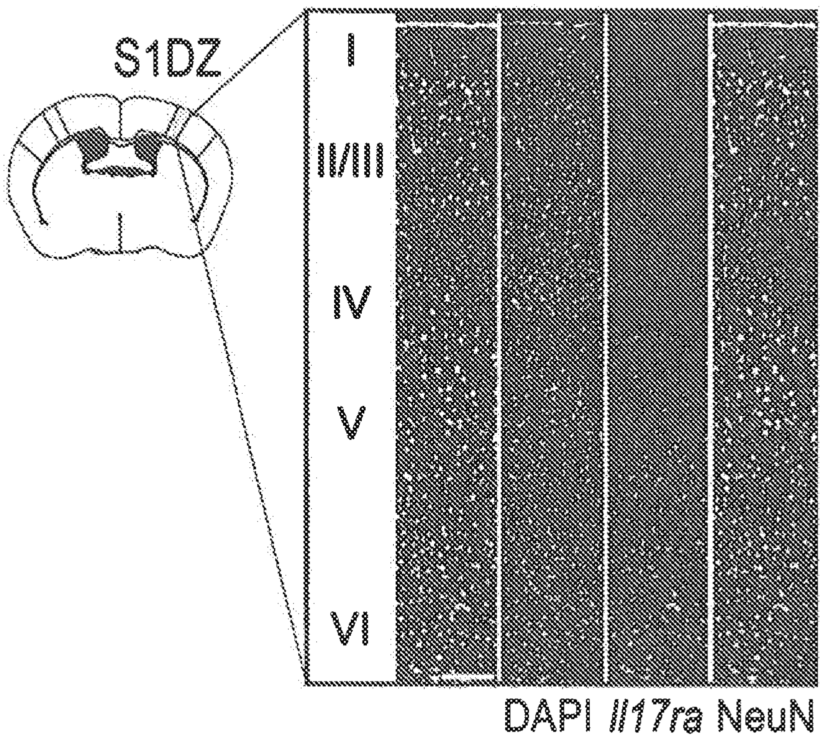
Figure 23D:
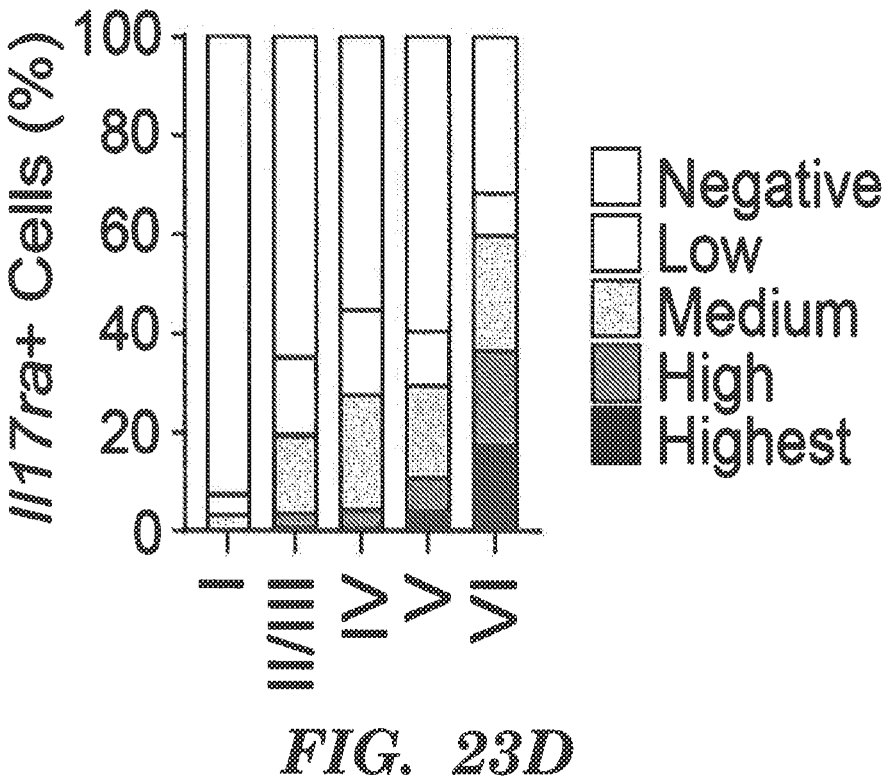
Figure 23E:
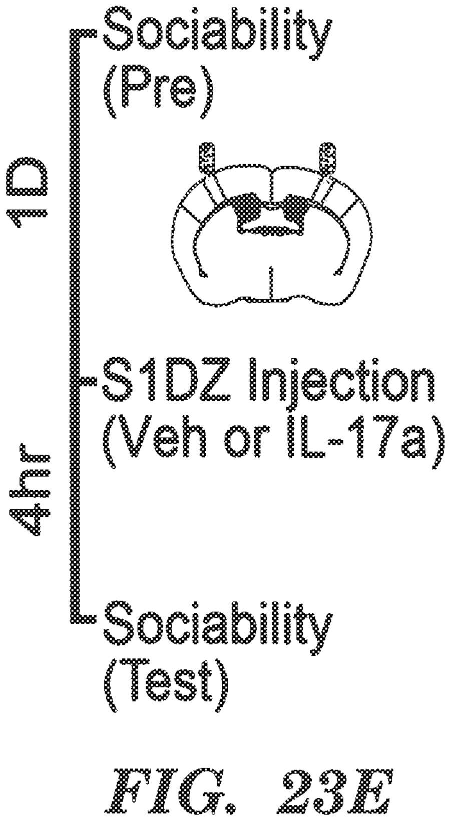
Figure 23F:
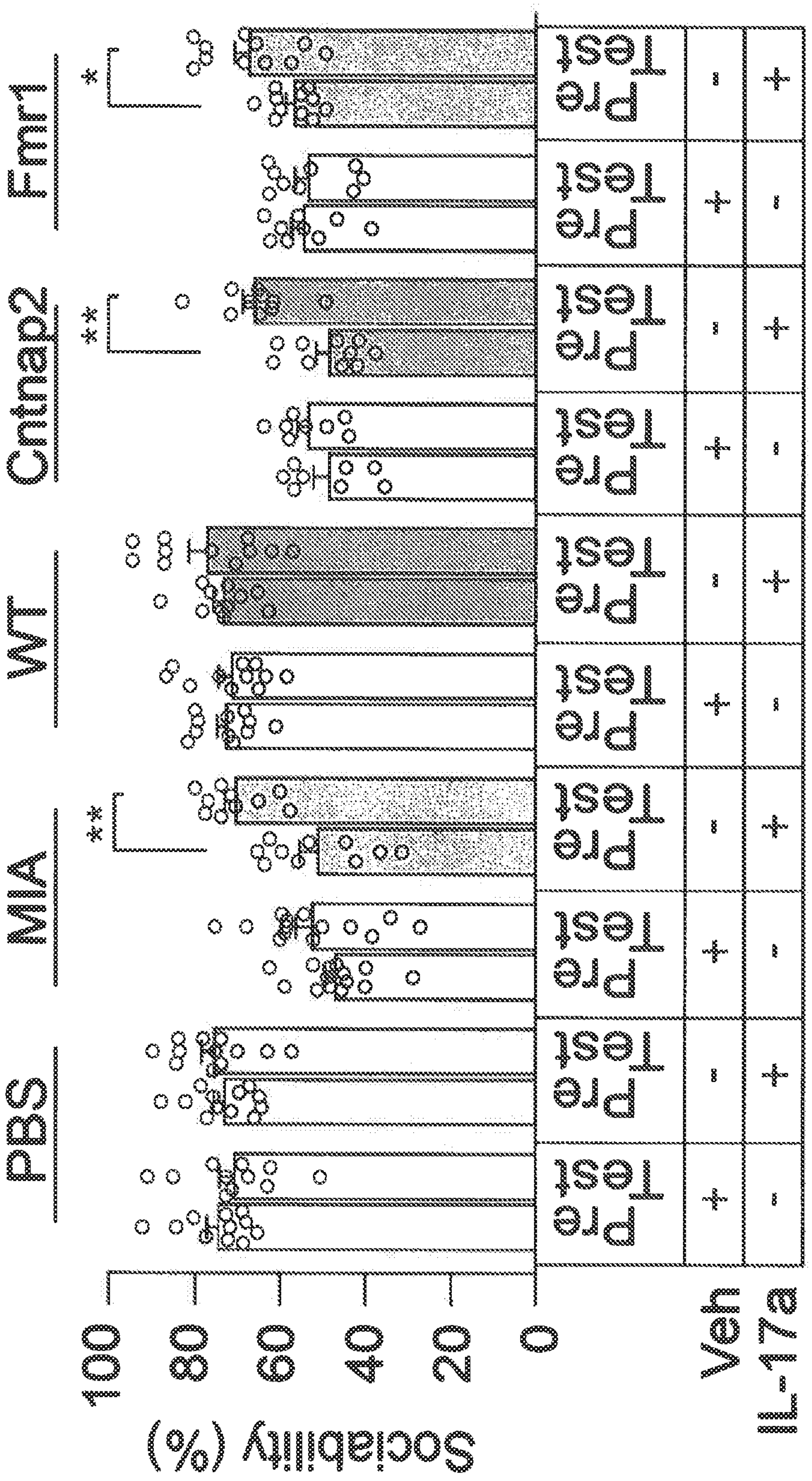

FIG. 23A-23F show IL-17a rescues sociability deficits in both MIA offspring and monogenic mutant mice. FIG. 23A shows IFN-γ, IL-6, IL-17a, and TNF-α levels in plasma following Veh or LPS injection (PBS-Veh n=6, PBS-LPS n=8, MIA-Veh n=6, MIA-LPS n=8, WT-Veh n=6, WT-LPS n=7, Cntnap2-Veh n=4, Cntnap2-LPS n=5, Fmr1-Veh n=5, Fmr1-LPS n=6, Shank3-Veh n=7, Shank3-LPS n=7; from 3 independent experiments). FIG. 23B shows Il17ra expression in WT and IL-17Ra KO animals at AP−0.58 mm. Scale bar represents 1 mm. FIG. 23C shows co-labeling of Il17ra and NeuN in the S1DZ. Scale bar represents 100 μm. FIG. 23D shows the quantification of Il17ra expression within the S1DZ according to cortical layer in PBS offspring (n=8). FIG. 23E-23F, shows that mice were tested for sociability one day prior to injection (Pre) and following bilateral administration of Veh or IL-17a into the S1DZ (Test). (PBS-Veh n=11, PBS-IL-17a n=12, MIA-Veh n=14, MIA-IL-17a n=10, WT-Veh n=11, WT-IL-17a n=11, Cntnap2-Veh n=8, Cntnap2-IL-17a n=10, Fmr1-Veh n=9, Fmr1-IL-17a n=11; from 6 independent experiments). *P<0.05, P<0.01 calculated by two-way ANOVA with Dunnett's post-hoc test (FIG. 23A) and two-way repeated measures ANOVA with Sidak's post-hoc test (FIG. 23**F). Graphs indicate mean±s.e.m.

Figure 24A:
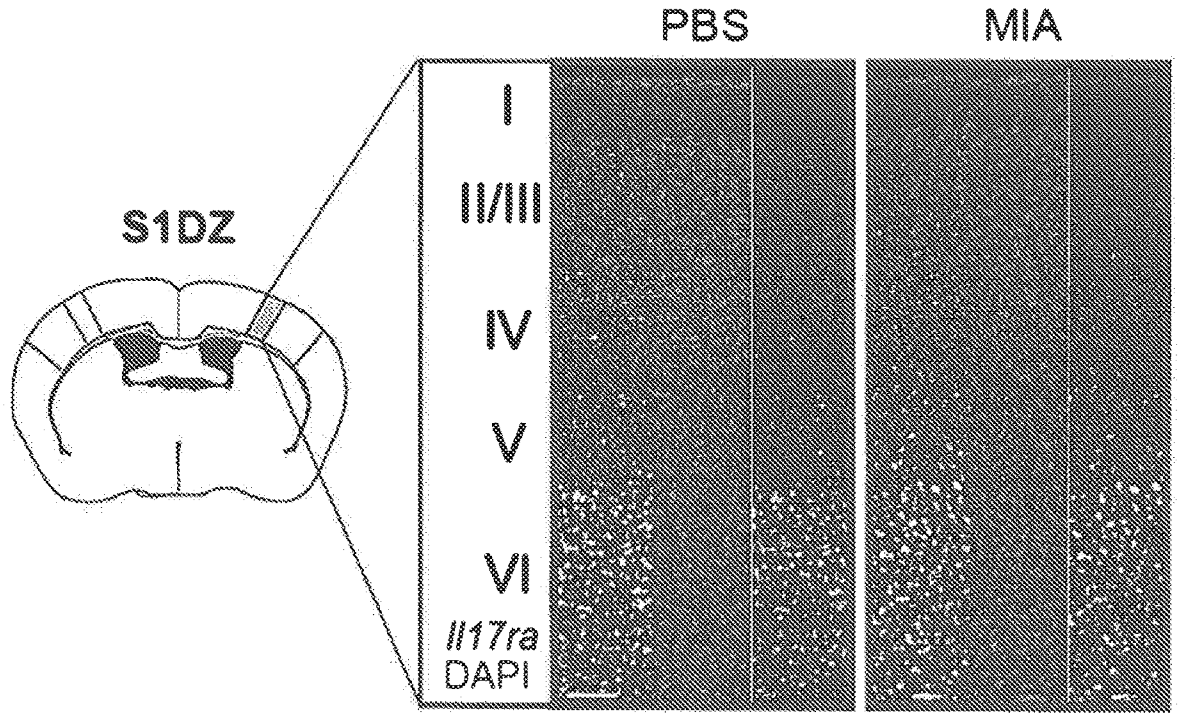
Figure 24B:
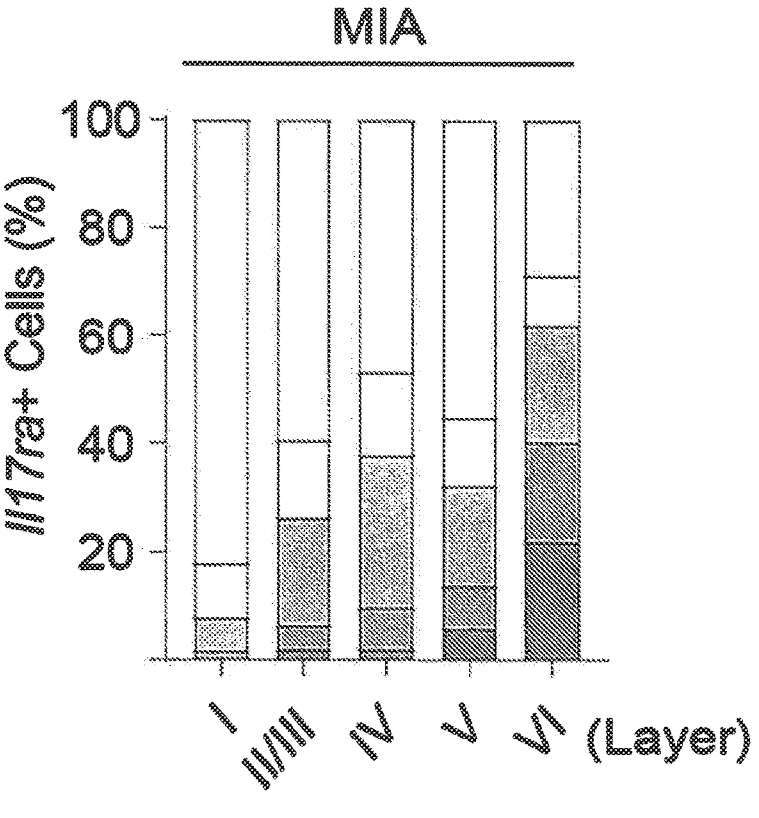
Figure 24C:
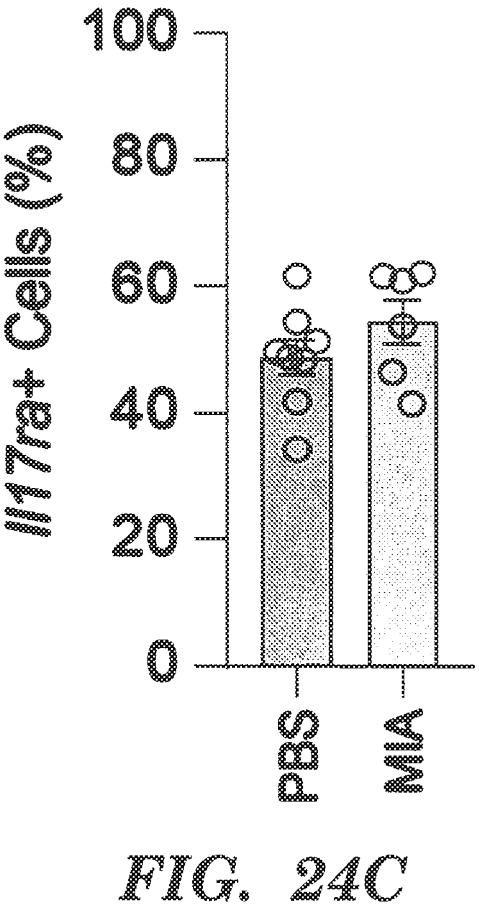
Figure 24D:
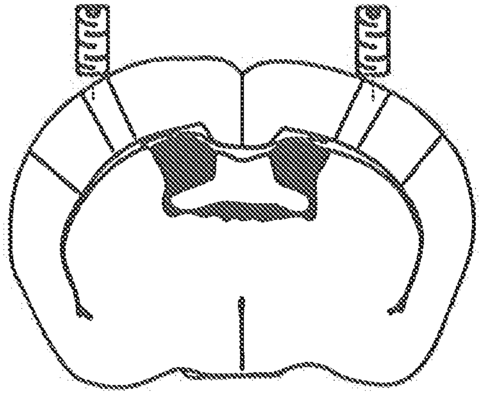
Figure 24E:
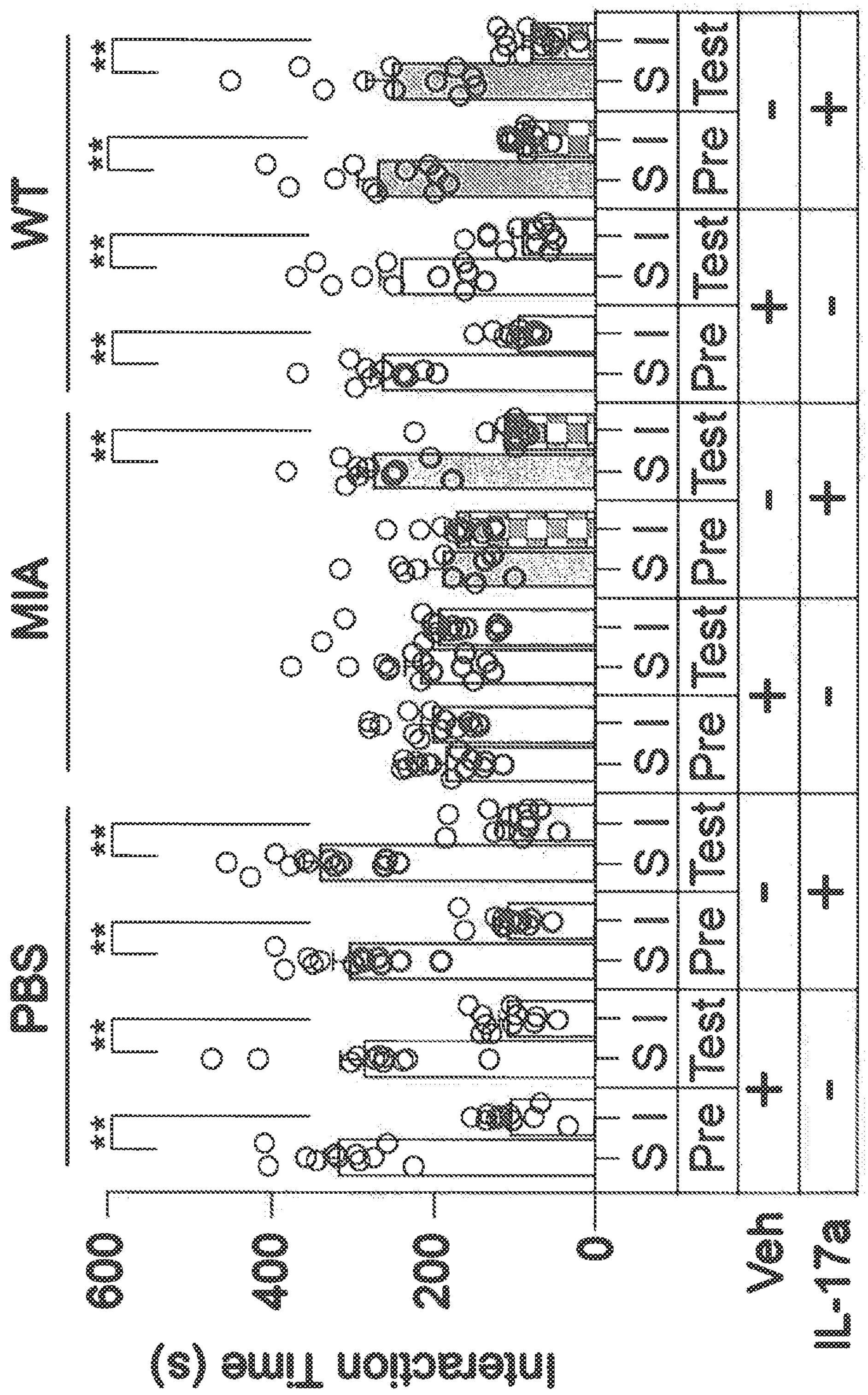
Figure 24E:
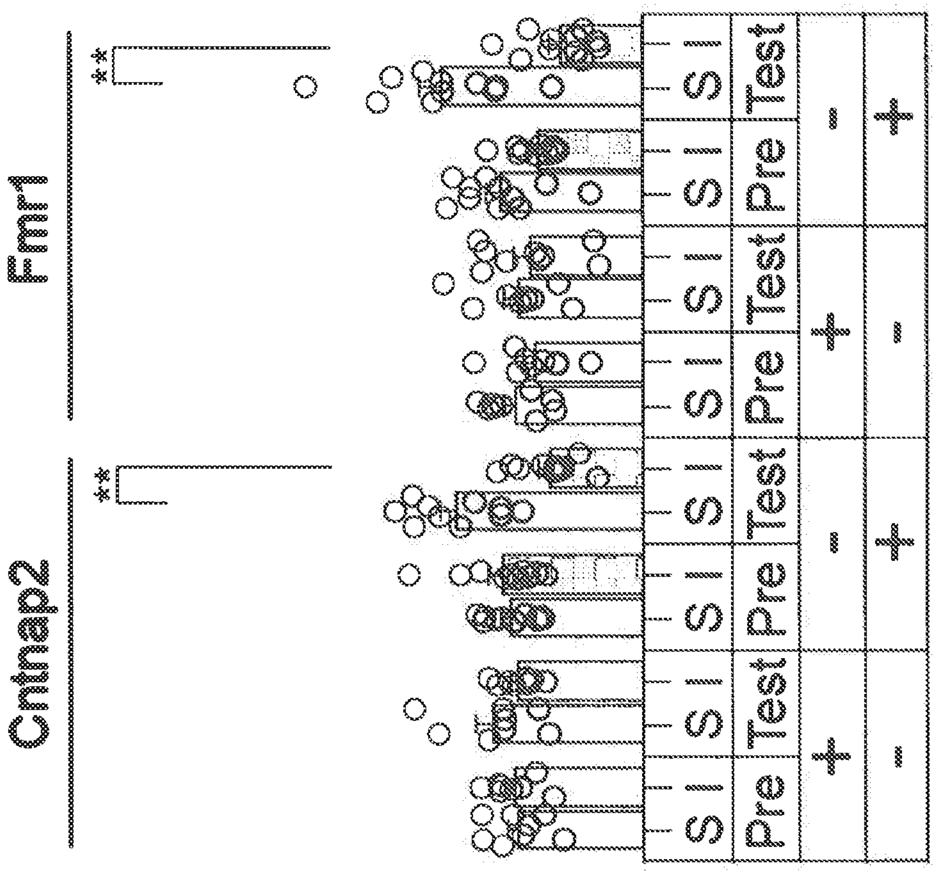
Figure 24F:
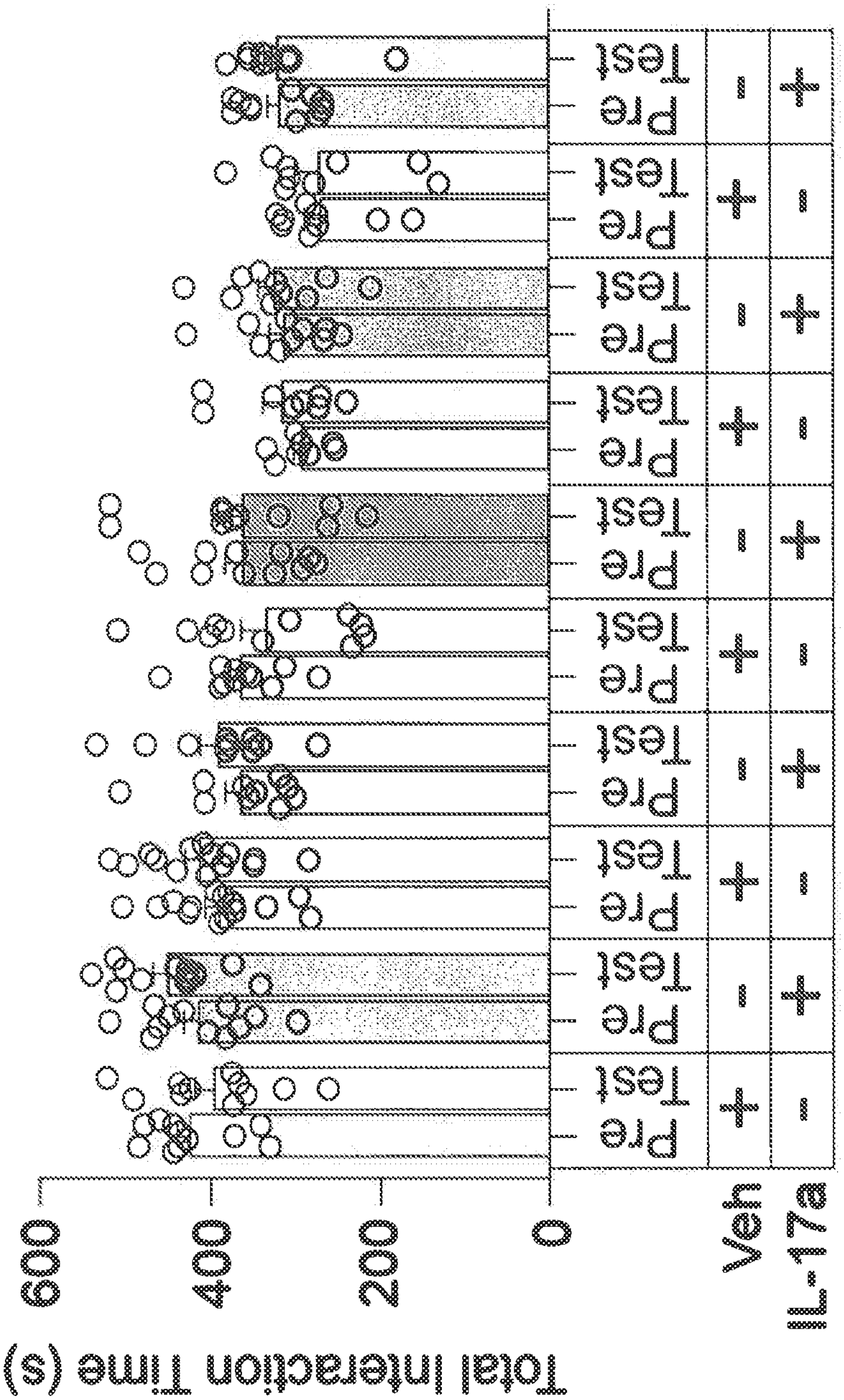
Figure 24G:
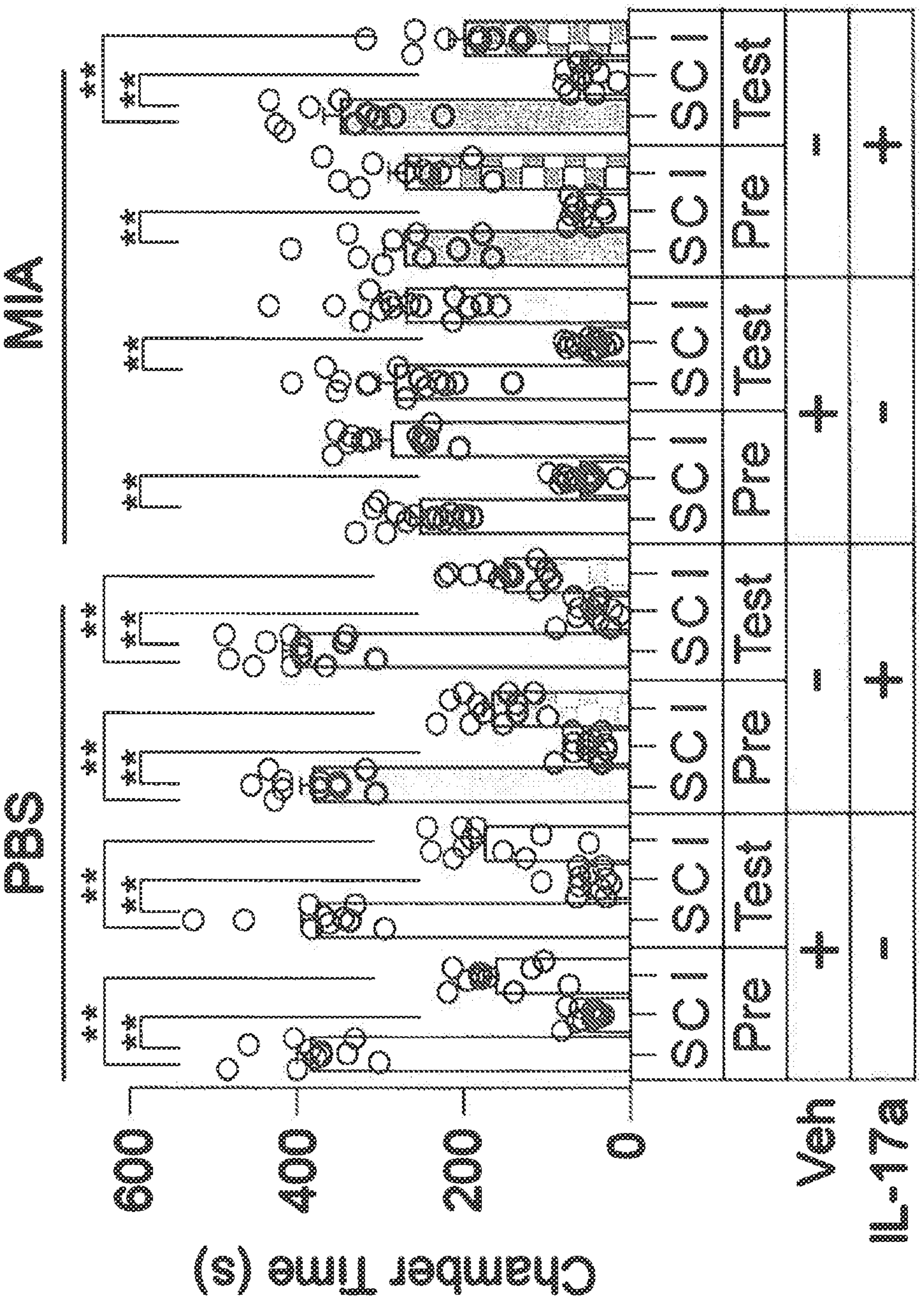
Figure 24G:
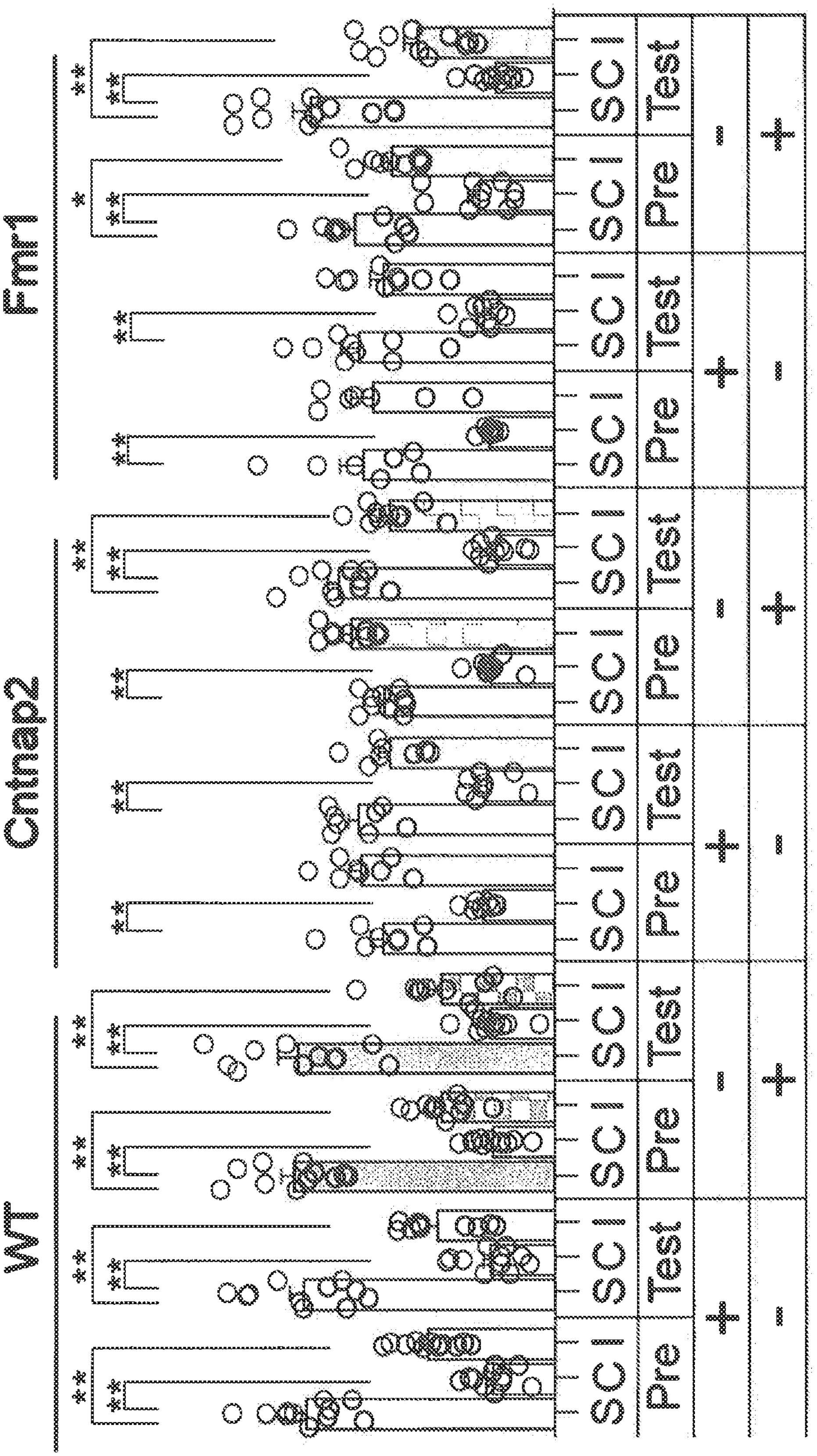
Figure 24H:
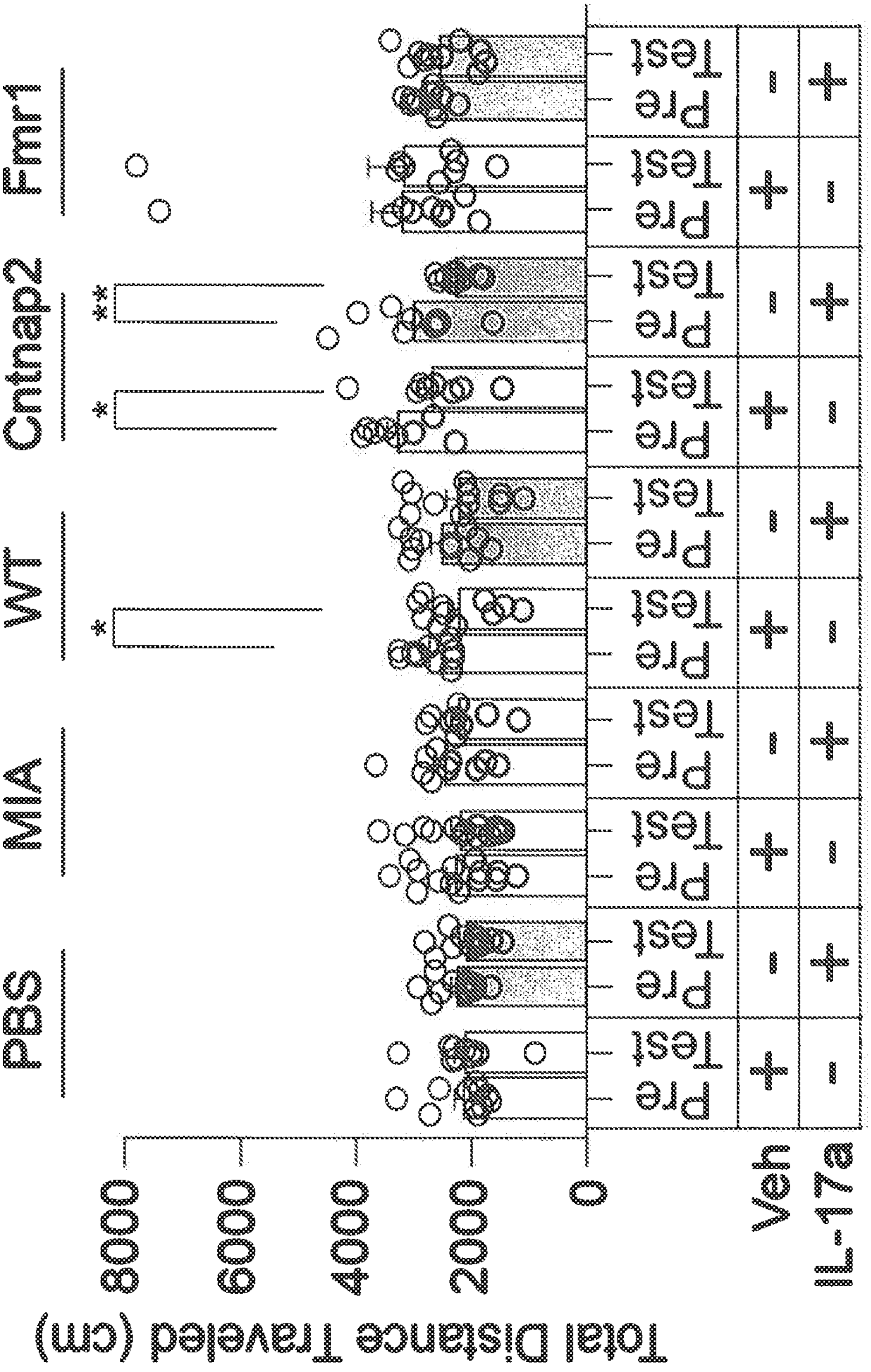

FIG. 24A-24H shows Il17ra expression in the S1DZ of PBS and MIA offspring. Further behavioral analyses of S1DZ IL-17a rescue of sociability in MIA offspring and monogenic mutant mice. FIG. 24A shows representative images of Il17ra expression in the S1DZ of PBS and MIA offspring. Scare bar represents 1 mm. FIG. 24B shows the quantification of Il17ra expression within the S1DZ of MIA offspring according to cortical layer. FIG. 24C shows the quantification of overall Il17ra expression in the S1DZ of PBS and MIA offspring. FIG. 24D-24H demonstrates further behavioral analyses of experiments described in FIG. 23F; Time spent investigating social (S) versus inanimate (I) objects (FIG. 24E), total interaction time (FIG. 24F), time spent in social (S), center (C) or inanimate (I) chamber (FIG. 24G), and distance traveled (FIG. 24H). *p<0.05, p<0.01 as calculated by unpaired two-tailed t test (FIG. 24C), two-way ANOVA with Sidak's (FIG. 24**E) and Dunnett's (FIG. 24G) post-hoc tests, and two-way repeated measures ANOVA with Sidak's post-hoc test (FIG. 24F, 24H). Graphs indicate mean±s.e.m.

Figure 25A:
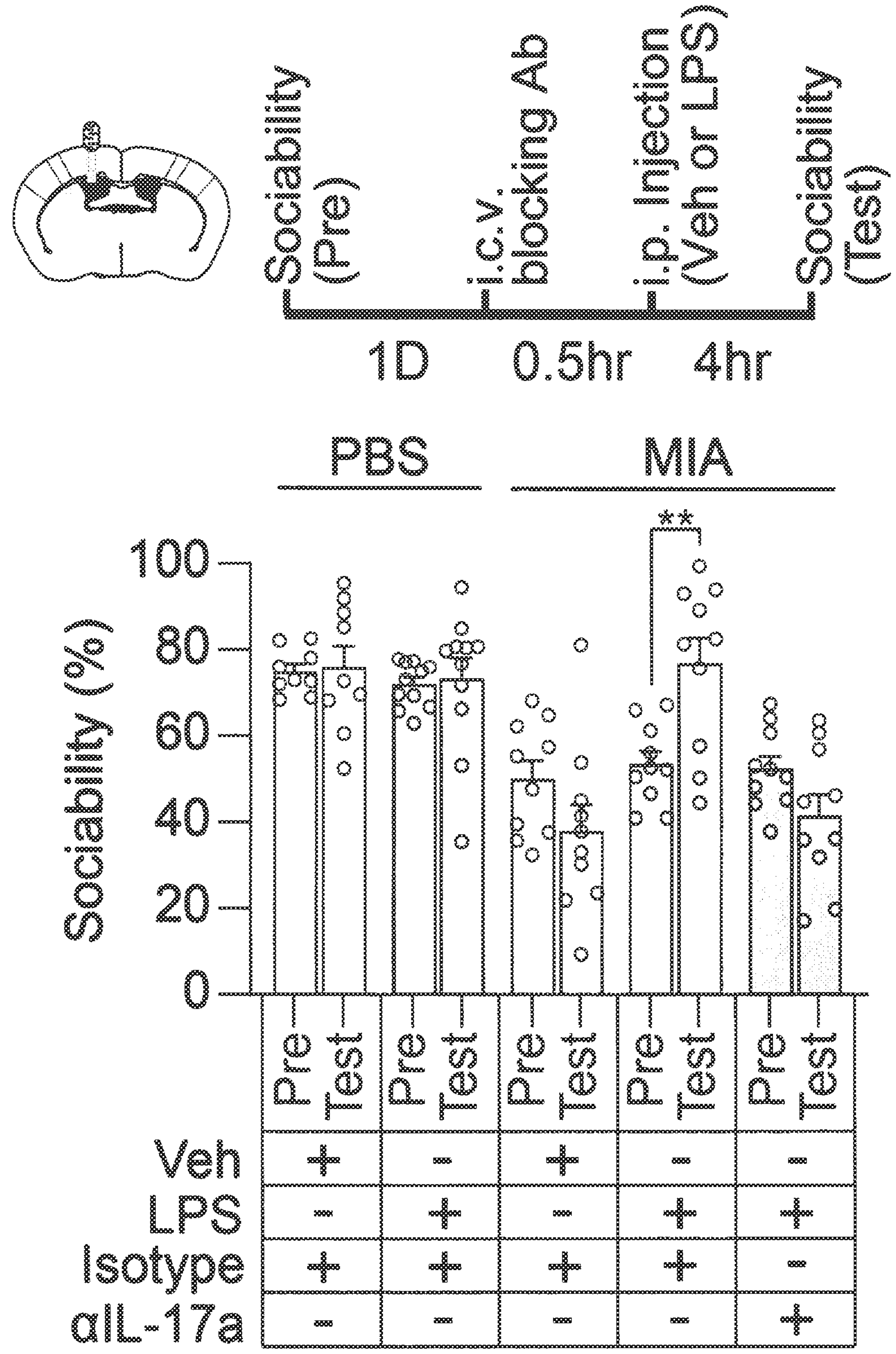
Figure 25B:
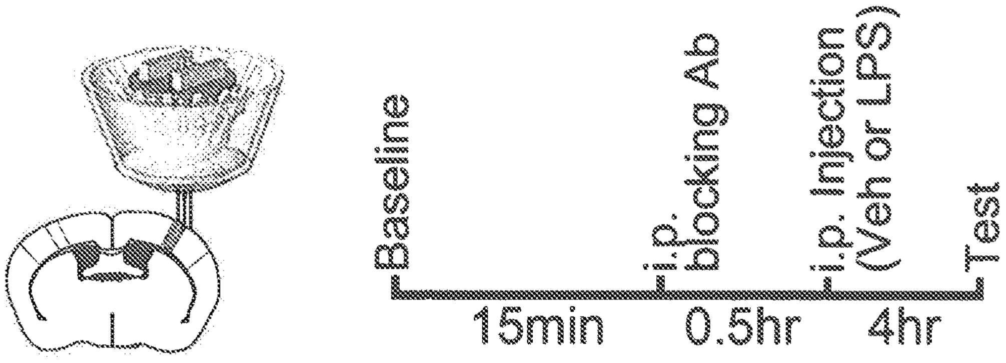
Figure 25C:
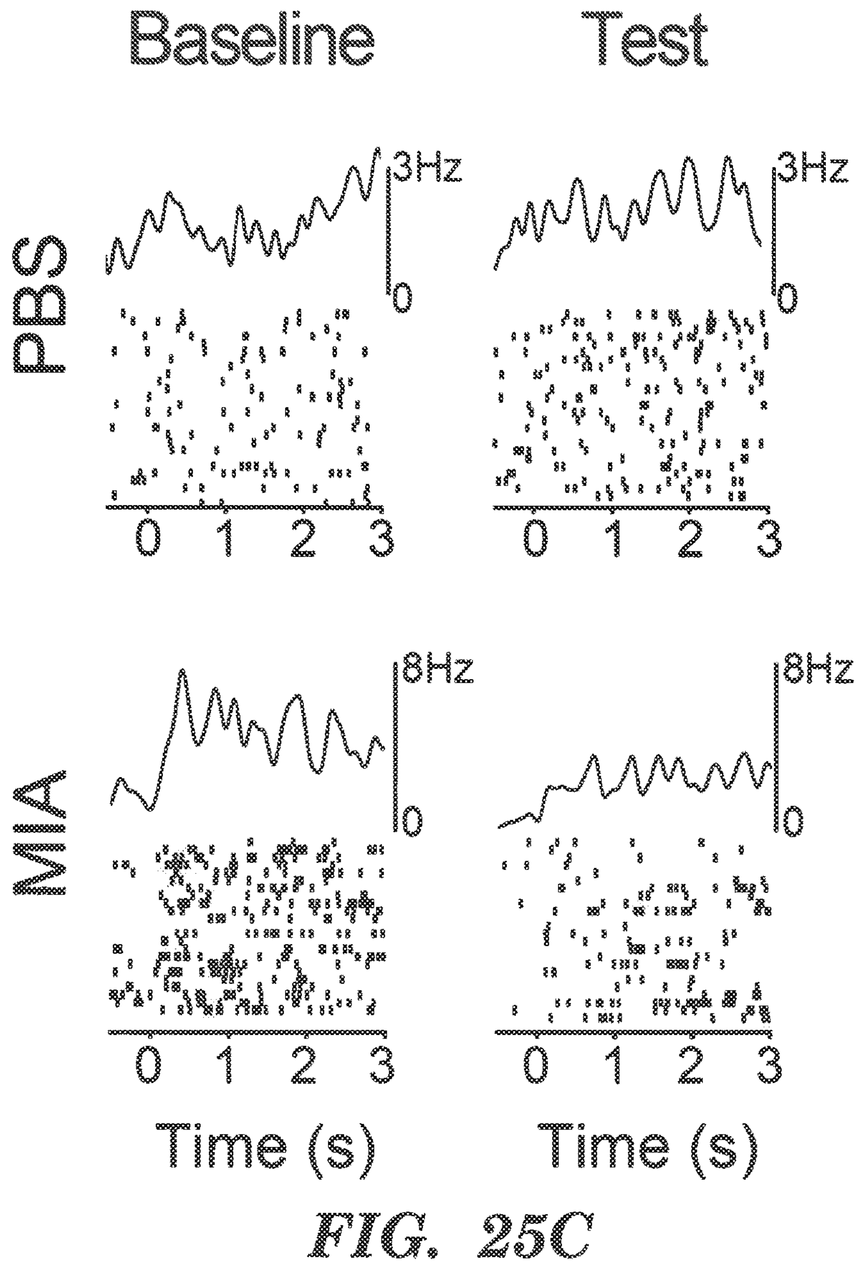
Figure 25D:
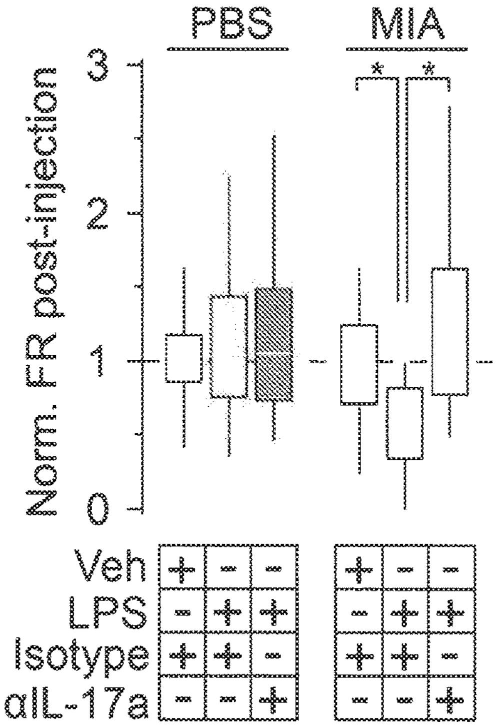
Figure 25E:
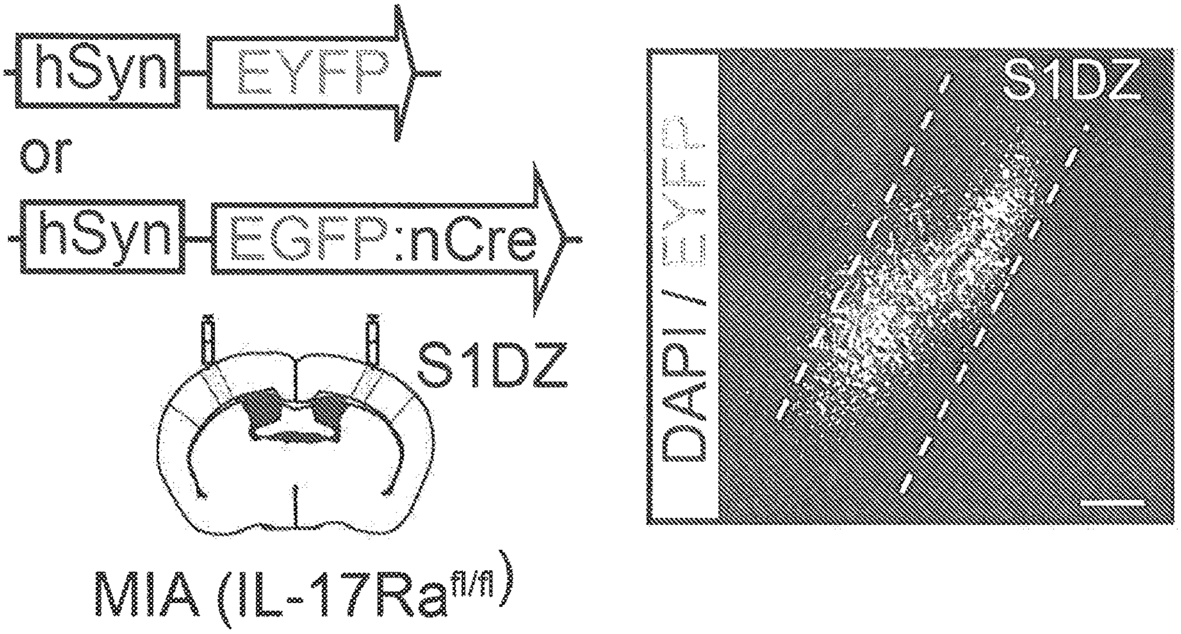
Figure 25F:
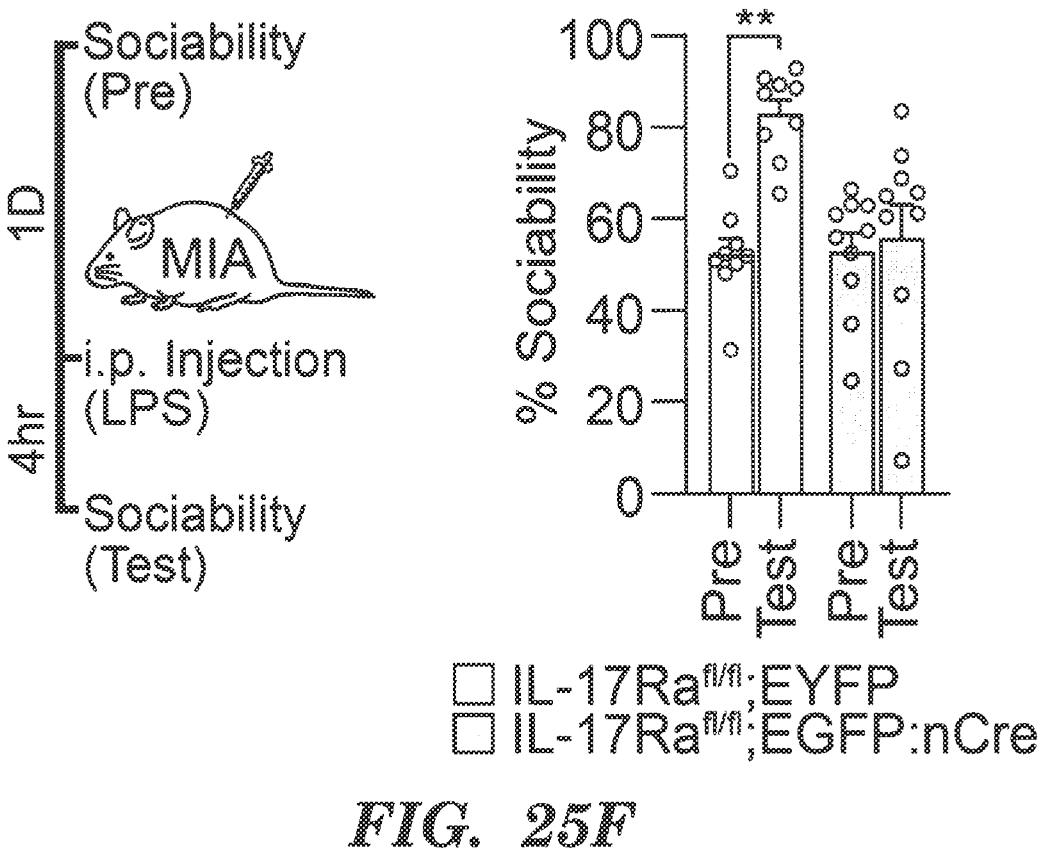

FIG. 25A-25G shows IL-17a is necessary for LPS-induced rescue of sociability deficits and reduction of S1DZ neural activity in MIA offspring. FIG. 25A demonstrates that mice were tested for sociability one day prior to injection (Pre). The following day blocking antibody against IL-17a (aIL-17a) or control isotype antibody was administered i.e.v. 30 minutes prior to Veh or LPS injection. Sociability was assessed four hours following Veh or LPS injection (Test) (PBS-Veh-Isotype n=9, PBS-LPS-Isotype n=11, MIA-Veh-Isotype n=10, MIA-LPS-Isotype n=10, MIA-LPS-aIL-17a n=10; from 7 independent experiments). FIG. 25B-25D shows the firing rate of S1DZ neurons before and four hours after Veh or LPS injection in PBS and MIA offspring pretreated with isotype control antibody or blocking antibody against IL-17a. FIG. 25C shows an example raster plot with firing rate profile before and after LPS treatment from an PBS and MIA mouse pretreated with isotype control antibody. At time 0 mice began walking on the wheel rotating at 7.5 cm/s. Data collected between 1-2 seconds were included in analysis. FIG. 25D demonstrates the normalized firing rate change following treatment represented as box-whisker plots indicating median, interquartile range, and data limits as defined by Tukey (PBS-Veh-Isotype n=65 cells, PBS-LPS-Isotype n=42 cells, PBS-LPS-aIL-17a n=40 cells, MIA-Veh-Isotype n=75 cells, MIA-LPS-Isotype n=48 cells, MIA-LPS-aIL-17a n=43 cells; from 2 MIA offspring and 2 PBS offspring in 12 independent experiments). FIG. 25E shows the lentivirus encoding either EYFP or EGFP fused to nuclear Cre (nCre) was bilaterally injected into the S1DZ of IL-17Ra$^{fl/fl}$ MIA offspring. Scale bar represents 200 μm. FIG. 25F-25G shows that mice were tested for sociability one day prior to injection (Pre). The following day, mice were tested for sociability four hours after LPS injection (Test). (IL-17Ra$^{fl/fl}$,EYFP n=9, IL-17Ra$^{fl/fl}$, EGFP:nCre n=10; from 5 independent experiments). *P<0.05, **P<0.01 calculated by two-way repeated measures ANOVA with Bonferroni's post-hoc test (FIG. 25A, 25F) and two-way ANOVA with Tukey's post-hoc test (FIG. 25D). Graphs indicate mean±s.e.m.

Figure 26A:
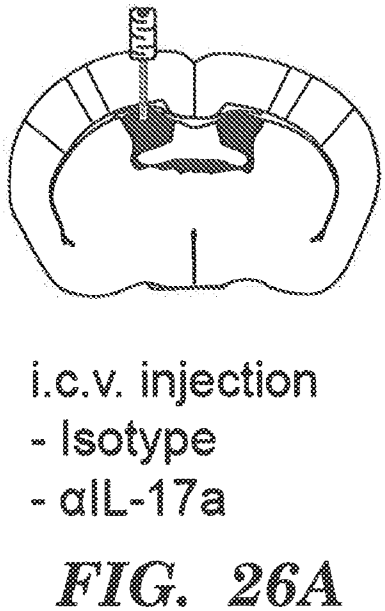
Figure 26B:
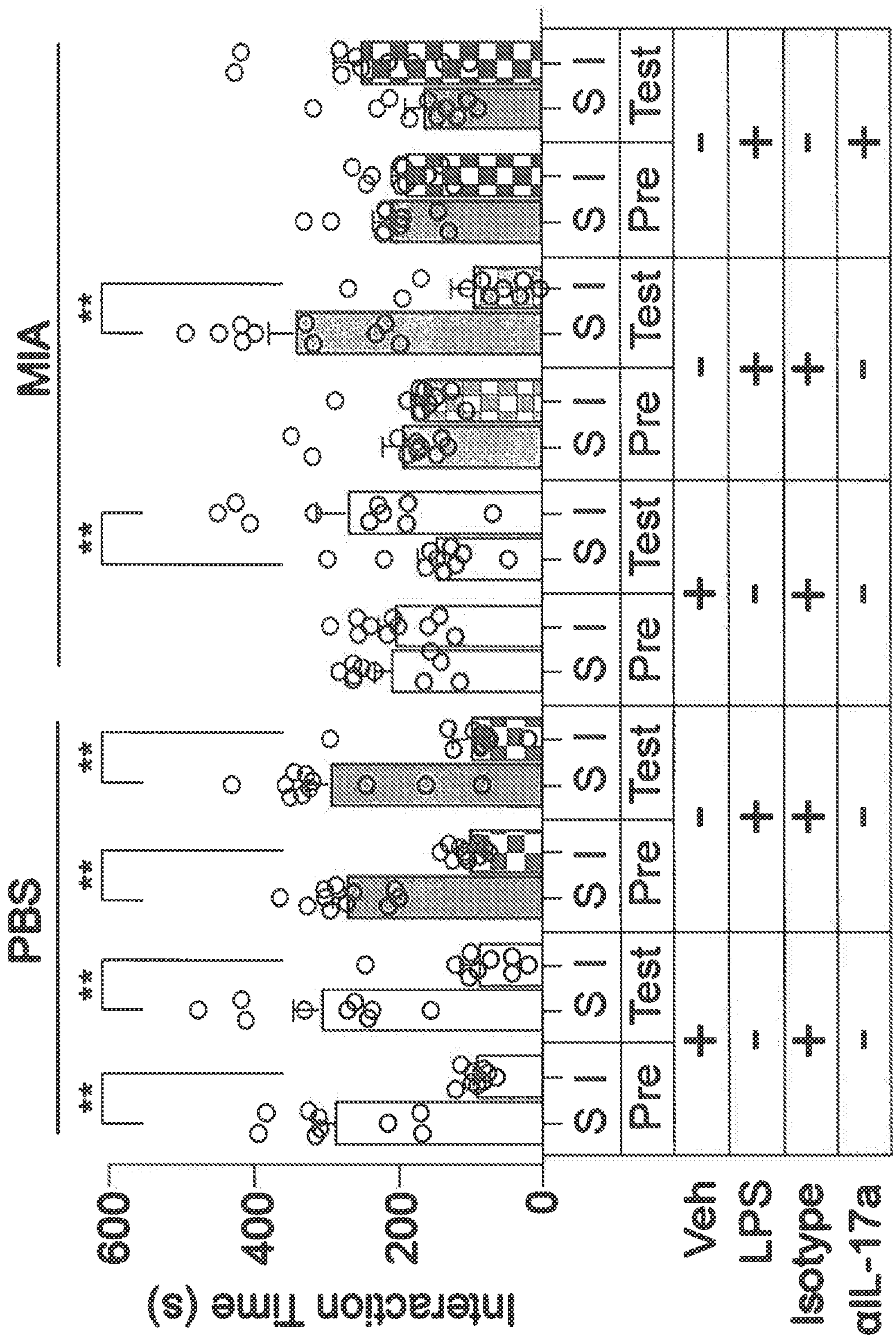
Figure 26C:
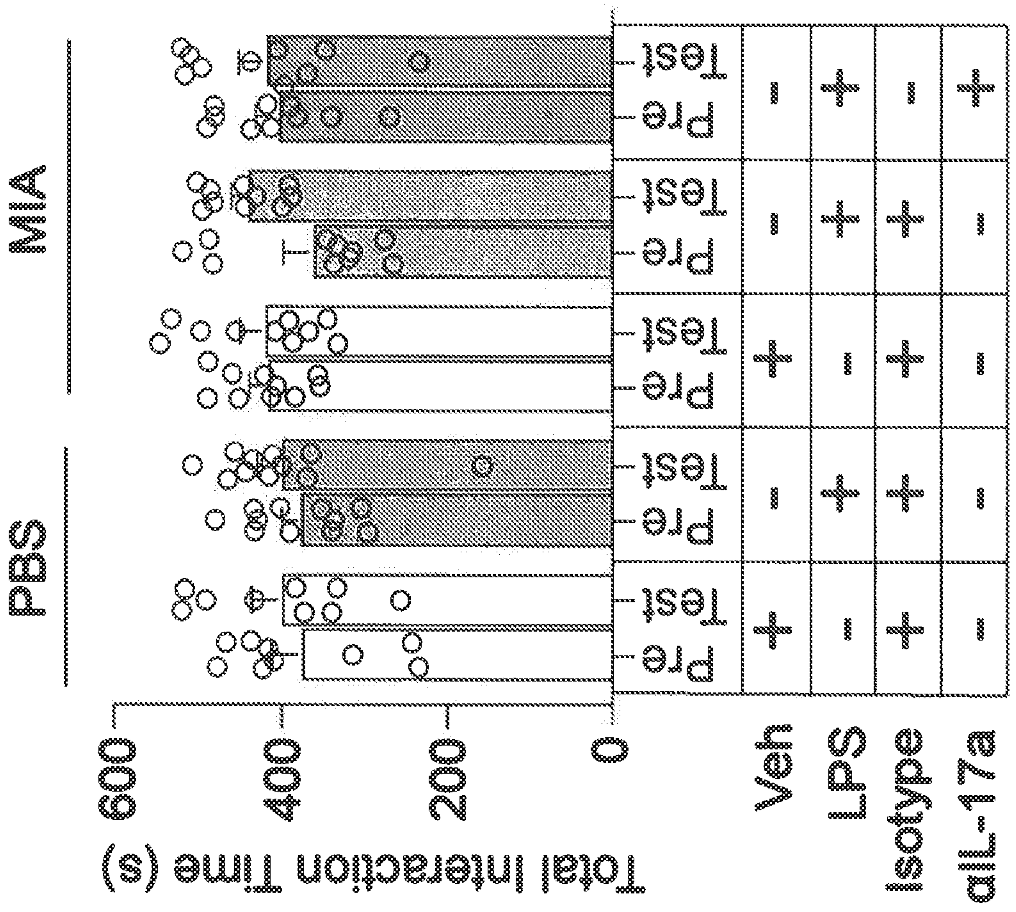
Figure 26D:
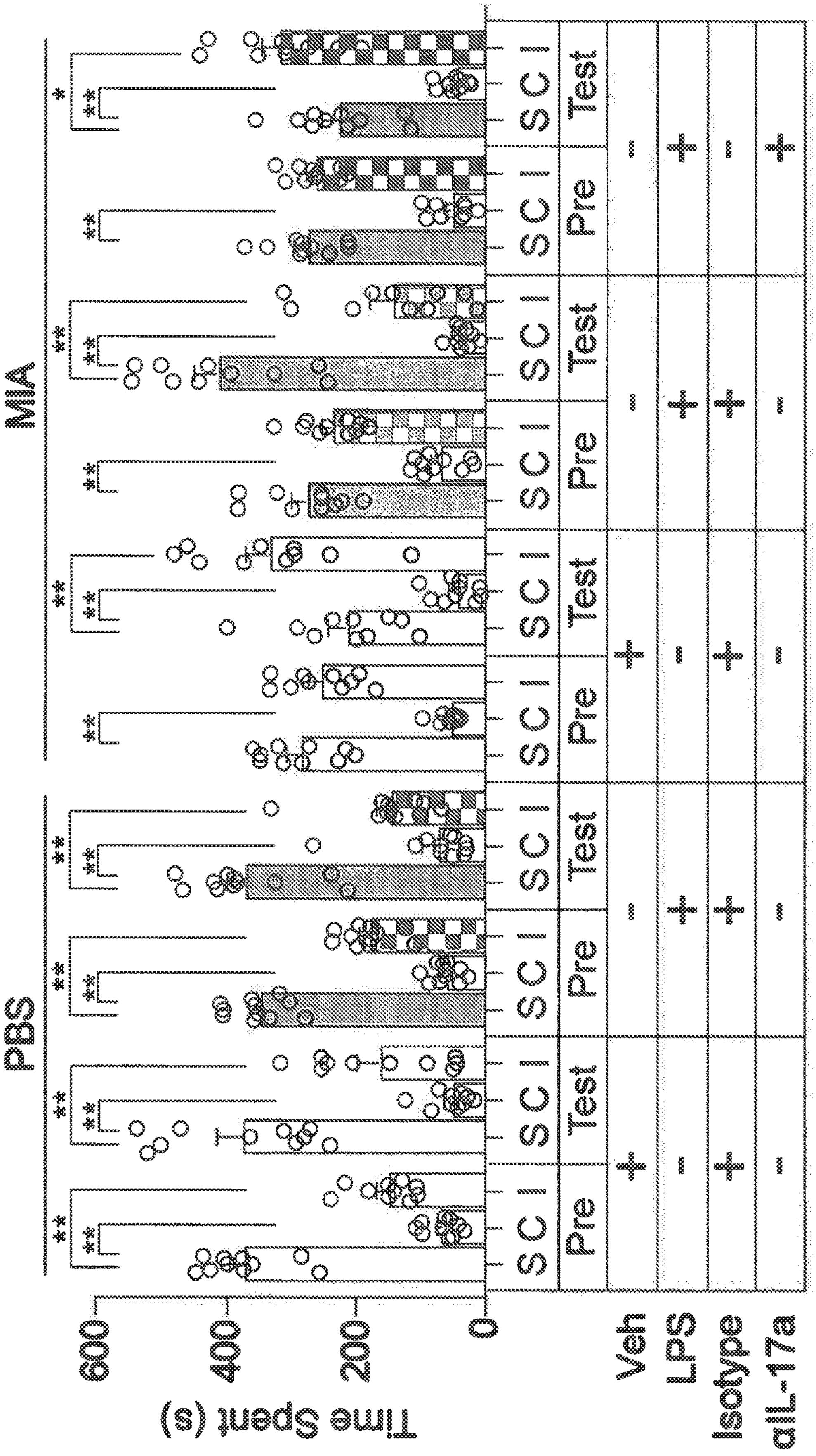
Figure 26E:
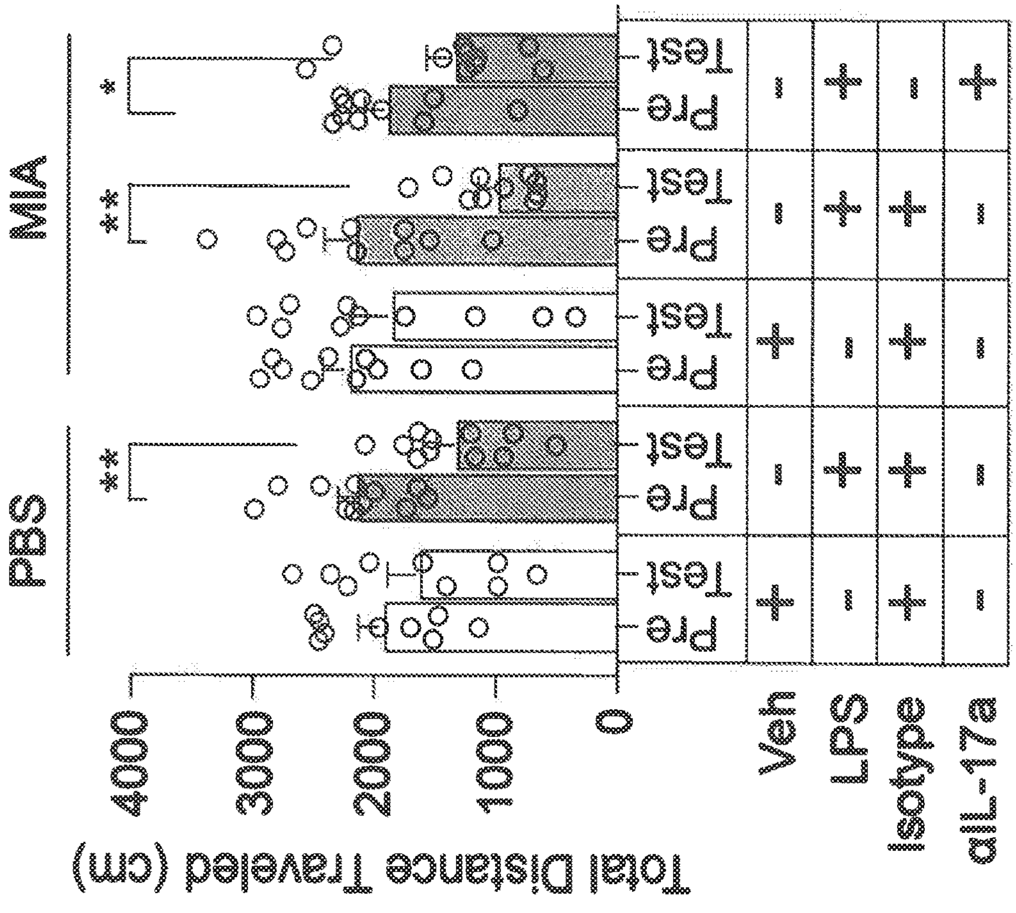
Figure 26F:
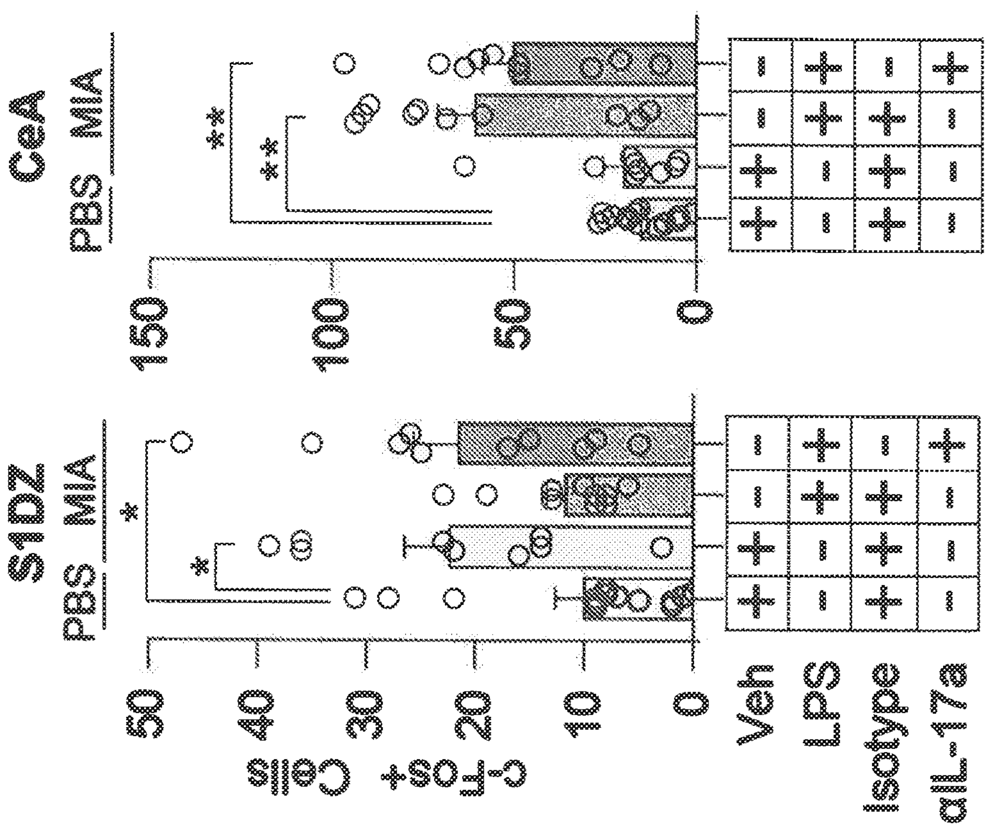

FIG. 26A-26E demonstrates that IL-17a is necessary for LPS-induced behavioral rescue and reduction of c-Fos expression in MIA offspring. FIG. 26A-26E demonstrates further behavioral analyses of experiments described in FIG. 4*a*; Time spent investigating social (S) versus inanimate (I) objects (FIG. 26B), total interaction time (FIG. 26C), time spent in social (S), center (C) or inanimate (I) chamber (FIG. 26D), and distance traveled (FIG. 26E). FIG. 26F shows the quantification of c-Fos expressing cells in the S1DZ and CeA following Veh or LPS injection in MIA offspring pretreated i.e.v. with isotype control antibody or blocking antibody against IL-17a (aIL-17a). *p<0.05, **p<0.01 as calculated by two-way ANOVA with Sidak's (FIG. 26B) and Dunnett's (FIG. 26D) post-hoc tests, two-way repeated measures ANOVA with Sidak's post-hoc tests (FIG. 26C, 26E), and one-way ANOVA with Dunnett's post-hoc test (FIG. 26F). Graphs indicate mean±s.e.m.

Figure 27A:
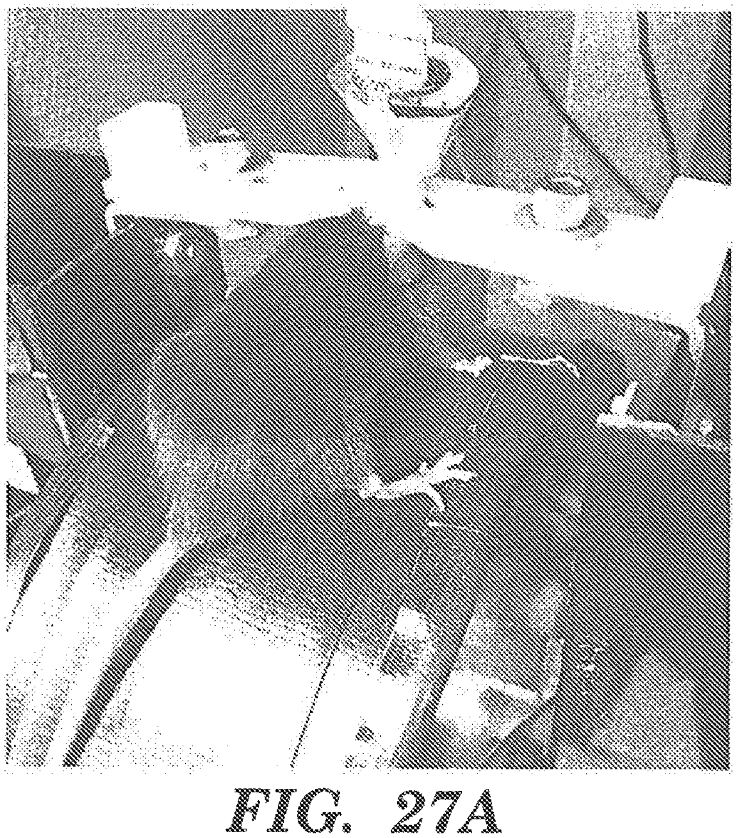
Figure 27B:
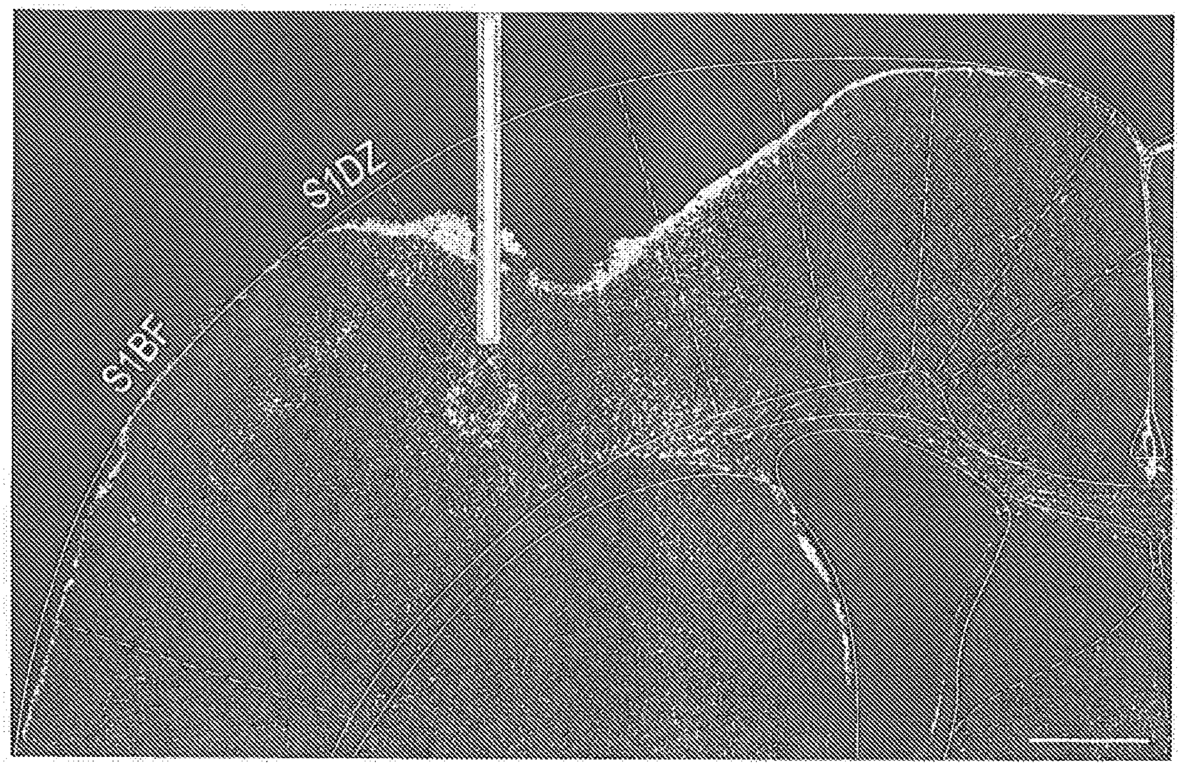
Figure 27C:
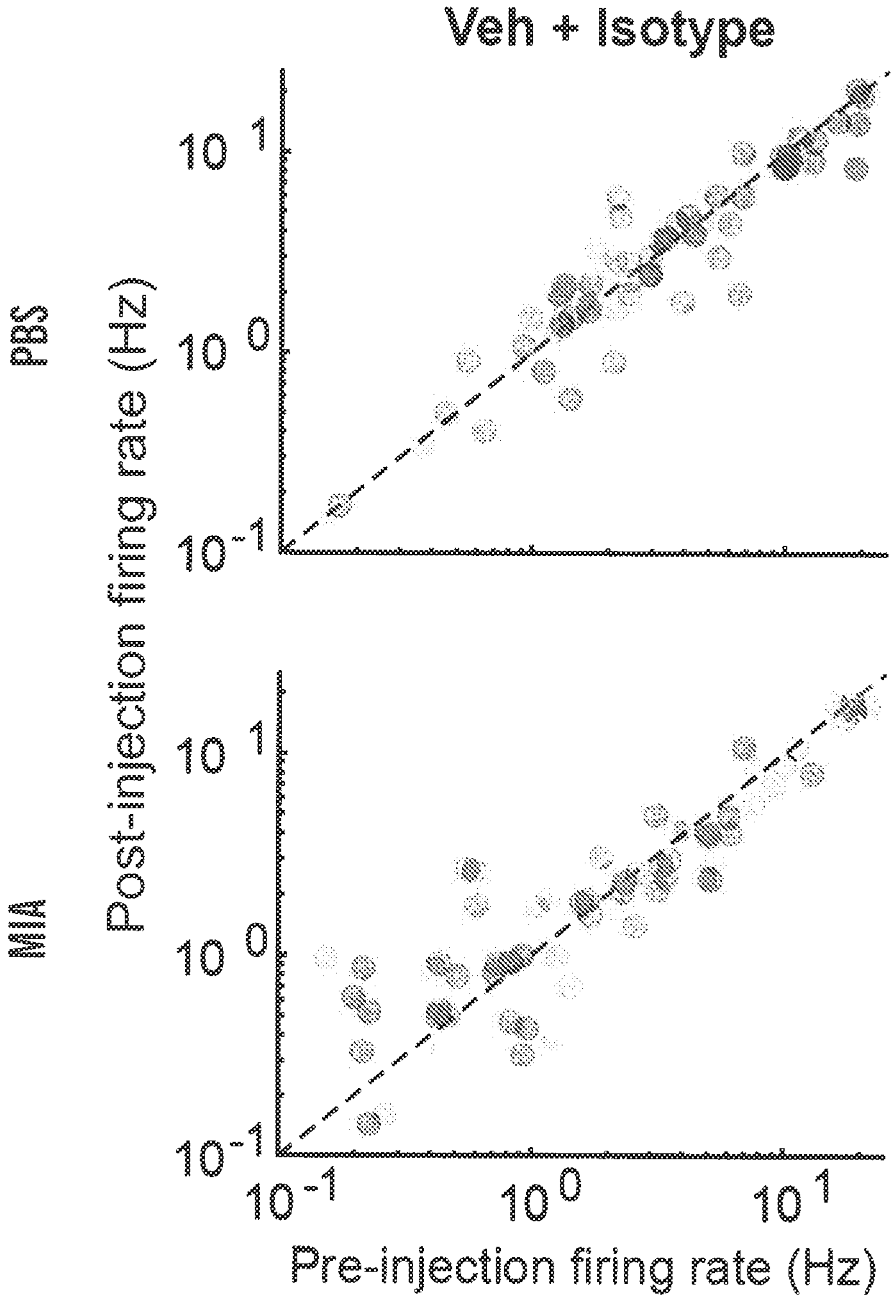
Figure 27C:
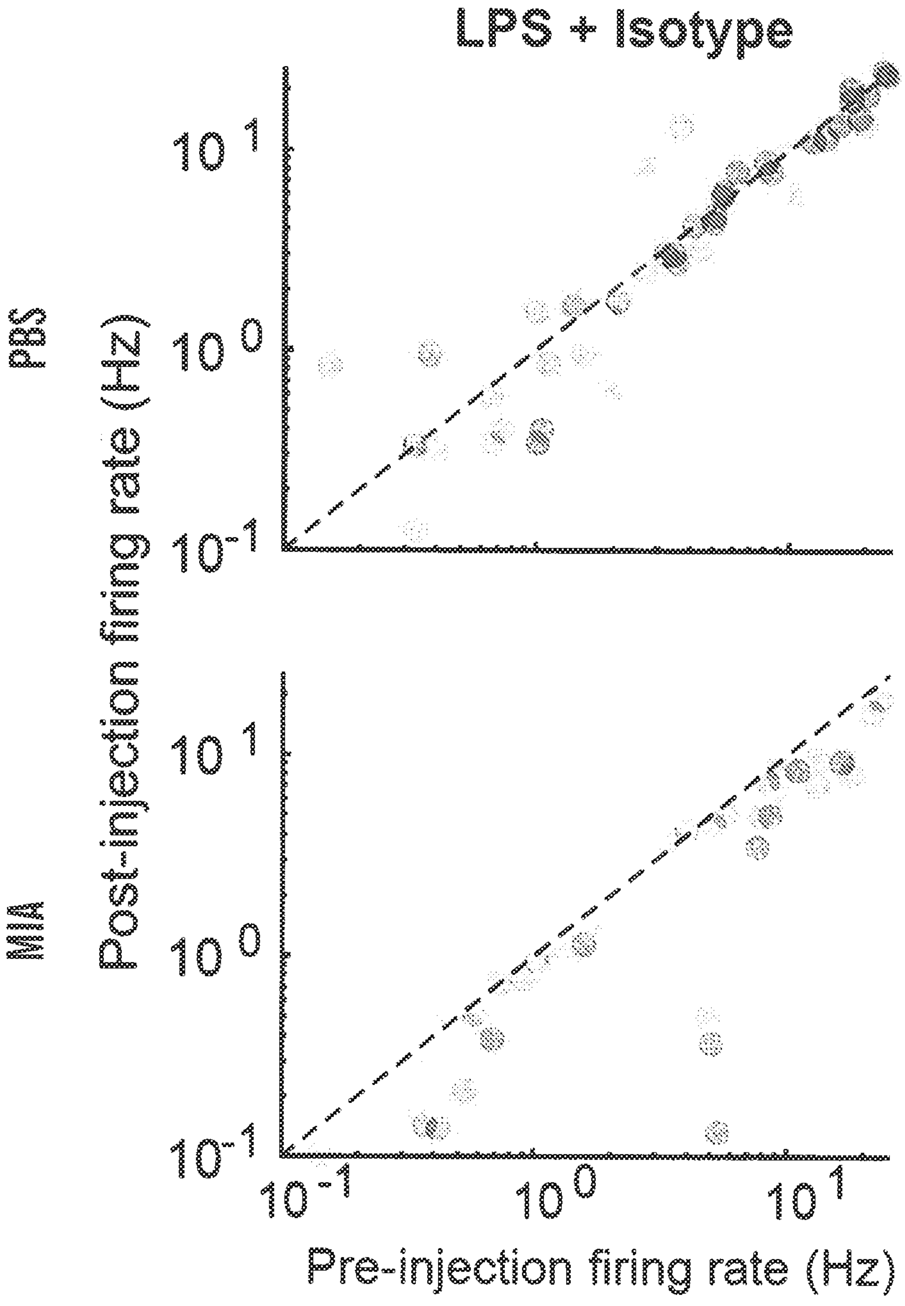
Figure 27C:
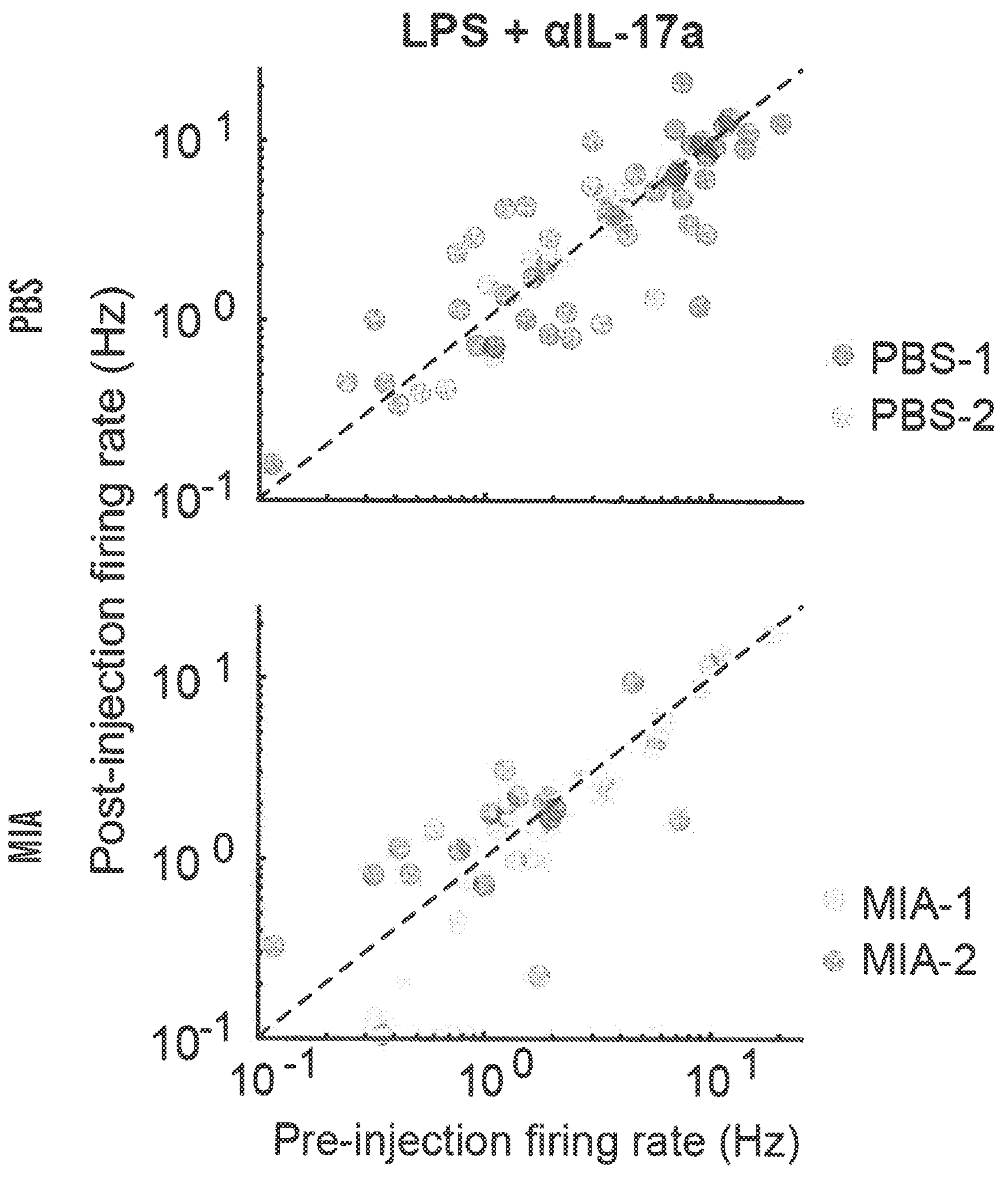
Figure 27D:
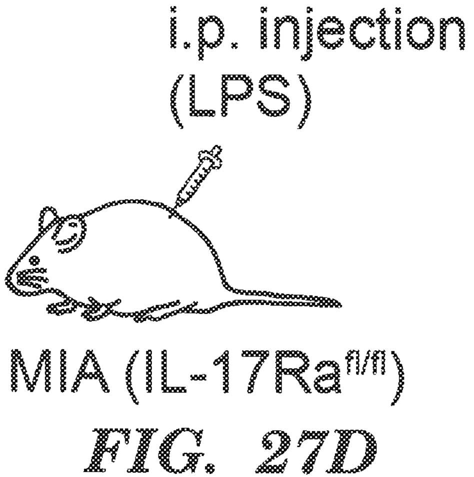
Figure 27E:
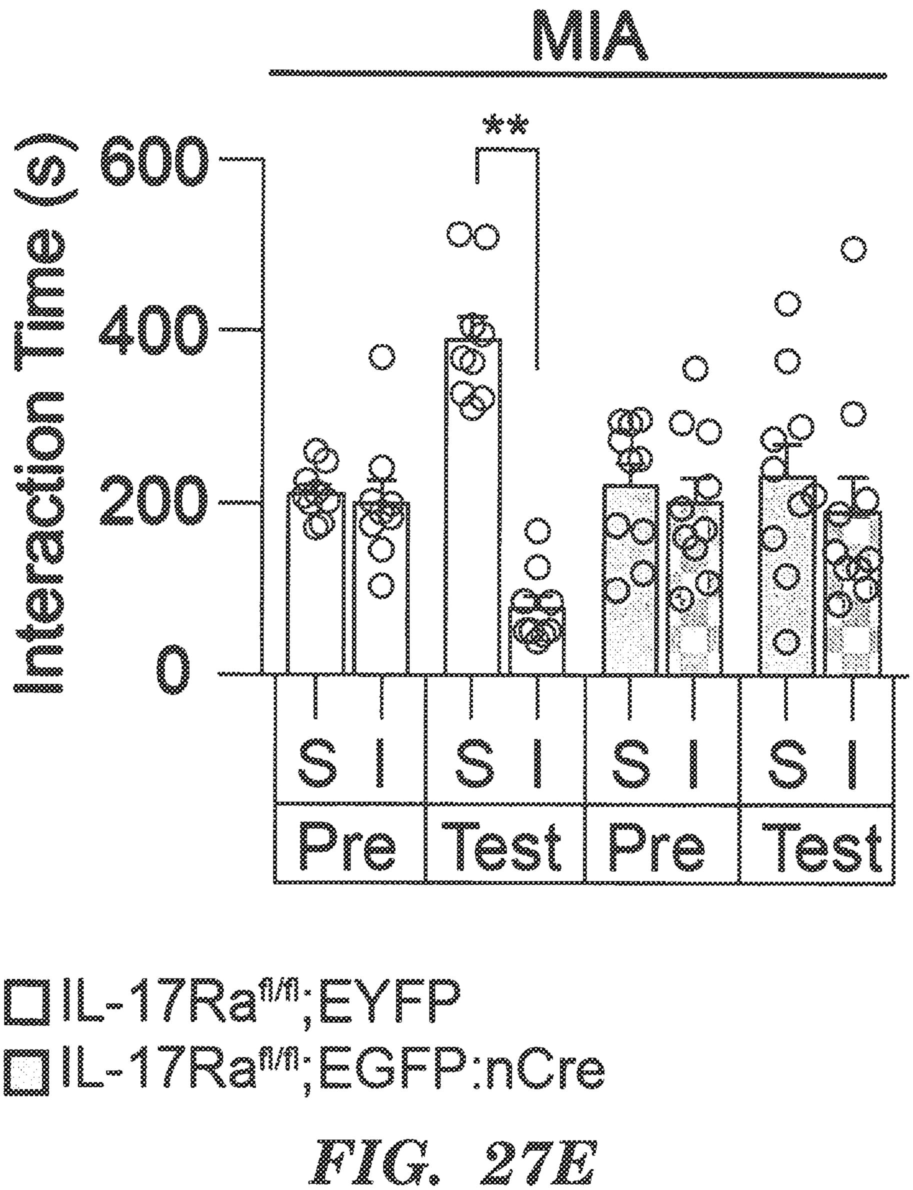
Figure 27F:
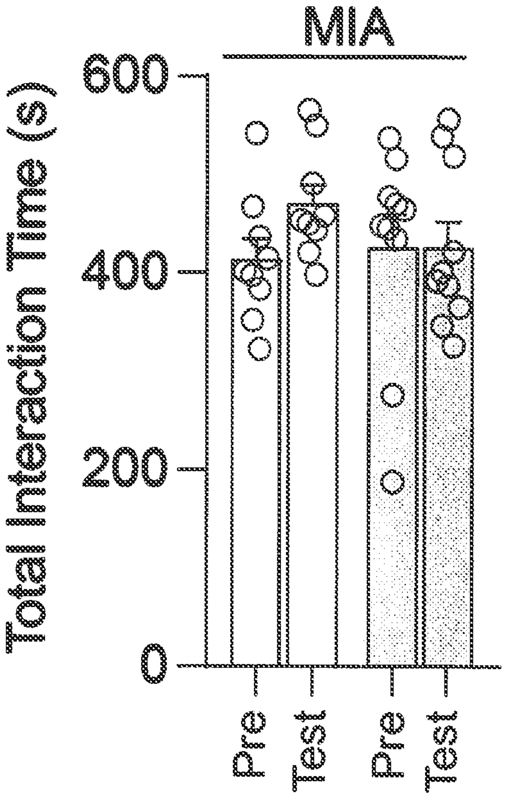
Figure 27G:
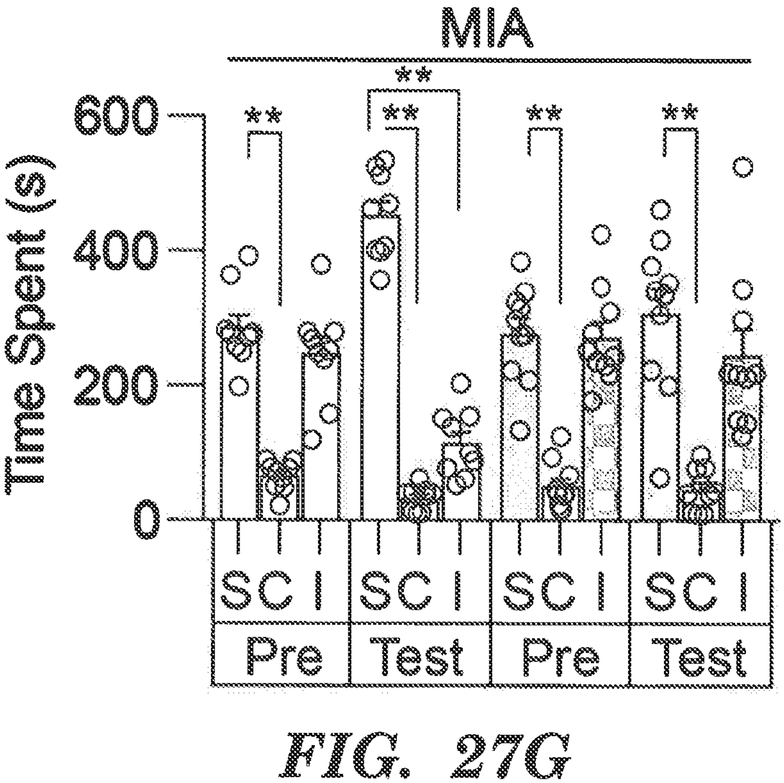
Figure 27J:
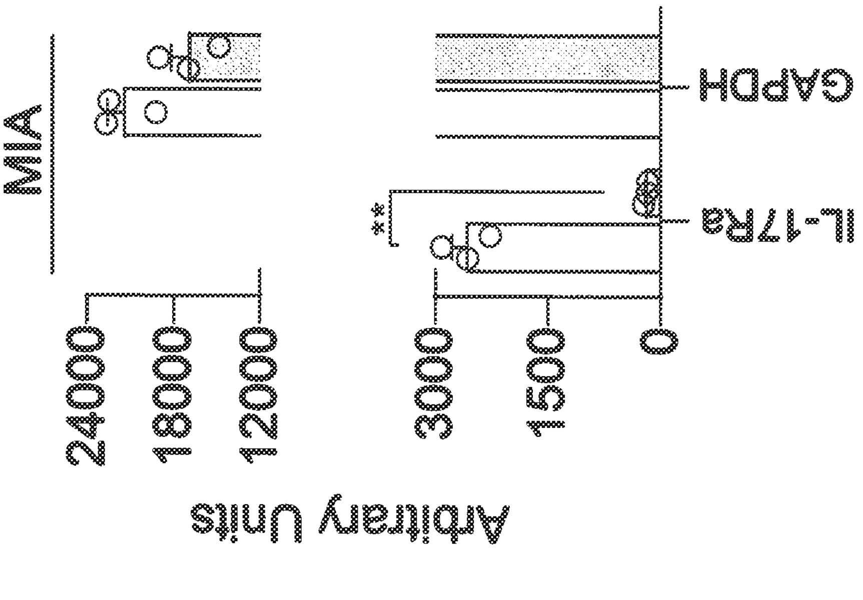
Figure 27I:
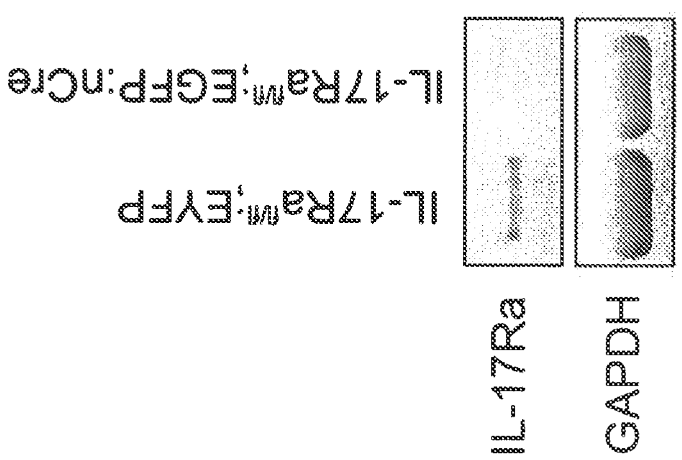
Figure 27H:
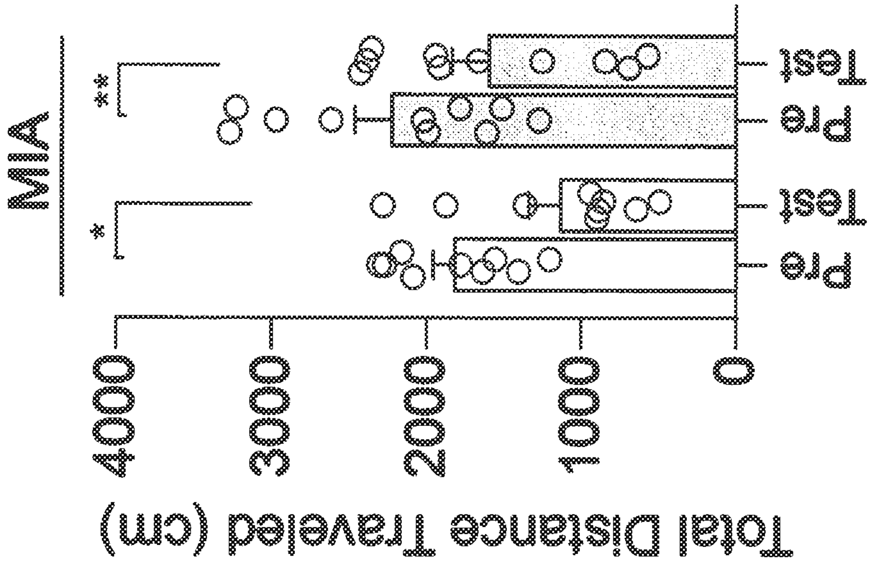

FIG. 27A-27J shows further analyses of the necessity of IL-17a for the LPS-induced reduction of firing rate in the S1DZ, and the necessity of S1DZ IL-17Ra expression for the LPS-induced rescue of sociability deficits in MIA offspring. FIG. 27A-27C demonstrates further analyses for experiments described in FIG. 25D. FIG. 27A shows an example of a head-fixed mouse on the running wheel used during single-unit recording. FIG. 27B shows a representative image of a tetrode placement in the S1DZ. Scale bar represents 500 μm. FIG. 27C shows the firing rate for individual cells before and 4 hrs after vehicle or LPS injection in PBS and MIA offspring pretreated with isotype control antibody or blocking antibody against IL-17a (aIL-17a). FIG. 27D-27H demonstrates further analyses for experiments described in FIG. 4*e-f*. Time spent investigating social (S) versus inanimate (I) objects (FIG. 27E), total interaction time (FIG. 27F), time spent in social (S), center (C) or inanimate (I) chambers (FIG. 27G), and distance traveled (FIG. 27H). FIG. 27I-27J shows representative images (FIG. 27I) and corresponding quantification (FIG. 27J) of Il17ra and Gapdh amplicon following PCR using cDNA derived from cells isolated from the cortical region centered on S1DZ of IL-17Ra$^{fl/fl}$, EYFP and IL-17Ra$^{fl/fl}$, EGFP:nCre mice (n=3 for all groups; from 1 experiment). *p<0.05, **p<0.01 as calculated by two-way ANOVA with Sidak's post-hoc test (FIG. 27E, 27G), two-way repeated measures ANOVA with Sidak's post-hoc tests, (FIG. 27F, 27H) and unpaired two-tailed t test (FIG. 27J). Graphs indicate mean±s.e.m.

Figure 28:
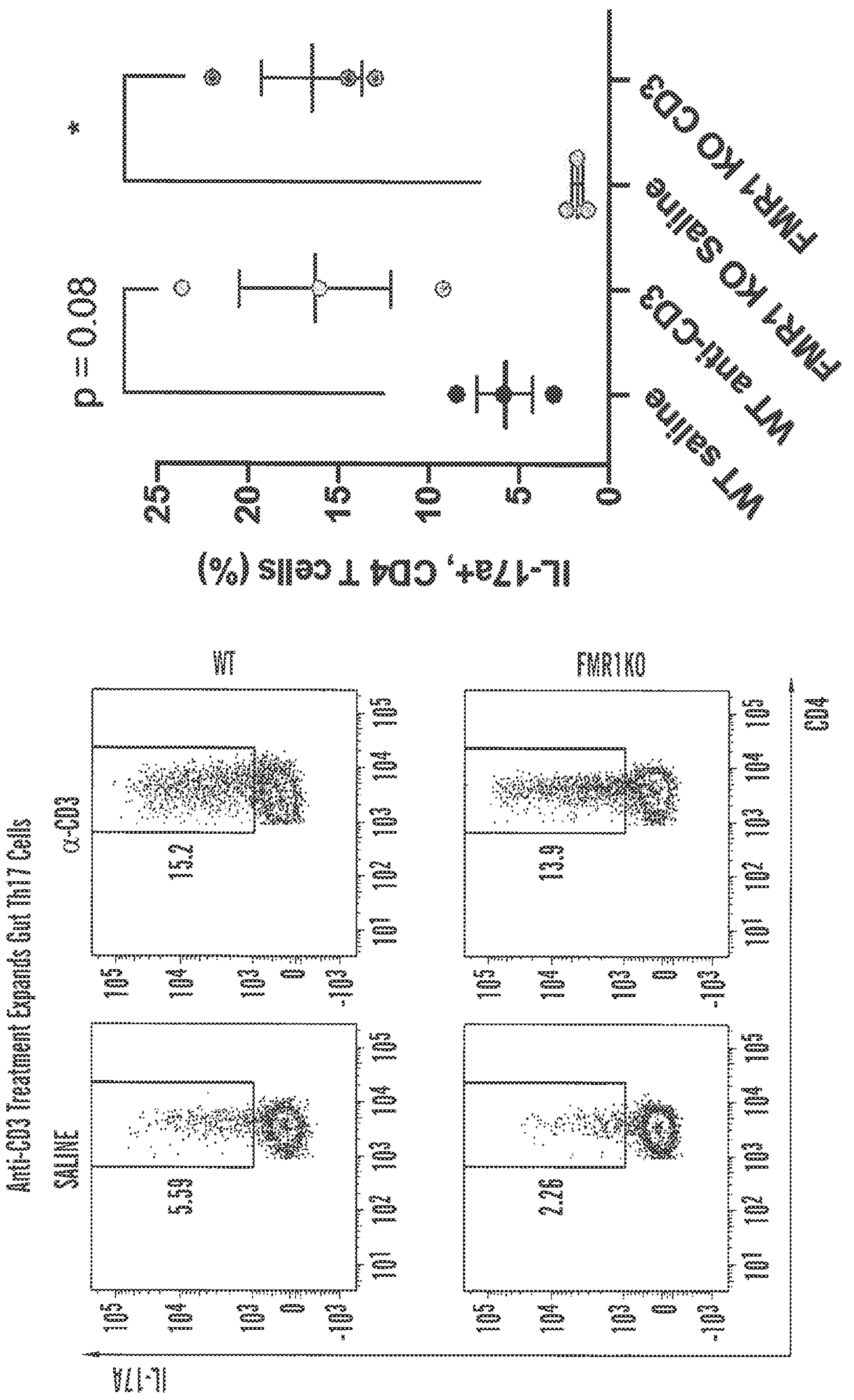

FIG. 28 shows that anti-CD3 treatment expands gut Th17 cells in WT and FMR1 KOs.

Figure 29:
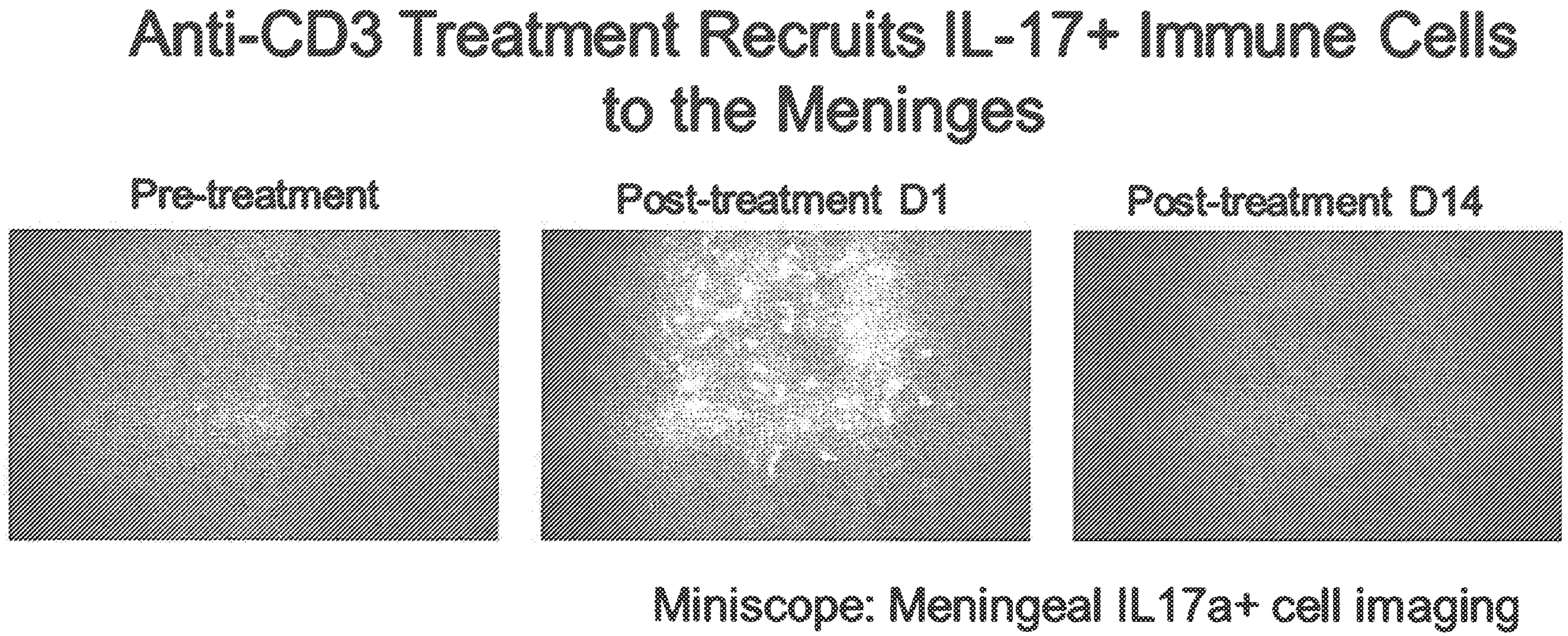

FIG. 29 demonstrates that anti-CD3 treatment recruits IL-17+ immune cells to the meninges.

Figure 30:
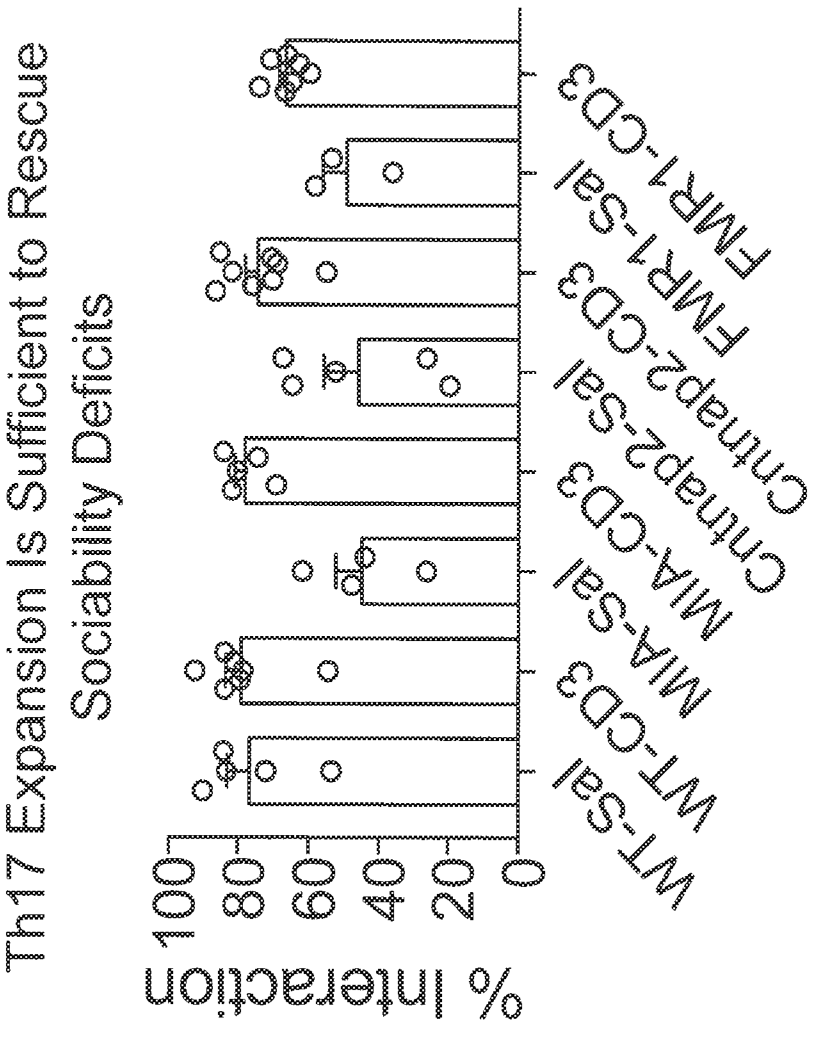

FIG. 30 shows that Th17 expansion is sufficient to rescue sociability deficits.

DETAILED DESCRIPTION

Although fever has been correlated with the behavioral improvements seen in human patients with neurodevelopmental disorders (e.g., autism spectrum disorders), it is not the driver of the rescue observed in MIA offspring upon LPS administration. The methods provided herein are based, in part, on the discovery that a systemic upregulation of proinflammatory cytokines IL-17a and IFN-γ are important factors underlying the rescue of neurodevelopmental disorders.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006;

Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

As used herein, the terms "treat," "treatment," "treating," or "amelioration" refer to therapeutic treatments, wherein the object is to reverse, alleviate, ameliorate, inhibit, slow down or stop the progression or severity of a condition associated with a neurodevelopmental disorder, e.g. autism spectrum disorder (ASD). The term "treating" includes reducing or alleviating at least one adverse effect or symptom of neurodevelopmental disorder, for example, lack of socialability, learning delays, repetitive movements, anxiety, sensitivity to sound, etc. Treatment is generally "effective" if one or more symptoms or clinical markers are reduced. Alternatively, treatment is "effective" if the progression of a disease or disorder is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein "preventing" or "prevention" refers to any methodology where the disease state does not occur due to the actions of the methodology (such as, for example, administration of an agent as described herein). In one aspect, it is understood that prevention can also mean that the disease is not established to the extent that occurs in untreated controls. Accordingly, prevention of a disease encompasses a reduction in the likelihood that a subject can develop the disease, relative to an untreated subject (e.g. a subject who is not treated with the methods or compositions described herein).

As used herein, the terms "administering," and "injecting" are used interchangeably in the context of the placement of an agent (e.g. a small molecule) described herein, into a subject, by a method or route which results in at least partial localization of the agent at a desired site, such as the gastrointestinal tract or a region thereof, such that a desired effect(s) is produced (e.g., increase IL-17a level or activity). The agent described herein can be administered by any appropriate route which results in delivery to a desired location in the subject. The half-life of the agent after administration to a subject can be as short as a few minutes, hours, or days, e.g., twenty-four hours, to a few days, to as long as several years, i.e., long-term. In some embodiments of any of the aspects, the term "administering" refers to the administration of a pharmaceutical composition comprising one or more agents. The administering can be done by direct injection (e.g., directly administered to a target cell or tissue), subcutaneous injection, muscular injection, oral, or nasal delivery to the subject in need thereof. Administering can be local or systemic.

The terms "patient", "subject" and "individual" are used interchangeably herein, and refer to an animal, particularly a human, to whom treatment, including prophylactic treatment is provided. The term "subject" as used herein refers to human and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment of any of the aspects, the subject is human. In another embodiment, of any of the aspects, the subject is an experimental animal or animal substitute as a disease model. In another embodiment, of any of the aspects, the subject is a domesticated animal including companion animals (e.g., dogs, cats, rats, guinea pigs, hamsters etc.). A subject can have previously received a treatment for a neurodevelopmental disease, or has never received treatment for a neurodevelopmental disease. A subject can have previously been diagnosed with having a neurodevelopmental disorder, or has never been diagnosed with a neurodevelopmental disorder.

The terms "decrease", "reduced", "reduction", or "inhibit" are all used herein to mean a decrease or lessening of a property, level, or other parameter by a statistically significant amount. In some embodiments, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased," "increase," "increases," or "enhance" or "activate" are all used herein to generally mean an increase of a property, level, or other parameter by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level. For example, increasing activity can refer to activating IL-17a or increasing levels of IL-17a in the brain directly or indirectly.

As used herein, a "reference level" refers to a normal, otherwise unaffected cell population or tissue (e.g., a biological sample obtained from a healthy subject, or a biological sample obtained from the subject at a prior time point, e.g., a biological sample obtained from a patient prior to being diagnosed with a neurodevelopmental disorder, or a biological sample that has not been contacted with an agent or composition disclosed herein).

As used herein, an "appropriate control" refers to an untreated, otherwise identical cell or population (e.g., a biological sample that was not contacted by an agent or composition described herein, or not contacted in the same manner, e.g., for a different duration, as compared to a non-control cell).

The term "pharmaceutically acceptable" can refer to agents and compositions which can be administered to a subject (e.g., a mammal or a human) without undue toxicity.

As used herein, the term "neurodevelopmental disease" and "neurodevelopmental disorder" are used interchangeably to refer to any disease or disorder that affects the brain of a subject. The neurodevelopmental disorder can cause at least one symptom of the disease or disorder. These symptoms can include but are not limited to, lack of socialability, learning delays, repetitive movements, anxiety, sensitivity to sound, memory loss, or any other symptom associated with a neurodevelopmental disease in a subject. Non-limiting examples of neurodevelopmental disorders include autism spectrum disorder (ASD), Asperger's syndrome, learning disabilities, anxiety disorders, schizophrenia, attention deficit hyperactivity disorder (ADHD), sensory processing disorder, epilepsy, fragile X syndrome, sleep disorder, obsessive compulsive disorder (OCD), and non-verbal learning disorder.

As used herein, the term "inflammation" or "inflamed" refers to activation or recruitment of the immune system or immune cells (e.g., T cells, B cells, macrophages). A tissue that has inflammation can become reddened, white, swollen, hot, painful, exhibit a loss of function, or have a film or mucus. Immune cells may secrete cytokines and interferons to signal other immune cells and promote phagocytosis of the microorganism and infected cells. Methods of identifying inflammation are well known in the art. Inflammation typically occurs following injury or infection by a microorganism. Inflammation can result in the release of cytokines by T cells. These cytokines are known to have various effects on the immune response and target tissues (e.g. the brain).

As used herein, the term "cytokine" refers to a small protein (~5-20 kDa) that acts through a target cytokine receptor to modulate the immune response, cell growth, or other cellular functions.

As used herein, the term "neural activity" refers to any functional property of neuronal cells. Examples of neural activity include neurotransmitter release, electrophysiological function (e.g., action potential generation or field potentials), calcium signaling, expression of neuronal markers (e.g., c-Fos), modulation signals from functional Magnetic Resonance Imaging (fMRI), magnetoencephalography (MEG) and/or electroencephalography (EEG). Methods of measuring neural activity are well known in the art.

Figure 9A:
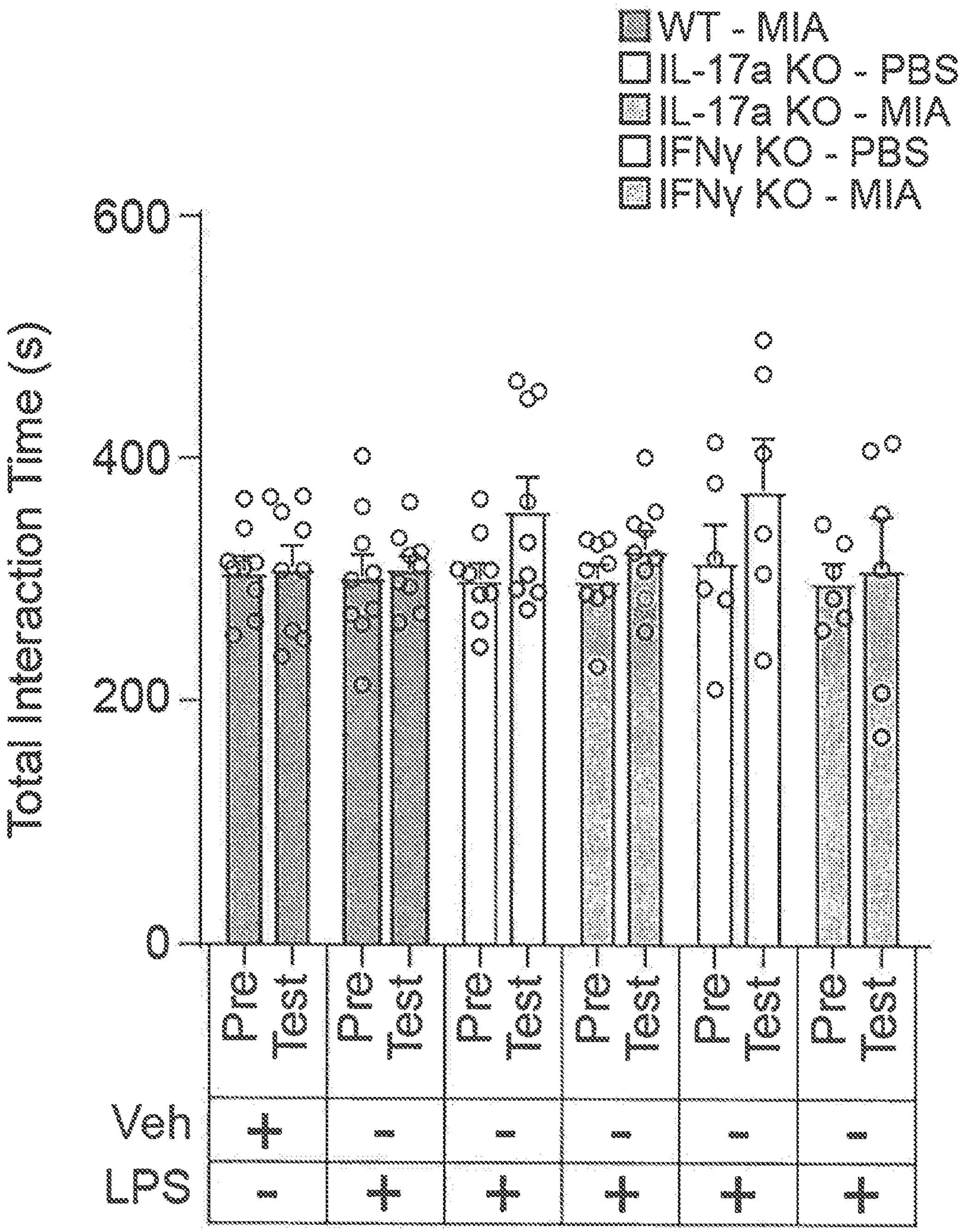
FIGS. 9A-9B shows total interaction time (FIG. 9A) and total distance traveled (FIG. 9B) in WT, IFNγ KO, and IL-17a KO offspring as described in FIG. 2E. (WT-MIA-Veh n=9, WT-MIA-LPS n=9, IL-17a KO-PBS-LPS n=6, IL-17a KO-MIA-LPS n=6, IFNγ KO-PBS-LPS n=9, IFNγ KO-MIA-LPS n=9; from 3 independent experiments).
Figure 9B:
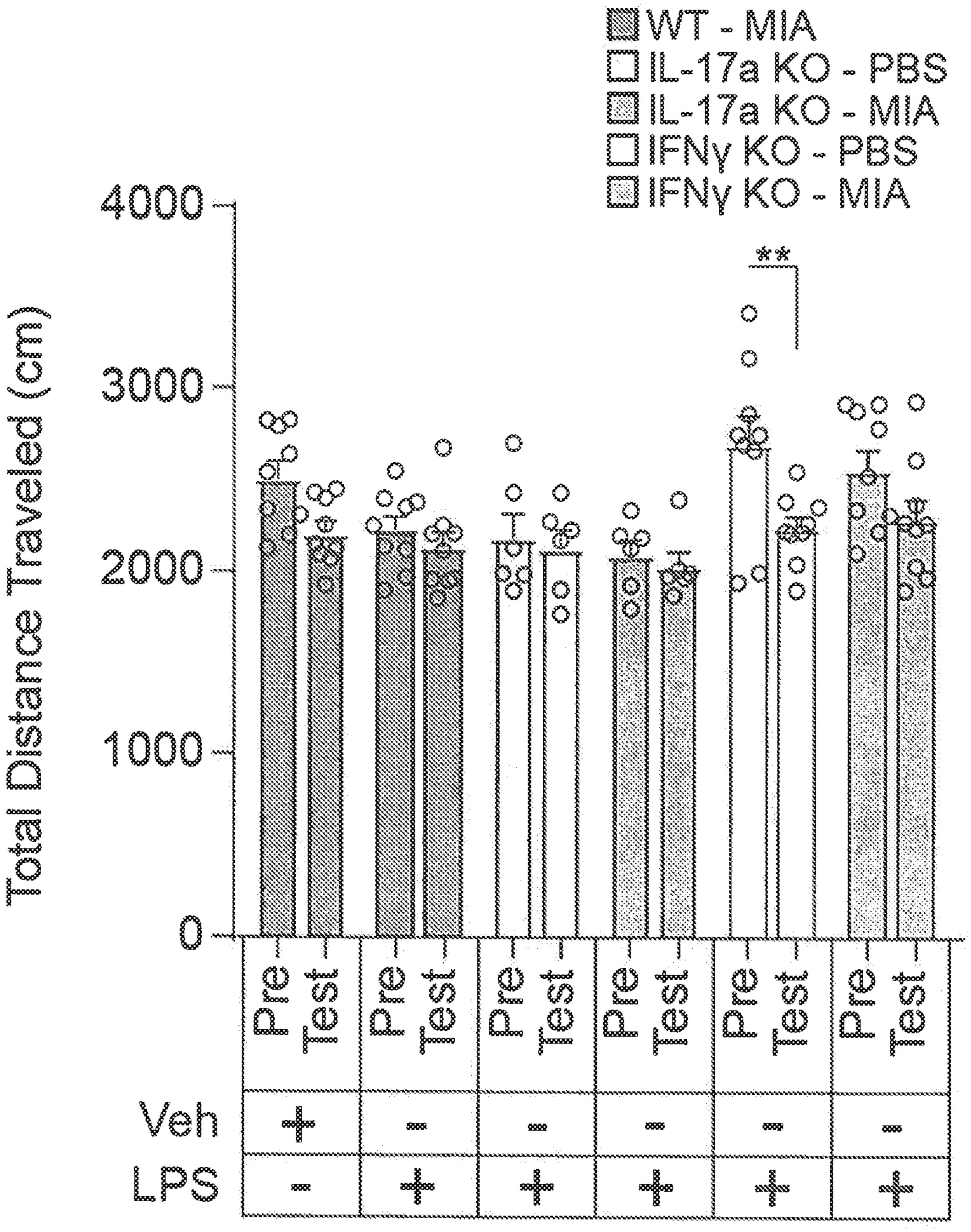

As used herein, the term "brain region" refers to any region or part of the brain in a subject. Mainly, the brain regions described herein are responsible for processing sensory inputs such as sight, sound, or touch. The anatomy of the somatosensory cortex is known in the art (See, for example, Purves et al., *Neuroscience, 2nd edition;* 2001, FIGS. 9.8 and FIGS. 9.9 which is incorporated by reference herein in its entirety). Non-limiting examples of brain regions include but are not limited to the dysgranular zone of the primary somatosensory cortex (S1DZ), prefrontal cortex (PFC), cerebellum, temporal association cortex (TeA), temporal parietal junction (TPJ), secondary somatosensory cortex, and the parietal association area.

The term "statistically significant" or "significantly" refers to statistical significance and generally means a two standard deviation (2SD) or greater difference.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin Exempli gratia, and is used herein to indicate a non-limiting example. Thus, the abbreviation "e.g." is synonymous with the term "for example."

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean±1%.

Unless otherwise explained, all technical and scientific terms used herein have the same meaning as commonly understood by one of ordinary skill in the art to which this disclosure belongs.

It should be understood that this disclosure is not limited to the particular methodology, protocols, and reagents, etc., described herein and as such may vary. The terminology used herein is for the purpose of describing particular embodiments only, and is not intended to limit the scope of the present disclosure, which is defined solely by the claims.

Methods of Treating and Preventing Neurodevelopmental Disorders

In one aspect, provided herein is a method of treating or preventing a neurodevelopmental disease or disorder in a subject. In one embodiment of any of the aspects, the neurodevelopmental disease is autism spectrum disorder (ASD), Asperger's syndrome, learning disabilities, anxiety disorders, schizophrenia, attention deficit hyperactivity disorder (ADHD), sensory processing disorder, epilepsy, fragile X syndrome, sleep disorder, obsessive compulsive disorder (OCD), non-verbal learning disorder, or any other neurodevelopmental disease known in the art.

In another aspect, described herein is a method of treating or preventing a neurodevelopmental disorder in a subject in need thereof, the method comprising: administering to the subject an agent that increases the level or activity of interleukin (IL)-17a (IL-17a) in the brain.

In some embodiments of any of the aspects, the agent increases the level or activity of the interleukin-17 receptor (IL-17Ra) in the brain.

In another aspect, described herein is method of treating a neurodevelopmental disorder in a subject in need thereof, the method comprising: administering IL-17a and IFNγ to the subject.

Generally, a neurodevelopmental disease is characterized and diagnosed by behavioral, brain imaging, or brain activity analysis. The diagnosis can be carried out by a physician, psychologist, or psychiatrist with any number of cognitive, behavioral, or developmental evaluations. For example, in autism spectrum disorders many behavioral signs are present at a young age in a human subject such as limited or no eye contact, lack of joyful expressions or smiling, little or no back and forth of sharing sounds, little to no babbling or speaking, unusual reactions to sounds, repetitive behaviors, and delayed language development. These symptoms can be detrimental to the patient's ability to care for themselves, maintain a career, or live independently over the long term. Furthermore, prior to the methods and compositions described herein, the current treatments for most neurodevelopmental diseases are largely ineffective and there is no cure for diseases such as autism.

With regard to brain imaging analysis, focal patches of abnormal laminar cytoarchitecture and cortical disorganization of neurons have been described in the neurodevelopmental disorders such as autism and can specifically affect the prefrontal cortex. Hyperactivity of the dysgranular zone of the somatosensory cortex (S1DZ) in mice has been previously implicated in the manifestation of maternal immune activation (MIA) behavioral phenotypes such as lack of socialability.

As used herein, a "subject" means a human or animal. Usually the animal is a vertebrate such as a primate, rodent, domestic animal or game animal. Primates include, for example, chimpanzees, cynomolgus monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of disease e.g., diabetic or obesity model. A subject can be male or female.

A subject can be one who has been previously diagnosed with or identified as suffering from or having a disease or disorder in need of treatment (e.g., a neurodevelopmental disorder) or one or more complications related to such a disease or disorder, and optionally, have already undergone treatment for the disease or disorder or the one or more complications related to the disease or disorder. Alternatively, a subject can also be one who has not been previously diagnosed as having such disease or disorder or related complications. For example, a subject can be one who exhibits one or more risk factors for the disease or disorder or one or more complications related to the disease or disorder or a subject who does not exhibit risk factors.

Described herein, is a method of detecting a neurodevelopmental disease in a subject. The method comprises detecting the level or activity of IL-17a, IL-17Ra, or IFNγ in a subject, in particular, within the brain.

In one aspect, described herein is a method of treating a subject with a neurodevelopmental disease, the method comprises: receiving the results of an assay that indicates that the subject has decreased levels or activity of IL-17a; and administering an agent that increases the levels or activity of IL-17a.

In some embodiments, the method further comprises identifying a subject with symptoms of a neurodevelopmental disease. In some embodiments, the method further comprises identifying a subject with a reduced level or activity of Th17 cells or reduced IL-17 secretion. In some embodiments of any of the aspects described herein, the methods further comprise performing a behavioral analysis to identify the subject with symptoms of a neurodevelopmental disease. Behavioral tests are well known in the art for neurodevelopmental disease.

Accordingly, in another aspect, described herein is the method of screening for a therapeutic agent that modulates at least one functional property of neural activity, the method comprises: (a) contacting a biological sample with an agent; (b) detecting the level or activity of IL-17a or IL-17Ra; and/or (c) detecting neural activity of the biological sample. In some embodiments, the biological sample is brain tissue. In some embodiments, the brain tissue is derived from the rodent somatosensory cortex dysgranular zone (S1DZ), somatosensory cortex barrel field (S1BF), secondary motor cortex (M2), primary motor cortex (M1), secondary auditory cortex dorsal part (AuD), central amygdala (CeA), medial prefrontal cortex (mPFC), prelimbic cortex (PrL), infralimbic cortex (IL), primary visual cortex (V1). In some embodiments, the brain tissue is derived from the mammalian or human prefrontal cortex (PFC), cerebellum, temporal association cortex (TeA), temporal parietal junction (TPJ), secondary somatosensory cortex, and the parietal association area.

In some embodiments, prior to step a, is a step of isolating a biological sample from a subject.

In some embodiments, the detecting of neural activity is done by measuring the level of neurotransmitter release, electrophysiological function (e.g. action potential generation or field potentials), calcium signaling, expression of neuronal markers (e.g. c-Fos), modulation of signals from functional Magnetic Resonance Imaging (fMRI), magnetoencephalography (MEG) and/or electroencephalography (EEG) in a cell, tissue, biological sample, or subject. These methods can be accomplished in vitro, in vivo, or ex vivo. For example, methods such as whole-cell patch clamp electrophysiology or microelectrode arrays can be employed in vitro or ex vivo to detect neural activity. A number of methods for detecting neural activity are known in the art.

In some embodiments of any of the aspects, the detecting of IL-17a or IL-17Ra in a subject or biological sample can be done by enzyme-linked immunosorbent assay (ELISA), flow cytometry, immunohistochemistry, Western blotting, next generation sequencing, reverse transcriptase-polymerase chain reaction (RT-PCR), or any other assay known in the art.

In some embodiments of any of the aspects, the methods described herein further comprise detecting the level of IFNγ, RORγt, IL-17f, IL-25, IL-26, IL-6, IL-21, IL-23, IL-1β, CCR6, RORα, IL-23R, IL-1R in a subject or biological sample.

In some embodiments, the biological sample is a blood sample, buffy coat, population of cells, or tissue sample. In some embodiments, the cell or tissue are derived from the brain or gastrointestinal tract.

Agents

The methods and compositions described herein are agents that are formulated for use in the treatment of a neurodevelopmental disease. In some embodiments or any of the aspects, the neurodevelopmental disease is an autism spectrum disorder (ASD). In some embodiments of any of the aspects, the neurodevelopmental disease results in a decreased level or acitivy of IL-17a in the brain.

As used herein, the term "agent" as used herein means any compound or substance such as, but not limited to, a small molecule, nucleic acid, polypeptide, peptide, drug, ion, etc. An "agent" can be any chemical, entity or moiety, including without limitation, synthetic and naturally-occurring proteinaceous and non-proteinaceous entities. In some embodiments of any of the aspects, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

The agent can be a molecule from one or more chemical classes, e.g., organic molecules, which may include organometallic molecules, inorganic molecules, genetic sequences, etc. Agents may also be fusion proteins from one or more proteins, chimeric proteins (for example domain switching or homologous recombination of functionally significant regions of related or different molecules), synthetic proteins or other protein variations including substitutions, deletions, insertion and other variants.

In one embodiment of any of the aspects, the agent is IL-17a or a ligand of IL-17Ra. In another embodiment of any of the aspects, the agent increases the level or activity of IL-17a or IL-17Ra. In another embodiment of any of the aspects, the levels or activity of IL-17a or IL-17Ra is increased by at least 50%, at least 60%, at least 70%, at least 80%, at least 90%, or more as compared to an appropriate control upon administration of the agent described herein.

In another embodiment of any of the aspects, the agent increases the level or activity of the interleukin-17 receptor (IL-17Ra) in the brain. In another embodiment of any of the aspects, the agent is an agonist of IL-17Ra. In another embodiment of any of the aspects, the agent increases the level or activity of Th17 cells.

As used herein, the term "interleukin-17a (IL-17a)," or "IL-17a," refers to an interleukin-17 cytokine that is responsible for immune responses in the body and activates the IL-17 receptor (IL-17Ra). Specifically, IL-17 can regulate numerous cell-specific functions. For example, as described herein, IL-17a is involved in cell signaling events related to brain activity, inflammation, and the like. Sequences for IL-17a, are known for a number of species, e.g., human IL-17A (NCBI GeneID: 3605) polypeptide and mRNA (e.g., NCBI Reference Sequences: NP_002181.1 and NM_002190.3). IL-17Ra can refer to human IL-17a, including naturally occurring variants, molecules, genetically engineered IL-17a, and alleles thereof. IL-17a refers to the mammalian IL-17a of, e.g., mouse, rat, rabbit, dog, cat, cow, horse, pig, and the like. The amino acid sequence of human IL-17a is shown in SEQ ID NO: 1.

As used herein, the term "interleukin-17 receptor," or "IL-17Ra," refers to a interleukin-17 receptor that is expressed in the brain, hematopoietic, bone marrow, thymus, spleen, intestine, and lung, among many others. Specifically, IL-17Ra can regulate numerous cell-specific functions. For example, as described herein, IL-17Ra is involved in cell signaling events related to brain activity, inflammation, and the like. Sequences for IL-17Ra, are known for a number of species, e.g., human IL-17RA (NCBI GeneID: 23765) polypeptide and mRNA (e.g., NCBI Reference Sequences: NM_014339.6; NM_001289905.1; NP_055154.3; and NP_001276834.1). IL-17Ra can refer to human IL-17Ra, including naturally occurring variants, molecules, genetically engineered IL-17Ra, and alleles thereof. IL-17Ra refers to the mammalian IL-17Ra of, e.g., mouse, rat, rabbit, dog, cat, cow, horse, pig, and the like. The amino acid sequence of human IL-17Ra is shown in SEQ ID NO: 2 for isoform 1 and SEQ ID NO: 3 for isoform 2.

As used herein, "Th17 cells" or "T helper-17 cells" refers to a subset of memory T cells, a type of immune cell, found in the gastrointestinal tract. Th17 cells play a role in the induction of tissue inflammation and destruction. Th17 cells are generally characterized by the expression of CD4 and secretion of IL-17, IL-22, and IL-26, among others. Described herein is an agent that increases the number, population, or activity of Th17 cells in a subject.

In another embodiment of any of the aspects, the agent is selected from the group consisting of a small molecule, an antibody, a peptide, a genome editing system, an antisense oligonucleotide, and an RNAi.

As used herein, the term "small molecule" refers to a organic or inorganic molecule, either natural (i.e., found in nature) or non-natural (i.e., not found in nature), which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. Examples of "small molecules" that occur in nature include, but are not limited to, taxol, dynemicin, and rapamycin. Examples of "small molecules" that are synthesized in the laboratory include, but are not limited to, compounds described in Tan et al., ("Stereoselective Synthesis of over Two Million Compounds Having Structural Features Both Reminiscent of Natural Products and Compatible with Miniaturized Cell-Based Assays" J. Am. Chem.

Soc. 120:8565, 1998; incorporated herein by reference). In certain other preferred embodiments, natural-product-like small molecules are utilized.

The term "RNAi" as used herein refers to interfering RNA or RNA interference. RNAi refers to a means of selective post-transcriptional gene silencing by destruction of specific mRNA by molecules that bind and inhibit the processing of mRNA, for example inhibit mRNA translation or result in mRNA degradation. As used herein, the term "RNAi" refers to any type of interfering RNA, including but are not limited to, siRNA, shRNA, endogenous microRNA and artificial microRNA. For instance, it includes sequences previously identified as siRNA, regardless of the mechanism of down-stream processing of the RNA.

In another embodiment of any of the aspects, the agent described herein is a polypeptide.

As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues provided herein are preferred to be in the "L" isomeric form. However, residues in the "D" isomeric form may be substituted for any L-amino acid residue provided the desired properties of the polypeptide are retained.

In one embodiment of any of the aspects, the peptide is a cytokine. In another embodiment of any of the aspects, the cytokine is IL-17a, IL-17f, or IL-25. In another embodiment of any of the aspects, the cytokine is recombinant.

As used herein, the term "recombinant" refers to a nucleic acid molecule or protein that has been engineered by methods of genetic recombination and molecular cloning to produce a gene product in a living cell. Proteins produced from expression of recombinant DNA are "recombinant proteins." Methods of producing a recombinant protein are known in the art (See, for example, U.S. Pat. No. 5,024, 939A, which is incorporated by reference herein in its entirety).

In another embodiment of any of the aspects, the agent described herein is an antibody, antibody reagent, or a fragment thereof. In another embodiment of any of the aspects, the agent is an anti-CD3 antibody.

As used herein, the term "antibody" refers to a polypeptide that includes at least one immunoglobulin variable domain or immunoglobulin variable domain sequence and which specifically binds a given antigen. An antibody or antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as $V_H$), and a light (L) chain variable region (abbreviated herein as $V_L$). In another example, an antibody includes two heavy (H) chain variable regions and two light (L) chain variable regions.

The term "antibody fragment," or "antigen-binding fragment" as used herein, refers to a protein fragment that comprises only a portion of an intact antibody, generally including an antigen binding site of the intact antibody and thus retaining the ability to bind antigen (e.g., CD3). Examples of antibody fragments encompassed by the present definition include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the $C_H1$ domain; (v) the Fv fragment having the $V_L$ and $V_H$ domains of a single arm of an antibody; (vi) the dAb fragment (Ward et al., *Nature* 341, 544-546 (1989)) which consists of a $V_H$ domain; (vii) isolated CDR regions; (viii) F(ab')2 fragments, a bivalent fragment including two Fab' fragments linked by a disulfide bridge at the hinge region; (ix) single chain antibody molecules (e.g., single chain Fv; scFv) (Bird et al., *Science* 242:423-426 (1988); and Huston et al., *PNAS* (USA) 85:5879-5883 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; and Hollinger et al., *Proc. Natl. Acad. Sci. USA,* 90:6444-6448 (1993)); (xi) "linear antibodies" comprising a pair of tandem Fd segments ($V_H$-$C_H1$-$V_H$-$C_H1$) which, together with complementary light chain polypeptides, form a pair of antigen binding regions (Zapata et al. Protein Eng. 8(10): 1057-1062 (1995); and U.S. Pat. No. 5,641,870).

The term "antibody reagent" encompasses antigen-binding fragments of antibodies (e.g., single chain antibodies, Fab and sFab fragments, F(ab')2, Fd fragments, Fv fragments, scFv, CDRs, and domain antibody (dAb) fragments (see, e.g. de Wildt et al., *Eur J. Immunol.* 1996; 26(3): 629-39; which is incorporated by reference herein in its entirety)) as well as complete antibodies.

An antibody can have the structural features of IgA, IgG, IgE, IgD, or IgM (as well as subtypes and combinations thereof). Antibodies can be from any source, including mouse, rabbit, pig, rat, and primate (human and non-human primate) and primatized antibodies. Antibodies also include broadly neutralizing antibodies, midibodies, nanobodies, humanized antibodies, chimeric antibodies, and the like. Furthermore, the antibody or antibody reagent as provided herein can comprise an amino acid sequence complementary to IL-17a, IL-17Ra, or IFN-γ (SEQ ID NOs: 1-4), or cluster of differentiation 3 (CD3).

The term "Fc region" is used to define the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a $C_H2$ domain, and a $C_H3$ domain, and optionally comprises a $C_H4$ domain. Replacements of amino acid residues in the Fc portion to alter antibody effector function are known in the art (U.S. Pat. Nos. 5,648,260 and 5,624,821).

As used herein, the term "Complementarity Determining Regions" ("CDRs"), i.e., CDR1, CDR2, and CDR3) refers to the amino acid residues of a heavy or light chain variable domain the presence of which are necessary for specific antigen binding. Each variable domain typically has three CDR regions identified as CDR1, CDR2 and CDR3. Each complementarity determining region can comprise amino acid residues from a "complementarity determining region" as defined by Kabat (i.e., about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e., about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). In some instances, a complementarity determining region can include amino acids from both a CDR region defined according to Kabat and a hypervariable loop. The term "CDR set" as used herein refers to a group of three CDRs that occur in a single heavy or light chain variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, *J. Mol. Biol,* 196:901-917 (1987) and Chothia et al., Nature 342:877-883 (1989)) found that certain sub-portions within Kabat CDRs adopt nearly identical peptide backbone conformations, in spite of great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (*FASEB*). 9:133-139 (1995)) and MacCallum (*J Mol Biol* 262(5): 732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. CDRs can also be described as comprising amino acid residues from a "complementarity determining region" as defined by the IMGT or Abysis, in some embodiments. The compositions and methods described herein may utilize CDRs defined according to any of these systems known in the art. Nonetheless, the boundaries of the CDRs are clear in reference to either of these numbering conventions.

An immunoglobulin constant (C) domain refers to a heavy ($C_H$) or light ($C_L$) chain constant domain. Murine and human IgG heavy chain and light chain constant domain amino acid sequences are known in the art. With respect to the heavy chain, in some embodiments of the aspects described herein, the heavy chain of an antibody described herein can comprise an alpha (α), delta (Δ), epsilon (ε), gamma (γ) or mu (μ) heavy chain. Non-limiting examples of human constant region sequences have been described in the art, e.g., see U.S. Pat. No. 5,693,780 and Kabat E A et al., (1991) supra.

As used herein, the terms "donor" and "donor antibody" refer to an antibody providing one or more CDRs. In an exemplary embodiment, the donor antibody is an antibody from a species different from the antibody from which the framework regions are obtained or derived. In some embodiments, the donor antibody is of a different isotype than the acceptor antibody. In the context of a humanized antibody, the term "donor antibody" refers to a non-human antibody providing one or more CDRs.

As used herein, the terms "acceptor" and "acceptor antibody" refer to the antibody providing or nucleic acid sequence encoding at least 80%, at least 85%, at least 90%, at least 95%, at least 98%, or 100% of the amino acid sequences of one or more of the framework regions. In some embodiments, the term "acceptor" refers to the antibody amino acid providing or nucleic acid sequence encoding the constant region(s). In yet another embodiment, the term "acceptor" refers to the antibody amino acid providing or nucleic acid sequence encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well known in the art or antibodies commercially available).

Human heavy chain and light chain acceptor sequences are known in the art. In some embodiments, the human heavy chain and light chain acceptor sequences are selected from the sequences listed from V-base (found on the worldwide web at vbase.mrc-cpe.cam.ac.uk) or from IMGT™ the international ImMunoGeneTics Information System™ (found on the worldwide web at imgt.cines.fr/textes/IMGTrepertoire/LocusGenes). In another embodiment of the technology disclosed herein, the human heavy chain and light chain acceptor sequences are selected from the sequences described in Table 3 and Table 4 of U.S. Patent Publication No. 2011/0280800, incorporated by reference herein in their entireties.

In some embodiments of any of the aspects described herein, the antibodies, antibody reagents, fragments thereof, and polypeptides described herein comprise human antigen-binding and constant domains.

The term "humanized antibody" refers to antibodies that comprise heavy and light chain variable domain sequences from a non-human species (e.g., a mouse) but in which at least a portion of the $V_H$ and/or $V_L$ sequence has been altered to be more "human-like", i.e., more similar to human germline variable sequences. Accordingly, "humanized" antibodies are a form of a chimeric antibody, that are engineered or designed to comprise minimal sequence derived from non-human immunoglobulin. For the most part, humanized antibodies are human immunoglobulins (recipient or acceptor antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies can comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., *Nature* 321: 522-525 (1986); Riechmann et al., *Nature* 332:323-329 (1988); and Presta, *Curr. Op. Struct. Biol.* 2:593-596 (1992).

The compositions and methods described herein can, in some embodiments, comprise "antigen-binding fragments" or "antigen-binding portions" of an antibody. The term "antigen-binding fragment" of an antibody refers to one or more fragments of an antibody that retain the ability to specifically bind to an antigen. Antigen-binding functions of an antibody can be performed by fragments of a full-length antibody. Such antibody fragment embodiments may also be incorporated in bispecific, dual specific, or multi-specific formats such as a dual variable domain (DVD-Ig) format; specifically binding to two or more different antigens. Non-limiting examples of antigen-binding fragments encompassed within the term "antigen-binding portion" of an antibody include (i) a Fab fragment, a monovalent fragment consisting of the $V_L$, $V_H$, $C_L$, and $C_H1$ domains; (ii) a F(ab')2 fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb fragment (Ward et al. (1989) *Nature,* 341:544-546; PCT Publication No. WO 90/05144), which comprises a single variable domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, for example, Bird et al. (1988) *Science* 242:423-426; and Huston et al. (1988) *Proc. Natl. Acad. Sci.* USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al. (1993) *Proc. Natl. Acad. Sci.* USA 90:6444-6448; Poljak (1994) *Structure* 2:1121-1123); Kontermann and Dubel eds., *Antibody Engineering*, Springer-Verlag, N.Y. (2001), p. 790 (ISBN 3-540-41354-5). In addition, single chain antibodies also include "linear antibodies" comprising a pair of tandem Fv segments ($V_H$-$C_H1$-$V_H$-$C_H1$) which, together with complementary light chain polypeptides, form a pair of antigen binding regions (Zapata et al. (1995) *Protein Eng.* 8(10): 1057-1062; and U.S. Pat. No. 5,641, 870).

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such humanized antibodies are chimeric antibodies (U.S. Pat. No. 4,816,567) where substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

In another embodiment of any of the aspects, the methods and compositions described herein further comprise administering an agent that increases the permeability of the blood brain barrier.

In another embodiment of any of the aspects, the agent is an interferon. In another embodiment of any of the aspects, the agent is IFNγ. In another embodiment, the IFNγ is recombinant. In another embodiment, the agent increases the level or activity of IFNγ.

As used herein, the term "interferon gamma" or "IFNγ," or "IFNG" refers to a dimerized soluble cytokine (interferon) that is responsible for immune responses in the body and activates interferon gamma receptors (IFNGR1 and IFNGR2). Specifically, IFNγ can regulate numerous cell-specific functions. For example, as described herein, IFNγ is involved in cell signaling events related to blood brain barrier permeability, inflammation, and the like. Sequences for IFNγ, are known for a number of species, e.g., human IFNG (NCBI GeneID: 3458) polypeptide and mRNA (e.g., NCBI Reference Sequences: NP_000610.2 and NM_000619.3). IFNγ can refer to human IFNγ, including naturally occurring variants, molecules, genetically engineered IFNγ, and alleles thereof. IFNγ refers to the mammalian IFNγ of, e.g., mouse, rat, rabbit, dog, cat, cow, horse, pig, and the like. The amino acid sequence of human IFNγ is shown in SEQ ID NO: 4.

Anti-CD3 Antibody Reagents

Cluster of differentiation 3 or CD3 is a receptor expressed on number of different cell types (e.g., thymocytes, stem cells, T cells, etc.). When CD3 is activated, this in turn activates cytotoxic T cells and T helper cells to increase inflammatory responses.

In one aspect, described herein is an antibody, antibody reagent, or fragment thereof that targets CD3 for use in the treatment and prevention of a neurodevelopmental disease or disorder.

In one embodiment of any of the aspects, the antibody, antibody reagent, or fragment thereof is an anti-CD3 antibody or antibody fragment. In another embodiment of any of the aspects, the antibody, antibody reagent, or fragment thereof promotes an increase in the level or activity of IL-17a or IL-17Ra in the brain of the subject.

In another embodiment of any of the aspects, the antibody, antibody reagent, or fragment thereof promotes an increase in the level or activity of Th17 cells in the gut of the subject, thereby increasing the level of IL-17+ immune cells in the brain.

In some embodiments of any of the aspects described herein, the antibody, antibody reagent, or antibody fragment increases the population of IL-17 positive immune cells in the brain.

Generally, the anti-CD3 antibody described herein in the working examples can increase IL17a+, CD4 T-cells in the gut of a subject.

Antibodies, antibody fragments, and antibody reagents that are therapeutic and/or specific for any particular target antigen (e.g., CD3) are readily selected by one of skill in the art from known antibodies or antibody reagents, e.g. from FDA-approved therapeutic antibody reagents and/or commercially available antibody reagents which are listed in catalogs according to their target specificity.

In another embodiment, the anti-CD3 antibody is any anti-CD3 antibody or antibody fragments of anti-CD3 antibodies known in the art. Non-limiting examples of anti-CD3 antibodies include otelixizumab and CD3e (145-2C11). The complementarity determining regions (CDR) of anti-CD3 antibodies are known in the art. See for example, WO2011/050104 A2; U.S. Pat. Nos. 7,041,289; and 6,406,696 B1 which are incorporated herein by reference in their entireties.

In some embodiments of any of the aspects, the antibody, antibody reagent, or fragment thereof is otelixizumab or CD3e (145-2C11).

Pharmaceutical Compositions

In one aspect, described herein is a pharmaceutical composition for use in the treatment of a neurodevelopmental disease or disorder. In one embodiment of any of the aspects, the agent as provided herein is formulated in a pharmaceutical composition.

As used herein, the term "pharmaceutical composition" can include any material or substance that, when combined with an active ingredient (e.g. IL-17a) allows the ingredient to retain biological activity and is non-toxic to the subject. Examples include, but are not limited to, any of the standard pharmaceutical carriers such as a phosphate buffered saline solution, emulsions such as oil/water emulsion, and various types of wetting agents. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. The term "pharmaceutically acceptable carrier" excludes tissue culture media. Each carrier must be "acceptable" in the sense of being compatible with the other ingredients of the formulation, for example the carrier does not decrease the impact of the agent on the treatment. In other words, a carrier is pharmaceutically inert. The terms "physiologically tolerable carriers" and "biocompatible delivery vehicles" are used interchangeably. Non-limiting examples of pharmaceutical carriers include particle or polymer-based vehicles such as nanoparticles, microparticles, polymer microspheres, or polymer-drug conjugates.

In some embodiments, the pharmaceutical composition is a liquid dosage form or solid dosage form. Liquid dosage forms for oral administration include, but are not limited to, pharmaceutically acceptable emulsions, microemulsions, solutions, suspensions, syrups and elixirs. In addition to the agent in liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the agent is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcelhdose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard-filled gelatin capsules using such excipients as lactose or milk sugar as well as high molecular weight polyethylene glycols, and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type can also be employed as fillers in soft and hard-filled gelatin capsules using such excipients as lactose or milk sugar as well as high molecular weight polyethylene glycols, and the like.

The agent can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms, the agent be admixed with at least one inert diluent such as sucrose, lactose and starch. Such dosage forms can also comprise, as in normal practice, additional substances other than inert diluents, e.g., tableting lubricants and other tableting aids such as magnesium stearate and microcrystalline cellulose. In the case of capsules, tablets and pills, the dosage forms can also comprise buffering agents. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The agents and pharmaceutical compositions described herein can be formulated to "restrict delivery of the agent to the brain," such that the formulation permits or facilitates the delivery to the subject's brain in viable form. This can be achieved, for example, by direct injection of the IL-17a polypeptide into the brain.

As another example, the agents and pharmaceutical compositions described herein can be "formulated to restrict delivery of the agent to the gastrointestinal tract," such that the formulation permits or facilitates the delivery to the colon, large intestine, or small intestine in viable form. This can be achieved, for example, by orally administering a microorganism or group of microorganisms as a solid dosage form with an enteric coating.

Enteric coatings or micro- or nano-particle formulations can facilitate such delivery as can, for example, buffer or other protective formulations. In some embodiments, the carrier or excipient restricts delivery of the composition to the gastrointestinal tract.

In some embodiments, the carrier or excipient is an enteric coating or enteric-coated drug delivery device. As used herein, the terms "enteric coating" or "enteric-coated drug delivery device" refers to any drug delivery method that can be administered orally but is not degraded or activated until the device enters the intestines. Such methods can utilize a coating or encapsulation that is degraded using e.g., pH dependent means, permitting protection of the delivery device and the agent to be administered or transplanted throughout the gastrointestinal tract until the device reaches the alkaline pH of the intestines (e.g. colon).

An enteric coating can be stable at low pH (such as in the stomach) and can dissolve at higher pH (for example, in the intestine). Material that can be used in enteric coatings includes, for example, alginic acid, cellulose acetate phthalate, plastics, waxes, shellac, and fatty acids (e.g., stearic acid, palmitic acid). Enteric coatings are described, for example, in U.S. Pat. Nos. 5,225,202, 5,733,575, 6,139,875, 6,420,473, 6,455,052, and 6,569,457, all of which are herein incorporated by reference in their entirety. The enteric coating can be an aqueous enteric coating. Examples of polymers that can be used in enteric coatings include, for example, shellac (trade name EmCoat 120 N, Marcoat 125); cellulose acetate phthalate (trade names AQUACOAT™, AQUACOAT ECD™, SEPIFILM™, KLUCEL™, and METOLOSE™); polyvinylacetate phthalate (trade name SURETERIC™); and methacrylic acid (trade names EUDRAGIT™, EUDRAGIT L 100-55™ from Evonik Industries, Germany).

Pharmaceutical compositions include formulations suitable for oral administration may be provided as discrete units, such as tablets, capsules, cachets, syrups, elixirs, prepared food items, microemulsions, solutions, suspensions, lozenges, or gel-coated ampules, each containing a predetermined amount of the active compound; as powders or granules; as solutions or suspensions in aqueous or non-aqueous liquids; or as oil-in-water or water-in-oil emulsions.

Accordingly, formulations suitable for rectal administration include gels, creams, lotions, aqueous or oily suspensions, dispersible powders or granules, emulsions, dissolvable solid materials, douches, and the like can be used. The formulations are preferably provided as unit-dose suppositories comprising the active ingredient in one or more solid carriers forming the suppository base, for example, cocoa butter. Suitable carriers for such formulations include petroleum jelly, lanolin, polyethyleneglycols, alcohols, and combinations thereof.

Efficacy, Dosage, and Administration

The term "effective amount" is used interchangeably with the term "therapeutically effective amount" or "amount sufficient" and refers to the amount of at least one agent (e.g., an agonist of IL-17Ra, e.g., IL-17a), at dosages and for periods of time necessary to achieve the desired therapeutic result, for example, to "attenuate", reduce or stop at least one symptom of a neurodevelopmental disease or disorder. For example, an effective amount using the methods as disclosed herein would be considered as the amount sufficient to reduce one or more symptoms of a neurodevelopmental disorder by at least 10%. An effective amount as used herein would also include an amount sufficient to prevent or delay the development of such a symptom, alter the course of a symptom disease (for example but not limited to, slow the progression of a symptom of the disease), or reverse a symptom of the disease in a subject suffering from a neurodevelopmental disorder.

Accordingly, the term "effective amount" or "therapeutically effective amount" as used herein refers to the amount of therapeutic agent (e.g. IL-17a) of a pharmaceutical composition to alleviate at least one symptom of a disease. Stated another way, "therapeutically effective amount" of an agonist of IL-17Ra as disclosed herein is the amount of an agonist which exerts a beneficial effect on, for example, the symptoms of the disease (e.g. a neurodevelopmental disorder). The dosage administered, as single or multiple doses, to an individual will vary depending upon a variety of factors, including pharmacokinetic properties of the inhibitor, the route of administration, conditions and characteristics (sex, age, body weight, health, size) of subjects, extent of symptoms, concurrent treatments, frequency of treatment and the effect desired. A therapeutically effective amount is also one in which any toxic or detrimental effects of the therapeutic agent are outweighed by the therapeutically beneficial effects. The effective amount in each individual case can be determined empirically by a skilled artisan according to established methods in the art and without undue experimentation. In general, the phrases "therapeutically-effective" and "effective for the treatment, prevention, or inhibition", are intended to qualify agonist as disclosed herein which will achieve the goal of reduction in the severity of a neurodevelopmental disorder or at one related symptom thereof.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of use or administration utilized.

The effective dose can be estimated initially from cell culture assays. A dose can be formulated in animals. Generally, the compositions are administered so that an agent or compound of the disclosure herein is used or given at a dose from 1 μg/kg to 1000 mg/kg; 1 μg/kg to 500 mg/kg; 1 μg/kg to 150 mg/kg, 1 μg/kg to 100 mg/kg, 1 μg/kg to 50 mg/kg, 1 μg/kg to 20 mg/kg, 1 g/kg to 10 mg/kg, 1 μg/kg to 1 mg/kg, 100 μg/kg to 100 mg/kg, 100 μg/kg to 50 mg/kg, 100 μg/kg to 20 mg/kg, 100 μg/kg to 10 mg/kg, 100 μg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. Further contemplated is a dose (either as a bolus or continuous infusion) of about 0.1 mg/kg to about 10 mg/kg, about 0.3 mg/kg to about 5 mg/kg, or 0.5 mg/kg to about 3 mg/kg. It is to be further understood that the ranges intermediate to those given above are also within the scope of this disclosure, for example, in the range 1 mg/kg to 10 mg/kg, for example use or dose ranges such as 2 mg/kg to 8 mg/kg, 3 mg/kg to 7 mg/kg, 4 mg/kg to 6 mg/kg, and the like.

The agents described herein can be administered at once, or can be divided into a number of smaller doses to be administered at intervals of time. It is understood that the precise dosage and duration of treatment will be a function of the location of where the composition is parenterally administered, the carrier and other variables that can be determined empirically using known testing protocols or by extrapolation from in vivo or in vitro test data. It is to be noted that concentrations and dosage values can also vary with the age of the individual treated. It is to be further understood that for any particular subject, specific dosage regimens can need to be adjusted over time according to the individual need and the professional judgment of the person administering or supervising the administration of the formulations. Hence, the concentration ranges set forth herein are intended to be exemplary and are not intended to limit the scope or practice of the claimed formulations.

In one embodiment of any of the aspects, the agent or composition is administered continuously (e.g., at constant levels over a period of time). Continuous administration of an agent can be achieved, e.g., by epidermal patches, continuous release formulations, or on-body injectors. The agent can be administered as a single bolus or multiple boluses, as a continuous infusion, or a combination thereof. For example, the agent can be administered as a single bolus initially, and then administered as a continuous infusion following the bolus. The rate of the infusion can be any desired rate. Some contemplated infusion rates include from 1 μg/kg/min to 100 mg/kg/min, or from 1 μg/kg/hr to 1000 mg/kg/hr. Rates of infusion can include 0.2 to 1.5 mg/kg/min, or more specifically 0.25 to 1 mg/kg/min, or even more specifically 0.25 to 0.5 mg/kg/min. It will be appreciated that the rate of infusion can be determined based upon the dose necessary to maintain effective plasma concentration and the rate of elimination of the agent, such that the agent is administered via infusion at a rate sufficient to safely maintain a sufficient effective plasma concentration of agent in the bloodstream.

The terms "co-administration" or the like, as used herein, are meant to encompass administration of the selected therapeutic agents to a single patient and are intended to include treatment regimens in which the agents are administered by the same or different route of administration or at the same or different time.

"Unit dosage form" as the term is used herein refers to a dosage for suitable one administration. By way of example a unit dosage form can be an amount of therapeutic disposed in a delivery device, e.g., a syringe or intravenous drip bag. In one embodiment of any of the aspects, a unit dosage form is administered in a single administration. In another embodiment, more than one unit dosage form can be administered simultaneously.

The dosage of the agent as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to administer further agents, discontinue treatment, resume treatment, or make other alterations to the treatment regimen. The dosage should not be so large as to cause adverse side effects, such as cytokine release syndrome. Generally, the dosage will vary with the age, condition, and sex of the patient and can be determined by one of skill in the art. The dosage can also be adjusted by the individual physician in the event of any complication.

In one embodiment of any of the aspects, the agent or compositions described herein are used as a monotherapy.

In another embodiment of any of the aspects, the agents described herein can be used in combination with other known agents and therapies for a neurodevelopmental disorder. Administered "in combination," as used herein, means that two (or more) different treatments are delivered to the subject during the course of the subject's affliction with the disorder, e.g., the two or more treatments are delivered after the subject has been diagnosed with the disorder (e.g. a neurodevelopmental disorder) and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." For example, as described herein, IFNγ delivered in combination with IL-17a increases the permeability of the blood brain barrier. The concurrent delivery allows for improved treatment of the sociability deficits in subjects with a neurodevelopmental disease.

In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. The agents described herein and at least one additional therapy can be administered simultaneously, in the same or in separate compositions, or sequentially. For sequential administration, the agent described herein can be administered first, and the additional agent can be administered second, or the order of administration can be reversed. The agent and/or other therapeutic agents, procedures or modalities can be administered during periods of active disorder, or during a period of remission or less active disease. The agent can be administered before another treatment, concurrently with the treatment, post-treatment, or during remission of the disorder.

Therapeutics currently used to treat or prevent a neurodevelopmental disorder include, but are not limited to, amisulpride, olanzapine, risperidone, clozapine and other treatments for neurodevelopmental disorders such as behavioral therapies are known in the art.

When administered in combination, the agent or composition and the additional agent (e.g., second or third agent), or all, can be administered in an amount or dose that is higher, lower or the same as the amount or dosage of each agent used individually, e.g., as a monotherapy. In certain embodiments, the administered amount or dosage of the agent, the additional agent (e.g., second or third agent), or all, is lower (e.g., at least 20%, at least 30%, at least 40%, or at least 50%) than the amount or dosage of each agent used individually. In other embodiments, the amount or dosage of agent, the additional agent (e.g., second or third agent), or all, that results in a desired effect (e.g., treatment of a neurodevelopmental disorder) is lower (e.g., at least 20%, at least 30%, at least 40%, or at least 50% lower) than the amount or dosage of each agent individually required to achieve the same therapeutic effect.

In some embodiments of any of the aspects, the additional agent is an interferon. In some embodiments of any of the aspects, the addition agent is IFNγ.

In some embodiments of any of the aspects, the agents described herein are administered by direct injection, subcutaneous injection, muscular injection, oral, or nasal administration. In some embodiments, the administering of the agent or pharmaceutical composition provided herein reduces the lack of sociability of a subject. In some embodiments, the socialability of the subject is increased by the agent or pharmaceutical composition described herein.

The terms "administered" and "subjected" are used interchangeably in the context of treatment of a disease or disorder.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "administer" refers to the placement of a composition into a subject by a method or route which results in at least partial localization of the composition at a desired site such that desired effect is produced. An agent or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebral spinal, and intrasternal injection and infusion. In preferred embodiments, the compositions are administered orally.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebral spinal, and intrasternal injection, infusion and other injection or infusion techniques, without limitation. Without limitations, oral administration can be in the form of solutions, suspensions, tablets, pills, capsules, sustained-release formulations, oral rinses, powders and the like.

Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

In some embodiments of any of the aspects, described herein is an agent or pharmaceutical composition that is administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control the agent's onset of action, duration of action, plasma levels within the therapeutic window, and peak blood levels. In particular, controlled- or extended-release dosage forms or formulations can be used to ensure that the maximum effectiveness of an agent is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with any agent described herein. Examples include, but are not limited to, those described in U.S. Pat. Nos. 3,845,770; 3,916,899; 3,536,809; 3,598,123; 4,008,719; 5674,533; 5,059,595; 5,591,767; 5,120,548; 5,073,543; 5,639,476; 5,354,556; 5,733,566; and 6,365,185, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed agents and thus effect controlled delivery of the drug. Examples of specific anion exchangers include, but are not limited to, DUOLITE® A568 and DUOLITE® AP143 (Rohm&Haas, Spring House, Pa. USA).

The efficacy of the agents described herein, e.g., for the treatment of a neurodevelopmental disorder, can be determined by the skilled practitioner. However, a treatment is considered "effective treatment," as the term is used herein, if one or more of the signs or symptoms of a neurodevelopmental disorder are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g., sociability. Efficacy can also be measured by a failure of an individual to worsen as assessed by hospitalization, or need for medical interventions (i.e., progression of the symptoms). Methods of measuring these indicators are known to those of skill in the art and/or are described herein.

Efficacy can be assessed in animal models of a condition described herein, for example, a mouse model or an appropriate animal model of a neurodevelopmental disorder, as the case may be. When using an experimental animal model, efficacy of treatment is evidenced when a statistically significant change in a marker is observed, e.g., reduced anxiety or increased sociability.

Microorganisms that Increase the Levels of IL-17a

As described herein and described in the working examples, gut microbiota-dependent production of peripherally-induced cytokines can modulate the expression of neurodevelopmental disorders by affecting the activity in the central nervous system. In one embodiment of any of the aspects, the microorganism increases the population of T helper-17 cells (Th17) in the gut.

In one aspect, described herein is a method of treating a neurodevelopmental disorder in a subject in need thereof, the method comprises: administering to the subject at least one microorganism or population thereof.

The term "microorganism" as used herein refers to any microscopic-organism, matter, or component that is derived, originated from, or secreted by a microbe. Non-limiting examples of microorganisms include viruses, prokaryotic organisms (e.g. bacterium), or eukaryotic organisms (e.g. yeast, fungus, etc.). In some embodiments, a population of microorganisms are used (e.g., segmented filamentous bacteria).

In one embodiment of any of the aspects, the microorganism is genetically engineered. In another embodiment of any of the aspects, the microorganism expresses an agent that increases the level or activity of interleukin (IL)-17a (IL-17a).

The term "genetically engineered microorganism" as used herein refers to a microorganism that has been transformed by a small molecule, gene editing system, vector, plasmid, DNA, RNA, microRNA, lipoproteins, polypeptides, or the like to alter their functional properties (e.g. promoting the secretion of IL-17a from Th17 cells). Examples of methods and compositions related to genetically engineered microorganisms are known in the art such as U.S. Pat. Nos. 7,354,592B2, 4,190,495A, 6,015,703A, US20080038805A1, and U.S. Pat. No. 5,733,540A, the contents of which are all incorporated by reference herein in their entireties.

In some embodiments of any of the aspects, the microorganism is a bacterium. In some embodiments, the bacterium is one that is found in the gastrointestinal tract. Exemplary bacteria include, but are not limited to *Clostridium, Lactobacillus, Escherichia*, Proteobacteria, Actinobacteria, Firmicutes, Bacteroidetes, *Saccharomyces, Bifidobacterium, Faecalibacterium, Prevotella, Ruminococcus, Bacteroides*, Candidatus, or any other bacteria known in the art. The bacteria can be genetically modified using methods known in the art (e.g. molecular cloning) to increase the production of IL-17a and/or IFNγ by cells in the gut.

In another embodiment of any of the aspects, the microorganism is administered by oral administration. In another embodiment of any of the aspects, the genetically engineered microorganism is formulated in a pharmaceutical composition, as described herein.

In another embodiment of any of the aspects, the pharmaceutical composition is formulated to restrict delivery of the agent to the gastrointestinal tract. As used herein, the term "restricts delivery of the genetically engineered microorganism to the gastrointestinal tract" refers to a formulation that permits or facilitates the delivery of the agent, microorganism, or pharmaceutical composition described herein to the colon, large intestine, or small intestine in viable form.

Some embodiments of the various aspects described herein can be described as in the following numbered paragraphs:

1) A method of treating a neurodevelopmental disorder in a subject in need thereof, the method comprising: administering to the subject an agent that increases the level or activity of interleukin (IL)-17a (IL-17a) in the brain.

2) The method of paragraph 1, wherein the agent increases the level or activity of the interleukin-17 receptor (IL-17Ra) in the brain.

3) The method of any of paragraphs 1-2, wherein the agent is selected from the group consisting of: a small molecule, an antibody, a peptide, a genome editing system, a vector, a miRNA, and a siRNA.

4) The method of any of paragraphs 1-3, wherein the peptide is a cytokine.

5) The method of any of paragraphs 1-4, wherein the cytokine is IL-17a, IL-17f, or IL-25.

6) The method of any of paragraphs 1-5, wherein the cytokine is recombinant.

7) The method of any of paragraphs 1-6, wherein the antibody is an anti-CD3 antibody.

8) The method of any of paragraphs 1-7, further comprising administering an agent that increases the permeability of the blood brain barrier.

9) The method of any of paragraphs 1-8, wherein the agent is selected from the group consisting of: a small molecule, an antibody, a peptide, a genome editing system, a vector, a miRNA, and a siRNA.

10) The method of any of paragraphs 1-9, wherein the peptide is an interferon.

11) The method of any of paragraphs 1-10, the interferon is interferon gamma (IFNγ).

12) The method of any of paragraphs 1-11, wherein the agent modulates the neural activity in a brain region selected from the group consisting of: the dysgranular zone of the primary somatosensory cortex (S1DZ), prefrontal cortex (PFC), cerebellum, temporal association cortex (TeA), temporal parietal junction (TPJ), secondary somatosensory cortex, and the parietal association area.

13) The method of any of paragraphs 1-12, wherein the neurodevelopmental disorder is selected from the group consisting of: autism spectrum disorder (ASD), Asperger's syndrome, learning disabilities, anxiety disorders, schizophrenia, attention deficit hyperactivity disorder (ADHD), sensory processing disorder, epilepsy, fragile X syndrome, sleep disorder, obsessive compulsive disorder (OCD), and non-verbal learning disorder.

14) The method of any of paragraphs 1-13, wherein the agent is formulated in a pharmaceutical composition.

15) The method of any of paragraphs 1-14, wherein the pharmaceutical composition is formulated to restrict delivery of the agent to the brain.

16) The method of any of paragraphs 1-15, wherein the agent is administered by direct injection, subcutaneous injection, muscular injection, oral, or nasal administration.

17) The method of any of paragraphs 1-16, wherein the level or activity of IL-17a is increased by at least 50%, at least 60%, at least 70%, at least 80%, at least 90%, or more as compared to an appropriate control.

18) The method of any of paragraphs 1-17, wherein the subject is a mammal. 19) The method of any of paragraphs 1-18, wherein the subject is a human.

20) A method of treating a neurodevelopmental disorder in a subject in need thereof, the method comprising: administering IL-17a and IFNγ to the subject.

21) The method of paragraph 20, wherein the agent is administered by direct injection, subcutaneous injection, muscular injection, oral, or nasal administration.

22) The method of any of paragraphs 20-21, wherein the IL-17a and IFNγ are recombinant.

23) The method of any of paragraphs 20-22, wherein the neurodevelopmental disorder is selected from the group consisting of: autism spectrum disorder (ASD), Asperger's syndrome, learning disabilities, anxiety disorders, schizophrenia, attention deficit hyperactivity disorder (ADHD), sensory processing disorder, epilepsy, fragile X syndrome, sleep disorder, obsessive compulsive disorder (OCD), and non-verbal learning disorder.

24) The method of any of paragraphs 20-23, wherein the IL-17a and IFNγ are formulated in a pharmaceutical composition.

25) The method of any of paragraphs 20-24, wherein the subject is a mammal.

26) The method of any of paragraphs 20-25, wherein the subject is a human.

27) A method of treating a neurodevelopmental disorder in a subject in need thereof, the method comprising: administering to the subject at least one genetically engineered microorganism or population thereof, that expresses an agent that increases the level or activity of interleukin (IL)-17a (IL-17a).

28) The method of paragraph 27, wherein the genetically engineered microorganism is a bacterium.

29) The method of any of paragraphs 27-28, wherein the genetically engineered microorganism increases the population of T helper-17 cells (Th17) in the gut.

30) The method of any of paragraphs 27-29, wherein the neurodevelopmental disorder is selected from the group consisting of: autism spectrum disorder (ASD), Asperger's syndrome, learning disabilities, anxiety disorders, schizophrenia, attention deficit hyperactivity disorder (ADHD), sensory processing disorder, epilepsy, fragile X syndrome, sleep disorder, obsessive compulsive disorder (OCD), and non-verbal learning disorder.

31) The method of any of paragraphs 27-30, wherein the genetically engineered microorganism is administered by oral administration.

32) The method of any of paragraphs 27-31, wherein the genetically engineered microorganism is formulated in a pharmaceutical composition.

33) The method of any of paragraphs 27-32, wherein the pharmaceutical composition is formulated to restrict delivery of the agent to the gastrointestinal tract.

34) The method of any of paragraphs 27-33, wherein the subject is a mammal.

35) The method of any of paragraphs 27-34, wherein the subject is a human.

36) A method of treating a neurodevelopmental disorder in a subject in need thereof, the method comprising: administering to the subject an antibody or antibody fragment thereof that increases the level or activity of interleukin (IL)-17a (IL-17a).

37) The method of paragraph 36, wherein the antibody is an anti-CD3 antibody.

38) The method of any of paragraphs 36-37, wherein the antibody increases the population of T helper-17 cells (Th17) in the gut of the subject.

39) The method of any of paragraphs 36-38, wherein the antibody increases the level of IL-17a in the brain of the subject.

40) A pharmaceutical composition formulated for the treatment of a neurodevelopmental disease, the pharmaceutical composition comprising:

a. an agent that increases the level or activity of IL-17a in the brain of a subject; and b. a pharmaceutically acceptable carrier.

41) The pharmaceutical composition of paragraph 40, wherein the agent is selected from the group consisting of a small molecule, an antibody reagent, a peptide, a genome editing system, a vector, and a nucleic acid.

42) The pharmaceutical composition of any of paragraphs 40-41, wherein the agent is an anti-CD3 antibody reagent.

43) The pharmaceutical composition of any of paragraphs 40-42, wherein the agent is a microorganism or group of microorganisms.

44) The pharmaceutical composition of any of paragraphs 40-43, wherein the pharmaceutical composition increases the population of T helper-17 cells (Th17) in the gut of the subject.

45) The pharmaceutical composition of any of paragraphs 40-44, wherein the microorganism or group of microorganisms comprises at least one commensal bacteria.

46) The pharmaceutical composition of any of paragraphs 40-45, wherein the microorganism is genetically engineered.

47) The pharmaceutical composition of any of paragraphs 40-46, wherein the pharmaceutical composition is formulated to restrict delivery of the agent to the gastrointestinal tract.

48) The pharmaceutical composition of any of paragraphs 40-47, further comprising an enteric coating.

All patents and other publications identified are expressly incorporated herein by reference for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The present invention is further illustrated by the following Examples, which in no way should be construed as further limiting.

Examples

Example 1: Inflammation Restores Sociability in a Mouse Model of Neurodevelopmental Disorders

SUMMARY

The beneficial effects of infection and ensuing inflammation on neurological disorders have been noted throughout history[1]. For example, a subset of human children with autism spectrum disorder (ASD) exhibit temporary but significant improvement of their behavioral symptoms during episodes of fever, a sign of systemic inflammation[2,3]. Here the molecular and neural mechanisms that underlie the beneficial effects of inflammation on abnormal social behavior were elucidated. A mouse model of neurodevelopmental disorders was used in which offspring were exposed to maternal immune activation (MIA) during embryogenesis, resulting in behavioral abnormalities, including deficits in sociability[4]. It is demonstrated that social behavior deficits can be temporarily rescued upon administration of lipopolysaccharide (LPS), which induces inflammatory responses[5]. At the neural level, LPS-induced behavioral rescue was accompanied by a reduction in neural activity in the dysgranular zone of the primary somatosensory cortex (S1DZ). S1DZ hyperactivity was previously implicated in the manifestation of MIA behavioral phenotypes[6]. At the molecular level, LPS increased plasma levels of inflammatory cytokines, such as interleukin-17a (IL-17a) and interferon-gamma (IFNγ), both of which are required for the LPS-dependent rescue of abnormal social behavior. More specifically, it was demonstrated that circulating IFNγ is required for the LPS-induced increase in blood brain-barrier (BBB) permeability, allowing IL-17a to act directly upon the S1DZ. Delivery of exogenous IL-17a in the S1DZ rescued sociability deficits, while abrogating expression of the IL-17 receptor subunit a (IL-17Ra) in S1DZ eliminated the ability of LPS to reverse the sociability phenotype. Lastly, it was shown that LPS-induced rescue in MIA offspring is dependent on the presence of gut bacteria that promote biogenesis of Th17 cells, a peripheral source of IL-17a. The data suggest a novel mechanism whereby the gut microbiota-dependent production of peripherally-induced cytokines can modulate the expression of neurodevelopmental disorders by affecting the activity in the central nervous system.

Introduction and Results

Figure 1A:
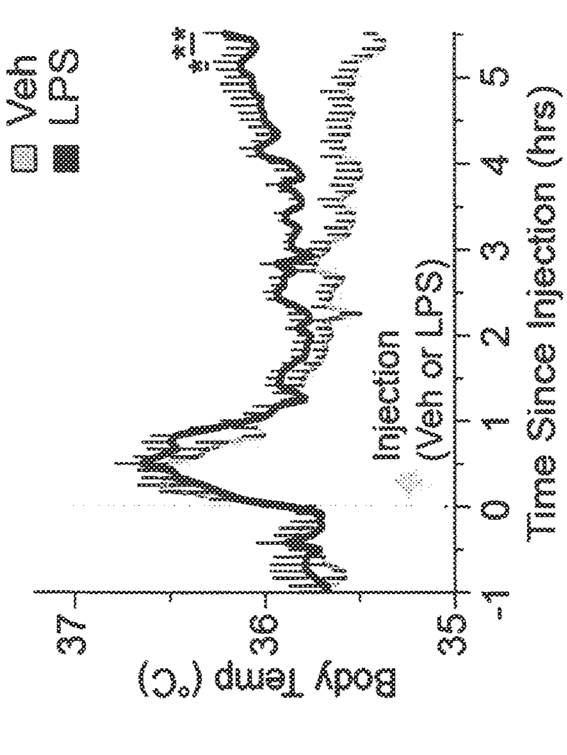
FIG. 1A-1F demonstrate that LPS injection rescues sociability deficits in MIA offspring.
Figure 1B:
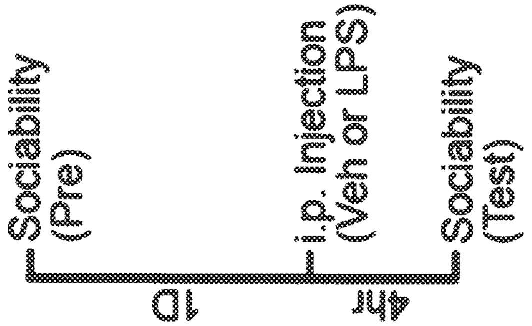
Figure 1C:
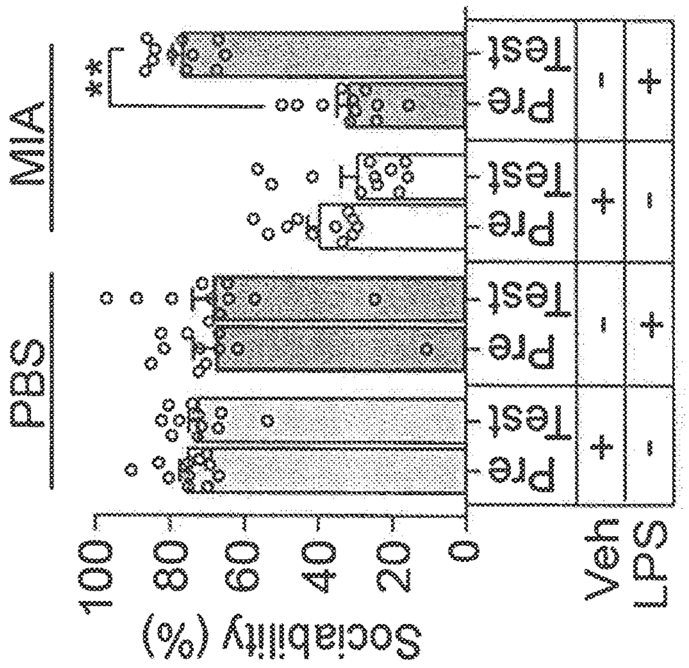
Figure 5B:
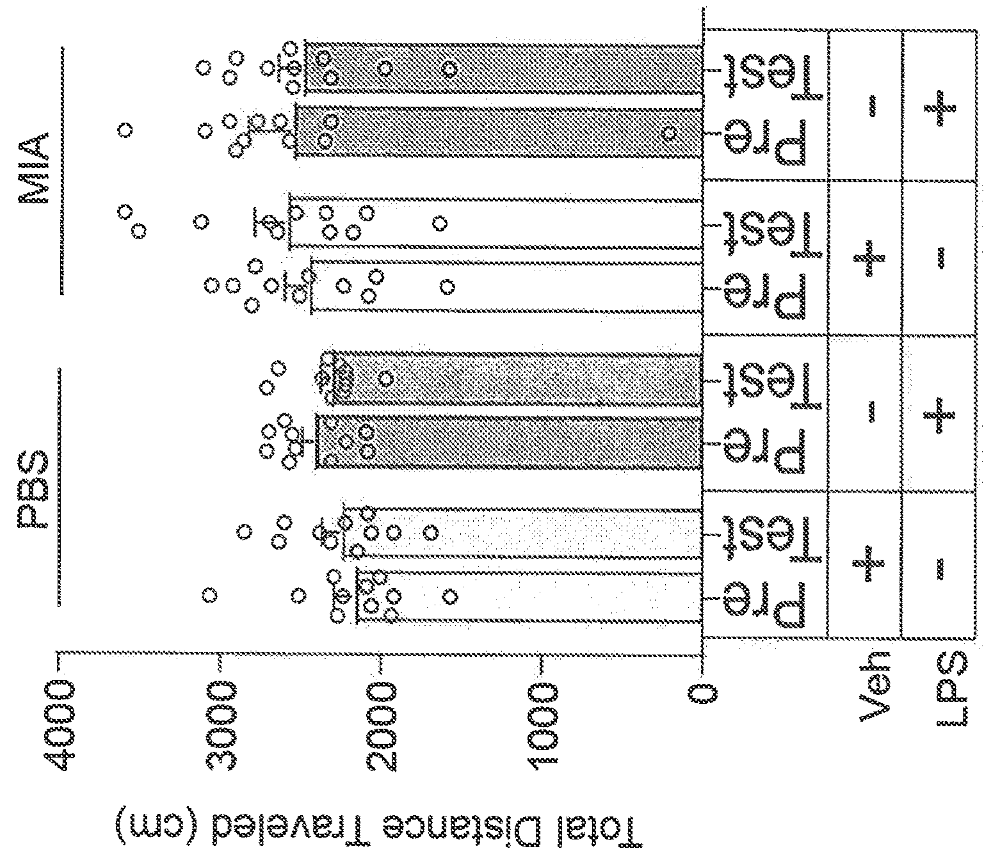
FIG. 5A-5B shows total interaction time (FIG. 5A) and total distance traveled (FIG. 5B) during the sociability assay for offspring described in FIG. 1C (n=11 for all groups; from 3 independent experiments).
Figure 5A:
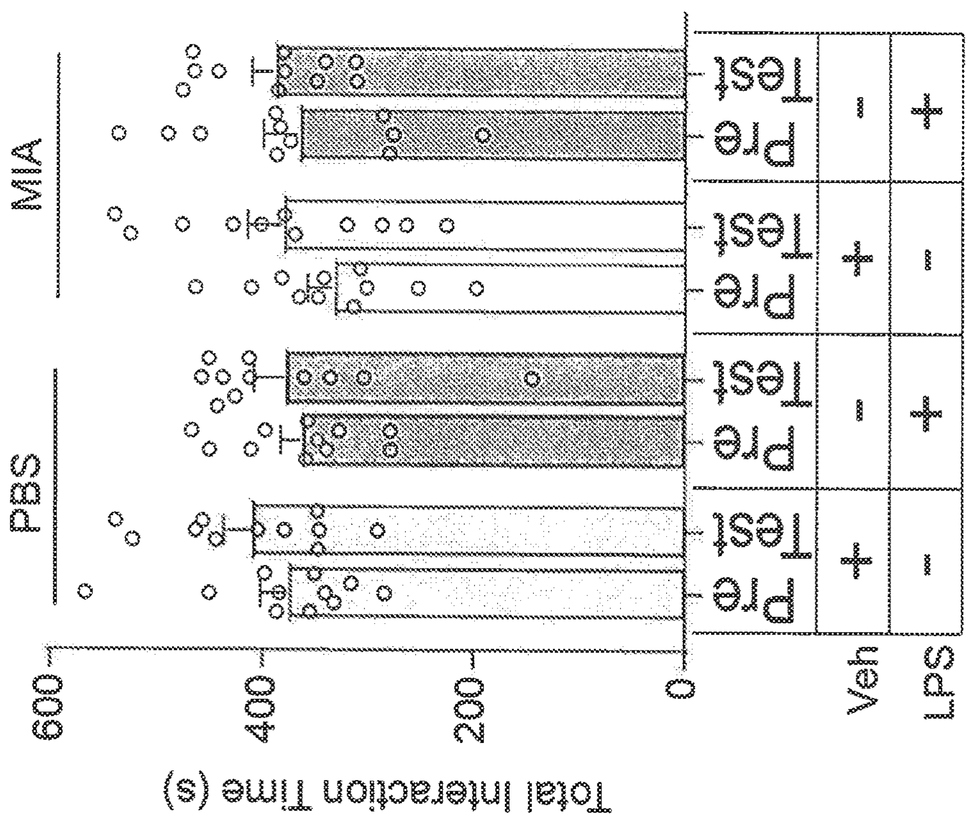
Figure 5C:
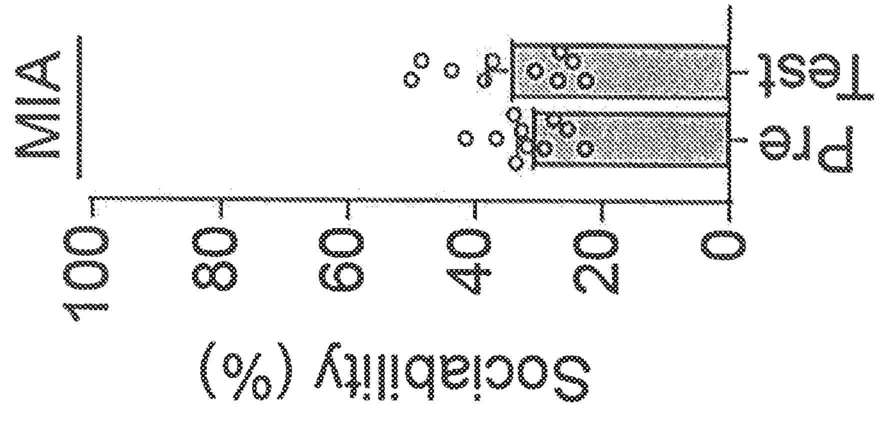
FIG. 5C-5E shows performance on sociability (FIG. 5C), total interaction time (FIG. 5D), and total distance traveled (FIG. 5E) one day prior to and 72 hrs after LPS injection in MIA offspring (n=10 for all groups, from 2 independent experiments). Data analyzed using three-way repeated measures ANOVA (FIGS. 5A-5B) and paired two-tailed t-test (FIGS. 5C-5E). Graphs indicate mean±s.e.m.
Figure 5D:
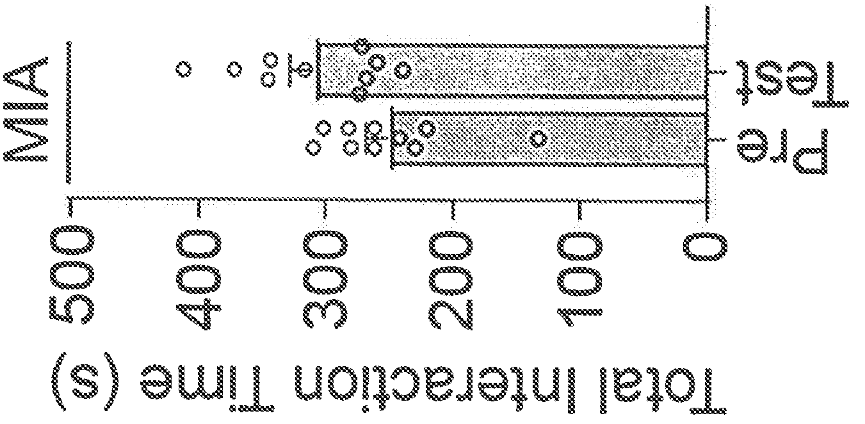
Figure 5E:
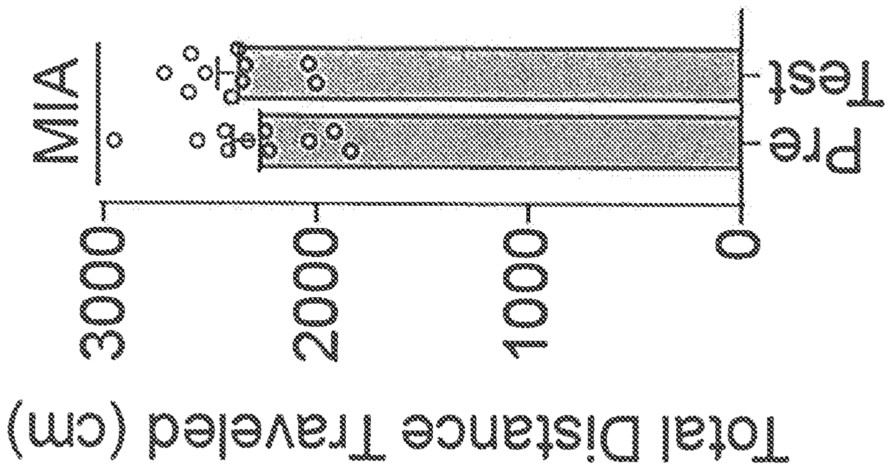
Figure 6A:
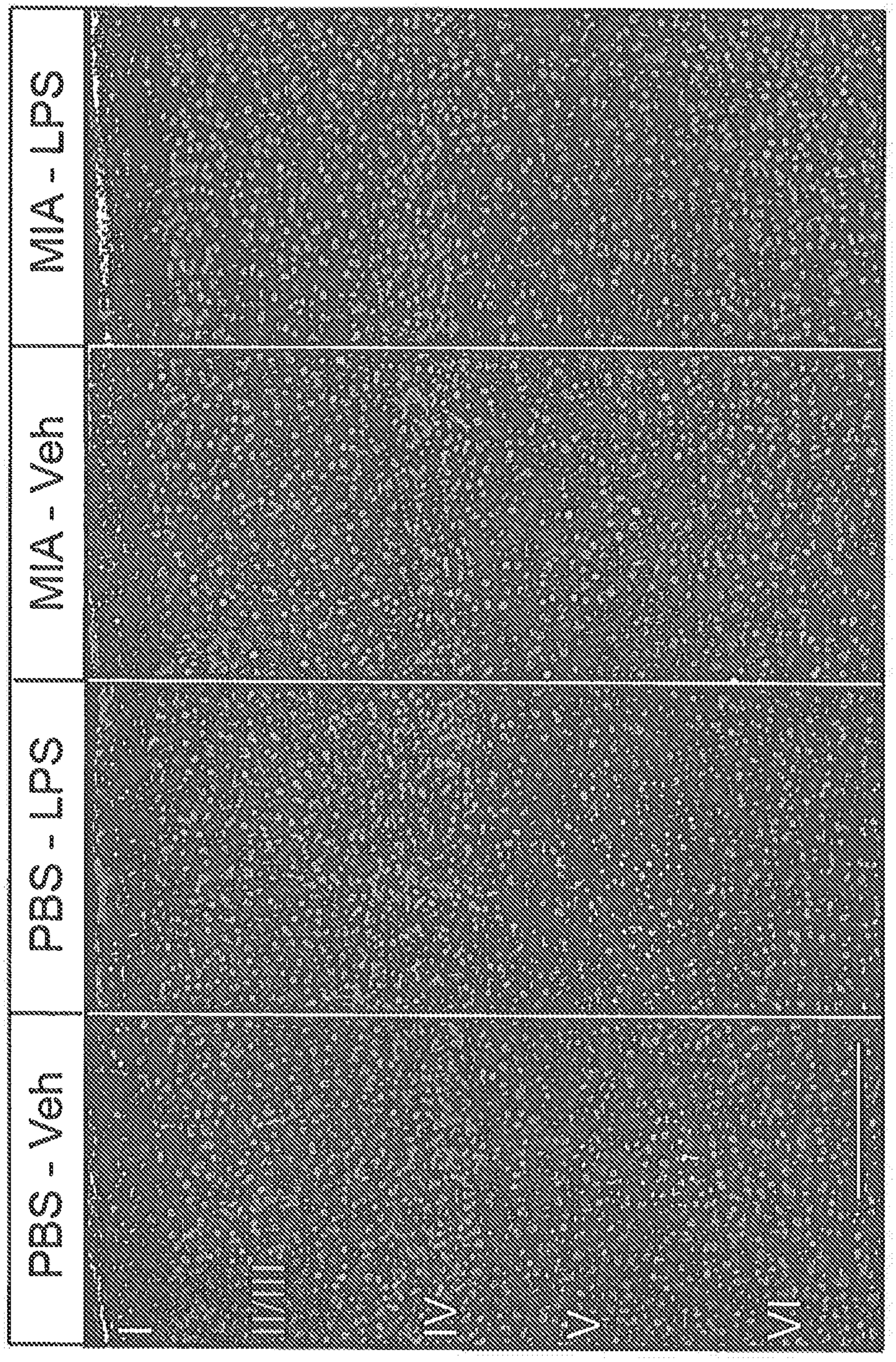
FIG. 6A-6C shows LPS-induced c-Fos expression in PBS and MIA offspring. Representative images illustrating c-Fos expression in a series of cortical regions and the central amygdala following Veh or LPS injection in PBS or MIA offspring. Sections are stained for c-Fos and DAPI. Images in FIG. 6A-6B are the same as those in FIG. 1D with entire cortical depth shown. Scale bar represents 200 μm. S1BF, Primary somatosensory cortex, barrel field; M1, Primary motor cortex; M2, Secondary motor cortex; mPFC, medial prefrontal cortex (PrL, IL); AuD, Primary auditory cortex; V1, Primary visual cortex; CeA, Central amygdala.
Figure 6B:
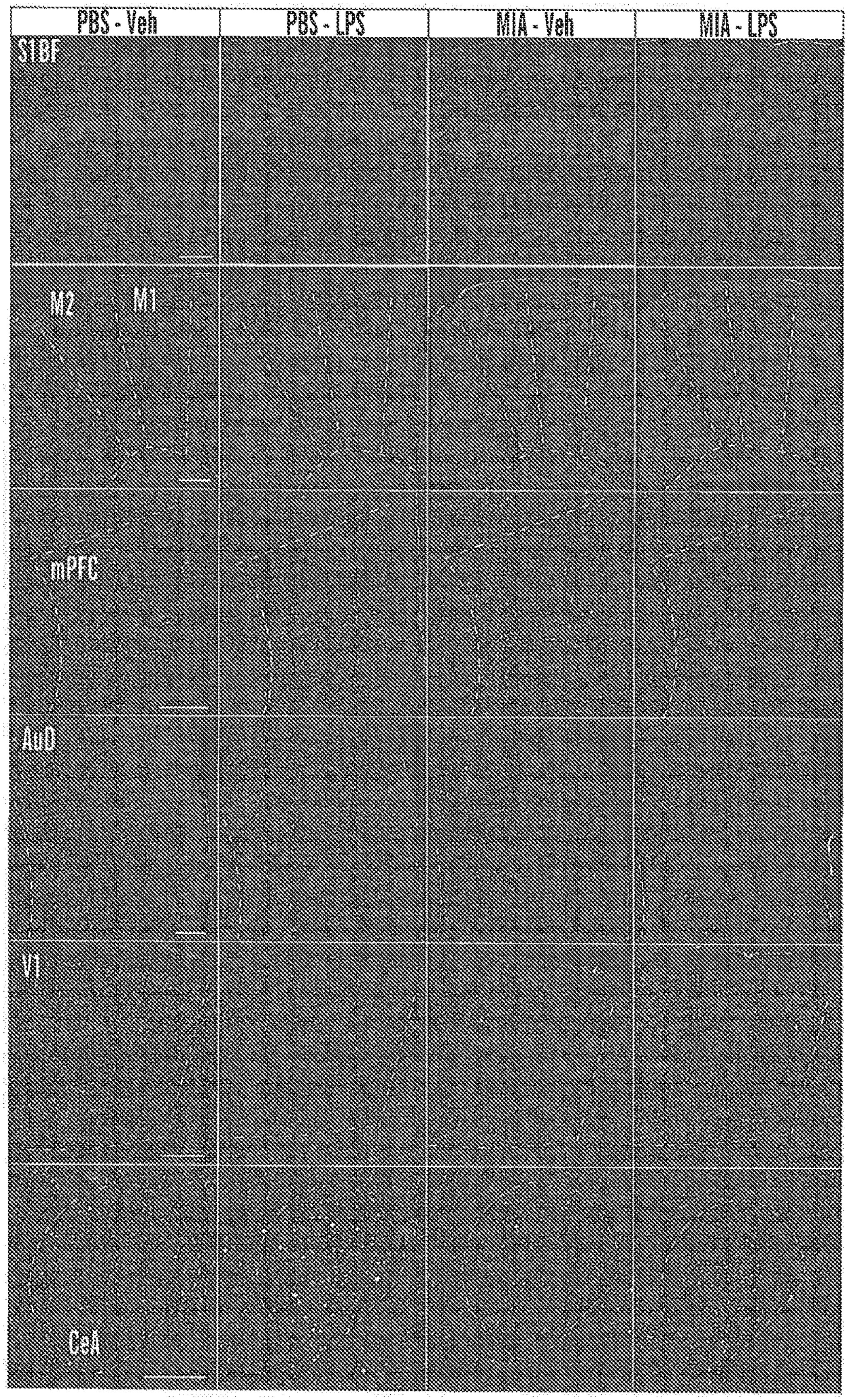
Figure 6C:
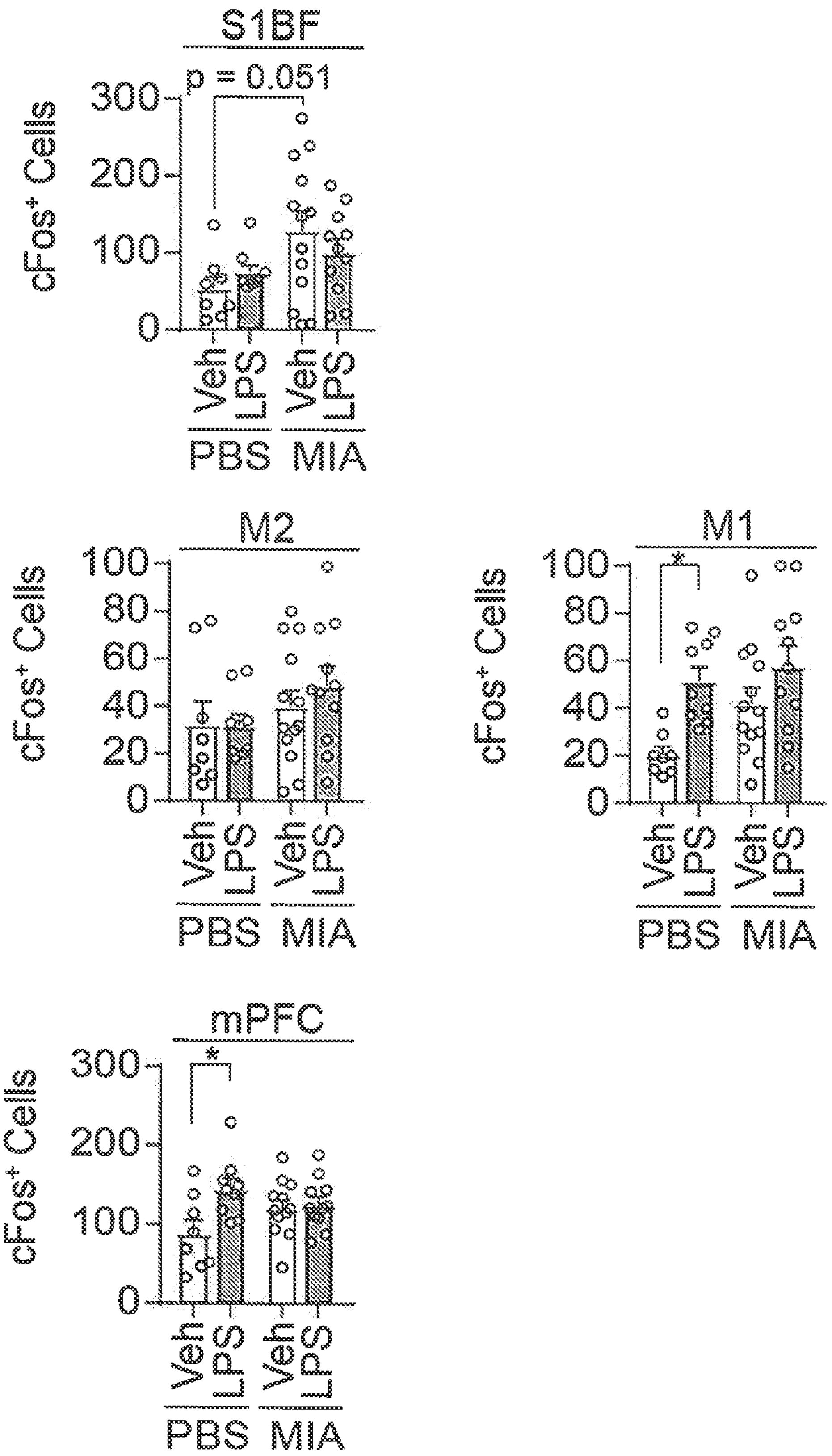
Figure 6C:
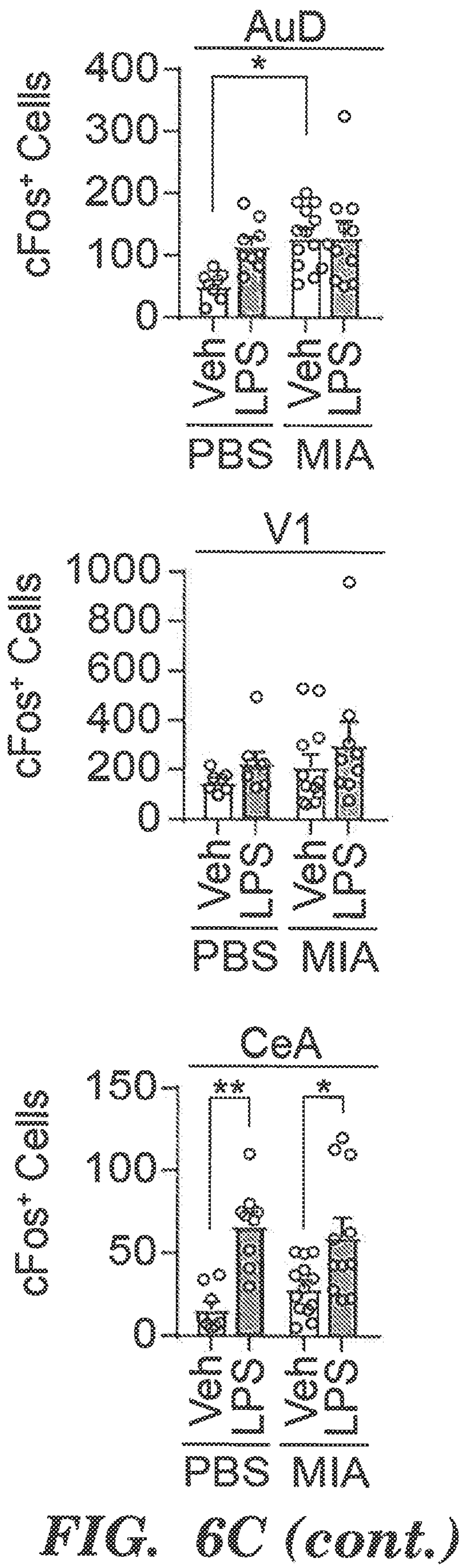

In humans, a surprising respite for children with ASD is apparent during episodes of fever, a symptom of systemic inflammation. This phenomenon has been appreciated by parents of ASD children as well as doctors for decades[7]. More recent clinical studies confirmed that the core symptoms of ASD improve during the course of fever[2,3]. A mechanistic understanding of how fever-associated immune responses translate into behavioral improvements both at the molecular and neural circuit-level is still lacking. It was first sought to determine whether the MIA mouse model is a suitable system to explore the mechanisms that allow for inflammation-associated behavioral rescue of impaired sociability[4,8] (defined as the natural inclination toward social objects). A low dose of LPS produces febrile responses without marked changes in locomotor activity[9]. Indeed, following a handling-induced temperature spike (0-1 hrs), intraperitoneal (i.p.) LPS administration at a low dose (50 μg/kg) in control animals—offspring born to mothers injected with PBS (PBS offspring)—led to an increase in body temperature of ~0.5-1.0 0C, ~4-5 hours after the treatment (FIG. 1A). To investigate whether LPS injection induces changes in social behavior, the sociability in adult male offspring was assessed a day before LPS injection (pretest, Pre) and 4 hours after injection (Test), when the increase in body temperature initiates (FIG. 1B). Unlike vehicle treatment, LPS injection in MIA offspring born to mothers injected with Poly(I:C) (polyinosinic: polycytidylic acid) robustly rescued their characteristic deficit in sociability; these animals display an interest in social objects indistinguishable from controls (FIG. 1C). Neither vehicle nor LPS injection affected baseline sociability in PBS offspring, and MIA offspring injected with LPS did not display changes in overall activity, measured as total investigation time and total distance traveled, when compared to vehicle-treated groups (FIG. 5A-B). Furthermore, the behavioral rescue was absent 72 hours following LPS treatment, paralleling the transient nature of fever-associated improvement observed in ASD children[2] (FIG. 5C-E).

Figure 1D:
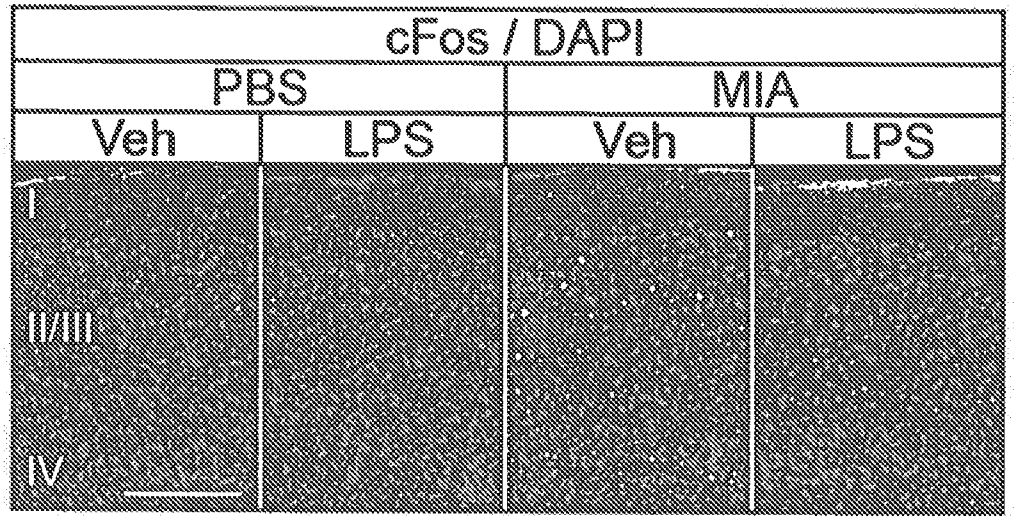
Figure 1E:
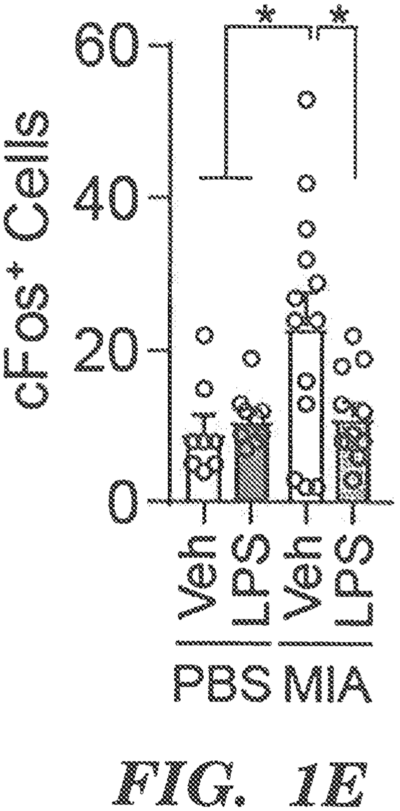
Figure 1F:
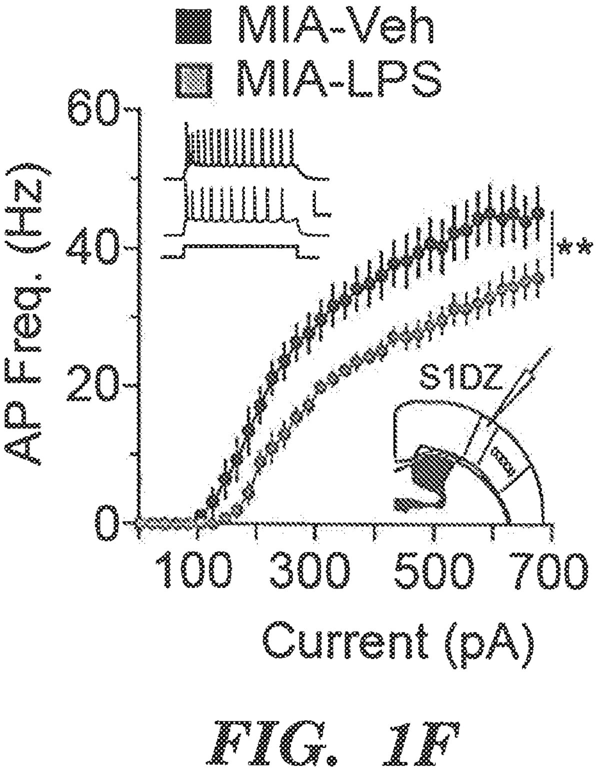

It was previously demonstrated that adult MIA offspring display cortical abnormalities in S1DZ accompanied by an overall increase in neural activity. Suppressing this increase in neural activity can temporarily rescue MIA-induced deficits in social behaviors[6]. Therefore, it was investigated whether LPS-induced behavioral rescue is characterized by changes in neural activity in MIA offspring. MIA offspring exhibited an increase in the number of S1DZ neurons expressing c-Fos, a marker for neuronal activation, relative to PBS offspring. However, in LPS-treated MIA offspring, the number of c-Fos+S1DZ neurons was indistinguishable from that of PBS offspring (FIG. 1D, 1E). LPS injections did not have a generalizable, brain-wide effect on c-Fos expression in the MIA offspring; the number of c-Fos-expressing neurons either remained unchanged, as in other cortical regions examined, or increased, as in the central amygdala (CeA), a region known to be activated by LPS10 (FIG. 6). Whole-cell patch-clamp recordings in MIA offspring demonstrate that the LPS-induced reduction in c-Fos expression is paralleled by changes in the functional input-output relationship of S1DZ pyramidal neurons. Neurons from LPS-injected animals exhibited reduced spiking in response to depolarizing current injections (FIG. 1F). These results indicate that intraperitoneal i.p. injection of LPS reduces S1DZ neural activity, contributing to the rescue of sociability deficits in MIA offspring.

Figure 2A:
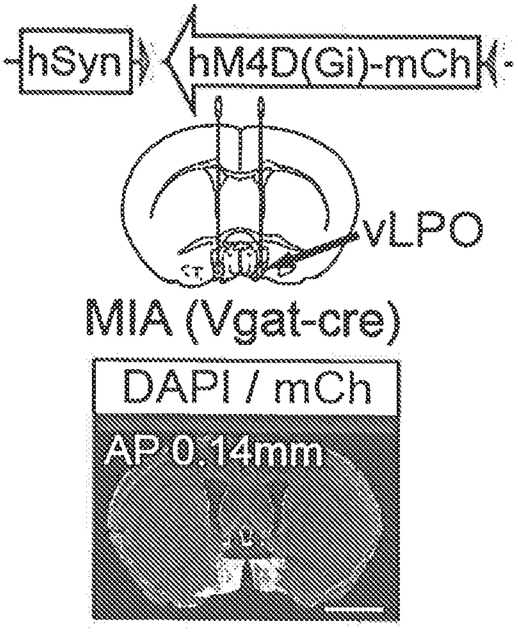
FIG. 2A-2E shows cytokine induction is necessary for LPS-induced rescue of MIA sociability deficits.
Figure 2B:
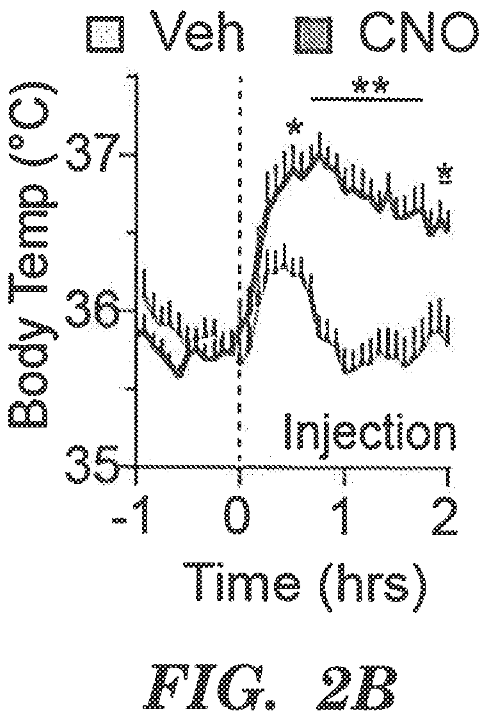
Figure 2C:
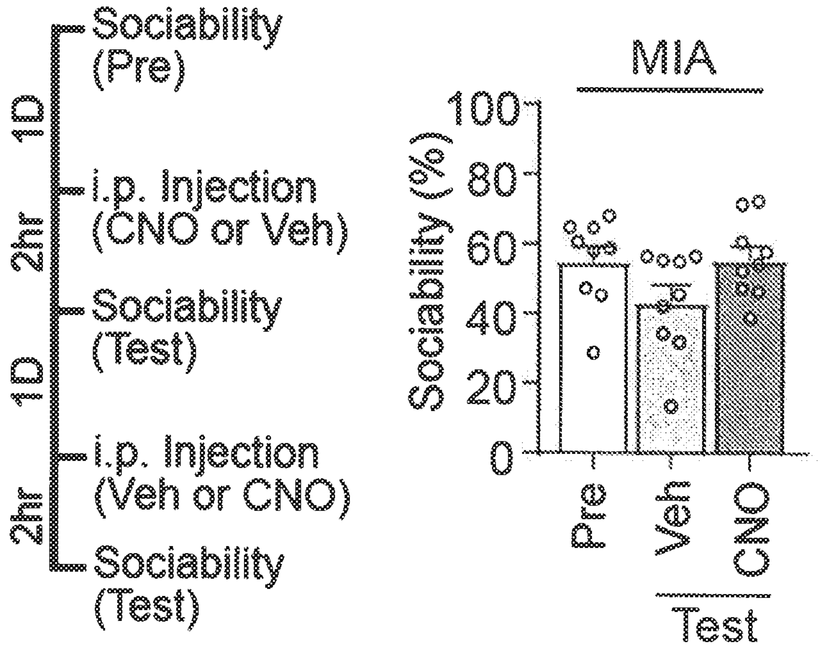
Figure 7A:
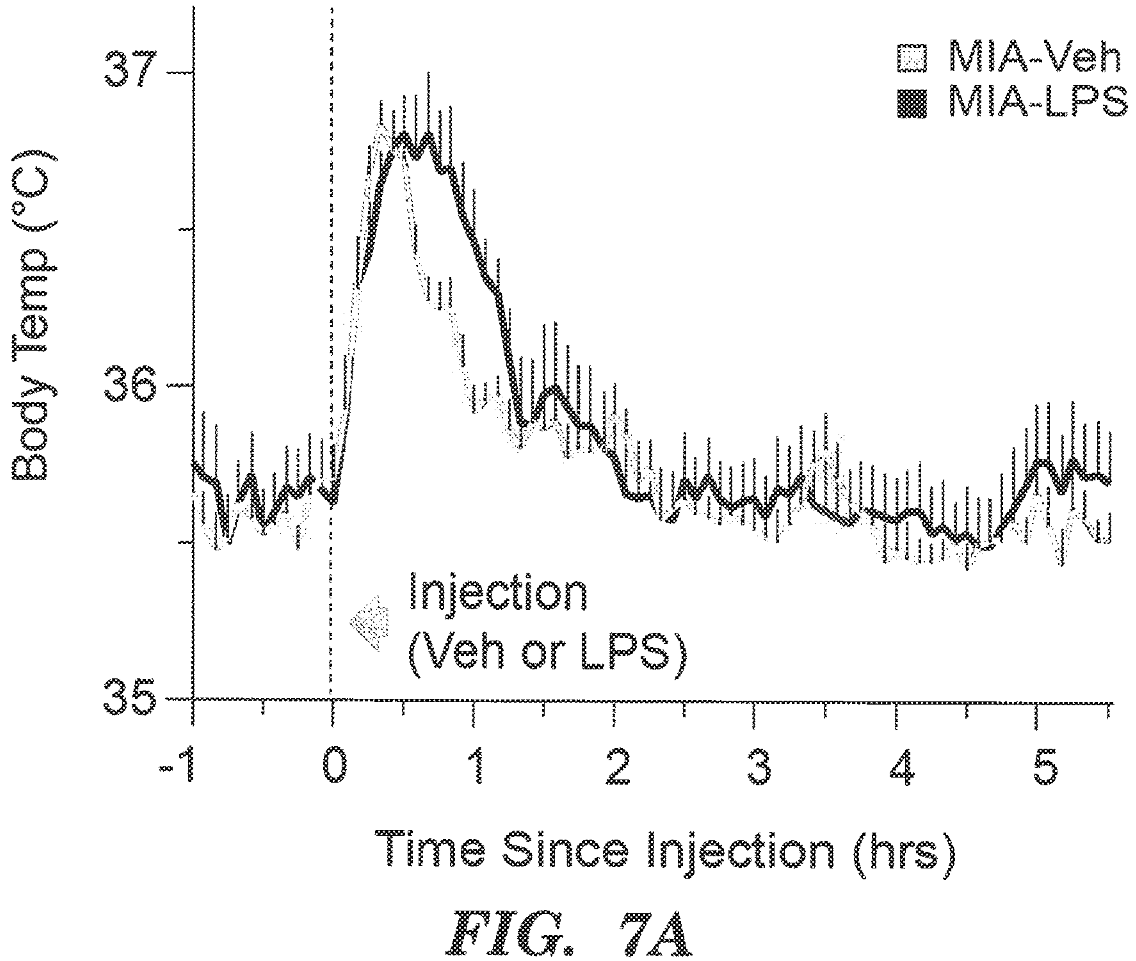
FIG. 7A shows body temperature profile following Veh or LPS injection in MIA-offspring (MIA-Veh n=10, MIA-LPS n=10; from 5 independent experiments).
Figure 7B:
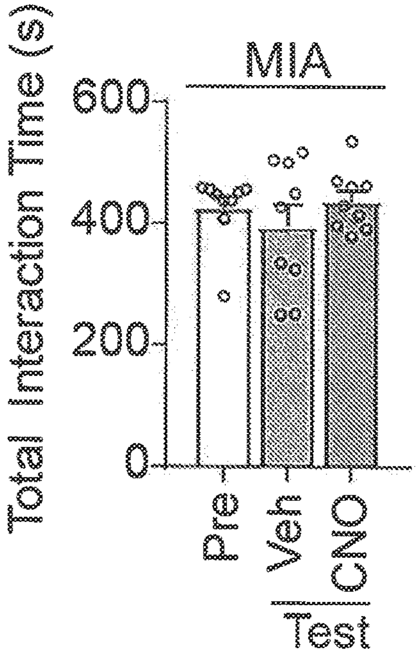
FIG. 7B-7C shows total interaction time (FIG. 7B) and total distance traveled (FIG. 7C) during the sociability assay for offspring described in FIG. 2C. (n=9 for all groups; from 2 independent experiments). Data analyzed by two-way repeated measures ANOVA (FIG. 7A) and one-way repeated measures ANOVA (FIG. 7B-7C). Graphs indicate mean±s.e.m.
Figure 7C:
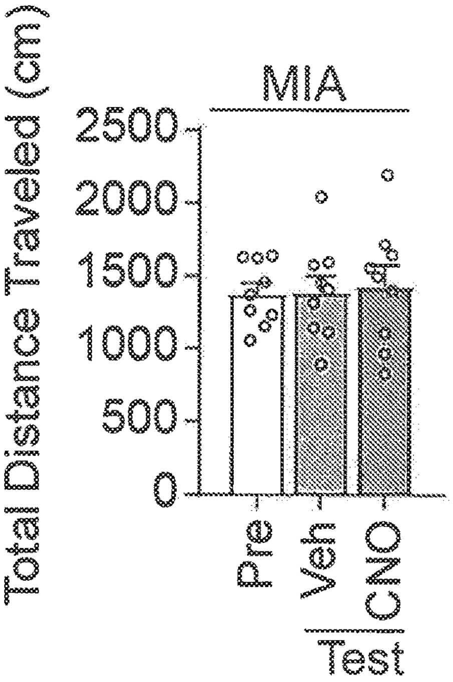

Next, the molecular mechanisms underlying the LPS-dependent behavioral rescue of sociability were explored. Unlike in PBS offspring, LPS treatment failed to induce changes in body temperature in MIA animals (FIG. 7A), suggesting that the febrile response might not be the main factor contributing to the rescue. To confirm this notion, it was sought to increase the animals' body temperature without inducing systemic inflammation. Inhibitory DREADDs[11] (designer receptors exclusively activated by designer drugs) were targeted to GABAergic neurons in the ventral part of the lateral preoptic nucleus (vLPO), using a Vgat-Cre transgenic mouse line[12] (FIG. 2A). As previously reported[13], inhibition of these neurons led to a robust increase in body temperature of ~1° C. (FIG. 2B). This febrile response, however, failed to restore social preference in MIA offspring (FIG. 2C, and FIG. 7B-7C), suggesting that fever per se does not drive the LPS-induced rescue of sociability deficits.

Figure 8A:
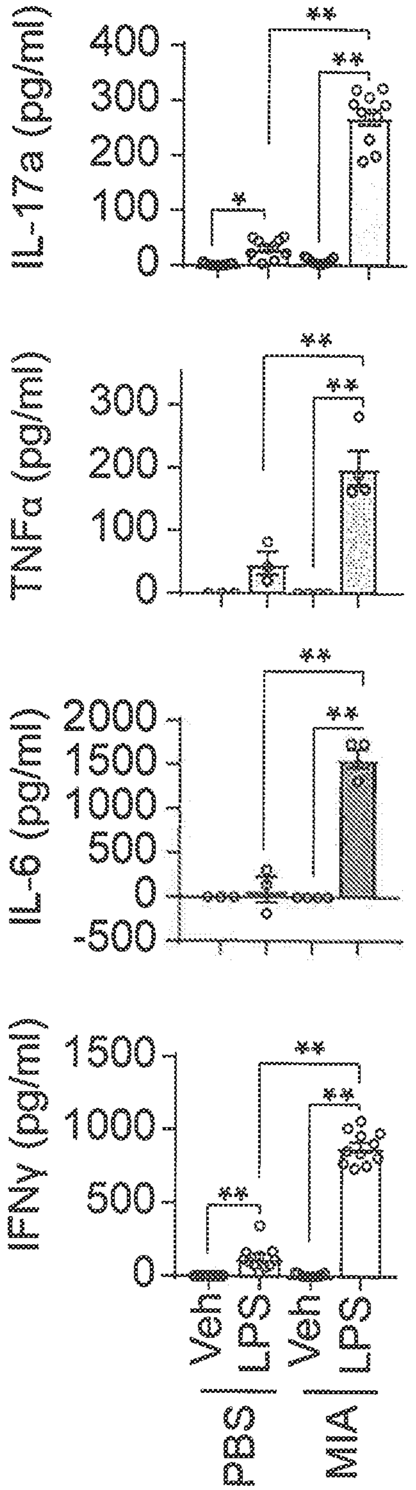
FIG. 8A demonstrates induction of cytokine following Veh or LPS injection in PBS and MIA offspring (For IFNγ and IL-17a; n=11 for all groups; from 3 independent experiments, For IL-6; PBS-Veh n=3, PBS-LPS n=3, MIA-Veh n=4, MIA-LPS n=4; from 1 experiment, For TNFα; PBS-Veh n=3, PBS-LPS n=3, MIA-Veh n=4, MIA-LPS n=4; from 1 experiment).
Figure 8B:
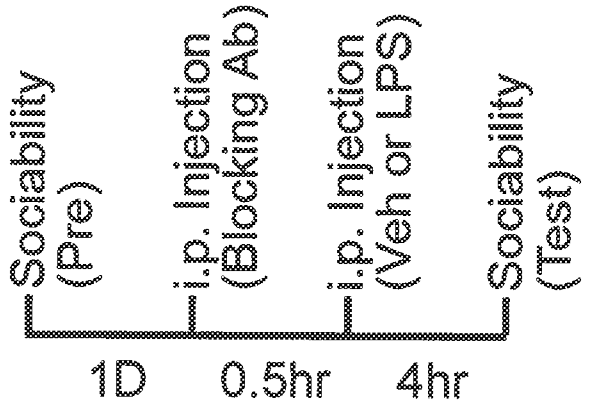
FIG. 8B shows that mice were tested for sociability one day prior to injections (Pre). The following day, mice were injected with blocking antibody or isotype control antibody 30 min before Veh or LPS injection. Four hours after Veh or LPS injection, sociability was assessed (Test).
Figure 8C:
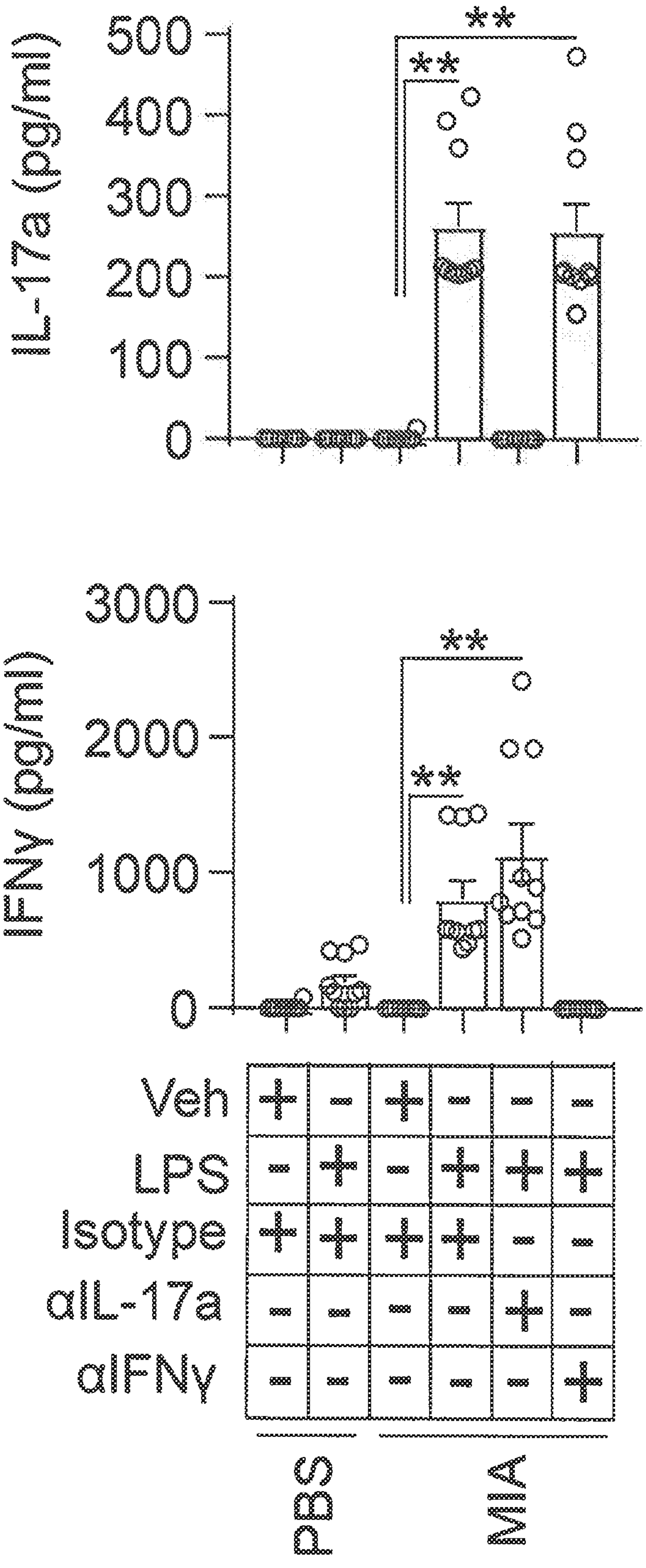
FIG. 8C shows cytokine induction following administration of blocking or isotype control antibody 30 min before Veh or LPS injection in PBS and MIA offspring (n=10 for all groups; from 3 independent experiments).
Figure 8D:
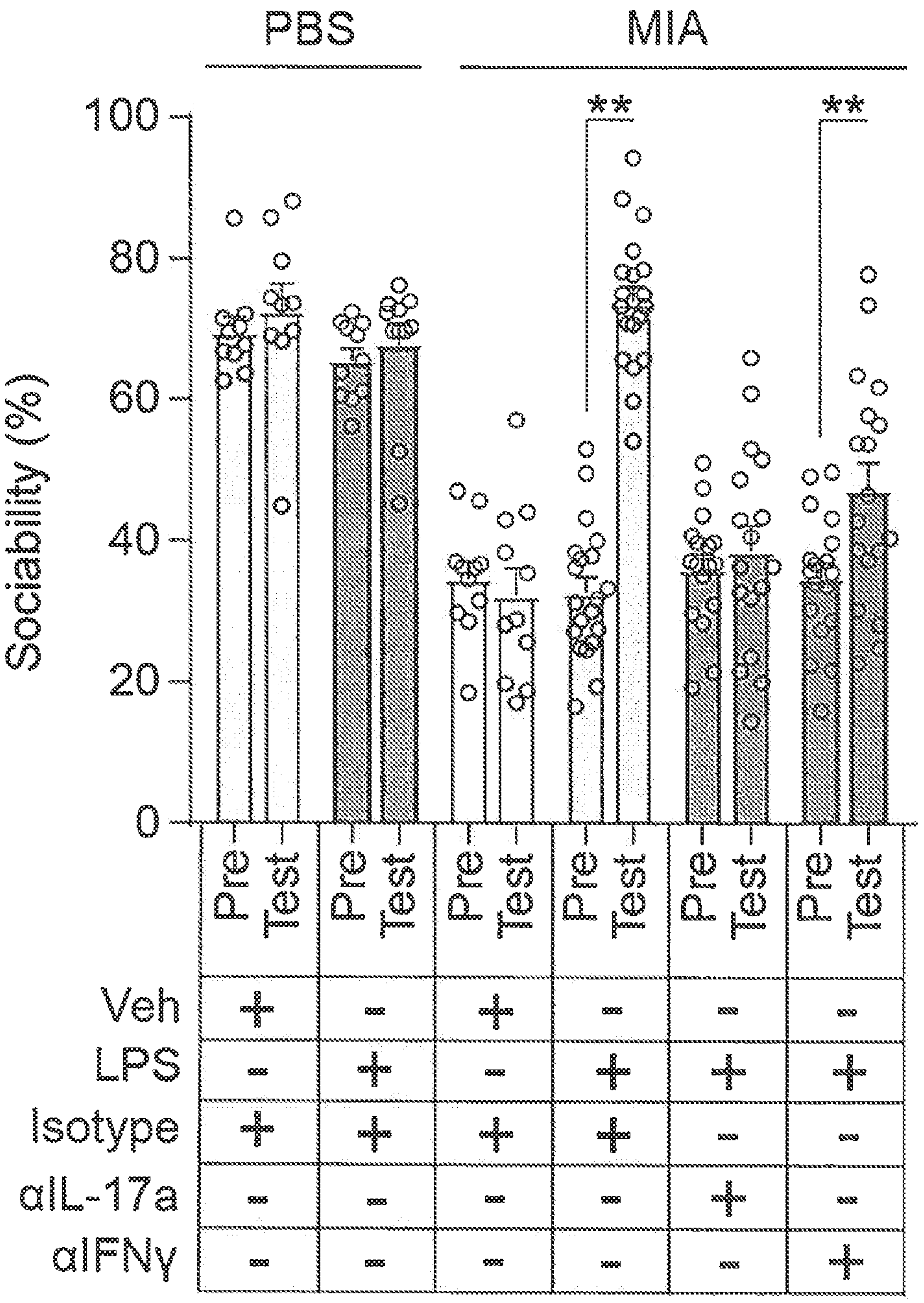
FIG. 8D-8F shows the performance on sociability (FIG. 8D), total interaction time (FIG. 8E), and total distance traveled (FIG. 8F) for mice described in (FIG. 8B) (PBS-Veh-Isotype n=10, PBS-LPS-Isotype n=11, MIA-Veh-Isotype n=11, MIA-LPS-Isotype n=20, MIA-LPS-aIL-17a n=17, MIA-LPS-aIFNγ n=18; from 3 independent experiments). *p<0.05, **p<0.01 as calculated by two-way ANOVA with Tukey's post-hoc test (FIG. 8A), one-way ANOVA with Tukey's post-hoc test (FIG. 8C), and two-way repeated measures ANOVA with Bonferroni's post-hoc test (FIGS. 8D-8F). Graphs indicate mean±s.e.m.
Figure 8E:
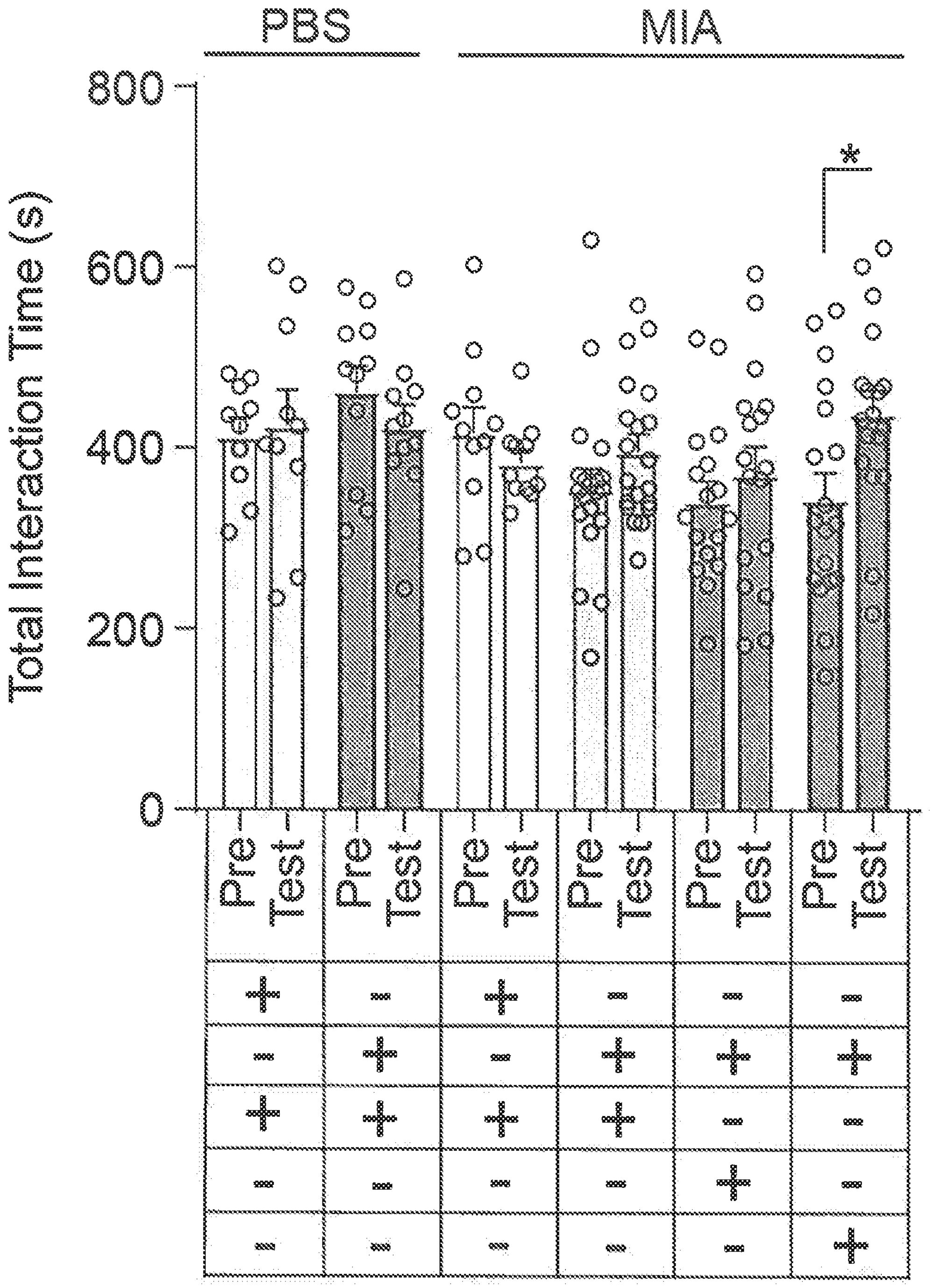
Figure 8F:
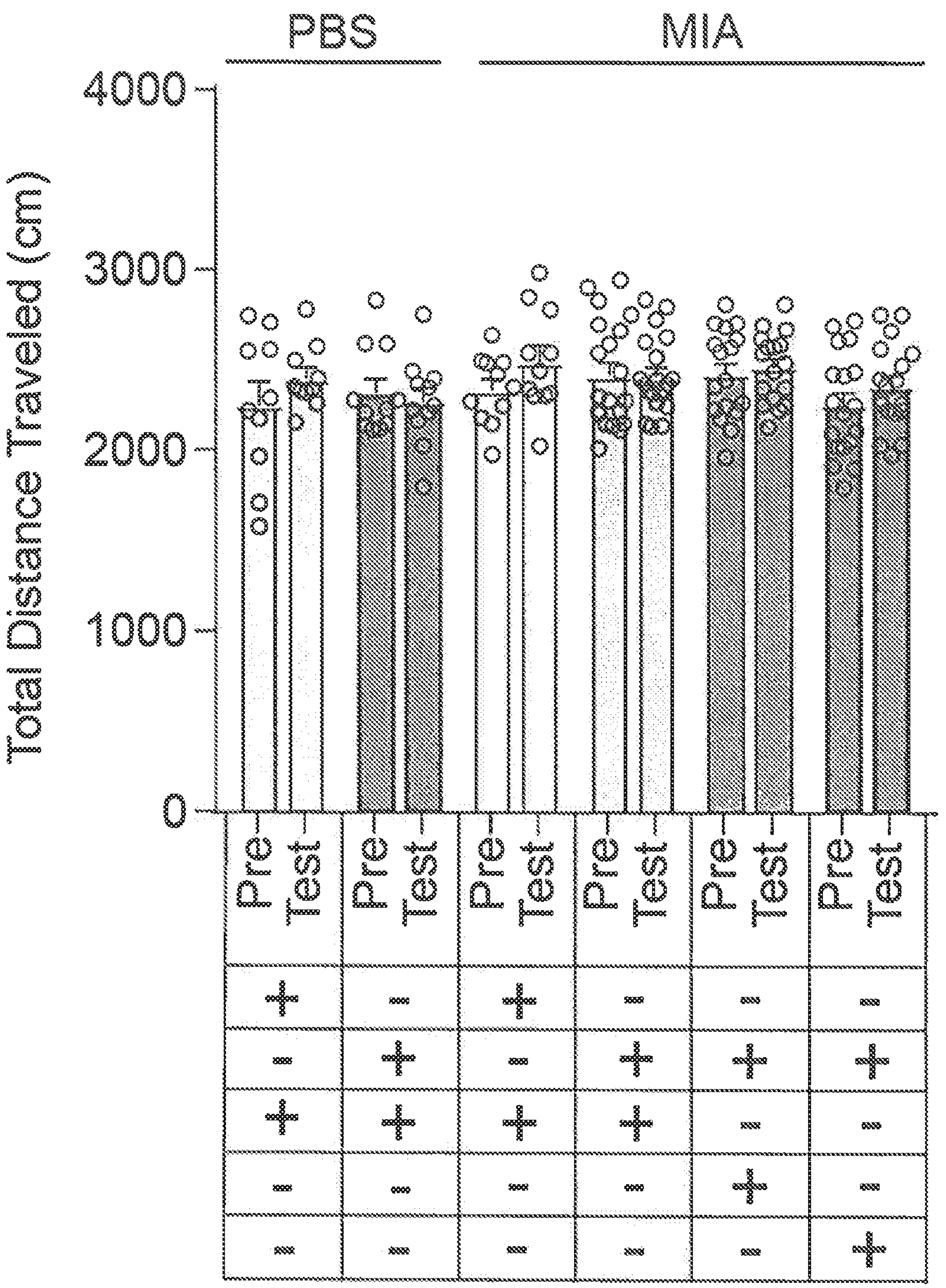

LPS injection also increases production of inflammatory cytokines[14]. A dose of LPS was used that is insufficient to produce high levels of inflammatory cytokines in the plasma of PBS offspring (FIG. 8A). However, consistent with the observation that immune cells in MIA offspring produce elevated amounts of cytokines during an inflammatory insult[15], administration of LPS in MIA offspring resulted in a robust increase in plasma levels of IFNγ, IL-6, TNFα and IL-17a (FIG. 8A). Importantly, both IFNγ in mice[16] and the IL-17 orthologue in *C. elegans*[17] have previously been implicated in promoting social behavior. Therefore, it was assessed whether a systemic increase in IFNγ or IL-17a levels is involved in mediating the behavioral rescue observed in LPS-treated MIA offspring. MIA offspring were pretreated with an i.p. injection of isotype control, IFNγ, or IL-17a blocking antibodies prior to treatment with vehicle or LPS (FIG. 8B). As expected, pretreatment with IFNγ or IL-17a blocking antibody suppressed the LPS-mediated increase in plasma IFNγ or IL-17a levels, respectively (FIG. 8C). Pretreatment with blocking antibodies against either cytokine also prevented the LPS-induced full reversal of sociability deficit in MIA offspring. Of note, a small, yet significant increase in sociability in MIA offspring was observed for the group pretreated with blocking antibody against IFNγ (FIG. 8D-8F).

Figure 2E:
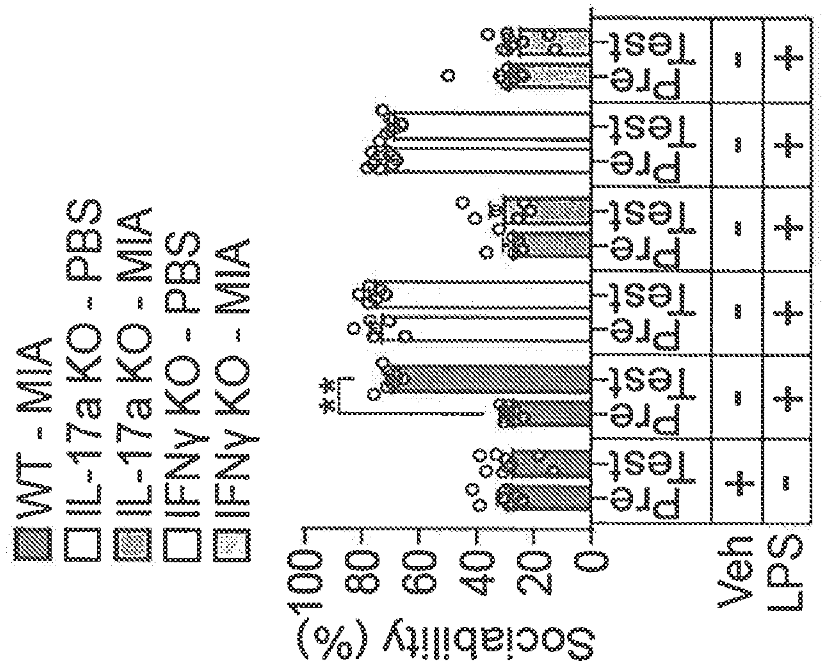
Figure 2D:
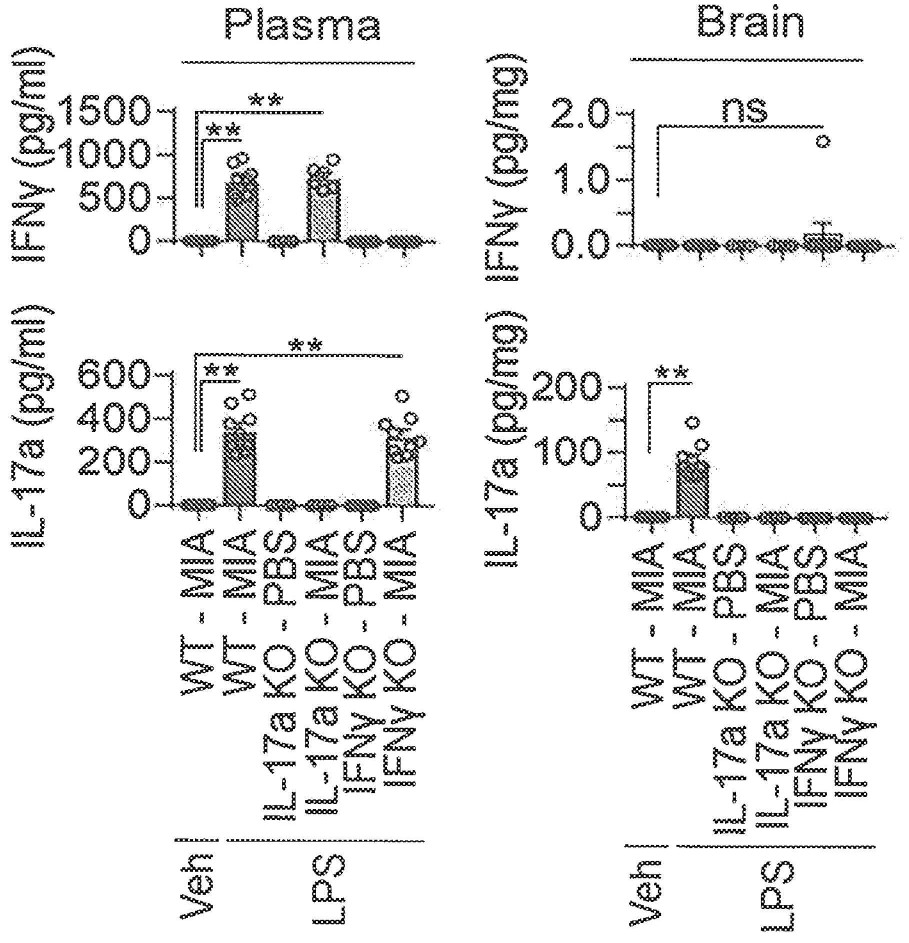
Figure 3A:
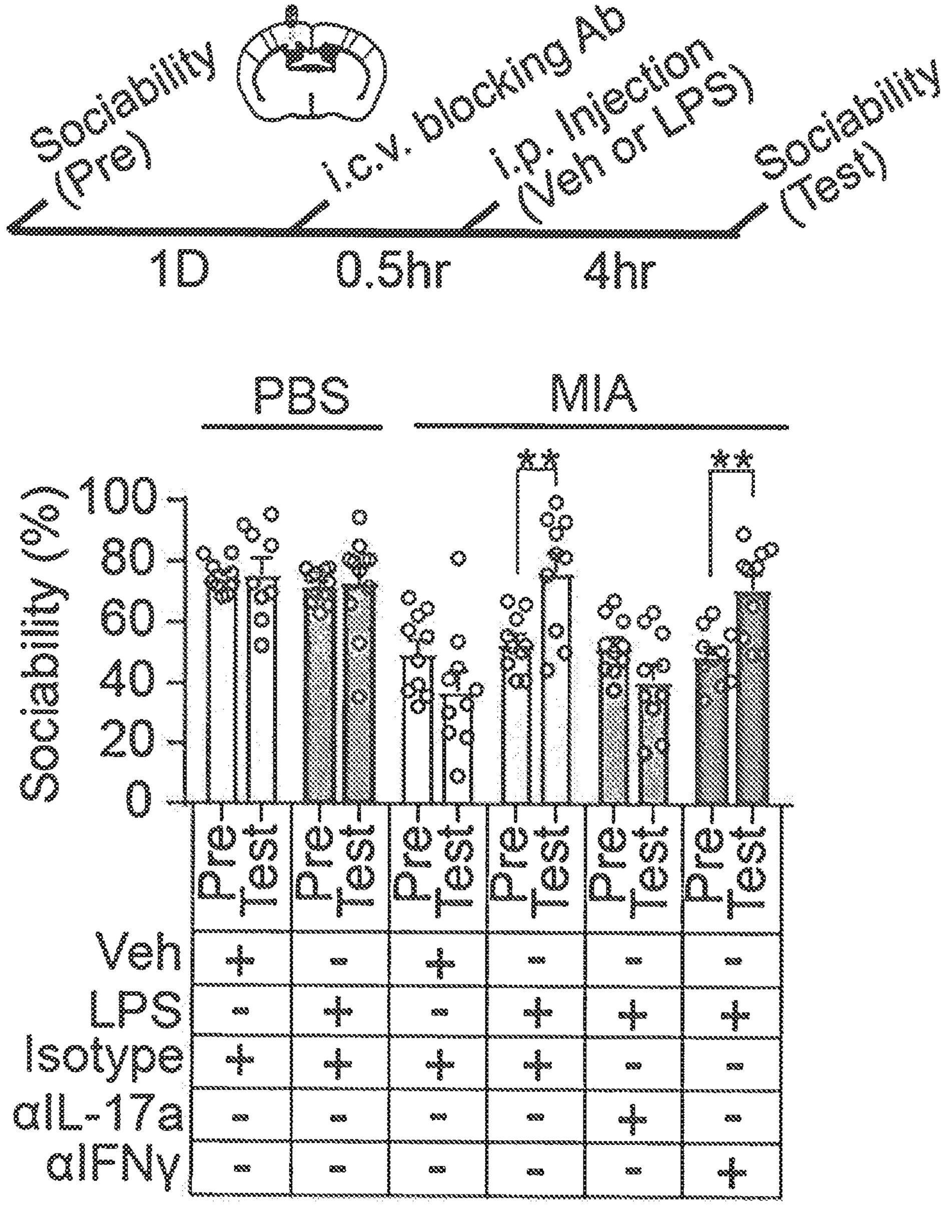
FIG. 3A-3D shows IL-17a is necessary and sufficient to rescue sociability deficits in MIA offspring.
Figure 3B:
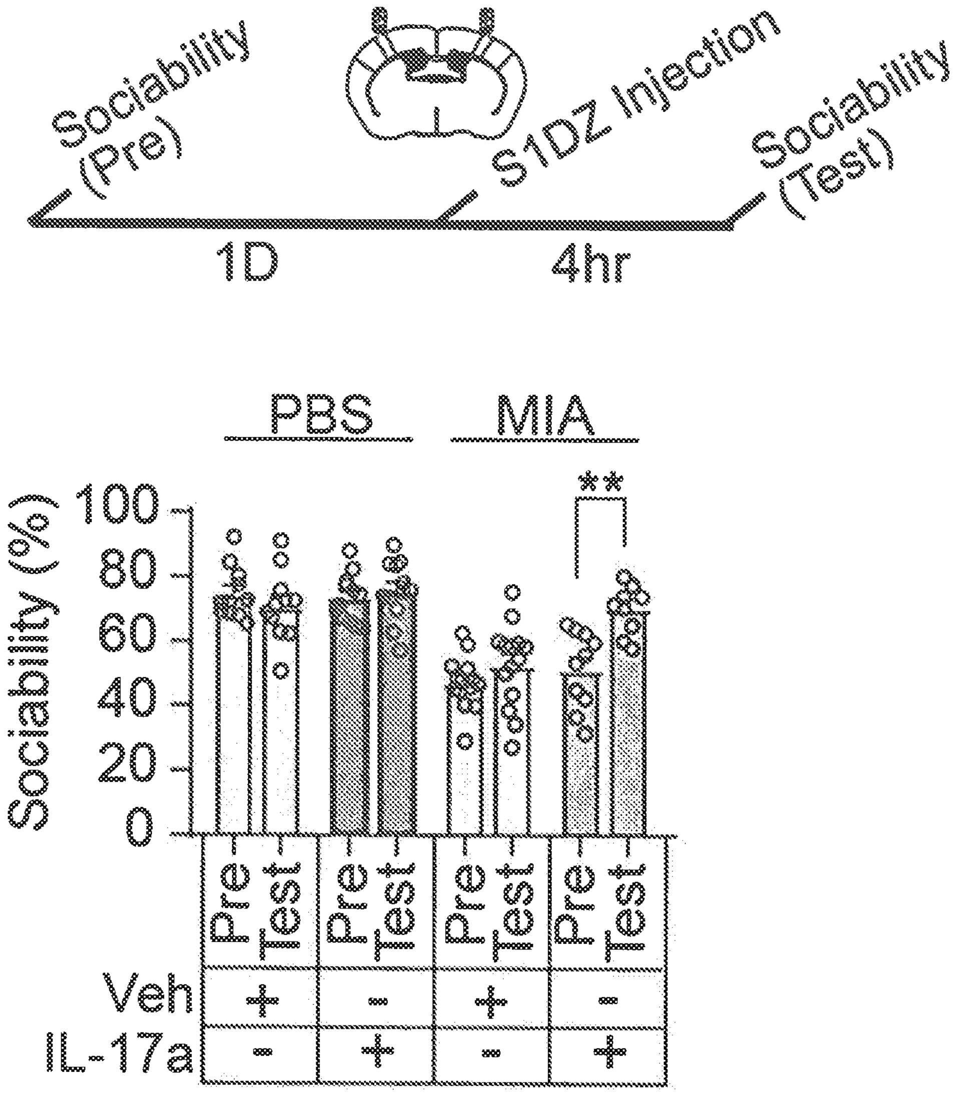
Figure 3C:
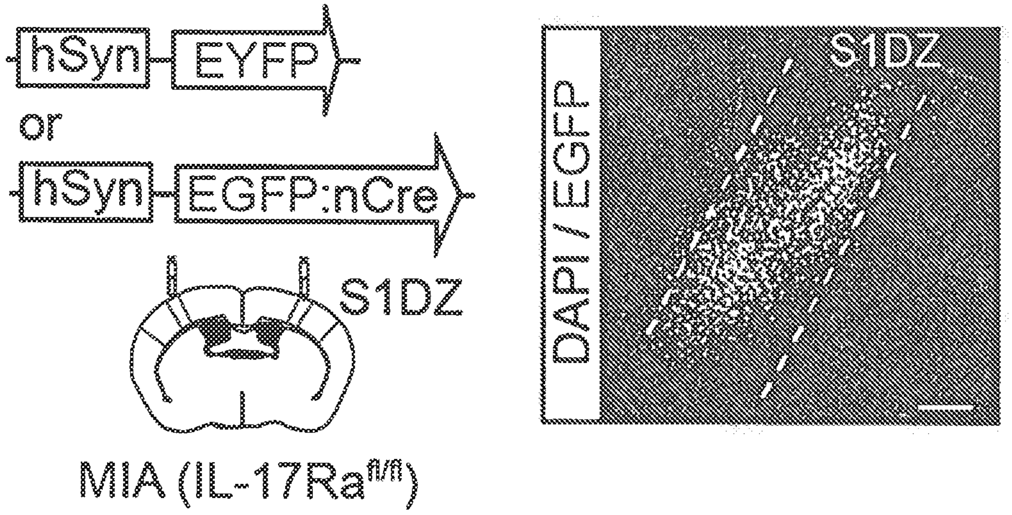
Figure 3D:
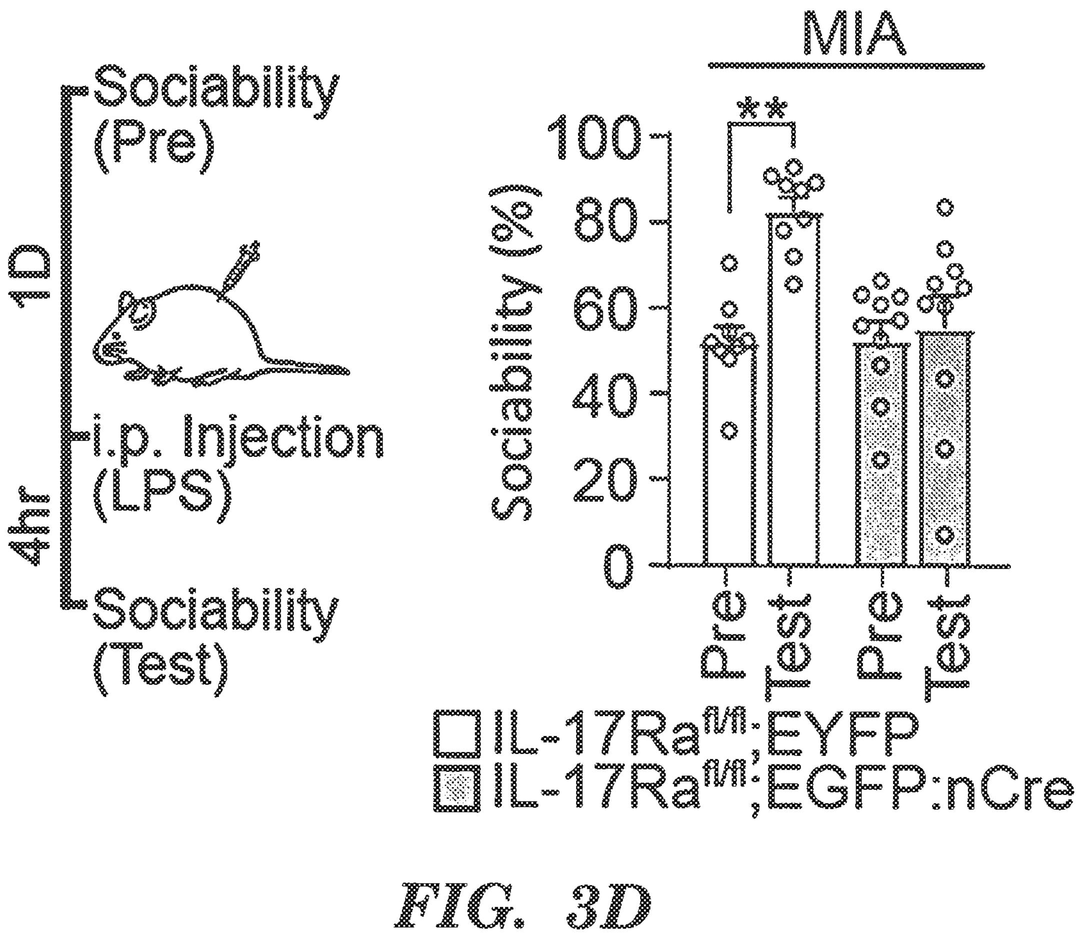
Figure 10A:
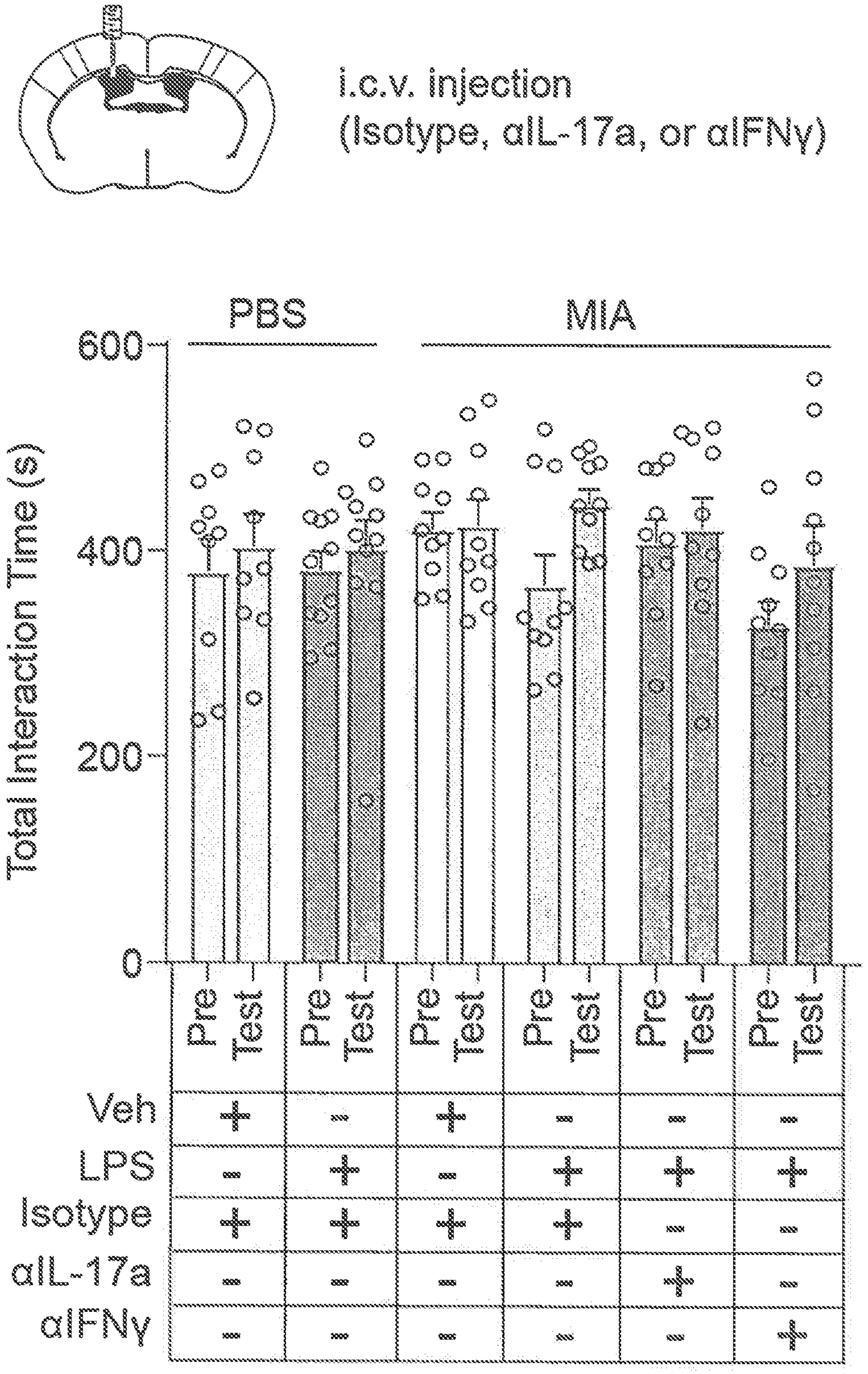
FIGS. 10A-10D shows total interaction time (FIG. 10A, 10C) and distance traveled (FIG. 10B, 10D) during the sociability assay for offspring described in FIG. 3A-3B (For FIG. 10A-10B, PBS-Veh-Isotype n=9, PBS-LPS-Isotype n=11, MIA-Veh-Isotype n=10, MIA-LPS-Isotype n=10, MIA-LPS-aIL-17a n=10, MIA-LPS-aIFNγ n=10; from 7 independent experiments. For FIG. 10C and FIG. 10D, PBS-Veh n=11, PBS-IL-17a n=12, MIA-Veh n=14, MIA-IL-17a n=10; from 9 independent experiments). **p<0.01 as calculated by two-way repeated measures ANOVA with Bonferroni's post-hoc test (FIG. 10A-10B) and three-way repeated measures ANOVA with Bonferroni's post-hoc test (FIG. 10C-10D). Graphs indicate mean±s.e.m.
Figure 10B:
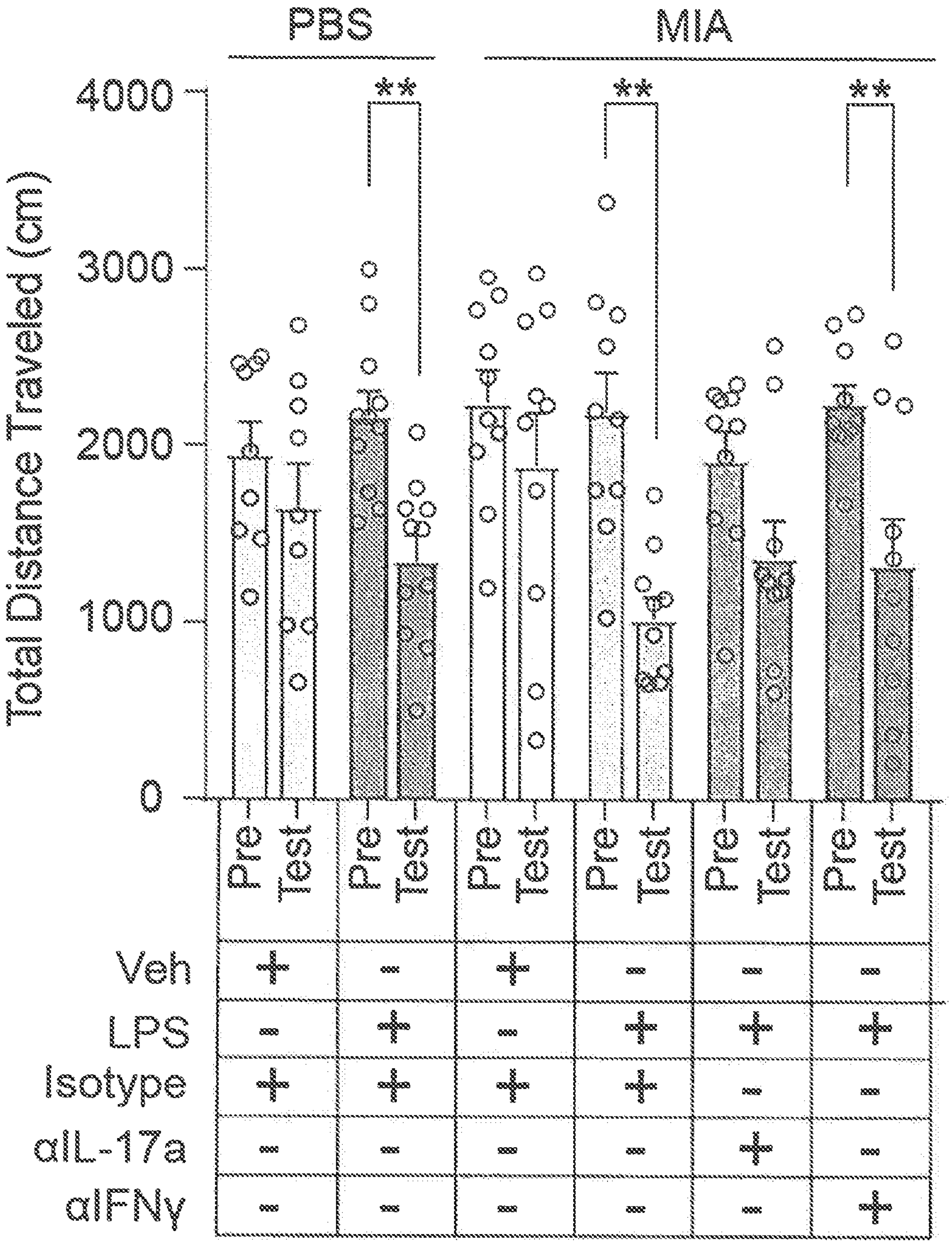
Figure 10C:
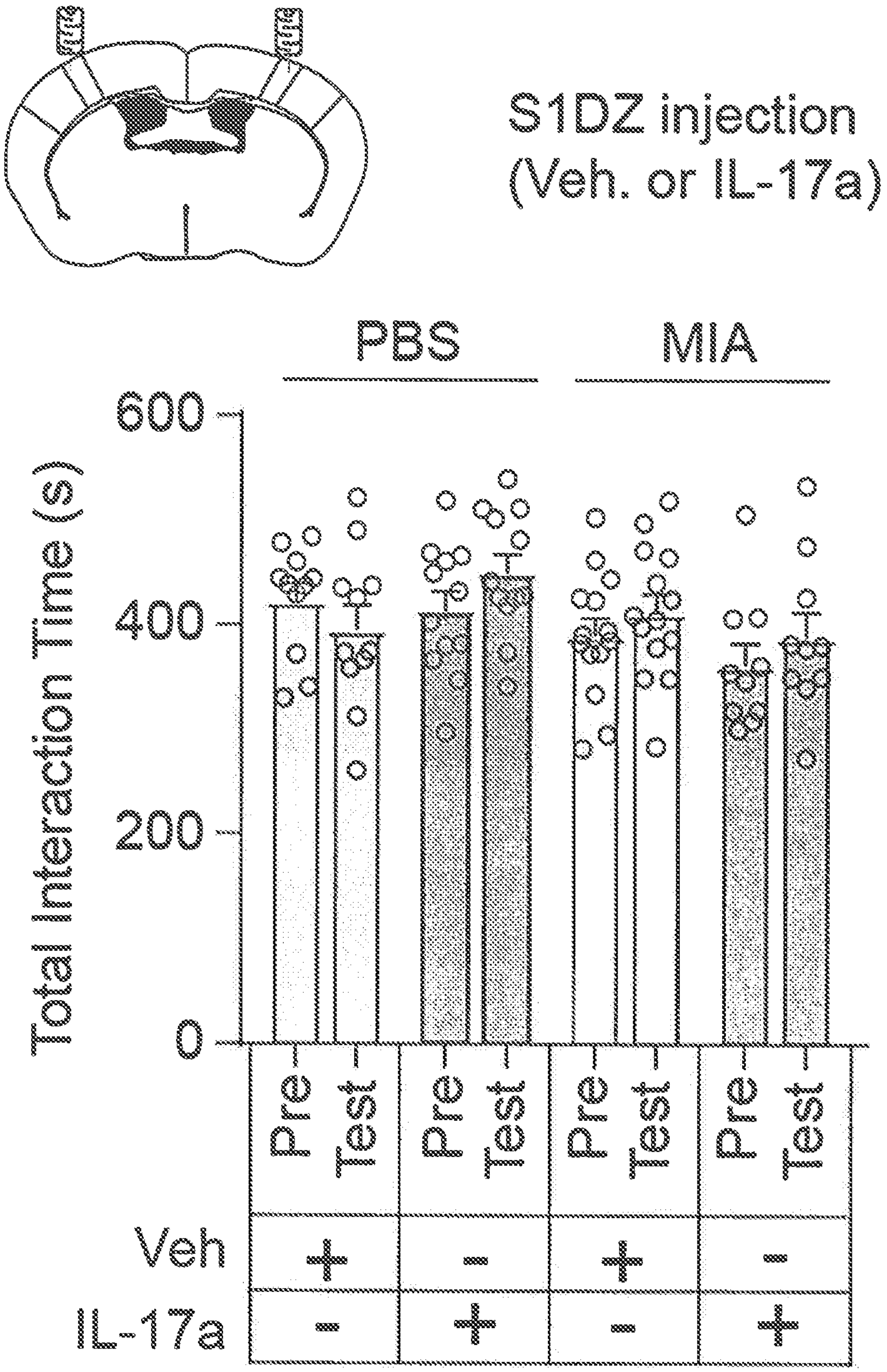
Figure 10D:
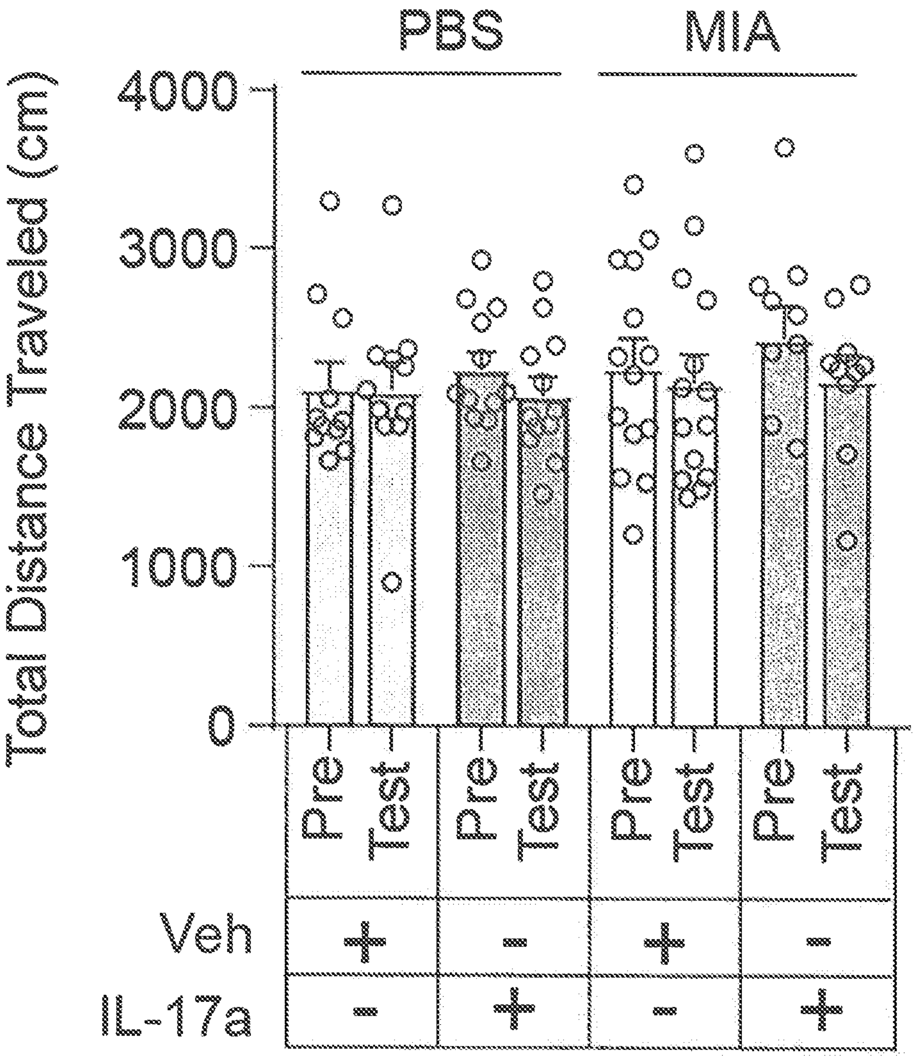
Figure 11B:
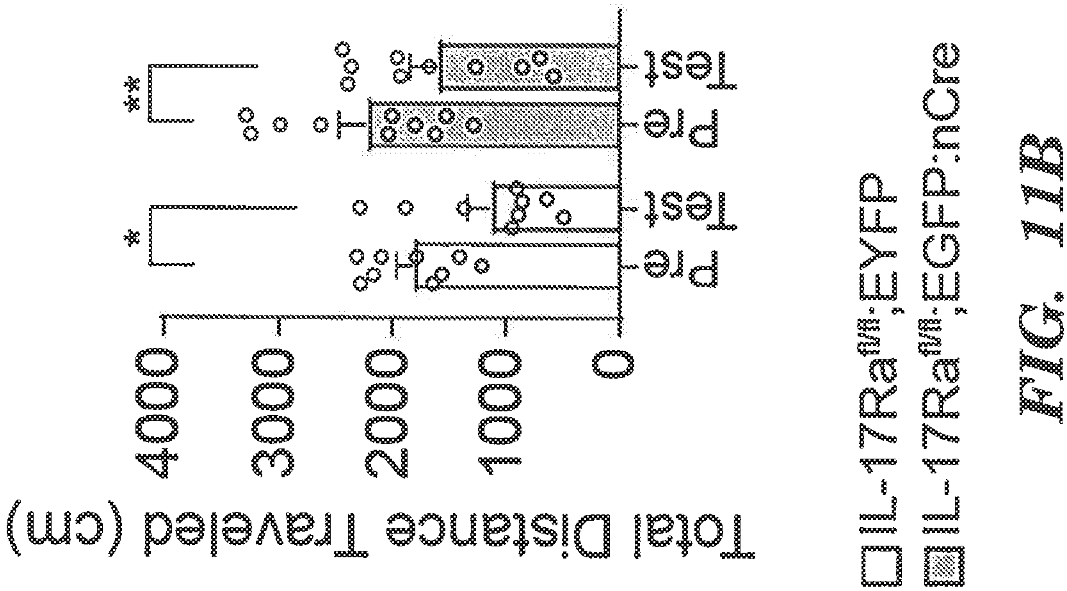
FIG. 11A-11B shows total interaction time (FIG. 11A) and distance traveled (FIG. 11B) during the sociability assay for offspring described in FIG. 3D (IL-17Ra$^{fl/fl}$, EYFP n=9, IL-17Ra$^{fl/fl}$;EGFP:nCre n=10; from 5 independent experiments).
Figure 11A:
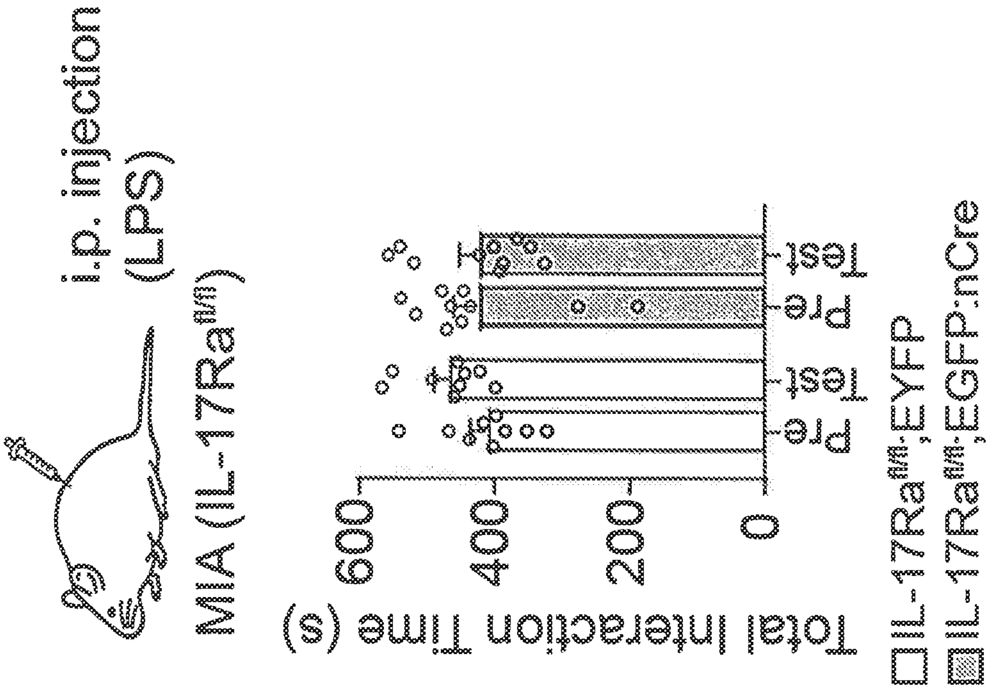
Figure 11D:
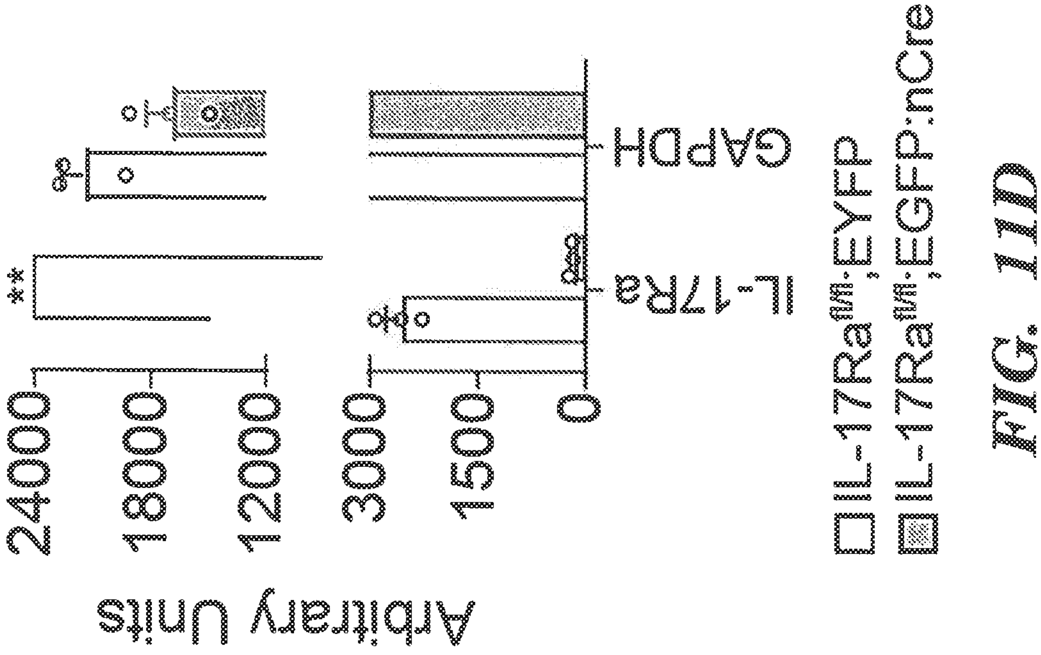
FIG. 11C-11D shows representative images (FIG. 11C) and corresponding quantification (FIG. 11D) of IL-17Ra and GAPDH amplicon following PCR using cDNA derived from cells isolated from the cortical region centered on S1DZ of IL-17Ra$^{fl/fl}$, EYFP and IL-17Ra$^{fl/fl}$, EGFP:nCre mice (n=3 for all groups; from 1 experiment). *p<0.05, p<0.01 as calculated by two-way repeated measures ANOVA with Bonferroni's post-hoc test (FIG. 11A-B) and unpaired two-tailed t-test (FIG. 11**D). Graphs indicate mean±s.e.m.
Figure 11C:
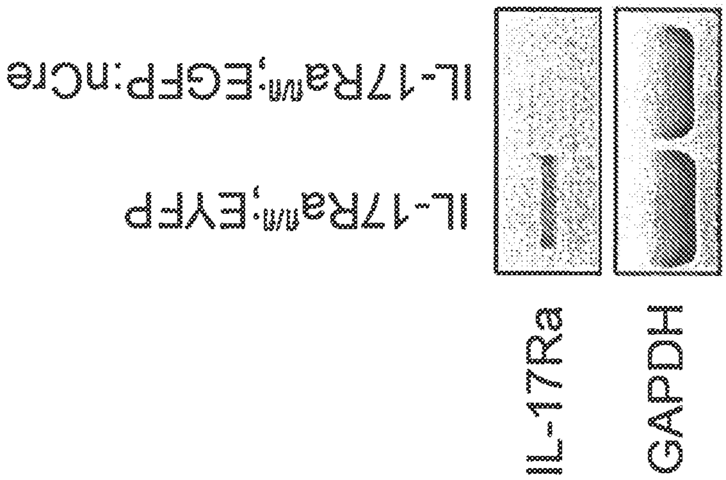

Next, the necessity of these cytokines in the LPS-induced rescue were investigated by using MIA offspring genetically deficient for IFNγ or IL-17a, which did not exhibit elevated levels of the respective cytokine upon LPS treatment (FIG. 2D, Plasma). While LPS injection restored sociability in wild-type (WT) MIA offspring, the same treatment failed to rescue the sociability deficits in IFNγ or IL-17a knockout (KO) MIA offspring (FIG. 2E, and FIG. 9A-9B), demonstrating that elevated levels of IFNγ and IL-17a are required for the LPS-induced behavioral rescue. Notably, MIA offspring injected with LPS displayed elevated levels of IL-17a, but not IFNγ, in the brain (FIG. 2D, Brain). Consistent with this observation, intracerebroventricular (i.c.v.) injection of blocking antibody against IL-17a, but not IFNγ, into the brain in MIA offspring prevented the LPS-induced rescue of sociability (FIG. 3A, and FIG. 10A-10B). Of note, LPS injection into i.c.v. blocking antibody-pretreated animals resulted in reduced total distance traveled without affecting total interaction time (FIG. 10A-B). These data indicate that IL-17a may directly act on the brain, and perhaps on S1DZ, to mediate the effects of LPS on sociability. Indeed, direct delivery of recombinant IL-17a protein into S1DZ was sufficient to rescue the sociability phenotype of MIA offspring in the absence of LPS administration (FIG. 3B, and FIG. 10C-10D). Lastly, LPS injection failed to restore sociability to MIA offspring deficient for IL-17Ra in the S1DZ region (FIG. 3C-3D, and FIG. 11A-11D). It was concluded that upon LPS treatment, elevated levels of IL-17a in the brain act directly upon IL-17Ra-expressing cells in S1DZ, restoring sociability in MIA offspring.

Figure 9C:
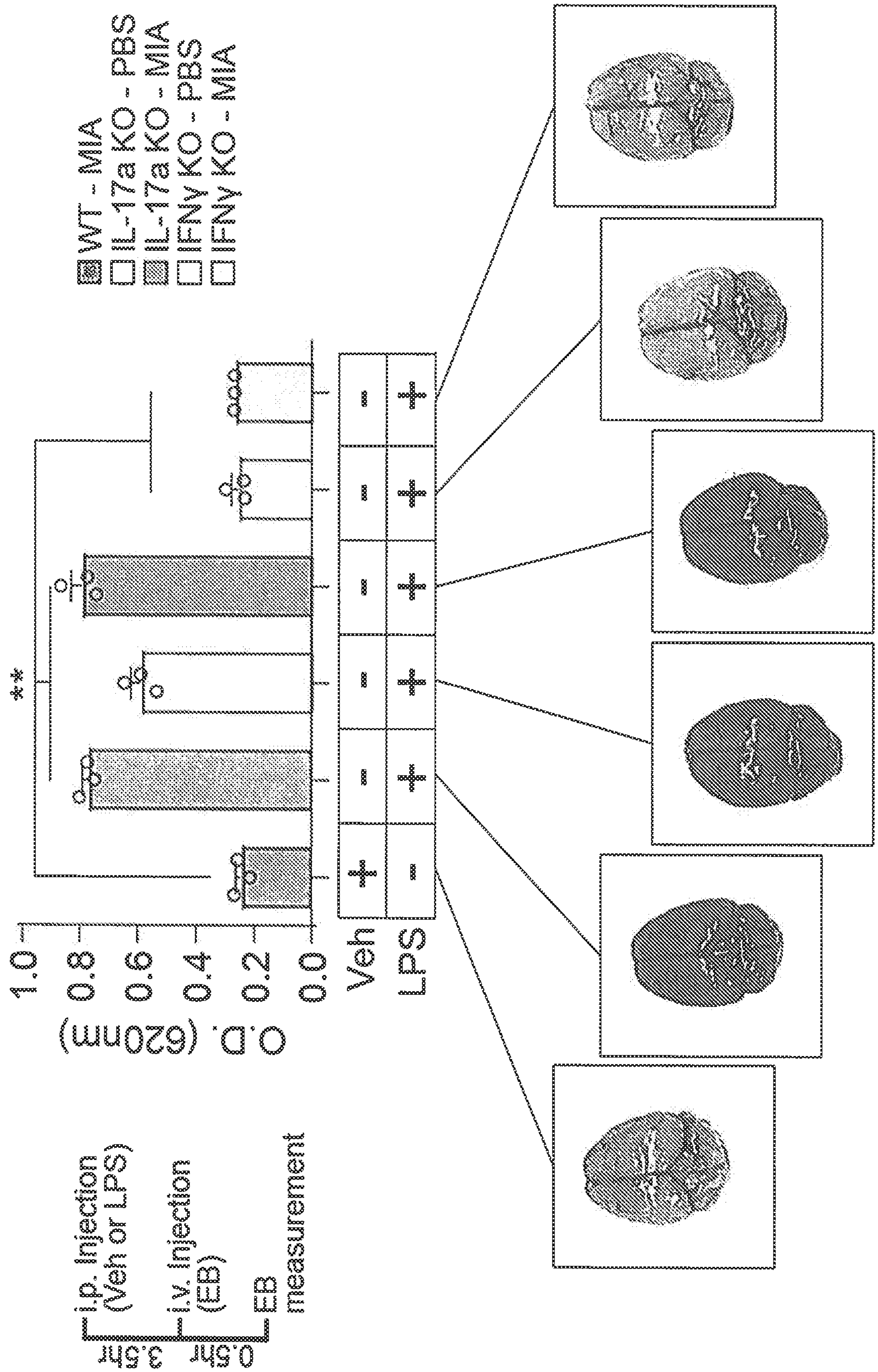
FIG. 9C shows mice were injected with Veh or LPS 3.5 hr before administration of Evan Blue (EB). Optical density (O.D.) values and representative images of Evans Blue detected in the brain of PBS or MIA offspring with WT, IL-17a KO, or IFNγ KO genetic background, following Veh or LPS injection (n=3 for all groups; from 1 experiment). **p<0.01 as calculated by two-way repeated measures ANOVA with Bonferroni's post-hoc test (FIGS. 9A-9B), and one-way ANOVA with Tukey's post-hoc test (FIG. 9C). Graphs indicate mean±s.e.m.

Next, it was investigated how increased IFNγ production at the periphery could contribute to the LPS-induced sociability rescue, as IFNγ is undetectable in the brain (FIG. 2D). IFNγ has been previously associated with increased permeability of the BBB upon viral infection[18]. It was observed that LPS injection can increase BBB permeability, as visualized by increased leakage of intravenously (i.v.) injected Evans Blue (EB) into the brain of MIA offspring (FIG. 9C). LPS-induced increase in EB leakage, however, was prevented in animals genetically deficient for IFNγ, but not IL-17a (FIG. 9C). Furthermore, IL-17a was no longer detectable in the brain of IFNγ KO MIA offspring upon LPS treatment (FIG. 2D, Brain), suggesting that IFNγ in the blood mediates the sociability rescue by allowing IL-17a to gain access to the brain.

Figure 4G:
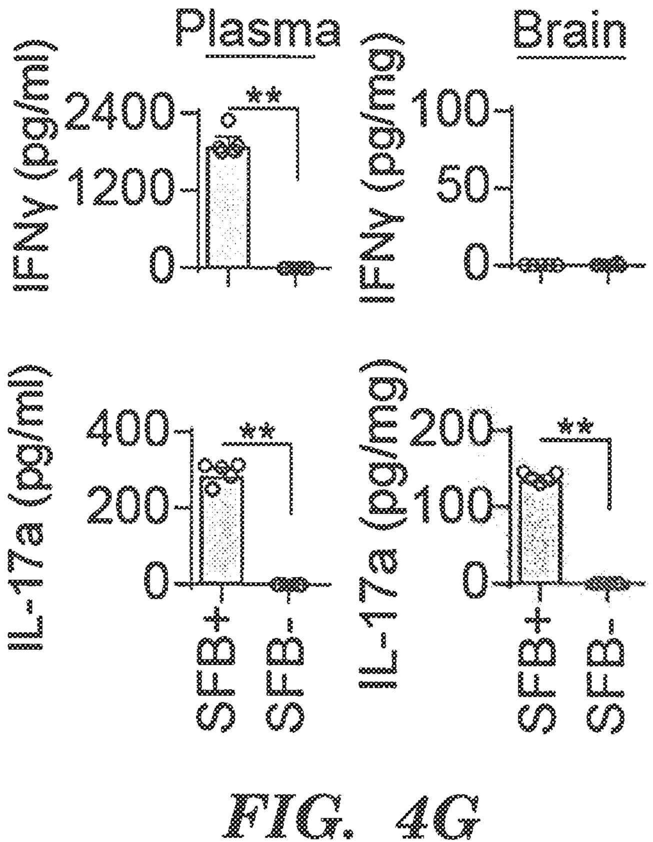

Finally, it was determined if LPS-dependent behavioral rescue could be influenced by the presence of gut commensals. The MIA offspring were treated with broad spectrum antibiotics, such as vancomycin or metronidazole, prior to LPS administration (FIG. 4A). Pretreating LPS-injected MIA offspring with vancomycin, but not metronidazole, prevented the reversal of the sociability phenotype (FIG. 4B, and FIG. 12A-12B) and suppressed the systemic increase in plasma and brain levels of IL-17a as well as the plasma levels of IFNγ (FIG. 4C). Mouse commensal segmented filamentous bacteria (SFB) is known to be sensitive to vancomycin, but not metronidazole treatment, and is also involved in differentiation of intestinal Th17 cells[19,20]. Indeed, qPCR analyses of mouse fecal samples showed that intestinal colonization by SFB is severely reduced upon vancomycin, but not metronidazole, treatment (FIG. 12C). These results were further confirmed by scanning electron microscopy (SEM), showing the lack of SFB associated with intestinal epithelial cells of the ileum[19] in the vancomycin-treated MIA offspring. SFB was still attached to the ileal mucosa of the vehicle- or metronidazole-treated mice (FIG. 12D). Therefore, it was investigated whether the presence of SFB in the MIA offspring is specifically required for the LPS-induced behavioral rescue. Whereas C57BL/6 (B6) mice from Taconic Biosciences (Tac) are colonized with SFB in their small intestine, those from Jackson Laboratories (Jax) lack SFB[19-21]. Because the presence of SFB in mothers is crucial for the induction of MIA behavioral phenotypes in offspring[21], a cross-fostering scheme was used to generate SFB-absent MIA offspring that were born to SFB-present mothers exposed to MIA. Upon birth, the offspring of SFB-present Tac mothers were injected with poly(I:C) and transferred to cages containing SFB-absent Jax mothers (FIG. 4D). For one week prior to behavioral testing, a subset of these offspring were subjected to an SFB colonization protocol (FIG. 4E, and FIG. 13A). Upon LPS injection, both behavioral rescue and increase in plasma and brain IL-17a levels were observed only in MIA offspring that had been colonized with SFB (FIG. 4F-G and FIG. 13B-C). They also exhibited increased levels of intestinal Th17 cells (FIG. 13D). Of note, SFB colonization also led to increased production of IFNγ in the circulation of LPS-treated MIA offspring (FIG. 4G). These data collectively suggest that Th17 cell-inducing gut bacteria (SFB) are required for the systemic increase in IL-17a (and IFNγ) levels in the plasma of MIA offspring upon exposure to an inflammatory stimulus, eventually mediating the behavioral rescue of sociability.

The previous data suggested that maternal gut microbial communities that promote Th17 cell biogenesis may represent a risk factor for the development of neurodevelopmental disorders in their offspring[21]. Based on the current findings, it is proposed that the presence of the same type of Th17 cell-promoting gut bacteria in offspring may be beneficial to ameliorate sociability symptoms in the event of inflammation. LPS injected in control offspring failed to increase IL-17a and IFNγ levels in the blood, implying that inflammatory responses may result in beneficial effects only among a subset of ASD patients, who not only carry Th17 cell-promoting bacteria in their guts, but also have their immune systems primed by prenatal exposure to inflammation or by other environmental factors. A better understanding of the role of gut-residing microbiota and a primed immune system among patients with neurodevelopmental disorders may provide opportunities to devise novel treatments for behavioral symptoms.

Example 2: Methods

Animals:

All experiments were performed according to Guide for the Care and Use of Laboratory Animals and were approved by the National Institutes of Health and the Committee on Animal Care at Harvard Medical School and Massachusetts Institute of Technology. C57BL/6 were purchased from Taconic Biosciences. $Ifng^{KO}$ (002287) and Vgat-Cre (028862) were purchased from Jackson Laboratories. $Il17a^{KO}$ and $IL\text{-}17Ra^{fl/fl}$ were described previously[22,23].

Maternal Immune Activation:

Mice were mated overnight and females carrying SFB in their guts[21] were checked daily for the presence of seminal plugs, noted as embryonic day 0.5 (E 0.5). On E12.5, pregnant female mice were weighed and injected with a single dose (20 mg/kg i.p.) of poly(I:C) (Sigma Aldrich) or PBS vehicle. Each dam was returned to its cage and left undisturbed until the birth of its litter. All pups remained with the mother until weaning on postnatal day 21-28 (P21-P28), at which time mice were group housed at a maximum of 5 per cage with same-sex littermates. Matings between IFNγ(−/−) mice were used to generate IFNγ KO MIA offspring. Matings between IL-17(−/−) males and IL-17a(+/−) females were used to generate IL-17a KO MIA mice. Matings between Vgat-Cre(c/c) males and WT females were used to make MIA Vgat-Cre mice.

Stereotaxic Surgery:

Surgeries were carried out using aseptic technique. Mice were anesthetized using a mixture of ketamine (100 mg/kg, i.p.) and xylazine (10 mg/kg, i.p.). Mice were given pre-operative slow-release buprenorphine (1.0 mg/kg s.c.). For manipulating body temperature with vLPO inhibition, Vgat-Cre mice received bilateral stereotaxic injections of virus (200 nl/side) at rates of <0.1 ml/min ($AAV_2$-hSyn-DIO-hM4Di-mCherry (Addgene™). Virus was bilaterally targeted to the vLPO (AP+0.15, ML±0.50, DV−4.9, lambda was raised 600 μm above bregma). For experiments involving genetic knockdown of IL-17Ra in S1DZ, $IL\text{-}17Ra^{fl/fl}$ mice received bilateral stereotaxic injections of virus (800nl/side) at a rate of <0.1 ml/min (pLenti-hSyn-EYFP, pLenti-hSyn-EGFP:nCre). Viruses were bilaterally targeted to the S1DZ (AP+0.50, ML±2.6, DV−0.80, lambda was level with bregma). All lentiviruses were made in house.

For administration of cytokines into S1DZ, cannula (PlasticsOne) were implanted superficially within S1DZ (AP−0.50, ML±2.6, DV−0.10). For central administration of blocking antibodies, cannula were implanted above the right lateral ventricle (AP−0.30, ML±1.0, DV−1.35). Cannula were fitted with dummy cannula (PlasticsOne®) to maintain cannula patency following surgery.

Tracking of Body Temperature:

Body temperature was measured using the Anipill remote temperature monitoring system (007894-001, DSI). Adult male mice were implanted with an Anipill capsule in the abdominal cavity. Experiments were carried out >3 weeks following surgery. Mice were singly housed the day before the experiment. Ambient temperature was maintained at 23.5° C., consistent with the ambient temperature of the vivarium. Body temperature was sampled in 5 minute increments. LPS or saline (Veh) injections occurred between 11:00-13:00 for experiments assaying the effects of LPS on body temperature in PBS and MIA offspring.

Immunohistochemistry:

Animals were transcardially perfused with cold PFA (4% in PBS). Brains were kept in PFA overnight at 4° C. prior to vibratome sectioning (Leica VT1000s®). Brains were cut at 50 μm thickness for cFos quantification. Brains were cut at 100 μm thickness for all other experiments.

Prior to antibody labeling, sections were incubated in blocking solution (0.4% Triton X-100 and 2% goat serum in PBS) for 30 min. Sections were then incubated in blocking solution containing primary antibodies overnight at room temperature. Primary antibodies used were chicken anti-GFP (1:1000, Ab5450, Abcam®), rabbit anti-cFos (1:500, ABE457, Millipore®), rabbit anti-DsRed (1:1000, 632496, Clontech®). Sections were washed in wash buffer (0.4% Triton X-100 in PBS) three times before secondary antibody labeling. Sections were incubated in blocking solution containing secondary antibodies and DAPI (1:5000, D1306, Thermofisher™) for three hours at room temperature. Images of stained slices were acquired using a confocal microscope (LSM710, Carl Zeiss®) with a 10× or 20× objective lens.

Behavioral Analysis:

Animals were tested during the light cycle in a room with lighting maintained at 230 Lux. Animals were transferred to the testing area at least one hour prior to the initiation of experiments. Tracking of mouse behavior was done using Etho Vision XT™ (Noldus®) tracking system.

Three-Chamber Social Approach Assay:

Adult male mice were assayed for sociability using a three-chamber social approach assay. The arena was constructed of white acrylic (50 cm×35 cm×30 cm). Wire cups (Spectrum Diversified®) were placed in the back left and right corner of the arena beneath water-filled 1L bottles (Nalgene®). On Day 0, mice were habituated to the arena for 10 min. Immediately following habituation, mice were singly housed. On Day 1 (Pre), mice were placed in the center of the arena and allowed to freely explore. Following 10 min, mice were confined to the center of the arena. An inanimate object (rubber stopper) or a male conspecific were placed beneath the wire cups. Placement of the inanimate object and social target were alternated. Mice were then allowed to freely explore the arena for 10 min. Interaction time was defined as time spent in the areas circumscribing the wire cups (<2 cm). Sociability was defined as interaction time with the social target divided by total interaction time and expressed as a percentage. For experiments involving LPS injections, mice were injected with LPS (50 μg/kg, i.p., L2630, Sigma) on Day 2 (Test), four hours prior to testing.

Behavioral Analysis with DREADD Manipulation:

Adult male Vgat-Cre mice were bilaterally injected with virus encoding the inhibitory DREADD receptor fused to mCherry into the vLPO. Following >3 weeks of recovery, mice were assayed on the three-chamber social approach assay outlined above. Baseline sociability was assayed on day 1 (Pre). On day 2 and day 3, mice were injected with either vehicle or CNO (1.5 mg/kg i.p., Enzo®) dissolved in saline, two hours prior to initiation of behavior. Injection order was counterbalanced. Following behavioral experiments, post-mortem histology was used to confirm mCherry expression within the vLPO.

IL-17a or IFNγ Blockade:

For peripheral cytokine blockade experiments, monoclonal IL-17a blocking antibody (clone 50104; R&D), monoclonal IFN-g blocking antibody (clone 37895; R&D®) or isotype control antibody (IgG2a, clone 54447; R&D®) were administered (300 μg/animal) intraperitoneally 30 min prior to LPS injection. Four hours following LPS administration, mice were assayed for sociability.

For central cytokine blockade experiments, adult male mice were implanted with cannula into the lateral ventricle and allowed to recover for >2 weeks prior to behavioral experiments. On Day 1 (Pre), mice were tested for baseline sociability. On Day 2 (Test) mice were injected with IL-17a blocking antibody, IFNγ blocking antibody, or isotype control antibody. Antibodies were dissolved in saline and administered intracerebroventricularly at 1 mg/kg in 500nl at a rate of 180nl/min through 750 μm-projecting injector tips (PlasticsOne®). Blocking antibody was administered 30 min prior to LPS administration. Four hours following LPS administration, mice were assayed for sociability.

S1DZ IL-17a Administration Experiments:

Adult male mice were implanted with cannula into S1DZ and allowed to recover for >2 weeks prior to behavioral experiments. On Day 1 (Pre) mice were assayed for sociability. On Day 2 (Test), mice were anesthetized briefly using isoflurane and either vehicle or IL-17a (50 ng/side in 1 μl at a rate of 180nl/min, 7956-ML/CF, R&D®) was administered bilaterally into S1DZ through 250 μm-projecting injector tips (PlasticsOne®). Four hours after vehicle or IL-17a administration, mice were assayed for sociability. Cannula placements were verified using histology.

BBB Permeability:

BBB permeability was assessed with Evans blue (Sigma Aldrich®). The Evans blue dye binds to serum albumin (69,000 Da) to become a high-molecular-weight protein tracer. Mice were injected with 100 μl of Evans blue solution (10 mg/kg in PBS) intravenously. After 30 min, all injected mice were sacrificed. Whole brains were then removed and photographed. The brain tissues were disrupted in lysis buffer at full speed for 60 seconds using a Micro-Homogenizer (VWR International®). The fluorescence was determined using a Spectrophotometer (BioTek Instruments®) with excitation at 620 nm and emission at 680 nm.

Enzyme-Linked Immunosorbent Assay (ELISA):

Mice were put under general anesthesia by intraperitoneal injection of Ketamine (100 mg/kg, i.p.) and xylazine (10 mg/kg, i.p.). Blood was collected by retro-orbital puncture, using clean heparinized microhematocrit capillary tubes (Fisher Scientific®). Once the tube was withdrawn, slight pressure was applied on the eyelid with gauze to prevent further bleeding. All blood samples were centrifuged at 15,000 g for 3 min at room temperature. For quantification of cytokines in brain lysate, samples were disrupted in cold lysis buffer with protease inhibitor cocktail for 60 seconds using the Micro-Homogenizer (VWR International) and centrifuged for 30 min at 15,000×g to remove insoluble precipitates. All samples were stored at −80° C. until further analysis. Plasma and brain lysate cytokines concentrations were measured using an ELISA kit (Biolgened™), following the manufacturer's instructions.

SFB-Gavaged and Antibiotics-Gavaged Mice:

For SFB-gavaging experiments, four fecal pellets of SFB mono-colonized mice were dissolved in 20 ml sterile PBS and filtered through a 100-μm cell strainer. 200 μl of fecal suspensions were gavaged via oral route into 8 to 9-week-old male cross-fostered mice. Control mice were gavaged with PBS. The SFB colonization was tested on day 7 following SFB-gavaging. For antibiotics treatments, Taconic-derived male mice were orally gavaged with vancomycin hydrochloride (Fisher) (2.5 mg/kg) or metronidazole (10 mg/kg) (Sigma Aldrich®) every two days, starting 21 days before behavioral test. Mouse fecal pellets were collected and stored at −80° C. before and after vancomycin and metronidazole treatments.

Cross-Fostering:

The day on which pups were born was considered P0. Pups were cross-fostered between P0 and P1. Entire litters were removed from the original mothers. Pups were gently mixed with the bedding of the recipient cage before being introduced to the cage with a foster mother.

*Lamina Propria* Mononuclear Cell Preparation:

For mononuclear cell isolations, both mesenteric fat tissues and Peyer's patches were carefully removed from intestinal tissues. Terminal ileal or colonic tissues were incubated in 5 mM EDTA in PBS containing 1 mM DTT at 37° C. on a shaker (200 r.p.m.) for 20 min. Tissues were washed one more time. Tissues were then further digested for 30 min at 37° C. in RPMI containing 10% fetal bovine serum, collagenase D (1.0 mg/ml) (Roche) and DNase I (100 μg/ml) (Sigma). Digested tissues were then filtered using a 100 μm cell strainer and incubated for additional 10 min at 37° C. Mononuclear cells were isolated from an interphase of percoll gradients (40:80 gradient).

Flow Cytometry:

Mononuclear cells were incubated with phorbol myristate acetate (PMA) (50 ng/ml) (Sigma) and ionomycin (500 ng/ml) (Sigma) in the presence of GolgiStop (BD) in complete T cell media at 37° C. for 4 h. Intracellular cytokine staining was performed according to the manufacturer's protocol. Cells were stained with Alexa Fluor 700-conjugated anti-CD4 (RM-5) (Invitrogen®), PerCP-Cy5.5-conjugated anti-CD8a (53-6.7) (eBioscience®), Brilliant Violet 605 anti-TCR β (Biolegend®). Cells were further stained intracellularly with APC-conjugated anti-RORγ (B2D) (eBioscience®), PE-Cy7-conjugated anti-IL-17a (eBio17B7) and Pacific-Blue-conjugated anti-IFNγ (XMG1-2) (Biolegend®) using Foxp3 staining/permeabilization buffer (eBioscience®). Flow cytometric analysis was performed on an LSRII (BD Biosciences®). All data were re-analyzed using FlowJo™ (Tree Star®).

PCR for Assaying IL-17R Knockdown:

$IL17Ra^{fl/fl}$ male mice were bilaterally injected with virus encoding nCre fused to EGFP or control virus encoding only EYFP into the S1DZ. Following >3 weeks, injection sites were dissected from the somatosensory cortex. Single cells were dissociated from brain tissue using a modified version[24] of the Papain Dissociation Kit protocol (LK003153, Worthington) and sorted on a BD FACS Aria™ (BD Biosciences®) based on EGFP/EYFP expression. RNA was extracted from sorted cells using a Quick-RNA micro-prep Kit™ (Zymo®). 20 ng of RNA was converted to cDNA using oligodT (Protoscript First Strand CDNA Synthesis Kit™, NEB). IL17R mRNA expression was analyzed using PCR. 1 μl of cDNA was diluted in a 20 μl reaction volume. il17ra and gapdh mRNA expression were assessed using the following primers: Il17Ra 5'-AGATGCCAG-CATCCTGTACC-3' (SEQ ID NO: 5) and 5'-CACAGT-CACAGCGTGTCTCA-3' (SEQ ID NO: 6); Gapdh 5'-GACTTCAACAGCCTCCCACTCTTCC-3' (SEQ ID NO: 7) and 5'-TGGGTGGTCCAGGTTTCTTACTCCTT-3' (SEQ ID NO: 8). Cycling conditions for IL17Ra: 95° C.×5 min (1 cycle), 95° C.×20 s, 60° C.×30 s, 72° C.×30s (32 cycles), 72° C.×5 min (1 cycle) and 4° C. hold. Cycling conditions for GAPDH: 95° C.×5 min (1 cycle), 95° C.×20 s, 60° C.×30 s, 72° C.×30s (28 cycles), 72° C.×5 min (1 cycle) and 4° C. hold. Band intensity from gel images were quantified using ImageJ™.

16S rRNA Quantitative PCR Analysis:

Bacterial genomic DNA was isolated from the fecal pellets of mice with phenol-chloroform extraction. qPCR was performed to quantify relative abundance of segmented filamentous bacteria (SFB). The following primers were used (SFB; forward sequence-GACGCTGAGGCATGAT-GAGAGCAT (SEQ ID NO: 9), reverse sequence-GACGGCACGGATTGTTATTCA (SEQ ID NO: 10), Universal; forward sequence-ACTCCTACGGGAGGCAGCAGT (SEQ ID NO: 11), reverse sequence-ATTACCGCGGCTGCTGGC (SEQ ID NO: 12)). Cycling conditions for both SFB and universal: 95° C. for 3 min, 45 cycles at 95° C. for 30s and 60° C. for 30 s, using Roche (Light cycler 96). A melting curve analysis was performed in order to validate primer pairs and amplification conditions. Data were analysed using Roche (Lightcylcler® 96 SW1.1) Software and the relative quantification (fold) of SFB DNA was performed using the ΔΔCt method.

Scanning Electron Microscopy (SEM):

Terminal ileum tissues from mice (8-10 weeks old) were cut open and fixed with 2.5% glutaraldehyde in 0.1 M cacodylate buffer (pH 7.4) overnight and processed for standard scanning electron microscopy. All samples were analysed on a Hitachi S-4800 Type II Field Emission Scanning Electron Microscope™.

Effect of LPS on cFos Expression:

Adult male mice were sacrificed five hours after LPS injection. c-Fos+ cells were quantified using the Cell Counter plugin in Fiji[25]. All cells were counted within a single coronal section of each respective brain region as defined by the Paxinos and Franklin Mouse Atlas[26]. Regions quantified include mPFC (Including only PrL and IL) (AP+1.98), S1DZ (AP−0.48), S1BF (AP−0.48), M1 (AP−0.46), M2 (AP−0.46), AuD (AP−1.94), CeA (AP−1.94), and V1 (AP−3.64). Somatosensory cortex dysgranular zone (S1DZ), somatosensory cortex barrel field (S1BF), secondary motor cortex (M2), primary motor cortex (M1), secondary auditory cortex dorsal part (AuD), central amygdala (CeA), medial prefrontal cortex (mPFC), prelimbic cortex (PrL), infralimbic cortex (IL), primary visual cortex (V1).

Brain Slice Preparation:

Male offspring from Poly: IC-injected mothers were sacrificed at 3-4 months of age by deep anesthesia with sodium pentobarbital and transcardially perfused with ice-cold dissection solution containing (in mM): sucrose 180, $NaHCO_3$28, glucose 7, $MgCl_2$ 7, sodium pyruvate 3, KCl 2.5, $NaH_2PO_4$ 1.25, $CaCl_2$ 1, and sodium ascorbate 1; 287 mOsm; saturated with 95% $O_2$ and 5% $CO_2$. Coronal 300 μm slices containing S1DZ were prepared in dissection solution using a vibratome (Leica VT1200). Brain slices were allowed to recover at 35.5° C. for 25 minutes in artificial cerebrospinal fluid (aCSF) containing (in mM): NaCl 120, $NaHCO_3$25, glucose 19.5, KCl 3, sodium pyruvate 3, $NaH_2PO_4$ 1.25, $MgCl_2$ 1.2, $CaCl_2$ 1.2, and sodium ascorbate 1; 304 mOsm; saturated with 95% $O_2$ and 5% $CO_2$. The slice-holding chamber was then stored at room temperature for at least 40 minutes before recording.

Whole-Cell Patch Clamp Recordings:

Slices were transferred to the recording chamber which was continuously perfused with aCSF at 2 mL per minute, maintained at 32° C. Neurons were visualized through an upright microscope (Scientifica SliceScope Pro 2000™) equipped with IR-DIC optics and a water-immersion lens (40×, 0.8 NA, Olympus). Electrophysiological signals were obtained with a Multiclamp 700B™ amplifier, filtered at 10 kHz and digitized at 20 kHz using a Digidata 1550B™, and recorded using Clampex 10.6™. The cortical region S1DZ was targeted by its relative medial position to the barrel field in the somatosensory cortex, which was observable under DIC optics. Whole-cell patch clamp recordings were made from layer 2/3 pyramidal neurons within S1DZ using thick-walled glass electrodes (1.5 mm OD, 0.84 mm ID; resistance 4-6 M2). Pipettes were loaded with internal solution containing (in mM): 100 K-gluconate, 20 KCl, 10 HEPES, 0.2 EGTA, 4 Mg-ATP, 0.3 Na-GTP, 10 sodium phosphocreatine and 0.1 Alexa-488 (Life Technologies®) with pH adjusted to 7.25 with 1 M KOH and osmolarity adjusted to ~295 mOsm by the addition of sucrose. Pipette capacitance was neutralized prior to break in, and the bridge was balanced. Series resistances ranged from 16-20 MΩ; cells with series resistance greater than 20 MΩ were discarded. Recording quality was monitored throughout the experiments with −50 pA hyperpolarizing current pulses. All current-clamp experiments were conducted at the cell's resting potential (zero holding current). Current-frequency (F-I) relation was generated by injecting 350 ms steps of current from −120 pA to +680 pA in 20 pA steps. The F-I curve (FIG. 1F) was generated from the action potential frequency over the duration of the step, from currents 0 pA to 680 pA. Cells were imaged at 40× and 4× through DIC and 470 nm light to document position, pyramidal morphology, and presence of spines. Sections were fixed with 4% PFA and stained using DAPI and their exact location with respect to S1DZ was determined by a third-party blinded to the identity and properties of the cells.

Statistics: Statistical analyses were performed using GraphPad Prism™

REFERENCES

1. Whitrow, M. Wagner-Jauregg and fever therapy. Med. Hist. (1990). doi: 10.1017/S0025727300052431
2. Curran, L. K. et al. Behaviors associated with fever in children with autism spectrum disorders. Pediatrics 120, e1386-e1392 (2007).
3. Grzadzinski, R., Lord, C., Sanders, S. J., Werling, D. & Bal, V. H. Children with autism spectrum disorder who improve with fever: Insights from the Simons Simplex Collection. Autism Res. 11, 175-184 (2018).
4. Smith, S. E. P., Li, J., Garbett, K., Mirnics, K. & Patterson, P. H. Maternal Immune Activation Alters Fetal Brain Development through Interleukin-6. J. Neurosci. (2007). doi: 10.1523/JNEUROSCI.2178-07.2007
5. Alexander, C. & Rietschel, E. T. Bacterial lipopolysaccharides and innate immunity. J. Endotoxin Res. (2001). doi: 10.1179/096805101101532675
6. Shin Yim, Y. et al. Reversing behavioural abnormalities in mice exposed to maternal inflammation. Nature (2017). doi: 10.1038/nature23909

7. Sullivan, R. et al. Parents speak. J Autism Dev Disord 10, 231-241 (1980).
8. Malkova, N. V., Yu, C. Z., Hsiao, E. Y., Moore, M. J. & Patterson, P. H. Maternal immune activation yields offspring displaying mouse versions of the three core symptoms of autism. Brain. Behav. Immun. (2012). doi: 10.1016/j.bbi.2012.01.011
9. Kozak, W., Conn, C. A. & Kluger, M. J. Lipopolysaccharide locomotor activity induces fever and depresses in unrestrained mice. Am. J. Physiol. Integr. Comp. Physiol. (1994). doi: 10.1152/ajpregu.1994.266.1.R125
10. Cai, H., Haubensak, W., Anthony, T. E. & Anderson, D. J. Central amygdala PKC-δ+neurons mediate the influence of multiple anorexigenic signals. Nat. Neurosci. (2014). doi: 10.1038/nn.3767
11. Armbruster, B. N., Li, X., Pausch, M. H., Herlitze, S. & Roth, B. L. Evolving the lock to fit the key to create a family of G protein-coupled receptors potently activated by an inert ligand. Proc. Natl. Acad. Sci. (2007). doi: 10.1073/pnas.0700293104
12. Vong, L. et al. Leptin Action on GABAergic Neurons Prevents Obesity and Reduces Inhibitory Tone to POMC Neurons. Neuron (2011). doi: 10.1016/j.neuron.2011.05.028
13. Zhao, Z.-D. et al. A hypothalamic circuit that controls body temperature. Proc. Natl. Acad. Sci. (2017). doi: 10.1073/pnas. 1616255114
14. Erickson, M. A. & Banks, W. A. Cytokine and chemokine responses in serum and brain after single and repeated injections of lipopolysaccharide: Multiplex quantification with path analysis. Brain. Behav. Immun. (2011). doi: 10.1016/j.bbi.2011.06.006
15. Hsiao, E. Y., McBride, S. W., Chow, J., Mazmanian, S. K. & Patterson, P. H. Modeling an autism risk factor in mice leads to permanent immune dysregulation. Proc. Natl. Acad. Sci. (2012). doi: 10.1073/pnas.1202556109
16. Filiano, A. J. et al. Unexpected role of interferon-γ 3 in regulating neuronal connectivity and social behaviour. Nature (2016). doi: 10.1038/nature18626
17. Chen, C. et al. IL-17 is a neuromodulator of *Caenorhabditis elegans* sensory responses. Nature (2017). doi: 10.1038/nature20818
18. Too, L. K., Ball, H. J., McGregor, I. S. & Hunt, N. H. The pro-inflammatory cytokine interferon-gamma is an important driver of neuropathology and behavioural sequelae in experimental pneumococcal meningitis. Brain. Behav. Immun. (2014). doi: 10.1016/j.bbi.2014.02.020
19. Ivanov, I. I. et al. Induction of Intestinal Th17 Cells by Segmented Filamentous Bacteria. Cell (2009). doi: 10.1016/j.cell.2009.09.033
20. Ivanov, I. I. et al. Specific Microbiota Direct the Differentiation of IL-17-Producing T-Helper Cells in the Mucosa of the Small Intestine. Cell Host Microbe (2008). doi: 10.1016/j.chom.2008.09.009
21. Kim, S. et al. Maternal gut bacteria promote neurodevelopmental abnormalities in mouse offspring. Nature (2017). doi: 10.1038/nature23910
22. Nakae, S. et al. Antigen-specific T cell sensitization is impaired in Il-17-deficient mice, causing suppression of allergic cellular and humoral responses. Immunity (2002). doi: 10.1016/S1074-7613(02)00391-6
23. El Malki, K. et al. An alternative pathway of imiquimod-induced psoriasis-like skin inflammation in the absence of interleukin-17 receptor a signaling. J. Invest. Dermatol. (2013). doi: 10.1038/jid.2012.318
24. Hrvatin, S. et al. Publisher Correction: Single-cell analysis of experience-dependent transcriptomic states in the mouse visual cortex. Nature Neuroscience (2018). doi: 10.1038/s41593-018-0112-6
25. Schindelin, J. et al. Fiji: An open-source platform for biological-image analysis. Nature Methods (2012). doi: 10.1038/nmeth.2019
26. Paxinos, G. & Franklin, K. B. J. Mouse brain in stereotaxic coordinates. Academic Press (2001). doi: 10.1016/S0306-4530(03)00088-X.

Example 3: Interleukin-17A Restores Sociability in Several Mouse Models for Neurodevelopmental Disorders The beneficial effects of infection and ensuing inflammation on neurological disorders have been noted[1]. For example, a subset of children with autism spectrum disorder (ASD) exhibit temporary but significant improvement of their behavioral symptoms during episodes of fever, a sign of systemic inflammation[2,3]. Here the molecular and neural mechanisms that underlie the beneficial effects of inflammation on social behavior deficits were elucidated. Here, an environmental model of neurodevelopmental disorders in which mice were exposed to maternal immune activation (MIA) during embryogenesis[4] were compared with mice genetically deficient for Contactin-associated protein-like 2 (Cntnap2)[5], Fragile X mental retardation-1 (Fmr1)[6], and Sh3 and multiple ankyrin repeat domains 3 (Shank3)[7]. It was established that social behavior deficits in MIA-exposed offspring can be temporarily rescued by the inflammatory response elicited by lipopolysaccharide (LPS) administration. This behavioral rescue was accompanied by a reduction in neural activity in the primary somatosensory cortex dysgranular zone (S1DZ), whose hyperactivity was previously implicated in the manifestation of MIA behavioral phenotypes[8]. In contrast, an LPS-induced rescue of social deficits in monogenic models was not observed, even though the severity of their sociability deficits positively correlated with increased neural activity in the S1DZ and reduction of neural activity in the S1DZ was sufficient to restore sociability in mutant mice. It is demonstrated herein that the differences in responsivity to the LPS treatment between the MIA and the monogenic models emerge from differences in the levels of cytokine production. LPS treatment in monogenic mutant mice did not induce comparable amounts of interleukin-17a (IL-17a) as in MIA offspring, and bypassing this difference by directly delivering recombinant IL-17a into S1DZ was sufficient to promote sociability in monogenic mutant mice as well as in MIA offspring. Conversely, abrogation of IL-17 receptor subunit a (IL-17Ra) expression in the S1DZ neurons eliminated the ability of LPS to reverse the sociability phenotypes in MIA offspring. Lastly, blocking IL-17a in the brain prevented LPS-induced reduction of neural activity in the S1DZ of MIA offspring. This data supports a novel neuroimmune mechanism underlying neurodevelopmental disorders, whereby production of IL-17a during inflammation can ameliorate the expression of social behavior deficits by directly affecting neural activity in the central nervous system.

While the improvement of behavioral symptoms for children with ASD during episodes of fever has been appreciated by parents and doctors alike, a mechanistic understanding of how fever-associated immune responses translate into behavioral relief, both at the molecular and neural level, is still lacking. The mechanisms that allow for the inflammation-associated rescue of sociability deficits were explored using both genetic and environmental mouse models for neurodevelopmental disorders. A febrile response can be exogenously induced by injecting animals with a low dose of LPS[9]. Indeed, intraperitoneal (i.p.) LPS administration (50 μg/kg) in control animals—offspring born to mothers injected with PBS-led to a significant increase in body temperature (~0.5-1.0° C.) ~4-5 hours after the treatment (FIG. 1A). To investigate whether LPS injection can ameliorate sociability deficits, sociability in adult males one day before LPS injection (pretest, Pre) and 4 hours after injection (Test) were compared, when the increase in body temperature initiates (FIG. 1B). As previously reported, MIA offspring born to mothers injected with Poly(I:C) (polyinosinic: polycytidylic acid) at embryonic day 12.5 (E12.5) exhibited impaired social approach behavior during the pretest[10-12]. The Cntnap2, Fmr1 and Shank3 monogenic models also displayed sociability deficits albeit with a marked variability during the pretest (FIGS. 15A-15D). The MIA offspring were compared to monogenic mutant animals that exhibited a sociability index lower than ~62%, the mean value for the three monogenic lines (FIG. 15A).

LPS injection in MIA offspring robustly rescued their characteristic deficits in sociability; these animals displayed an interest in social objects indistinguishable from controls (FIG. 1C, FIG. 14, and FIG. 16A-16D). LPS injection did not affect baseline sociability in control offspring. LPS-induced sociability rescue was absent 72 hours following the treatment, paralleling the transient nature of fever-associated improvement observed in ASD children[2] (FIG. 17A-17E). Furthermore, LPS-induced rescue was observed in both young (2-5 months) and aged (9-12 month) mice (FIG. 14 and FIG. 17F-17J), suggesting that this is a generalizable phenomenon, not confined to early adulthood. LPS-induced rescue of MIA sociability deficits was also evident when assayed using a reciprocal social interaction test (FIG. 17K). Lastly, LPS treatment in MIA offspring also rescued an enhanced marble burying behavior (FIG. 17L), showing that inflammation can relieve several MIA-associated behavioral symptoms.

Next, it was probed whether fever has a role in the observed behavioral rescue. Unlike in control offspring, LPS treatment did not induce changes in body temperature in MIA animals (FIG. 18A), suggesting that the febrile response might not be the main factor contributing to the rescue. To directly test whether fever is dispensable, the animals' body temperature was experimentally increased without inducing systemic inflammation by targeting inhibitory DREADDs (designer receptors exclusively activated by designer drugs)[13] to GABAergic neurons in the ventral part of the lateral preoptic nucleus (vLPO), using a Vgat-Cre transgenic mouse line[14] (FIG. 2A). As previously reported[15], inhibition of these neurons led to an increase in body temperature of ~1° C. (FIG. 2B). Induction of febrile response alone, however, failed to promote social preference in MIA offspring (FIG. 2C and FIG. 18B-18E), confirming that fever per se is not the main driver of the LPS-induced rescue. Of note, MIA Vgat-Cre mice exhibited comparable sociability deficits, were unaffected by CNO treatment and showed an increase in sociability upon LPS treatment (FIG. 18F-18J). Intriguingly, unlike in MIA offspring, LPS treatment failed to restore sociability in mutant mice deficient for Cntnap2, Fmr1, and Shank3 (FIG. 14 and FIG. 16A-16D), indicating that rescue by LPS-driven inflammation may be applicable only to a subset of animal models for neurodevelopmental disorders.

It was established that adult MIA offspring display cortical abnormalities preferentially localized to S1DZ, a subregion of the S1 cytoarchitecturally defined by the absence of a discernable fourth layer (FIG. 19A-19B). The cortical phenotype is characterized by an overall increase in neural activity, that, when reduced, can acutely rescue MIA-induced deficits in social behaviors[8]. Next, it was investigated whether LPS-induced behavioral rescue in MIA offspring is accompanied by changes in S1DZ neural activity. MIA offspring exhibited an increase in the number of S1DZ cells expressing c-Fos, a marker for neuronal activation, relative to control offspring. However, in LPS-treated offspring, the number of c-$Fos^+$ S1DZ neurons was reduced to levels of control offspring (FIG. 20A-20B and FIG. 21). LPS injections did not elicit a generalized, brain-wide effect on c-Fos expression in MIA offspring; the number of c-$Fos^+$ neurons either remained unchanged, as in several cortical regions examined, or increased, such as in the central amygdala (CeA), a region known to be activated by LPS16 (FIG. 20A, 20C and FIG. 21D, 21E). Therefore, LPS-induced behavioral rescue in MIA offspring was accompanied by a reduction in S1DZ neural activity.

Dysregulation of neural activity and deficits in interneuron function in S1 have been previously associated with various genetic mouse models for neurodevelopmental disorders[17-19] Therefore, the next step was to determine whether increased neural activity can also be observed in the S1DZ of monogenic mutant mice. The number of c-$Fos^+$ S1DZ neurons was increased compared to that of WT animals, and the magnitude of this increase correlated with the severity of the sociability deficits, notably in Cntnap2 and Fmr1 mutant animals (FIG. 22A-22B). These data suggest that increased neural activity in S1DZ may contribute to the expression of sociability deficits also in monogenic mutant mice. Therefore, it was tested whether reducing neural activity in the S1DZ of monogenic mutant mice could correct their sociability deficits. Enhanced yellow fluorescent protein (EYFP) or halorhodopsin (NpHR) were virally targeted to the S1DZ and assayed sociability while optically inhibiting the S1DZ at 3-min intervals (FIG. 20D-20F). A rescue of the sociability deficits in Cntnap2 and Fmr1 mutant animals was observed. Shank3 mutant mice showed an increase in sociability upon photoinhibition, but it was not significantly different from that of control animals expressing EYFP (FIG. 20F and FIG. 22C-22F). Therefore, reducing neural activity in the S1DZ was sufficient to rescue sociability deficits in Cntnap2 and Fmr1 mutant mice as well as in MIA offspring[8]. Unlike in MIA offspring, however, LPS treatment failed to reduce the number of S1DZ c-$Fos^+$ neurons in monogenic mutant mice (FIG. 20G-20I).

LPS injection is known to increase production of inflammatory cytokines[20]. Administration of LPS results in a robust increase in plasma levels of IFN-γ, IL-6, and TNF-α (FIG. 23A). Intriguingly, IL-17a, whose orthologue in *C. elegans*[21] has previously been implicated in promoting social behaviors, was prominently upregulated in MIA offspring, but not in monogenic mutant mice or in control animals (FIG. 23A). Furthermore, it was noted that the receptor subunit A for IL-17a (IL-17Ra) is expressed in cortical neurons, including in the S1DZ (FIG. 23B-23D and FIG. 24A-24C). These data suggested that the increased levels of IL-17a upon LPS treatment in MIA, but not in mutant mice, may directly impact the S1DZ to restore sociability. Consistent with this idea, direct administration of recombinant IL-17a into the S1DZ was sufficient to rescue the sociability phenotypes of not only MIA offspring, but also of Cntnap2 and Fmr1 mutant mice (FIG. 23E, 23F and FIG. 24D-24H).

To further determine whether IL-17a mediates LPS-driven behavioral rescue, IL-17a activity in the brain was inhibited via intracerebroventricular (i.e.v.) injection of blocking antibodies. Antibodies against IL-17a prevented both the LPS-induced rescue of sociability (FIG. 25A and FIG. 26A-26E) and the reduction of c-Fos expression in the S1DZ of MIA offspring (FIG. 26F). To directly assay the effects of LPS on neural activity multi-electrode arrays were used to measure the firing rate of S1DZ neurons in awake animals (FIG. 27A, 27B). Upon LPS treatment, a decrease in overall firing rate was observed that was prevented by blocking IL-17a in MIA offspring. Neither LPS nor IL-17a blocking antibody treatment changed the firing rate in the S1DZ of control offspring (FIG. 25B-25D and FIG. 27C). Furthermore, LPS injection failed to restore sociability to MIA offspring deficient for IL-17Ra in the S1DZ neurons (FIG. 25E, 25F). IL-17Ra knockdown was mediated by viral delivery of Cre-recombinase, expressed under the control of the human synapsin (hSyn) promoter, into the S1DZ of IL-17Ra$^{fl/fl}$ MIA offspring (FIG. 25E, 25F and FIG. 27D-27J). This data collectively demonstrates that IL-17a mediates the restoring effects of inflammation on social behaviors by directly acting on IL17Ra$^{+}$ S1DZ neurons.

The data presented herein further supports that increased IL-17a production in the pregnant mothers present a risk factor for neurodevelopmental disorders in offspring[22,23]. LPS treatment led to an increase in IL-17a levels in the blood selectively in MIA offspring, but not in other monogenic mutant mice, suggesting that inflammatory responses can result in beneficial effects for individuals who have their immune systems primed by prenatal exposure to inflammation or by other environmental factors.

Example 4: Experimental Methods

Animals:

All experiments were performed according to Guide for the Care and Use of Laboratory Animals and were approved by the National Institutes of Health and the Committee on Animal Care at Massachusetts Institute of Technology. C57BL/6 were purchased from Taconic Biosciences for generating PBS and MIA offspring. Vgat-Cre (028862) were purchased from Jackson Laboratories and inbred. For monogenic experiments, C57BL/6, Cntnap2 (017482), Fmr1 (003025), and Shank3 (017688) mice were purchased from Jackson Laboratories and inbred after colonizing with SFB from donor mice. IL-17Ra$^{fl/fl}$ and IL-17Ra KO were previously described[24,25]. All mice were males aged 2-5 months, unless otherwise specified.

Maternal Immune Activation:

Mice were mated overnight with females carrying SFB in their guts[22]. On E12.5, pregnant female mice were weighed and injected with a single dose (20 mg/kg i.p.) of poly(I:C) (P9582, Sigma Aldrich) or PBS vehicle. Each dam was returned to its cage and left undisturbed until the birth of its litter. All pups remained with the mother until weaning on postnatal day 21-28 (P21-P28), at which time mice were group housed at a maximum of 5 per cage with same-sex littermates. Mating between Vgat-Cre(c/c) males and WT females were used to make MIA Vgat-Cre mice.

Stereotaxic Surgery:

Surgeries were carried out using aseptic technique. Mice were anesthetized using a mixture of ketamine (100 mg/kg, i.p.) and xylazine (10 mg/kg, i.p.). Mice were given pre-operative slow-release buprenorphine (1.0 mg/kg s.c.). For manipulating body temperature with vLPO inhibition, Vgat-Cre mice received bilateral stereotaxic injections of virus (200nl/side) at rates of <0.1 ml/min (AAV$_2$-hSyn-DIO-hM4Di-mCherry (Addgene)). Virus was bilaterally targeted to the vLPO (AP+0.15, ML±0.50, DV−4.9, lambda was raised 600 μm above bregma). For experiments involving optical manipulation in S1DZ, WT, Cntnap2, Fmr1, and Shank3 mice received bilateral stereotaxic injections of virus (400 μl/side) at a rate of <0.1 ml/min (AAV$_2$-hSyn-EYFP, AAV2-hSyn-eNpHR3.0-EYFP). Viruses were bilaterally targeted to the S1DZ (AP−0.50, ML±2.6, DV−0.80, lambda was level with bregma). In order to deliver light into the S1DZ, a 300 μm optic fiber was superficially implanted in the S1DZ. For experiments involving genetic knockdown of IL-17Ra in S1DZ, IL-17Ra$^{fl/fl}$ mice received bilateral stereotaxic injections of virus (800nl/side) at a rate of <0.1 ml/min (pLenti-hSyn-EYFP, pLenti-hSyn-EGFP:nCre). Viruses were bilaterally targeted to the S1DZ. All lentiviruses were made in house. For administration of cytokines into S1DZ, cannula (PlasticsOne) were implanted superficially within the S1DZ. For central administration of blocking antibodies, cannula were implanted above the right lateral ventricle (AP−0.30, ML±1.0, DV−1.35, lambda was raised 600 μm above bregma). Cannula were fitted with dummy cannula (PlasticsOne®) to maintain cannula patency following surgery.

Tracking of Body Temperature:

Body temperature was measured using the Anipill remote temperature monitoring system (007894-001, DSI). Adult male mice were implanted with an Anipill capsule in the abdominal cavity. Experiments were carried out >3 weeks following surgery. Mice were singly housed the day before the experiment. Ambient temperature was maintained at 23.5° C., consistent with the ambient temperature of the vivarium. Body temperature was sampled in 5-minute increments. LPS or saline (Veh) injections occurred between 11:00-13:00 for experiments assaying the effects of LPS on body temperature in PBS and MIA offspring.

Immunohistochemistry:

Animals were transcardially perfused with cold PFA (4% in PBS). Brains were kept in PFA overnight at 4° C. prior to vibratome sectioning (Leica VT1000s). Brains were cut at 50 μm thickness for c-Fos quantification. Brains were cut at 100 μm thickness for all other experiments.

Prior to antibody labeling, sections were incubated in blocking solution (0.4% Triton X-100 and 2% goat serum in PBS) for 30 min. Sections were then incubated in blocking solution containing primary antibodies overnight at room temperature. Primary antibodies used were chicken anti-GFP (1:1000, Ab5450, Abcam), rabbit anti-c-Fos (1:500, ABE457, Millipore®), rabbit anti-DsRed (1:1000, 632496, Clontech), and mouse anti-NeuN (1:1000, MAB377, Millipore®). Sections were washed in wash buffer (0.4% Triton X-100 in PBS) three times before secondary antibody labeling. Sections were incubated in blocking solution containing secondary antibodies and DAPI (1:5000, D1306, Thermofisher) for three hours at room temperature. Images of stained slices were acquired using a confocal microscope (LSM710, Carl Zeiss®) with a 10×, 20×, or 40× objective lens.

In Situ Hybridization

Animals were transcardially perfused with cold PBS. Brains were extracted and embedded in optimal cutting temperature (OCT) compound on dry ice. Sections were cut at 20 μm thickness on a cryostat. In situ hybridizations were performed using RNAscope 2.5 HD Assay-Red kit (322350, Advanced Cell Diagnostics®) using a probe targeting the Il17ra transcript (Mm-Il17ra-O1, 566131, Advanced Cell Diagnostics®). The probe was designed to target region 444-882 of the Il17ra transcript (NM_008359.2). Modifications to the kit protocol to improve adherence of tissue to the slide include an extension of fixation time to 30 min and the addition of a humidified bake step at 40° C. immediately prior to probe hybridization. Sections were counterstained with DAPI. Images were acquired using a confocal microscope (LSM710, Carl Zeiss®) with a 10× or 20× objective lens. Il17ra and DAPI expression was quantified using QuPath[26]. Cells were divided into the following categories based on level of Il17ra expression: low=1-3 puncta, medium=>3-9 puncta, high=>9-15 puncta, highest=>15 puncta.

In Situ Hybridization Followed by Immunohistochemistry

For experiments assaying the overlap of Il17ra and NeuN expression, immunohistochemistry for NeuN was performed following a modified in situ hybridization protocol. The RNAscope 2.5 HD Assay-Red kit in situ protocol was modified in the following ways: Sections were baked at 60° C., followed by a 10 min fixation step with 4% PFA at room temperature. Sections were then stored in 70% ethanol at 4° C. overnight. Sections were permeabilized in 8% SDS for 10 min. Sections were washed twice with PBS between each step. Following SDS treatment, the RNAscope 2.5 HD Assay-Red kit protocol was followed from the probe hybridization step. Following the completion of the in situ protocol, sections were incubated in blocking buffer containing NeuN antibody overnight at 4° C. Sections were then incubated in blocking buffer containing DAPI and secondary antibody for 2 hrs at room temperature.

Behavioral Analysis:

Male mice were tested during the light cycle in a room with lighting maintained at 230 Lux. Animals were transferred to the testing area at least one hour prior to the initiation of experiments. Tracking of mouse behavior was done using Etho Vision XT (Noldus®) tracking system.

Three-Chamber Social Approach Assay:

Adult male mice were assayed for sociability using a three-chamber social approach assay. The arena was constructed of white acrylic (50 cm×35 cm×30 cm). Wire cups (Spectrum Diversified®) were placed in the back left and right corner of the arena beneath water-filled 1L bottles (Nalgene®). On day 0, mice were habituated to the arena for 10 min. Immediately following habituation, mice were singly housed. On day 1 (Pre), mice were placed in the center of the arena and allowed to freely explore. Following 10 min, mice were confined to the center of the arena. An inanimate object (rubber stopper) or a male conspecific were placed beneath the wire cups. Placement of the inanimate object and social target were alternated. Mice were then allowed to freely explore the arena for 10 min. Interaction time was defined as time spent in the areas circumscribing the wire cups (<2 cm). Sociability was defined as interaction time with the social target divided by total interaction time and expressed as a percentage. For experiments involving LPS injections, mice were injected with either saline (Veh) or LPS (50 μg/kg, i.p., L2630, Sigma) on day 2 (Test), four hours prior to testing. For the experiment assaying sociability 72 hrs following LPS injection, mice used for 4 hr LPS sociability experiments were tested for sociability again at 72 hrs.

Three-Chamber Social Approach Assay with DREADD Manipulation:

Adult male Vgat-Cre MIA offspring were bilaterally injected with virus encoding the inhibitory DREADD receptor fused to mCherry into the vLPO. Following >3 weeks of recovery, mice were assayed on the three-chamber social approach assay outlined above. Baseline sociability was assayed on day 1 (Pre). On day 2 and day 3, mice were injected with either Saline (Veh) or CNO (1.5 mg/kg i.p., BML-NS105, Enzo Life Sciences®), two hours prior to initiation of behavior. Injection order was counterbalanced. Following behavioral experiments, post-mortem histology was used to confirm mCherry expression within the vLPO.

For experiments assaying the effect of CNO and LPS injection in Vgat-Cre PBS and MIA offspring that have not undergone surgery, baseline sociability was assessed on day 1. On day 2 and 3 mice received counterbalanced injections of CNO or vehicle. On day 4, mice were injected with LPS.

Three-Chamber Social Approach Assay with S1DZ IL-17a Administration:

Adult male mice were implanted with a cannula into S1DZ bilaterally and allowed to recover for >2 weeks prior to the behavioral experiments. On day 1 (Pre) mice were assayed for sociability. On day 2 (Test), mice were anesthetized briefly using isoflurane and either saline (Veh) or IL-17a (50 ng/side in 1 μl at a rate of 180nl/min, 7956-ML/CF, R&D) was administered bilaterally into S1DZ through 250 μm-projecting injector tips (PlasticsOne®). Four hours after vehicle or IL-17a administration, mice were assayed for sociability. Cannula placements were verified using histology.

Three-Chamber Social Approach Assay with S1DZ Optogenetic Inhibition:

After two weeks of recovery mice were allowed to freely explore the arena for 10 min. The following day, the mice were given 3 min of no stimulation ('off' session) and 3 min of laser stimulation ('on' session) (594 nm, 6 mW).

Three-Chamber Social Approach Assay with IL-17a Blocking Antibody:

For central cytokine blockade experiments, adult male mice were implanted with a cannula into the lateral ventricle and allowed to recover for >2 weeks prior to the behavioral experiments. On day 1 (Pre), mice were tested for baseline sociability. On day 2 (Test) mice were injected with IL-17a blocking antibody (clone 50104; R&D®) or isotype control antibody (IgG2a, clone 54447; R&D). Antibodies were dissolved in saline and administered intracerebroventricularly at 1 mg/kg in 500nl at a rate of 180nl/min through 750 μm-projecting injector tips (PlasticsOne®). Blocking antibody was administered 30 min prior to LPS administration. Four hours following LPS administration, mice were assayed for sociability.

Marble Burying Assay:

On day 1, mice were tested for their baseline marble burying phenotype. On day 2, four hours prior to beginning the marble burying assay, mice were treated with either LPS or vehicle. Marble burying assay was carried out as described previously[8]. Mice were placed into testing arenas (arena size: 40 cm×20 cm×30 cm, bedding depth: 3 cm) each containing 20 glass marbles (laid out in four rows of five marbles equidistant from one another). At the end of the 15 min exploration period mice were carefully removed from the testing cages and the number of marbles buried was recorded. The marble burying index was arbitrarily defined as the following: 1 for marbles covered >50% with bedding, 0.5 for marbles covered <50% with bedding, or 0 for anything less.

Reciprocal Social Interaction Assay:

Four hours prior to testing, mice were injected with vehicle or LPS. Two unfamiliar mice of the same treatment and background were placed in a fresh mouse cage and allowed to freely interact for 10 min. Videos were acquired using IC Capture (The Imaging Source®) at 640×480 aspect ratio and 25 fps. Social interaction (close following, push-crawl, nose-nose sniffing, and nose-anus sniffing) was scored by an observer blind to treatment and background[27].

Quantification of c-$Fos^+$ Cells in the Brain after LPS Administration:

Adult male mice were sacrificed five hours after LPS injection. c-$Fos^+$ cells were quantified using the Cell Counter plugin in Fiji[28]. All cells were counted within a single coronal section of each respective brain region as defined by the Paxinos and Franklin Mouse Atlas[29]. Regions quantified include mPFC (PrL and IL) (AP+1.98), S1DZ (AP−0.46), S1BF (AP−0.46), M1 (AP−0.46), M2 (AP-0.46), AuD (AP−1.94), CeA (AP−1.94), and V1 (AP−3.64). Medial prefrontal cortex (mPFC), prelimbic cortex (PrL), infralimbic cortex (IL), primary somatosensory cortex dysgranular zone (S1DZ), primary somatosensory cortex barrel field (S1BF), primary motor cortex (M1), secondary motor cortex (M2), secondary auditory cortex dorsal part (AuD), central amygdala (CeA), primary visual cortex (V1). For experiments testing IL-17a dependence of LPS-induced changes in c-Fos expression, mice were injected i.e.v. with control antibodies or blocking antibody against IL-17a 30 min prior to i.p. vehicle or LPS injection. Surgical and injection methods were identical to behavioral experiments.

Enzyme-Linked Immunosorbent Assay (ELISA):

After four hours of vehicle or LPS administration, mice were anesthetized by intraperitoneal injection of fatal plus (100 mg/kg). All blood samples were centrifuged at 10,000g for 10 min at 4C. All samples were stored at −80° C. until further analysis. Cytokines concentrations in plasma were measured using an ELISA kit (IFN-γ; 430804, TNF-α; 430904, IL-6; 431304, IL-17a; 432504, Biolegend®), following the manufacturer's instructions.

PCR for Assaying IL-17Ra Knockdown:

IL17Ra$^{fl/fl}$ male mice were bilaterally injected with virus encoding nuclear Cre fused to EGFP or control virus encoding only EYFP into the S1DZ. Following >3 weeks, injection sites were dissected from the primary somatosensory cortex. Single cells were dissociated from brain tissue using a modified version[30] of the Papain Dissociation Kit protocol (LK003153, Worthington®) and sorted on a BD FACS Aria (BD Biosciences®) based on EGFP/EYFP expression. RNA was extracted from sorted cells using a Quick-RNA microprep kit (Zymo®). 20 ng of RNA was converted into cDNA using oligodT (Protoscript First Strand CDNA Synthesis Kit, NEB). Il17ra mRNA expression was analyzed using PCR. 1 μl of cDNA was diluted in a 20 μl reaction volume. Il17ra and Gapdh mRNA expression were assessed using the following primers: Il17ra 5'-AGATGCCAGCATCCTGTACC-3' (SEQ ID NO: 5) and 5'-CACAGTCACAGCGTGTCTCA-3' (SEQ ID NO: 6); Gapdh 5'-GACTTCAACAGCCTCCCACTCTTCC-3' (SEQ ID NO: 7) and 5'-TGGGTGGTCCAGGTTTCTTACTCCTT-3' (SEQ ID NO: 8). Cycling conditions for Il17ra: 95° C.x5 min (1 cycle), 95° C.x20 s, 60° C.x30 s, 72° C.x30s (32 cycles), 72° C.x5 min (1 cycle) and 4° C. hold. Cycling conditions for Gapdh: 95° C.x5 min (1 cycle), 95° C.x20 s, 60° C.x30 s, 72° C.x30s (28 cycles), 72° C.x5 min (1 cycle) and 4° C. hold. Band intensity from gel images were quantified using ImageJ.

In Vivo Electrophysiology

Electrophysiological experiments were conducted in head-fixed mice trained to walk on a rotating running wheel. Prior to training, mice were implanted with custom crowns permitting head-fixing above the wheel and allowed to recover for one week before training. Mice were trained to walk on the wheel for three 10 min sessions daily for at least one week. Following training, mice were implanted with a multi-electrode array targeting the S1DZ and allowed to recover before testing. To assess IL-17a dependence of LPS-induced changes in neural activity, mice were injected i.p. with control antibodies or blocking antibody against IL-17a (1 mg/mouse), 30 min prior to i.p. vehicle or LPS injection. Baseline neural activity was measured while mice were running on the wheel immediately prior to the first injection. Following the first injection, mice were returned to their home cage. Post-injection (Test) neural activity during wheel running was measured 4 hrs after vehicle or LPS injection.

Multi-Electrode Array Construction and Implantation.

Custom multi-electrode array scaffolds (drive bodies) were designed using 3D CAD software (SolidWorks®) and printed in Accura 55 Plastic™ (American Precision Prototyping®) as described previously[31,32]. Prior to implantation, each array scaffold was loaded with 8-24 independently movable micro-drives carrying 12.5 μm nichrome (California Fine Wire Company®) tetrodes. Electrodes were pinned to custom-designed, 32- or 128-channel electrode interface boards (EIB, Sunstone Circuits®) along with a common reference wire (A-M systems).

Electrophysiological Recordings and Spike Sorting

Signals were acquired using a Neuralynx multiplexing digital recording System™ (Neuralynx®) through a combination of 32- and 64-channel digital multiplexing headstages plugged into the EIB of the implant. Signals from each electrode were amplified, filtered between 0.1 Hz and 9 kHz and digitized at 30 kHz. Initial spike sorting was performed using MountainSort, followed by manual quality control using MClust toolbox found on the world wide web at redishlab.neuroscience.umn.edu/mclust/MClust.html.

Analysis of Firing Rate

Firing rate was calculated across one second time windows during which animals were walking stably on the rotating wheel averaged across 25-50 trials per condition. The first second after wheel rotation onset was omitted to avoid firing rate changes due to acceleration. Firing rate was sampled with a Ims bin width passed through a box car filter (100 ms). The resulting PSTHs were then smoothed with a 50 ms Gaussian. To assess the effect of treatment on neural activity, changes in firing rates during wheel running 4 hrs after injection were normalized to the pre-injection baseline.

Statistics: Statistical analyses were performed using GraphPad® Prism™

Example 3-4 References

1. Whitrow, M. Wagner-Jauregg and fever therapy. Med. Hist. (1990). doi: 10.1017/S0025727300052431
2. Curran, L. K. et al. Behaviors associated with fever in children with autism spectrum disorders. Pediatrics 120, e1386-e1392 (2007).
3. Grzadzinski, R., Lord, C., Sanders, S. J., Werling, D. & Bal, V. H. Children with autism spectrum disorder who improve with fever: Insights from the Simons Simplex Collection. Autism Res. 11, 175-184 (2018).
4. Shi, L., Fatemi, S. H., Sidwell, R. W. & Patterson, P. H. Maternal influenza infection causes marked behavioral and pharmacological changes in the offspring. J. Neurosci. (2003).
5. Alarcón, M. et al. Linkage, Association, and Gene-Expression Analyses Identify CNTNAP2 as an Autism-Susceptibility Gene. Am. J. Hum. Genet. (2008). doi: 10.1016/j.ajhg.2007.09.005
6. The Dutch-Belgian Fragile X Consorthium et al. Fmr1 knockout mice: A model to study fragile X mental retardation. Cell (1994). doi: 10.1016/0092-8674 (94) 90569-X
7. Peça, J. et al. Shank3 mutant mice display autistic-like behaviours and striatal dysfunction. Nature (2011). doi: 10.1038/nature09965

8. Shin Yim, Y. et al. Reversing behavioural abnormalities in mice exposed to maternal inflammation. Nature (2017). doi: 10.1038/nature23909
9. Kozak, W., Conn, C. A. & Kluger, M. J. Lipopolysaccharide locomotor activity induces fever and depresses in unrestrained mice. Am. J. Physiol. Integr. Comp. Physiol. (1994). doi: 10.1152/ajpregu.1994.266.1.R125
10. Choi, G. B. et al. The maternal interleukin-17a pathway in mice promotes autism-like phenotypes in offspring. Science (80-.). (2016). doi: 10.1126/science.aad0314
11. Smith, S. E. P., Li, J., Garbett, K., Mirnics, K. & Patterson, P. H. Maternal Immune Activation Alters Fetal Brain Development through Interleukin-6. J. Neurosci. (2007). doi: 10.1523/JNEUROSCI.2178-07.2007
12. Malkova, N. V., Yu, C. Z., Hsiao, E. Y., Moore, M. J. & Patterson, P. H. Maternal immune activation yields offspring displaying mouse versions of the three core symptoms of autism. Brain. Behav. Immun. (2012). doi: 10.1016/j.bbi.2012.01.011
13. Armbruster, B. N., Li, X., Pausch, M. H., Herlitze, S. & Roth, B. L. Evolving the lock to fit the key to create a family of G protein-coupled receptors potently activated by an inert ligand. Proc. Natl. Acad. Sci. (2007). doi: 10.1073/pnas.0700293104
14. Vong, L. et al. Leptin Action on GABAergic Neurons Prevents Obesity and Reduces Inhibitory Tone to POMC Neurons. Neuron (2011). doi: 10.1016/j.neuron.2011.05.028
15. Zhao, Z.-D. et al. A hypothalamic circuit that controls body temperature. Proc. Natl. Acad. Sci. (2017). doi: 10.1073/pnas.1616255114
16. Cai, H., Haubensak, W., Anthony, T. E. & Anderson, D. J. Central amygdala PKC-δ+neurons mediate the influence of multiple anorexigenic signals. Nat. Neurosci. (2014). doi: 10.1038/nn.3767
17. Gogolla, N. et al. Common circuit defect of excitatory-inhibitory balance in mouse models of autism. J. Neurodev. Disord. (2009). doi: 10.1007/s11689-009-9023-x
18. Orefice, L. L. L. et al. Peripheral Mechanosensory Neuron Dysfunction Underlies Tactile and Behavioral Deficits in Mouse Models of ASDs. Cell (2016). doi: 10.1016/j.cell.2016.05.033
19. Selby, L., Zhang, C. & Sun, Q. Q. Major defects in neocortical GABAergic inhibitory circuits in mice lacking the fragile X mental retardation protein. Neurosci. Lett. (2007). doi: 10.1016/j.neulet.2006.11.062
20. Erickson, M. A. & Banks, W. A. Cytokine and chemokine responses in serum and brain after single and repeated injections of lipopolysaccharide: Multiplex quantification with path analysis. Brain. Behav. Immun. (2011). doi: 10.1016/j.bbi.2011.06.006
21. Chen, C. et al. IL-17 is a neuromodulator of *Caenorhabditis elegans* sensory responses. Nature (2017). doi: 10.1038/nature20818
22. Kim, S. et al. Maternal gut bacteria promote neurodevelopmental abnormalities in mouse offspring. Nature (2017). doi: 10.1038/nature23910
23. Lammert, C. R. et al. Cutting Edge: Critical Roles for Microbiota-Mediated Regulation of the Immune System in a Prenatal Immune Activation Model of Autism. J. Immunol. (2018). doi: 10.4049/jimmunol.1701755
24. El Malki, K. et al. An alternative pathway of imiquimod-induced psoriasis-like skin inflammation in the absence of interleukin-17 receptor a signaling. J. Invest. Dermatol. (2013). doi: 10.1038/jid.2012.318
25. Tusi, B. K. et al. Population snapshots predict early haematopoietic and erythroid hierarchies.
Nature (2018). doi: 10.1038/nature25741
26. Bankhead, P. et al. QuPath: Open source software for digital pathology image analysis. Sci. Rep. (2017). doi: 10.1038/s41598-017-17204-5
27. Silverman, J. L., Yang, M., Lord, C. & Crawley, J. N. Behavioural phenotyping assays for mouse models of autism. Nature Reviews Neuroscience (2010). doi: 10.1038/nrn2851
28. Schindelin, J. et al. Fiji: An open-source platform for biological-image analysis. Nature Methods (2012). doi: 10.1038/nmeth.2019
29. Paxinos, G. & Franklin, K. B. J. Mouse brain in stereotaxic coordinates. Academic Press (2001). doi: 10.1016/S0306-4530 (03) 00088-X
30. Hrvatin, S. et al. Publisher Correction: Single-cell analysis of experience-dependent transcriptomic states in the mouse visual cortex. Nature Neuroscience (2018). doi: 10.1038/s41593-018-0112-6
31. Halassa, M. M. et al. State-dependent architecture of thalamic reticular subnetworks. Cell (2014). doi: 10.1016/j.cell.2014.06.025
32. Brunetti, M. et al. Design and fabrication of ultralight weight, Adjustable multi-electrode probes for electrophysiological recordings in mice. J. Vis. Exp. (2014). doi: 10.3791/51675

Example 5: Anti-CD3 Treatment Recruits IL-17+ Immune Cells to the Meninges

In order to increase the level of IL-17 in the brain without direct injection, wild-type (WT) and Fragile X mental retardation mouse models (FMR1 KO) were treated with an anti-CD3 antibody (Purified Anti-Mouse CD3e (145-2C11); Tonbo Biosciences®, San Diego, CA) or a saline control.

Cells in the gut were analyzed by flow cytometry for IL-17A and CD4 expression for anti-CD3 treated and control mice. Both WT and FMR1 KO mice treated with anti-CD3 exhibited a significant increase in IL17a+, CD4 T-cells in the gut compared to mice that received saline control (FIG. 28).

Cell imaging of the meninges was performed to determine the localization of immune cells in the brain and whether immune cells have differential localization or expression of interleukins following anti-CD3 antibody treatment. Surprisingly, WT mice that received anti-CD3 antibody treatment exhibited an increase in IL-17+ immune cells in the meninges of the brain within 1 day of treatment (FIG. 29).

Following Th-17 cell expansion, it was discovered that WT, MIA, Cntap2, and FMR1 mice treated with anti-CD3 antibody displayed an increase in the percentage of interactions with other mice. Stated another way, Th17 expansion is sufficient to rescue socialability deficits in models of Fragile X mental retardation and autism spectrum disorders (FIG. 30).

Taken together, these results confirm that Th17 cell expansion in the gut can increase the expression and recruitment of IL-17+ immune cells in the brain and that IL-17a is sufficient to promote socialability across models (FIG. 23E-23F).

Sequences

SEQ ID NO: 1 (interleukin-17A precursor [Homo sapiens]; NCBI Reference Sequence: NP_002181.1)

```
  1 mtpgktslvs lllllsleai vkagitiprn pgcpnsedkn fprtvmvnln ihnrntntnp

 61 krssdyynrs tspwnlhrne dperypsviw eakcrhlgci nadgnvdyhm nsvpiqqeil

121 vlrrepphcp nsfrlekilv svgctcvtpi vhhva
```

SEQ ID NO: 2 (interleukin-17 receptor A isoform 1 precursor [Homo sapiens]; NCBI Reference Sequence: NP_055154.3)

```
  1 mgaarsppsa vpgpllglll lllgvlapgg aslrlldhra lvcsqpglnc tvknstcldd
 61 swihprnltp sspkdlqiql hfahtqqgdl fpvahiewtl qtdasilyle gaelsvlqln
121 tnerlcvrfe flsklrhhhr rwrftfshfv vdpdqeyevt vhhlpkpipd gdpnhqsknf
181 lvpdceharm kvttpcmssg slwdpnitve tleahqlrvs ftlwnesthy qilltsfphm
241 enhscfehmh hipaprpeef hqrsnvtltl rnlkgccrhq vqiqpffssc Indclrhsat
301 vscpempdtp epipdymplw vywfitgisi llvgsvilli vcmtwrlagp gsekysddtk
361 ytdglpaadl ippplkprkv wiiysadhpl yvdvvlkfaq flltacgtev aldlleeqai
421 seagvmtwvg rqkqemvesn skiivlcsrg trakwqallg rgapvrlrcd hgkpvgdlft
481 aamnmilpdf krpacfgtyv vcyfsevscd gdvpdlfgaa pryplmdrfe evyfriqdle
541 mfqpgrmhrv gelsgdnylr spggrqlraa ldrfrdwqvr cpdwfecenl ysaddqdaps
601 ldeevfeepl lppgtgivkr aplvrepgsq aclaidplvg eeggaavakl ephlqprgqp
661 apqplhtlvl aaeegalvaa vepgpladga avrlalageg eacpllgspg agrnsvlflp
721 vdpedsplgs stpmaspdll pedvrehleg lmlslfeqsl scqaqggcsr pamvltdpht
781 pyeeeqrqsv qsdqgyisrs spqppeglte meeeeeeeqd pgkpalplsp edleslrslq
841 rqllfrqlqk nsgwdtmgse segpsa
```

SEQ ID NO: 3 (interleukin-17 receptor A isoform 2 precursor [Homo sapiens]; NCBI Reference Sequence: NP_001276834.1)

```
  1 mgaarsppsa vpgpllglll lllgvlapgg aslrlldhra lvcsqpglnc tvknstcldd
 61 swihprnltp sspkdlqiql hfahtqqgdl fpvahiewtl qtdasilyle gaelsvlqln
121 tnerlcvrfe flsklrhhhr rwrftfshfv vdpdqeyevt vhhlpkpipd gdpnhqsknf
181 lvpdceharm kvttpcmssg slwdpnitve tleahqlrvs ftlwnesthy qilltsfphm
241 enhscfehmh hipaprpeef hqrsnvtltl rnlkgccrhq vqiqpffssc Indclrhsat
301 vscpempdtp epipgpgsek ysddtkytdg lpaadlippp lkprkvwiiy sadhplyvdv
361 vlkfaqfllt acgtevaldl leegaiseag vmtwvgrqkq emvesnskii vlcsrgtrak
421 wqallgrgap vrlrcdhgkp vgdlftaamn milpdfkrpa cfgtyvvcyf sevscdgdvp
481 dlfgaapryp lmdrfeevyf riqdlemfqp grmhrvgels gdnylrspgg rqlraaldrf
541 rdwqvrcpdw fecenlysad dqdapsldee vfeepllppg tgivkraplv repgsqacla
601 idplvgeegg aavaklephl qprgqpapqp lhtlvlaaee galvaavepg pladgaavrl
661 alagegeacp llgspgagrn svlflpvdpe dsplgsstpm aspdllpedv rehleglmls
721 lfeqslscqa qggcsrpamv ltdphtpyee eqrqsvqsdq gyisrsspqp pegltemeee
781 eeeeqdpgkp alplspedle slrslqrqll frqlqknsgw dtmgsesegp sa
```

SEQ ID NO: 4 (interferon gamma precursor [Homo sapiens]);
NCBI Reference Sequence: NP_000610.2)
1 mkytsyilaf qlcivlgslg cycqdpyvke aenlkkyfna ghsdvadngt lflgilknwk 61 eesdrkimqs qivsfyfklf knfkddqsiq ksvetikedm nvkffnsnkk krddfekltn 121 ysvtdlnvqr kaiheliqvm aelspaaktg krkrsqmlfr grrasq

---

The invention claimed is:

1. A method of treating a neurodevelopmental disorder in a subject in need thereof, the method comprising: administering to the subject:

i) an IL17a peptide and ii) an anti-CD3 antibody;

wherein the neurodevelopmental disorder is selected from the group consisting of:

autism spectrum disorder (ASD), Asperger's syndrome, and fragile X syndrome.

2. The method of claim 1, wherein the IL17a peptide is recombinant.

3. The method of claim 1, further comprising administering an interferon peptide.

4. The method of claim 3, wherein the interferon is interferon gamma (IFNγ).

5. The method of claim 1, wherein i) the IL17a peptide and ii) the anti-CD3 antibody are administered by direct injection, subcutaneous injection, muscular injection, oral, or nasal administration.

6. The method of claim 1, wherein the level or activity of IL-17 receptor is increased in the brain of the subject as compared to the level in a patient with the neurodevelopmental disorder that has not been treated with i) the IL17a peptide and ii) the anti-CD3 antibody.

7. The method of claim 1, wherein the neurodevelopmental disorder is ASD or fragile X syndrome.

8. A method of treating a neurodevelopmental disorder in a subject in need thereof, the method comprising: administering to the subject an anti-CD3 antibody; wherein the neurodevelopmental disorder is selected from the group consisting of:

autism spectrum disorder (ASD), Asperger's syndrome, and fragile X syndrome.

9. The method of claim 8, further comprising administering an interferon peptide.

10. The method of claim 9, wherein the interferon is interferon gamma (IFNγ).

11. The method of claim 8, wherein the anti-CD3 antibody is administered by direct injection, subcutaneous injection, muscular injection, oral, or nasal administration.

12. The method of claim 8, wherein the neurodevelopmental disorder is ASD or fragile X syndrome.

* * * * *